United States Patent
Wang et al.

(10) Patent No.: US 10,519,474 B2
(45) Date of Patent: Dec. 31, 2019

(54) RECOMBINANT MICROORGANISM FOR IMPROVED PRODUCTION OF FINE CHEMICALS

(71) Applicant: BASF SE, Ludwigshafen (DE)

(72) Inventors: Qingzhao Wang, Ardsley, NY (US); Shakir Siraj Ratani, Elmsford, NY (US); Zheyuan Guo, Tarrytown, NY (US); Hartwig Schroeder, Nussloch (DE); Holger Hartmann, Mannheim (DE); Markus Pompejus, San Diego, CA (US)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/579,291

(22) PCT Filed: Jun. 2, 2016

(86) PCT No.: PCT/EP2016/062457
§ 371 (c)(1),
(2) Date: Dec. 4, 2017

(87) PCT Pub. No.: WO2016/193351
PCT Pub. Date: Dec. 8, 2016

(65) Prior Publication Data
US 2018/0148748 A1 May 31, 2018

Related U.S. Application Data

(60) Provisional application No. 62/171,036, filed on Jun. 4, 2015.

(51) Int. Cl.
*C12P 13/06* (2006.01)
*C07K 14/245* (2006.01)
*C12N 1/20* (2006.01)
*C12N 15/70* (2006.01)

(52) U.S. Cl.
CPC ............ *C12P 13/06* (2013.01); *C07K 14/245* (2013.01); *C12N 1/20* (2013.01); *C12N 15/70* (2013.01)

(58) Field of Classification Search
None
See application file for complete search history.

(56) References Cited

U.S. PATENT DOCUMENTS

| 5,019,509 A | 5/1991 | Rozzell |
| 5,565,350 A | 10/1996 | Kmiec |
| 5,786,313 A | 7/1998 | Schneider et al. |
| 8,524,476 B2 * | 9/2013 | Smirnov ............... C12N 9/0069 435/116 |
| 2009/0098621 A1 * | 4/2009 | Rybak ..................... C12P 13/04 435/107 |
| 2010/0047878 A1 | 2/2010 | Nagai et al. |
| 2015/0376663 A1 | 12/2015 | Schroeder et al. |
| 2016/0304917 A1 | 10/2016 | Krawczyk et al. |
| 2016/0355829 A1 | 12/2016 | Schroder et al. |
| 2017/0211106 A1 | 7/2017 | Schroder et al. |
| 2018/0030418 A1 | 2/2018 | Dantas Costa et al. |

FOREIGN PATENT DOCUMENTS

| RU | 2268305 C2 | 1/2006 |
| RU | 2515044 C2 | 1/2006 |
| RU | 2006130318 A | 2/2008 |
| WO | WO-8903427 A1 | 4/1989 |
| WO | WO-94/29421 A1 | 12/1994 |
| WO | WO-00/15815 A1 | 3/2000 |
| WO | WO-2005071062 A1 | 8/2005 |
| WO | WO-2007/120198 A2 | 10/2007 |
| WO | WO-2008/119009 A2 | 10/2008 |
| WO | WO-2008141226 A2 | 11/2008 |
| WO | WO-2009022754 A1 | 2/2009 |
| WO | WO-2009/082029 A1 | 7/2009 |
| WO | WO-2012/150155 A1 | 11/2012 |
| WO | WO-2012/172822 A1 | 12/2012 |
| WO | WO-2014009435 A1 | 1/2014 |
| WO | WO-2015/028915 A1 | 3/2015 |
| WO | WO-2015/044818 A1 | 4/2015 |
| WO | WO-2015/087226 A1 | 6/2015 |
| WO | WO-2015/140226 A1 | 9/2015 |
| WO | WO-2016/063172 A1 | 4/2016 |
| WO | WO-2016/193351 A2 | 12/2016 |

OTHER PUBLICATIONS

International Search Report for PCT/EP2016/062457 dated Nov. 30, 2016.
Written Opinion of the International Searching Authority for PCT/EP2016/062457 dated Nov. 30, 2016.
International Search Report for PCT/EP2016/063172 dated Nov. 9, 2016.
Written Opinion of the International Searching Authority for PCT/EP2016/063172 dated Nov. 9, 2016.
U.S. Appl. No. 61/882,006, Qingzhao et al.
U.S. Appl. No. 61/882,007, Qingzhao et al.
U.S. Appl. No. 61/915,513, Qingzhao et al.
U.S. Appl. No. 61/915,516, Qingzhao et al.
U.S. Appl. No. 61/915,517, Qingzhao et al.
U.S. Appl. No. 61/915,525, Qingzhao et al.
U.S. Appl. No. 61/915,527, Qingzhao et al.
U.S. Appl. No. 61/915,528, Qingzhao et al.
U.S. Appl. No. 61/881,964, Qingzhao et al.
U.S. Appl. No. 61/881,966, Qingzhao et al.

(Continued)

*Primary Examiner* — Suzanne M Noakes
(74) *Attorney, Agent, or Firm* — Drinker Biddle & Reath LLP

(57) ABSTRACT

Recombinant microorganism for improved production of fine chemicals The present invention relates to a recombinant nucleic acid molecule, a recombinant micro-organism, to a method for producing alanine and to the use of the recombinant nucleic acid molecule or the recombinant microorganism for the fermentative production of alanine.

23 Claims, 23 Drawing Sheets
Specification includes a Sequence Listing.

(56) References Cited

OTHER PUBLICATIONS

U.S. Appl. No. 61/881,968, Qingzhao et al.
U.S. Appl. No. 61/881,967, Qingzhao et al.
U.S. Appl. No. 61/881,970, Qingzhao et al.
U.S. Appl. No. 61/881,972, Qingzhao et al.
U.S. Appl. No. 61/881,969, Qingzhao et al.
U.S. Appl. No. 61/915,518, Qingzhao et al.
U.S. Appl. No. 61/915,534, Qingzhao et al.
U.S. Appl. No. 16/915,535, Qingzhao et al.
U.S. Appl. No. 62/174,529, Qingzhao et al.
U.S. Appl. No. 15/735,875, Jaitzig et al.
Atabase EMBL [Online], Sequence 3 from Patent WO2009082029, XP002762308, retrieved from EBI accession No. EM PAT:HB463804, Database accession No. HB463804, 2009.
Fowler et al., "Increased Malonyl Coenzyme A Biosynthesis by Tuning the *Escherichia coli* Metabolic Network and Its Application to Flavanone Production," Applied and Environmental Microbiology, vol. 75, No. 18, pp. 5831-5839, 2009.
Guardiola et al., "*Escherichia coli* K-12 Mutants Altered in the Transport of Branched-Chain Amino Acids," Journal of Bacteriology, vol. 108, No. 3, pp. 1034-1044, 1971.
Lee et al., "Aerobic production of alanine by *Escherichia coli* aceF IdhA mutants expressing the Bacillus sphaericus alaD gene," Applied Genetics and Molecular Biotechnology, No. 65, pp. 56-60, 2004.
Smith et al., "Fed-batch two-phase production of alanine by a metabolically engineered *Escherichia coli*," Biotechnology Letters, vol. 28, pp. 1695-1700, 2006.
Hermann, "Industrial production of amino acids by coryneform bacteria," Journal of Biotechnology, vol. 104, pp. 155-172, 2003.
Xie et al., "Effect of transport proteins on L-isoleucine production with the L-isoleucine-producing strain *Corynebacterium glutamicum* YILW," Journal of Industrial Microbiology & Biotechnology, vol. 39, pp. 1549-1556, 2012.
Zhang et al., "Metabolic evolution of energy-conserving pathways for succinate production in *Escherichia coli*," Proceedings of the National Academy of Sciences, vol. 106, No. 48, pp. 20180-20185, 2009.
Zhang et al., "Production of L-alanine by metabolically engineered *Escherichia coli*," Applied Microbiology and Biotechnology, vol. 77, pp. 355-366, 2007.
Cahyanto et al., "Construction of Lactobacillus Plantarum Strain with Enhanced L-lysine Yield," Journal of Applied Microbiology, vol. 102, pp. 674-679, 2007.
Chen et al., "Cloning, Expression and Characterization of L-Aspartate ß-Decarboxylase Gene from *Alcaligenes faecalis* CCRC 11585," Journal of Industrial Microbiology and Biology & Biotechnology, vol. 25, pp. 132-140, 2000.
Raczynska-Pawelec et al., "Characterization of *Campylobacter jejuni* and Gene Cloned in *Escherichia coli*", Acta Microbiologica Polonica, vol. 44, No. 3/4, pp. 227-241, 1995.
Wang et al., "Molecular Cloning of the Aspartate 4-Decarboxylase Gene from *Pseudomonas* sp. ATCC 19121 and Characterization of the Bifunctional Recombinant Enzyme", Applied Microbiology and Biotechnology, vol. 73, pp. 339-349, 2006.

\* cited by examiner

A)

Figure 1:
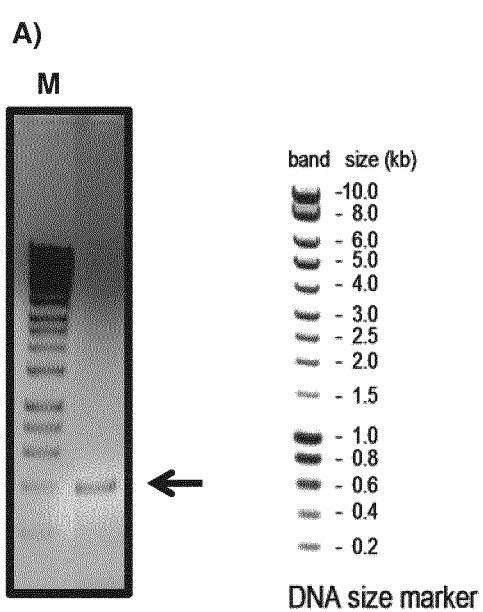

Figure 1 (continued):

B)

```
GTCTTTGAGTAATGCTGTCCCCGGCGAAACAAGCTAAAAAAATTAACAGAACGATTATCCGGCGTTGACAT gct tcacctcacttcacatataaagatt
                                                              <yfbV
caaaaatttgtgcaaattcacaactcagcggacaacgttcaaaacatttgtcttccataccactcagtatcctttagcagcctgaagcctaagtagtacata
ttcattgagtcgtcaaattcatatcattatgccattggctgaaattacgcaagatggcatagactcaagatattcttcctcatcatgcaagaaaaatttgcagtgcat
                                                                                     ackA>
gatgttaatcataaatgtcggtgtcatcatgcctatgctcctgacgttttttagccacgtatcaattataggtactt ATGTCGAGTAAGTTAGT
                                                                              ▶MetSerSerLysLeuVa
       P395-ackA-pta-check1>                               P395-ackA-pta-check2>
ACTGGTTCTGAACTGCGGTAGTTCTTCACTGAAATTTGCCATCATCGATGCAGTAAATGGTGAAGAGTACCTTTCTTGGTTAGCCGAATGTTTCCAC
▶LeuValLeuAsnCysGlySerSerLeuLysPheAlaIleIleAspAlaValAsnGlyGluTyrLeuLeuValSerPheHis
CTGCCCGAAGCACGTATCAAATGGACGGCAATAAACAGGAAGGCTTTAGGTGCAGGCCGCTCACAGCGAAGCGCTCAACTTTATCa
▶LeuProGluAlaArgIleLysTrpLysMetAspGlyAsnLysGlnGlyGlyPheArgCysArgProLeuThrAlaLysArgSerAsnPheIleA
  FRT>
attaacccctcactaaagggcgcgaagttcctattctctagaaagtatagaactcctcgagccctatagtgagtcgtattaGCCGATGCTGCAGGGTATGC
▶sn
GCAAGCCGGTTAACGACCTGTCCCGTGGCGCACTGGTTGACGATATCGTCTACACCATCGCGCGCTGACTCAGTCGCGATTCAGTCGCACAGCAGTAAtc
     <P395-ackA-pta-check5                   <P395-ackA-pta-check6
tcgtcatcatccgcagcttgcgtgccgatatctgaaccggaataatcactatctccgttttttattctcttaatctgcattaatcctttctgattatcttgctta
actgcgctgatcaatgaattggccattcacttgcatcttaccacttgtttgtgcaaggaatattgcgctatgtccgcaatcactgaatccaaaccaacaa
  yfcC>
gaagatgggcaATGCCCGATACGTTGGTGATTATCTTTTTTGTGCTATTTTAACCAGCCTTGCCACCT
```

Figure 2:
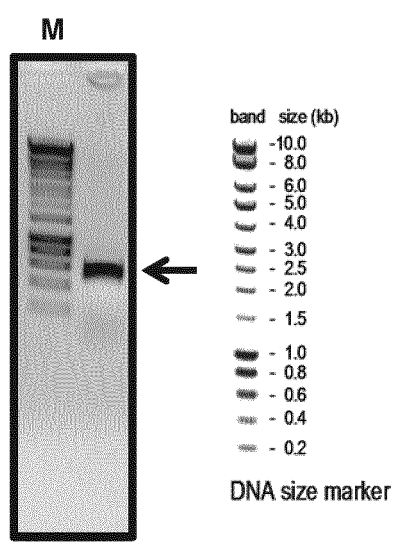

Figure 2 (continued):

B)

```
CAGGTTGGCTGTGTAAGGTTAGTTTTGTTTCGCGCTGCCGCTGTCTCTGATAACTGGTCATGCTGATAAAGACGGGAATAATCCCTACC
P395-adhE-check1>
GGGTTGACCAGCGCAAATAACCCGATGAAAATTTGAAGTAAACGGGAAATCAAAAAGGTCTGAATCACGgttagctccgaagca
aagccggataatgttagccataagatgttgaaaagacgcgctaacaatacgcctttgacagcattttcacctcctaaaattg
ctatcattcgttattgttatctagtgtgtgcaaaacatgctaatgtagcccaccaaatactactacaatttattaactgttagctataatggcgaaa
                                                  P395-adhE-check2>
agcgatgctgaaaggtgtcagctttgcaaaaatttgatttggatcacgtaatcagtaccagaagtgagtaatcttgcttacgccacctggaagt
gacgcattagagataataactctaatgtttaaactctttagtaaatcacagtgagtgcgagtaagcttttgatttcataggttaagc
                                                         adhE>   *ATGGCTGTTACTAA
aaatcatcaccgcactgactatactctcgtattcgagcagatgattactaaaaagtttaacattatcaggagagca  ↑MetAlaValThrAs
                      FRT>
TGTCGCTGAACTTAACGCACTCGTAGAGCGGTGTAAAaattaaccctcactaaagggcggaagttcctattctctagaaagtataggaactt
↑nValAlaGluLeuAsnAlaLeuArgValGluValLysIleAsnProHis
cgagccctaatgaactccgtgctaAAGAAGCCGCTCCCGGCTAAAGCTGAGAAAAAAGCGAAAAAAATCCGCTTAAtcagtagcgctgtct
ggcaatataaacggcccctcctgggccgttttttgttttacccaagcaacttcccataaaccgacattagccttcatcatattgcgac
                                                               <P395-adhE-check5
gatgtataacgcctaaacacaggatattgtactttacaggtcacaagtcacgtcgttaagagccctgtgaggcgtatagcggcgttaaa
aaactgccgagaagggtatatagcccggaagaagtgcgacaggataaaacgaactgacaggataaaagtgccctgctcaccctgtcagtaaagaaattctt
                         <P395-adhE-check6
aTTAATCGTGGCGATGCCTTTCCTGAATAGCCGTTAATGAGCCGACTTGTAACCGCCCTCTATATAGTGT
```

A)

Figure 3:
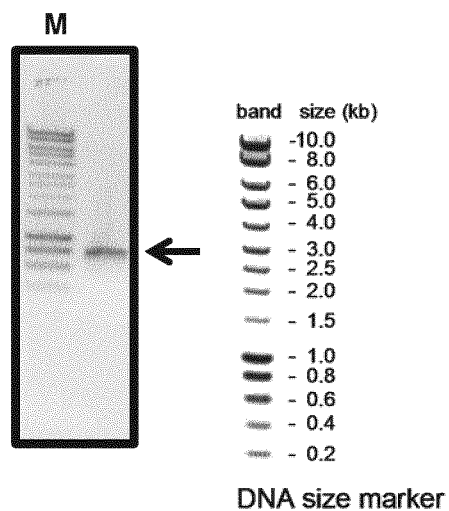

Figure 3 (continued):

B)

```
CCAGCAGGCGTTTCATATGGTATTCCGGGCTGGTCATTAACCAGAGATTCATCCCCTGCGAATGCCCGGGGCCAACGAAACGTGTCTCAAACGGGACC
AAATGAATATCGGTTACCGTCGCCTGGCTCATACAAGGCGTCTCCACCTGCGTCTCGCTTTCGCTCAGGATGCCGATCGGCAAAGAAACGGATCGCCCATAATCGC
                                                                    P395-frd-check1
                                                                                           <poxA
CGCGCGTTTAATAAGTTAGGAATGGATGCGCTCGGCTGCCAGGATGCCGTTTCGCTCATagtaatctccagtctttgacaaggcacgaagtctactcgc
aacgcgacggcgagacaaatttacgcaggaatcaaacagcggtgggcagtgactaaaaagcacgatctgatgttagtaattaatcatcttcagtgataat
ttagccctcttgcgcactaaaaaaatcgatctcgtcaaattcagactcgtcaatctgttgtacctataaaggagcagtgaatagcgttcgcagaccgta
                                                frdA
                                         GTGCAAACCTTTCAAGCCGATCTTGCCATTGTAGGCGCCGGTGG
                                         ValGlnThrPheGlnAlaAspLeuAlaIleValGlyAlaGlyGly
actttcaggtactacccctgaagtacgtgctgtgtgggataaaaacaatctgaggaatg'
                                                              FRT>
CGCGGGaattaaccctcactaaagggcggaagttcctattctctagaagtataggaactcgagccctaatgaactccgtgctaACGCGATGCACGATCTGAAAAT
▲yAlaGlyIleAsnProHis
TCACGTGCCTGCGGGCAAATGGGTTTTCTACGGTTCTACGGTTCCTGACCAGTTGTCACGCTGATTGGTTATCGTTACAATCTAAcgtatcgccaatgt
                                                    ampC>
                                                                            <P395-frd-check4
aaatccggccgcgcctatggcggccgttttgtatggaaaccagaccttATGTTCAAAACGAGCGCTCGCCTCGCGGCCTTATTAATTACCTCCTCCTTGCTCCACATTTG
CTGCCCCTCAACAAATCAACGATATTGTGCATCGCACAATTACCCCGCTTATAGAGACAACAAAAGATCCCGGTATGCGGTGGGGTAATTTATCAG
GGTAAACCTTATTACTTTACCTGGGGCTATGCGGACATCGCGAAAAGCAGCCCGTCACACACGCAAACGTTGTTTGAGTTAGGTTCGGTCAGCAAAAC
ATTTACG
```

A)

Figure 4:
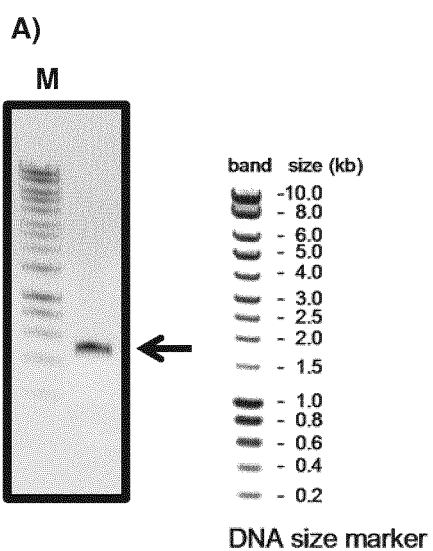

Figure 4 (continued):

B)

```
                                                                      P395-pf1B-check2>
TAATCCGCGACTTCGCATCCCGGAATTCTGGACCGCCTGTCGGTTCTGCACCGGAAAATTTTTCTCACCTGACCGTGATGAACTTCATCACTGATAACC
                                                P395-pf1B-check1>
TGATTCCGGTTACGATCGGTAATATATTATCGGCGGTGGTTTGTTGGTTGACATACTGGGTCATTTACCTGCGTGAAAACGATCACCATTAAtggt
                                                             pf1B>
                                            ATGTCCGAGCTTAATGAAAAGTTAGCCACAGCCTGGGAAGGTTTTACCAAaatta
tgtcgaagtacgcagtaagaaggtaggtgtt                                                                  
                                            ▶MetSerGluLeuAsnGluLysLeuAlaThrAlaTrpGluGlyPheThrLysIleA
    FRT>
accctcactaaagggcggaagttcctattctctagaaagtataggaactt cgagcccgtgctaAAGAACAGCAGGACGTTATTACTCGTACCT
▶snProHis                                                                                pf1A>
TCACTCAATCTATGTAAttagatttgactgaaatcgtacagtaaaaggctccacgaaagtgggccttttttagcacgagagccttttgtcagc
tatctatactttaaggtgactgccaaaacagactcgacgtagcctt cgagctgcgcaccaaacacgcctcagatgggccacatctggagaaacaccgcaATGTCAGTTAT
TGGTCGCATTCACTCCTTTGAATCCTGTGGAACCGTAGACGGCCCAGGTATTCGCTTTATCACCTTTTTCCAGGGCTGCCTGATGCGCTGCTGTATTG
                    <P395-pf1B-check4
TCATAACCGGCGACACCTGGGATACGCATGGC
        <P395-pf1B-check3
```

A)

Figure 5:
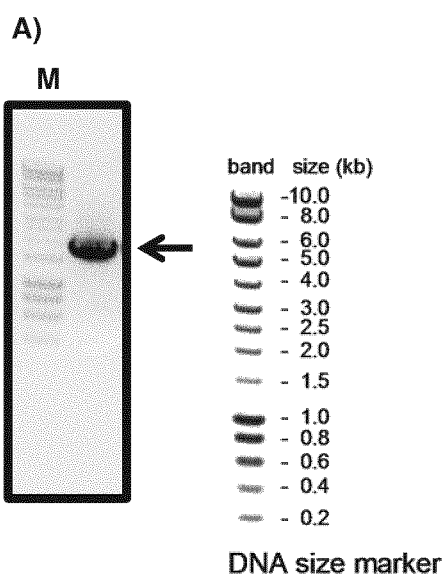
Figure 6:
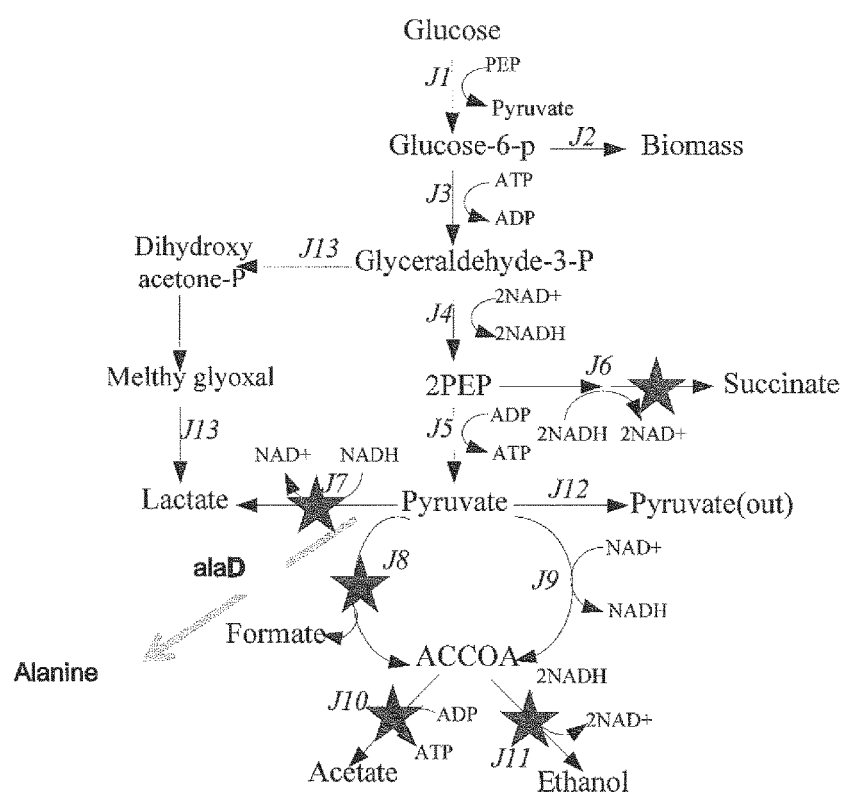

Figure 5 (continued):
B)

```
GAG GGT TTT TGG AGC AGC TGG CGA TTG CTC CGT CTG CGG CAA TTT CGC CAG ACA AGC AGA ATC AAG
    P395-ldhA-check1>
TTC TAC CGT GCC GAC GTT CAA TAA CCA GCG GCT GGG ATG TGA AAG GCT GGC GTT GGT GAT ATG CGC
                                                                P395-ldhA-check3>
AAG CTG ACA ATC TCC CAC CAG ATA ACG GAG ATC GGG AAT GAT TAA ACC TTT ACG CGT AAT GCG TGG
GCT TTC ATC TAA TGC AAT ACG TGT CCC GAG CGG TAG CCA GAT GCC CGC CAG CGT GGG AAC CCA CAG
CCC GAG CGT CAT CAG CAG CGT CAA CGG CAC AAG AAT AAT CAG TAA TAA CAG CGC GAG AAC GGC TTT
                                <ydbH
ATA TTT ACC CAG CAT gggtagttaatatcctgatttagcgaaaaattaagcattcaatacgggtattgtggcatgtttaaccgttcagttgaa
          ggttgcgcctacactaagcatagttgttgatgaattttcaatatcgccatagctttcaattatatttgaaatttgtaaaatattttagtagcttaaa
                              alaD gstear>
         tgtgattcaacatcactggagaaagtctt atg aaa att ggc atc cct aaa gag att aag aac aat gaa aac cgt
                                     ▶ M   K   I   G   I   P   K   E   I   K   N   N   E   N   R
  gta gca atc acc ccg gca ggt gtt atg act ctg gtt aaa gcg ggc cac gat gtg tac gtc gaa acc
▶ V   A   I   T   P   A   G   V   M   T   L   V   K   A   G   H   D   V   Y   V   E   T
  gaa gcg ggt gcc ggc agc ggc ttc agc gac agc gag tat gag aag gcg ggt gcg gtt att gtg act
▶ E   A   G   A   G   S   G   F   S   D   S   E   Y   E   K   A   G   A   V   I   V   T
  aag gcg gag gac gct tgg gca gcc gaa atg gtt ctg aag gtg aaa gaa ccg ctg gcg gag gag ttt
▶ K   A   E   D   A   W   A   A   E   M   V   L   K   V   K   E   P   L   A   E   E   F
  cgc tat ttt cgt ccg ggt ctg att ttg ttc acc tac ctg cac ctg gct gcg gcc gag gcg ctg acc
▶ R   Y   F   R   P   G   L   I   L   F   T   Y   L   H   L   A   A   A   E   A   L   T
  aag gca ctg gtg gag cag aag gtt gtt ggc atc gcg tac gaa acg gtt caa ctg gcg aat ggt tcc
▶ K   A   L   V   E   Q   K   V   V   G   I   A   Y   E   T   V   Q   L   A   N   G   S
  ctg ccg ctg ctg acc cct atg tct gaa gtt gcg ggt cgc atg agc gtt caa gtc ggc gct cag ttt
▶ L   P   L   L   T   P   M   S   E   V   A   G   R   M   S   V   Q   V   G   A   Q   F
  ctg gag aaa ccg cac ggt ggc aag ggc att ttg ctg ggt ggt gtt ccg ggt gtc cgc cgt ggt aaa
▶ L   E   K   P   H   G   G   K   G   I   L   L   G   G   V   P   G   V   R   R   G   K
  gtg acg atc att ggc ggt ggt acg gcc ggt acg aac gcg gcc aag att gcc gta ggt ctg ggt gca
▶ V   T   I   I   G   G   G   T   A   G   T   N   A   A   K   I   A   V   G   L   G   A
  gat gtg acc att ctg gac atc aac gcg gaa cgt ttg cgt gag ctg gac gat ctg ttt ggc gac caa
▶ D   V   T   I   L   D   I   N   A   E   R   L   R   E   L   D   D   L   F   G   D   Q
  gtc acc acc ctg atg agc aac agc tac cac atc gcg gag tgc gtc cgt gaa agc gat ttg gtc gtt
▶ V   T   T   L   M   S   N   S   Y   H   I   A   E   C   V   R   E   S   D   L   V   V
  ggt gcg gtg ctg atc ccg ggt gca aaa gcc ccg aaa ctg gtg acc gag atg gtc cgt agc atg
▶ G   A   V   L   I   P   G   A   K   A   P   K   L   V   T   E   E   M   V   R   S   M
  acc ccg ggt tcg gtt ctg gtc gac gtg gca att gac cag ggc ggt atc ttc gaa acc acc gac cgc
▶ T   P   G   S   V   L   V   D   V   A   I   D   Q   G   G   I   F   E   T   T   D   R
  gtc acg acc cat gat gac ccg acc tat gtg aaa cat ggc gtg gtt cac tat gcg gtc gcg aat atg
▶ V   T   T   H   D   D   P   T   Y   V   K   H   G   V   V   H   Y   A   V   A   N   M
  ccg ggt gca gtg ccg cgc acg tcc acg ttc gcg ctg acg aac gtg acg att cca tac gct ctg cag
▶ P   G   A   V   P   R   T   S   T   F   A   L   T   N   V   T   I   P   Y   A   L   Q
  atc gcc aat aag ggc tat cgt gcg gcg tgt ctg gat aat ccg gca ttg ctg aaa ggc atc aat acc
▶ I   A   N   K   G   Y   R   A   A   C   L   D   N   P   A   L   L   K   G   I   N   T
  ctg gat ggt cat atc gtt tac gag gct gtg gct gca gca cac aac atg ccg tac act gat gtc cat
▶ L   D   G   H   I   V   Y   E   A   V   A   A   H   N   M   P   Y   T   D   V   H
                                        FRT>
  agc ttg ctg caa ggc taa aattaaccctcactaaagggcggaagttcctattctctagaaagtataggaacttcgagccctaatgaactcc
▶ S   L   L   Q   G
 gtgctatcttgccgctcccctgcattccaggggagctgattcagataatccccaatgaccttcatcctctattcttaaaatagccctgagtcagaaact
            hslJ gene>                                              <P395-ldhA-check2
 gtaattgagaaccaca ATG AAG AAA GTA GCC GCG CTC GTT GCG CTA AGC CTG CTG ATG GCG GGA TGT GTA
 AGT AAT GAC AAA ATT GCT GTA ACG CCA GAA CAG TTA CAG CAT CAT CGT TTT GTG CTG GAA AGC GTA
         <P395-ldhA-check4
 AAC GGT AAG CCC GTG ACC AAC GAT AAA AAT CCG CCA GAA ATC
```

RECOMBINANT MICROORGANISM FOR IMPROVED PRODUCTION OF FINE CHEMICALS

RELATED APPLICATIONS

This application is a national stage application (under 35 U.S.C. § 371) of PCT/EP2016/062457, filed Jun. 2, 2016, which claims benefit of U.S. Application No. 62/171,036, filed Jun. 4, 2015.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 074008_1828_US_571581_SL_ST25 . The size of the text file is 140 KB and the text file was created on Jul. 19, 2019.

FIELD OF THE INVENTION

The present invention relates to a recombinant nucleic acid molecule, a recombinant microorganism, to a method for producing pyruvate, succinate, aspartate, malate, lactate, valine, leucine and/or alanine and to the use of the recombinant nucleic acid molecule or the recombinant microorganism for the fermentative production of pyruvate, succinate, aspartate, malate, lactate, valine, leucine and/or alanine.

DESCRIPTION OF THE INVENTION

Amino acids are organic compounds with a carboxy-group and an amino-group. The most important amino acids are the alpha-amino acids where the amino group is located next to the carboxy-group. Proteins are based on alpha-amino acids.

Alanine has drawn considerable interest because it has been used as an additive in the food, feed and pharmaceutical industries. Moreover alanine is a raw material for the industrial production of alanine, N,N-bis(carboxymethyl)-, trisodium salt (MGDA, trade name Trilon M) which is a strong chelating agent, showing an excellent performance at dissolving organic and inorganic scale (WO94/29421, WO2012/150155). Trilon M grades are readily biodegradable according to standard OECD tests. Due to the superb ecological and toxicological profile, Trilon M grades are particularly suitable for use in products for end-consumers and the demand for such biodegradable complex builders is constantly rising.

Alanine can be produced by fermentation with Coryneform bacteria (Hermann, 2003: Industrial production of amino acids by Coryneform bacteria, J. of Biotechnol, 104, 155-172) or E. coli. (WO2007/120198, WO2008/119009).

It has recently been described that overexpression of the ygaW gene improves fermentative alanine productivity of a microorganism (WO2012/172822).

Alanine production in E. coli is more efficient and widely used for industrial production of alanine as raw material for the chemical industry. As the demand of the chemical industry for alanine is increasing, there is a demand for improvement of productivity of fermentative production of alanine.

It is one object of the present invention to provide microorganisms which can be used in fermentative production of alanine with high yield and efficiency.

DETAILED DESCRIPTION OF THE INVENTION

A contribution to achieving the above mentioned aim is provided by a recombinant microorganism of the family of Escherichia coli (E. coli) having, compared to a respective reference microorganism, at least one of i) a reduced, repressed or deleted activity and/or expression of a brnQ gene and/or ii) an introduced, increased or enhanced activity and/or expression of an argP gene and/or iii) an introduced, increased or enhanced activity and/or expression of a gcvA gene and/or iv) a reduced, repressed or deleted activity and/or expression of a gcvB gene and/or v) an altered activity of an lpxD gene.

The term "reduced, repressed or deleted expression and/or activity of an enzyme", means a significantly reduced, repressed or deleted expression and/or activity and also encompasses an undetectable expression and/or activity of the respective enzymes.

The term "higher", "increase" or "enhanced" e.g. in reference to expression and/or activity of an enzyme or to yield or productivity, means a significantly higher, increased or enhanced expression and/or activity or yield or productivity.

The term "altered" expression and/or activity of an enzyme means an expression and/or activity of an enzyme in a recombinant microorganism that is significantly different from the expression and/or activity of the respective enzyme in a wild-type, non-recombinant microorganism.

Surprisingly, it has been discovered that a microorganism having at least one of i) a reduced, repressed or deleted expression and/or activity of a protein encoded by the brnQ gene and/or ii) an introduced, increased or enhanced activity and/or expression of an argP gene and/or iii) an introduced, increased or enhanced activity and/or expression of a gcvA gene and/or iv) a reduced, repressed or deleted activity and/or expression of a gcvB gene and/or v) an altered activity of an lpxD gene has a higher yield and/or productivity of alanine in fermentative production when compared to the same microorganism not comprising a reduced, repressed or deleted expression and/or activity of the respective brnQ gene and/or an introduced, increased or enhanced activity and/or expression of an argP gene and/or an introduced, increased or enhanced activity and/or expression of a gcvA gene and/or a reduced, repressed or deleted activity and/or expression of a gcvB gene and/or an altered activity of an lpxD gene.

Accordingly, one embodiment of the invention at hand is a recombinant microorganism comprising compared to a respective reference microorganism at least one of i) a reduced, repressed or deleted activity and/or expression of a brnQ gene encoding a brnQ protein having a branched chain amino acid transporter activity and/or ii) an introduced, increased or enhanced activity and/or expression of an argP gene encoding an argP protein having a DNA binding/transcription activating activity and/or iii) an introduced, increased or enhanced activity and/or expression of a gcvA gene encoding a DNA-binding protein and/or iv) a reduced, repressed or deleted activity and/or expression of a gcvB gene encoding a non-protein encoding RNA and/or v) an altered activity of an lpxD gene encoding an UDP3-O-(3-hydroxymyristoyl)-glucosamine N-acyltransferase protein and having compared to a respective reference microorganism a higher yield and/or productivity of alanine in fermentative production.

The term "reference microorganism" as used herein means a control microorganism to which the recombinant microorganism is compared. This reference microorganism has substantially the same genotype as the recombinant microorganism with the exception of the difference to be analyzed. Preferably the reference microorganism is the strain from which the recombinant microorganism is originated. For example, a gene has been introduced into a wild type microorganism, thus creating a recombinant microorganism, then the wild type would be a suitable reference microorganism for this recombinant microorganism. It is also possible, that into a recombinant microorganism A further mutation is introduced, thereby creating a recombinant microorganism B. The recombinant microorganism A would then be the suitable reference microorganism for recombinant microorganism B. In the event, the performance of a recombinant microorganism and the respective reference microorganism shall be compared both microorganisms are grown under substantially identical conditions.

It is obvious for the skilled person that a microorganism having an increased yield and/or productivity of alanine can also be used for the production of other metabolites that are closely related to alanine, for example metabolites that are intermediates in the alanine pathway, that share common intermediates with the alanine pathway or that are metabolites which use alanine as intermediate in their pathway. The microorganisms of the invention can also be easily adapted for having an increased yield and/or productivity of such related metabolites by increasing or introducing certain enzyme activities or by knocking out or decreasing certain enzyme activities.

Such metabolites are for example pyruvate, succinate, aspartate, malate, lactate, valine and leucine.

For example, in order to use the recombinant microorganism of the invention to produce succinate, the genes ldh, pfl, pta and adhE have to be knocked out and a PEP carboxylase gene and/or a pyruvate carboxylase gene have to be introduced in the genome of the microorganism of the invention. The respective pathway and necessary mutations are described for example in Zhang et al. (2009), PNAS (106) pp 20180-20185.

Accordingly, another embodiment of the invention at hand is a recombinant microorganism comprising compared to a respective reference microorganism at least one of i) a reduced, repressed or deleted activity and/or expression of a brnQ gene encoding a brnQ protein having a branched chain amino acid transporter activity and/or ii) an introduced, increased or enhanced activity and/or expression of an argP gene encoding an argP protein having a DNA binding/transcription activating activity and/or iii) an introduced, increased or enhanced activity and/or expression of a gcvA gene encoding a DNA-binding protein and/or iv) a reduced, repressed or deleted activity and/or expression of a gcvB gene encoding a non-protein encoding RNA and/or v) an altered activity of an lpxD gene encoding an UDP3-O-(3-hydroxymyristoyl)-glucosamine N-acyltransferase protein and having compared to a respective reference microorganism a higher yield and/or productivity of pyruvate, succinate, aspartate, malate, lactate, valine and/or leucine in fermentative production.

In some embodiments, the microorganism is a prokaryotic cell or a yeast cell. Suitable prokaryotic cells include Gram-positive, Gram negative and Gram-variable bacterial cells, preferably Gram-negative.

Thus, microorganisms that can be used in the present invention include, but are not limited to, *Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Brevibacterium ammoniagenes, Brevibacterium divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Micrococcus* sp. CCM825, *Morganella morganii, Nocardia opaca, Nocardia rugosa, Planococcus eucinatus, Proteus rettgeri, Propionibacterium shermanii, Pseudomonas synxantha, Pseudomonas azotoformans, Pseudomonas fluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus* sp. ATCC 15592, *Rhodococcus* sp. ATCC 19070, *Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces avermitilis, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Escherichia freundii, Microbacterium ammoniaphilum, Serratia marcescens, Salmonella typhimurium, Salmonella schottmulleri, Xanthomonas citri* and so forth.

In some embodiments, the microorganism is a eukaryotic cell. Suitable eukaryotic cells include yeast cells, as for example *Saccharomyces* spec, such as *Saccharomyces cerevisiae, Hansenula* spec, such as *Hansenula polymorpha, Schizosaccharomyces* spec, such as *Schizosaccharomyces pombe, Kluyveromyces* spec, such as *Kluyveromyces lactis* and *Kluyveromyces marxianus, Yarrowia* spec, such as *Yarrowia lipolytica, Pichia* spec, such as *Pichia methanolica, Pichia stipites* and *Pichia pastoris, Zygosaccharomyces* spec, such as *Zygosaccharomyces rouxii* and *Zygosaccharomyces bailii, Candida* spec, such as *Candida boidinii, Candida utilis, Candida freyschussii, Candida glabrata* and *Candida sonorensis, Schwanniomyces* spec, such as *Schwanniomyces occidentalis, Arxula* spec, such as *Arxula adeninivorans, Ogataea* spec such as *Ogataea minuta, Klebsiella* spec, such as *Klebsiella pneumonia.*

Numerous bacterial industrial strains are especially suitable for use in the methods disclosed herein. In some embodiments, the microorganism is a species of the genus *Corynebacterium*, e.g. *C. acetophilum, C. glutamicum, C. callunae, C. acetoacidophilum, C. aceto glutamicum.* In some embodiments, the microorganism is a species of the genus *Bacillus*, e.g., *B. thuringiensis, B. anthracis, B. megaterium, B. subtilis, B. lentils, B. circulans, B. pumilus, B. lautus, B. coagulans, B. brevis, B. firmus, B. alkaophius, B. licheniformis, B. clausii, B. stearothermophilus, B. halo-*

*durans*, *B. subtilis*, *B. pumilus*, and *B. amyloliquefaciens*. In some embodiments, the microorganism is a species of the genus *Erwinia*, e.g., *E. uredovora*, *E. carotovora*, *E. ananas*, *E. herbicola*, *E. punctata* and *E. terreus*. In some embodiments, the microorganism is a species of the genus *Escherichia*, e.g., *E. coli*. In other embodiments the microorganism is a species of the genus *Pantoea*, e.g., *P. citrea* or *P. agglomerans*. In still other embodiments, the microorganism is a species of the genus *Streptomyces*, e.g., *S. ambofaciens*, *S. achromogenes*, *S. avermitilis*, *S. coelicolor*, *S. aureofaciens*, *S. aureus*, *S. fungicidicus*, *S. griseus* or *S. lividans*. In further embodiments, the microorganism is a species of the genus *Zymomonas*, e.g., *Z. mobilis* or *Z. lipolytica*. In further embodiments, the microorganism is a species of the genus *Rhodococcus*, e.g. *R opacus*.

Preferably the microorganism is selected from the family of Enterobacteriaceae, preferably of the genus *Escherichia*, for example *Escherichia coli* (*E. coli*), preferably the strain *E. coli* W, which corresponds to DSMZ 1116, which corresponds to ATCC9637.

In addition to the reduced, repressed or deleted activity and/or expression of a brnQ gene encoding a brnQ protein having a branched chain amino acid transporter activity and/or the introduced, increased or enhanced activity and/or expression of an argP gene encoding an argP protein having a DNA binding/transcription activating activity and/or the introduced, increased or enhanced activity and/or expression of a gcvA gene encoding a DNA-binding protein and/or the reduced, repressed or deleted activity and/or expression of a gcvB gene encoding a non-protein encoding RNA and/or the altered activity of an lpxD gene encoding an UDP-3-O-(3-hydroxymyristoyl)-glucosamine N-acyltransferase protein, the recombinant microorganism of the invention may further comprise (a) a reduced, repressed or deleted activity and/or expression of a pflB gene encoding a pyruvate formate lyase I, wherein the reduction, repression or deletion of the activity and/or expression of the pflB gene is determined compared to a respective reference microorganism.

In addition to the reduced, repressed or deleted activity and/or expression of a brnQ gene encoding a brnQ protein having a branched chain amino acid transporter activity and/or the introduced, increased or enhanced activity and/or expression of an argP gene encoding an argP protein having a DNA binding/transcription activating activity and/or the introduced, increased or enhanced activity and/or expression of a gcvA gene encoding a DNA-binding protein and/or the reduced, repressed or deleted activity and/or expression of a gcvB gene encoding a non-protein encoding RNA and/or the altered activity of an lpxD gene encoding an UDP-3-O-(3-hydroxymyristoyl)-glucosamine N-acyltransferase protein, the recombinant microorganism of the invention may further comprise (b) a reduced, repressed or deleted activity and/or expression of a adhE gene encoding a bifunctional acetaldehyde-CoA dehydrogenase/iron-dependent alcohol dehydrogenase/pyruvate-formate lyase deactivase), wherein the reduction, repression or deletion of the activity and/or expression of the adhE gene is determined compared to a respective reference microorganism.

In addition to the reduced, repressed or deleted activity and/or expression of a brnQ gene encoding a brnQ protein having a branched chain amino acid transporter activity and/or the introduced, increased or enhanced activity and/or expression of an argP gene encoding an argP protein having a DNA binding/transcription activating activity and/or the introduced, increased or enhanced activity and/or expression of a gcvA gene encoding a DNA-binding protein and/or the reduced, repressed or deleted activity and/or expression of a gcvB gene encoding a non-protein encoding RNA and/or the altered activity of an lpxD gene encoding an UDP-3-O-(3-hydroxymyristoyl)-glucosamine N-acyltransferase protein, the recombinant microorganism of the invention may further comprise (c) a reduced, repressed or deleted activity and/or expression of a ldhA gene encoding a NAD-dependent fermentative D-lactate dehydrogenase, wherein the reduction, repression or deletion of the activity and/or expression of the ldhA gene is determined compared to a respective reference microorganism.

In addition to the reduced, repressed or deleted activity and/or expression of a brnQ gene encoding a brnQ protein having a branched chain amino acid transporter activity and/or the introduced, increased or enhanced activity and/or expression of an argP gene encoding an argP protein having a DNA binding/transcription activating activity and/or the introduced, increased or enhanced activity and/or expression of a gcvA gene encoding a DNA-binding protein and/or the reduced, repressed or deleted activity and/or expression of a gcvB gene encoding a non-protein encoding RNA and/or the altered activity of an lpxD gene encoding an UDP-3-O-(3-hydroxymyristoyl)-glucosamine N-acyltransferase protein, the recombinant microorganism of the invention may further comprise (d) a reduced, repressed or deleted activity and/or expression of a pta gene encoding a phosphate acetyltransferase, wherein the reduction, repression or deletion of the activity and/or expression of the pta gene is determined compared to a respective reference microorganism.

In addition to the reduced, repressed or deleted activity and/or expression of a brnQ gene encoding a brnQ protein having a branched chain amino acid transporter activity and/or the introduced, increased or enhanced activity and/or expression of an argP gene encoding an argP protein having a DNA binding/transcription activating activity and/or the introduced, increased or enhanced activity and/or expression of a gcvA gene encoding a DNA-binding protein and/or the reduced, repressed or deleted activity and/or expression of a gcvB gene encoding a non-protein encoding RNA and/or the altered activity of an lpxD gene encoding an UDP-3-O-(3-hydroxymyristoyl)-glucosamine N-acyltransferase protein, the recombinant microorganism of the invention may further comprise (e) a reduced, repressed or deleted activity and/or expression of a ackA gene encoding an acetate kinase, wherein the reduction, repression or deletion of the activity and/or expression of the ackA gene is determined compared to a respective reference microorganism.

In addition to the reduced, repressed or deleted activity and/or expression of a brnQ gene encoding a brnQ protein having a branched chain amino acid transporter activity and/or the introduced, increased or enhanced activity and/or expression of an argP gene encoding an argP protein having a DNA binding/transcription activating activity and/or the introduced, increased or enhanced activity and/or expression of a gcvA gene encoding a DNA-binding protein and/or the reduced, repressed or deleted activity and/or expression of a gcvB gene encoding a non-protein encoding RNA and/or the altered activity of an lpxD gene encoding an UDP-3-O-(3-hydroxymyristoyl)-glucosamine N-acyltransferase protein, the recombinant microorganism of the invention may further comprise (f) a reduced, repressed or deleted activity and/or expression of a frdA gene encoding a fumarate reductase, wherein the reduction, repression or deletion of the activity and/or expression of the frdA gene is determined compared to a respective reference microorganism.

In addition to the reduced, repressed or deleted activity and/or expression of a brnQ gene encoding a brnQ protein having a branched chain amino acid transporter activity and/or the introduced, increased or enhanced activity and/or expression of an argP gene encoding an argP protein having a DNA binding/transcription activating activity and/or the introduced, increased or enhanced activity and/or expression of a gcvA gene encoding a DNA-binding protein and/or the reduced, repressed or deleted activity and/or expression of a gcvB gene encoding a non-protein encoding RNA and/or the altered activity of an lpxD gene encoding an UDP-3-O-(3-hydroxymyristoyl)-glucosamine N-acyltransferase protein, the recombinant microorganism of the invention may further comprise (g) an introduced, increased or enhanced activity and/or expression of an alaD gene encoding an alanine dehydrogenase, wherein the increase or enhancement of the activity and/or expression of the alaD gene is determined compared to a respective reference microorganism.

In addition to the reduced, repressed or deleted activity and/or expression of a brnQ gene encoding a brnQ protein having a branched chain amino acid transporter activity and/or the introduced, increased or enhanced activity and/or expression of an argP gene encoding an argP protein having a DNA binding/transcription activating activity and/or the introduced, increased or enhanced activity and/or expression of a gcvA gene encoding a DNA-binding protein and/or the reduced, repressed or deleted activity and/or expression of a gcvB gene encoding a non-protein encoding RNA and/or the altered activity of an lpxD gene encoding an UDP-3-O-(3-hydroxymyristoyl)-glucosamine N-acyltransferase protein, the recombinant microorganism of the invention may further comprise (h) a reduced, repressed or deleted activity and/or expression of a dadX gene encoding a alanine racemase, wherein the reduction, repression or deletion of the activity and/or expression of the dadX gene is determined compared to a respective reference microorganism.

In addition to the reduced, repressed or deleted activity and/or expression of a brnQ gene encoding a brnQ protein having a branched chain amino acid transporter activity and/or the introduced, increased or enhanced activity and/or expression of an argP gene encoding an argP protein having a DNA binding/transcription activating activity and/or the introduced, increased or enhanced activity and/or expression of a gcvA gene encoding a DNA-binding protein and/or the reduced, repressed or deleted activity and/or expression of a gcvB gene encoding a non-protein encoding RNA and/or the altered activity of an lpxD gene encoding an UDP-3-O-(3-hydroxymyristoyl)-glucosamine N-acyltransferase protein, the recombinant microorganism of the invention may further comprise (i) an introduced, increased or enhanced activity and/or expression of an ygaW gene encoding an alanine transporter, wherein the increase or enhancement of the activity and/or expression of the ygaW gene is determined compared to a respective reference microorganism as described in WO2012/172822 and PCT/IB2014/064426 the latter being incorporated by reference.

In addition to the reduced, repressed or deleted activity and/or expression of a brnQ gene encoding a brnQ protein having a branched chain amino acid transporter activity and/or the introduced, increased or enhanced activity and/or expression of an argP gene encoding an argP protein having a DNA binding/transcription activating activity and/or the introduced, increased or enhanced activity and/or expression of a gcvA gene encoding a DNA-binding protein and/or the reduced, repressed or deleted activity and/or expression of a gcvB gene encoding a non-protein encoding RNA and/or the altered activity of an lpxD gene encoding an UDP-3-O-(3-hydroxymyristoyl)-glucosamine N-acyltransferase protein, the recombinant microorganism of the invention may further comprise (j) an introduced, increased or enhanced activity and/or expression of a zipA gene encoding a cell division protein involved in Z ring assembly, wherein the increase or enhancement of the activity and/or expression of the zipA gene is determined compared to a respective reference microorganism as described in PCT/IB2014/064426 which is incorporated by reference herein.

In addition to the reduced, repressed or deleted activity and/or expression of a brnQ gene encoding a brnQ protein having a branched chain amino acid transporter activity and/or the introduced, increased or enhanced activity and/or expression of an argP gene encoding an argP protein having a DNA binding/transcription activating activity and/or the introduced, increased or enhanced activity and/or expression of a gcvA gene encoding a DNA-binding protein and/or the reduced, repressed or deleted activity and/or expression of a gcvB gene encoding a non-protein encoding RNA and/or the altered activity of an lpxD gene encoding an UDP-3-O-(3-hydroxymyristoyl)-glucosamine N-acyltransferase protein, the recombinant microorganism of the invention may further comprise (k) an introduced, increased or enhanced activity and/or expression of an lpd gene encoding a encoding a lipoamide dehydrogenase, wherein the increase or enhancement of the activity and/or expression of the lpd gene is determined compared to a respective reference microorganism as described in PCT/IB2014/064426.

Preferably, the recombinant microorganism of the invention comprising at least one of the reduced, repressed or deleted activity and/or expression of a brnQ gene encoding a brnQ protein having a branched chain amino acid transporter activity and/or the introduced, increased or enhanced activity and/or expression of an argP gene encoding an argP protein having a DNA binding/transcription activating activity and/or the introduced, increased or enhanced activity and/or expression of a gcvA gene encoding a DNA-binding protein and/or the reduced, repressed or deleted activity and/or expression of a gcvB gene encoding a non-protein encoding RNA and/or the altered activity of an lpxD gene encoding an UDP-3-O-(3-hydroxymyristoyl)-glucosamine N-acyltransferase protein is additionally having at least two, preferably at least three, more preferably at least four, even more preferably at least five, even more preferably at least six, even more preferably at least seven, even more preferably at least eight most preferably all of the features selected from the group of (a) a reduced, repressed or deleted activity and/or expression of a pflB gene encoding a pyruvate formate lyase I and (b) a reduced, repressed or deleted activity and/or expression of a adhE gene encoding a bifunctional acetaldehyde-CoA dehydrogenase/iron-dependent alcohol dehydrogenase/pyruvate-formate lyase deactivase) and (c) a reduced, repressed or deleted activity and/or expression of a ldhA gene encoding a NAD-dependent fermentative D-lactate dehydrogenase and (d) a reduced, repressed or deleted activity and/or expression of a pta gene encoding a phosphate acetyltransferase and (e) a reduced, repressed or deleted activity and/or expression of an ackA gene encoding an acetate kinase and (f) a reduced, repressed or deleted activity and/or expression of a frdA gene encoding a fumarate reductase and (g) an introduced, increased or enhanced activity and/or expression of an alaD gene encoding an alanine dehydrogenase, (h) a reduced, repressed or deleted activity and/or expression of a dadX gene encoding a alanine reductase and (i) an introduced, increased or enhanced activity and/or expression of an ygaW gene encoding an alanine transporter and (j) an introduced, increased or enhanced activity and/or expression of a zipA gene encoding a cell division protein involved in Z ring assembly and
(k) an introduced, increased or enhanced activity and/or expression of an lpd gene encoding a encoding a lipoamide dehydrogenase,
wherein the reduction, repression, deletion, increase or enhancement of the activity and/or expression of a gene is determined compared to a respective reference microorganism.

The alaD gene may be derived from any organism or may be a synthetic gene designed by man, for example having codon usage optimized for expression in the recombinant microorganism of the invention or being optimized for enzyme activity, e.g. having improved Vmax or Km. Preferably the alaD gene is derived from a microorganism of one of the geni *Bacillus, Geobacillus, Paenibacillus, Halobacillus, Brevibacillus*. In a more preferred embodiment the alaD gene is derived from a microorganism of the genus *Geobacillus*. In a most preferred embodiment, the alaD gene is derived from *Geobacillus stearothermophllus*.

In a preferred embodiment the alaD gene has been codon optimized for the expression in the recombinant microorganism of the invention.

The microorganism of the invention may comprise further genetic modifications, such as mutations, knock-outs or enhanced or introduced enzyme activities that further improve yield and/or productivity of alanine, pyruvate, succinate, aspartate, malate, lactate, valine and/or leucine, preferably succinate or alanine, more preferably alanine.

In a further embodiment the brnQ gene encoding a brnQ protein having a branched chain amino acid transporter activity with a reduced, repressed or deleted activity and/or expression in the recombinant microorganism of the invention, is selected from the group of
(i) a nucleic acid molecule comprising a sequence of SEQ ID NO: 1, or
(ii) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 1, or
(iii) a nucleic acid molecule hybridizing to a nucleic acid molecule having SEQ ID NO: 1 under medium stringent conditions, more preferably under high stringent conditions, most preferably under very high stringent conditions, or
(iv) a nucleic acid molecule encoding a polypeptide of SEQ ID NO: 2, or
(v) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 2,
wherein the polypeptide encoded by (ii), (iii) or (v) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 2, and wherein the microorganism comprising the mutated gene and/or protein as defined above has an improved alanine yield in fermentation In one example, the brnQ gene encoding a brnQ protein having a branched chain amino acid transporter activity with a reduced, repressed or deleted activity and/or expression in the recombinant microorganism of the invention, is having the sequence of SEQ ID NO: 3, encoding the protein having SEQ ID NO: 4.

In a further embodiment the argP gene encoding an argP protein having a DNA binding/transcription activating activity with a introduced, increased or enhanced activity and/or expression in the recombinant microorganism of the invention, is selected from the group of
(i) a nucleic acid molecule comprising a sequence of SEQ ID NO: 45, or
(ii) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 45, or
(iii) a nucleic acid molecule hybridizing to a nucleic acid molecule having SEQ ID NO: 45 under medium stringent conditions, more preferably under high stringent conditions, most preferably under very high stringent conditions, or
(iv) a nucleic acid molecule encoding a polypeptide of SEQ ID NO: 46, or
(v) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 46,
wherein the polypeptide encoded by (ii), (iii) or (v) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 46, and
wherein the microorganism comprising the mutated gene and/or protein as defined above has an improved alanine yield in fermentation In one example, the argP gene encoding a argP protein having a DNA binding/transcription activating activity with a introduced, increased or enhanced activity and/or expression in the recombinant microorganism of the invention, is having the sequence of SEQ ID NO: 47, encoding the protein having SEQ ID NO: 48.

In a further embodiment the gcvA gene encoding a DNA-binding protein with an introduced, increased or enhanced activity and/or expression in the recombinant microorganism of the invention, is selected from the group of
(i) a nucleic acid molecule comprising a sequence of SEQ ID NO: 53, or
(ii) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 53, or
(iii) a nucleic acid molecule hybridizing to a nucleic acid molecule having SEQ ID NO: 53 under medium stringent conditions, more preferably under high stringent conditions, most preferably under very high stringent conditions, or
(iv) a nucleic acid molecule encoding a polypeptide of SEQ ID NO: 54, or (v) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 54, wherein the polypeptide encoded by (ii), (iii) or (v) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 54, and wherein the microorganism comprising the mutated gene and/or protein as defined above has an improved alanine yield in fermentation.

In a further embodiment the gcvB gene encoding a non-protein encoding RNA with a reduced, repressed or deleted activity and/or expression in the recombinant microorganism of the invention, is selected from the group of (i) a nucleic acid molecule comprising a sequence of SEQ ID NO: 58, or
(ii) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 58, or
(iii) a nucleic acid molecule hybridizing to a nucleic acid molecule having SEQ ID NO: 58 under medium stringent conditions, more preferably under high stringent conditions, most preferably under very high stringent conditions, or wherein the or non-protein encoding RNA encoded by (ii), (iii) or (v) is having at least 10%, 20% preferably at least 30% or 50%, more preferably at least 60% or 70%, even more preferably at least 75%, 80%, 85% or 90%, most preferred at least 95% of the activity as the or non-protein encoding RNA having SEQ ID NO: 58, and wherein the microorganism comprising the mutated gene as defined above has an improved alanine yield in fermentation.

In a further embodiment the lpxD gene encoding a UDP-3-O-(3-hydroxymyristoyl)-glucosamine N-acyltransferase protein with an altered activity and/or expression in the recombinant microorganism of the invention, is selected from the group of (i) a nucleic acid molecule comprising a sequence of SEQ ID NO: 49, or
(ii) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 49, or
(iii) a nucleic acid molecule hybridizing to a nucleic acid molecule having SEQ ID NO: 49 under medium stringent conditions, more preferably under high stringent conditions, most preferably under very high stringent conditions, or
(iv) a nucleic acid molecule encoding a polypeptide of SEQ ID NO: 50, or
(v) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 50, and wherein the codon of the genes under (i) to (v) corresponding to position 43 to 45 of SEQ ID NO: 49 is not encoding amino acid alanine and is not a stop codon or the amino acid of the proteins encoded by the genes under (i) to (v) corresponding to position 15 of SEQ ID NO: 50 is not alanine, and wherein the protein encoded by the gene as defined above in (1) to (5) has an altered activity and/or expression compared to the protein having SEQ ID NO: 50, and wherein the microorganism comprising the mutated gene and/or protein as defined above has an improved alanine yield in fermentation.

In one example, the lpxD gene encoding a UDP-3-O-(3-hydroxymyristoyl)-glucosamine N-acyltransferase protein with an altered activity and/or expression in the recombinant microorganism of the invention, is having the sequence of SEQ ID NO: 51, encoding the protein having SEQ ID NO: 52.

The recombinant microorganism of the invention comprising at least one of the reduced, repressed or deleted activity and/or expression of a brnQ gene encoding a branched chain amino acid transporter protein and/or the introduced, increased or enhanced activity and/or expression of an argP gene encoding an argP protein having a DNA binding/transcription activating activity and/or the introduced, increased or enhanced activity and/or expression of a gcvA gene encoding a DNA-binding protein and/or the reduced, repressed or deleted activity and/or expression of a gcvB gene encoding a non-protein encoding RNA and/or the altered activity of an lpxD gene encoding an UDP-3-O-(3-hydroxymyristoyl)-glucosamine N-acyltransferase protein may further comprise any one, two, three, four, five, six, seven, eight, nine or all of the features as defined above under (a) to (k), wherein the pflB gene is selected from the group consisting of (A) a nucleic acid molecule comprising a sequence of SEQ ID NO: 5, or
(B) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 5, or
(C) a nucleic acid molecule hybridizing to a nucleic acid molecule having SEQ ID NO: 5 under medium stringent conditions, more preferably under high stringent conditions, most preferably under very high stringent conditions, or
(D) a nucleic acid molecule encoding a polypeptide of SEQ ID NO: 6, or
(E) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 6, wherein the polypeptide encoded by (B), (C) or (E) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 6 and wherein the adhE gene is selected from the group consisting of (F) a nucleic acid molecule comprising a sequence of SEQ ID NO: 7, or
(G) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 7, or
(H) a nucleic acid molecule hybridizing to a nucleic acid molecule having SEQ ID NO: 7 under medium stringent conditions, more preferably under high stringent conditions, most preferably under very high stringent conditions, or
(I) a nucleic acid molecule encoding a polypeptide of SEQ ID NO: 8, or
(J) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 8,
wherein the polypeptide encoded by (G), (H) or (J) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 8 and wherein the ldhA gene is selected from the group consisting of
(K) a nucleic acid molecule comprising a sequence of SEQ ID NO: 9, or
(L) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 9, or
(M) a nucleic acid molecule hybridizing to a nucleic acid molecule having SEQ ID NO: 9 under medium stringent conditions, more preferably under high stringent conditions, most preferably under very high stringent conditions, or
(N) a nucleic acid molecule encoding a polypeptide of SEQ ID NO: 10, or
(O) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 10,
wherein the polypeptide encoded by (L), (M) or (O) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 10 and wherein the pta gene is selected from the group consisting of
(P) a nucleic acid molecule comprising a sequence of SEQ ID NO: 11, or
(Q) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 11, or
(R) a nucleic acid molecule hybridizing to a nucleic acid molecule having SEQ ID NO: 11 under medium stringent conditions, more preferably under high stringent conditions, most preferably under very high stringent conditions, or
(S) a nucleic acid molecule encoding a polypeptide of SEQ ID NO: 12, or
(T) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 12,
wherein the polypeptide encoded by (Q), (R) or (T) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 12 and wherein the ackA gene is selected from the group consisting of
(U) a nucleic acid molecule comprising a sequence of SEQ ID NO: 120, or
(V) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 120, or
(W) a nucleic acid molecule hybridizing to a nucleic acid molecule having SEQ ID NO: 120 under medium stringent conditions, more preferably under high stringent conditions, most preferably under very high stringent conditions, or
(X) a nucleic acid molecule encoding a polypeptide of SEQ ID NO: 121, or
(Y) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 121,
wherein the polypeptide encoded by (V), (W) or (Y) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 121 and
wherein the frdA gene is selected from the group consisting of
(Z) a nucleic acid molecule comprising a sequence of SEQ ID NO: 13, or
(AA) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 13, or
(BB) a nucleic acid molecule hybridizing to a nucleic acid molecule having SEQ ID NO: 13 under medium stringent conditions, more preferably under high stringent conditions, most preferably under very high stringent conditions, or
(CC) a nucleic acid molecule encoding a polypeptide of SEQ ID NO: 14, or
(DD) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 14, wherein the polypeptide encoded by (AA), (BB) or (DD) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 14 and wherein the alaD gene is selected from the group consisting of (EE) a nucleic acid molecule comprising a sequence of SEQ ID NO: 15, or (FF) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 15, or (GG) a nucleic acid molecule hybridizing to a nucleic acid molecule having SEQ ID NO: 15 under medium stringent conditions, more preferably under high stringent conditions, most preferably under very high stringent conditions, or (HH) a nucleic acid molecule encoding a polypeptide of SEQ ID NO: 16, or (II) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 16, wherein the polypeptide encoded by (FF), (GG) or (II) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 16 and wherein the dadX gene is selected from the group consisting of (JJ) a nucleic acid molecule comprising a sequence of SEQ ID NO: 118, or (KK) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 118, or (LL) a nucleic acid molecule hybridizing to a nucleic acid molecule having SEQ ID NO: 118 under medium stringent conditions, more preferably under high stringent conditions, most preferably under very high stringent conditions, or (MM) a nucleic acid molecule encoding a polypeptide of SEQ ID NO: 119, or (NN) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 119, wherein the polypeptide encoded by (KK), (LL) or (NN) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 119 and wherein the ygaW gene is selected from the group consisting of (OO) a nucleic acid molecule comprising a sequence of SEQ ID NO: 109, or (PP) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 109, or (QQ) a nucleic acid molecule hybridizing to a nucleic acid molecule having SEQ ID NO: 109 under medium stringent conditions, more preferably under high stringent conditions, most preferably under very high stringent conditions, or (RR) a nucleic acid molecule encoding a polypeptide of SEQ ID NO: 110, or (SS) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 110, wherein the polypeptide encoded by (PP), (QQ) or (SS) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 110 and wherein the zipA gene is selected from the group consisting of (TT) a nucleic acid molecule comprising a sequence of SEQ ID NO: 111, or (UU) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 111, or (VV) a nucleic acid molecule hybridizing to a nucleic acid molecule having SEQ ID NO: 111 under medium stringent conditions, more preferably under high stringent conditions, most preferably under very high stringent conditions, or (WW) a nucleic acid molecule encoding a polypeptide of SEQ ID NO: 112, or (XX) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 112, wherein the polypeptide encoded by (UU), (VV) or (XX) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 112 and wherein the lpd gene is selected from the group consisting of (YY) a nucleic acid molecule comprising a sequence of SEQ ID NO: 113, or (ZZ) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 113, or
(AAA) a nucleic acid molecule hybridizing to a nucleic acid molecule having SEQ ID NO: 113 under medium stringent conditions, more preferably under high stringent conditions, most preferably under very high stringent conditions, or
(BBB) a nucleic acid molecule encoding a polypeptide of SEQ ID NO: 114, or
(CCC) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 114,
  wherein the polypeptide encoded by (ZZ), (AAA) or (CCC) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 114.

Preferably, the nucleic acid molecule as defined in (EE) to (II) is under control of a sequence functioning as a promoter in a microorganism having the sequence of
(1) a nucleic acid molecule comprising a sequence of SEQ ID NO: 115 or 116, or
(2) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 115 or 116, or
(3) a nucleic acid molecule hybridizing to a nucleic acid molecule having SEQ ID NO: 115 or 116 under medium stringent conditions, more preferably under high stringent conditions, most preferably under very high stringent conditions or
(4) a fragment of at least 10 nucleotides, preferably at least 20 nucleotides, at least 30 nucleotides or at least 40 nucleotides, more preferably a fragment of at least 50 nucleotides, at least 75 nucleotides or at least 100 nucleotides, even more preferably at least 150 or at least 200 nucleotides of the nucleic acid molecule having SEQ ID NO: 115 or 116. Preferably the fragment of SEQ ID NO: 115 or 116 is a fragment comprising the 3' region of SEQ ID NO: 115 or 116, therefore the fragment comprises a deletion at the 5' end of SEQ ID NO: 115 or 116.

A further embodiment of the invention is a composition comprising one or more recombinant microorganisms of the invention as defined above. The composition may further comprise a medium that allows grow of the recombinant microorganism of the invention. The medium may additionally comprise a carbon source such as hexoses, pentoses or polyols for example sucrose, glucose, fructose, galactose, mannose, raffinose, xylose, arabinose, xylulose, glycerol, mannitol, arabitol, xylitol, starch, cellulose, lignocellulose or combinations thereof. Preferably the carbon source is glucose or sucrose, more preferably the carbon source is glucose.

In a preferred embodiment the composition comprises the microorganism of the invention and NBS medium, AM1 medium or PPM01 medium. More preferably the composition further comprises a carbon source, preferably a sugar. The ingredients of these media are known to a skilled person.

Preferably NBS medium comprises per liter
1-5 g, preferably 3.5 g $KH_2PO_4$ and
1-10 g, preferably 5.0 g $K_2HPO_4$ and
1-5 g, preferably 3.5 g $(NH_4)_2HPO_4$ and
0.1-1 g, preferably 0.25 g $MgSO_4\text{-}7H_2O$ and
5-25 mg, preferably 15 mg $CaCL_2\text{-}2H_2O$ and
0.1-1 mg, preferably 0.5 mg Thiamine and
0.1-5 ml, preferably 1 ml trace metal stock,
wherein the trace metal stock comprises 0.5-5 g, preferably 1.6 g $FeCL_3\text{-}6H_2O$; 0.05-0.5 g, preferably 0.2 g $CoCl_2\text{-}6H_2O$; 0.01-0.5 g, preferably 0.1 g $CuCl_2\text{-}2H_2O$; 0.1-0.5 g, preferably 0.2 g $ZnCl_2$; 0.05-0.5 g, preferably 0.2 g $NaMoO_4\text{-}2H_2O$; 0.001-0.1 g, preferably 0.05 g $H_3BO_3$ per liter 0.01-1 M, preferably 0.1 M HCL.

The preferred carbon source in the NBS medium is glucose or sucrose, preferably 2%-18% glucose or 2%-16% sucrose.

Preferably AM 1 medium comprises per liter 0.1-10 mM, preferably 1 mM betain solution
1-10 g, preferably 2.6 g $(NH_4)_2HPO_4$ and
0.1-5 g, preferably 0.87 g $NH_4H_2PO_4$ and
0.05-2.5 g, preferably 0.15 g KCl and
0.05-5 g, preferably 0.37 g $MgSO_4\text{-}7H_2O$ and
0.1-5 ml, preferably 1 ml trace metal stock,
wherein the trace metal stock comprises per liter 0.01-1 M, preferably 0.12 M HCL, 1-5 g, preferably 2.4 g $FeCL_3\text{-}6H_2O$; 0.1-1 g, preferably 0.3 g $CoCl_2\text{-}6H_2O$; 0.1-1 g, preferably 0.21 g $CuCl_2\text{-}2H_2O$; 0.1-1 g, preferably 0.3 g $ZnCl_2$; 0.1-1 g, preferably 0.27 g $NaMoO_4\text{-}2H_2O$; 0.01-0.5 g, preferably 0.068 g $H_3BO_3$ and 0.1-1 g, preferably 0.5 g $MnCl_2\text{-}4H_2O$, and optionally 1-30 g, preferably 15 g $(NH_4)_2SO_4$.

The preferred carbon source in the NBS medium is glucose or sucrose, preferably 2%-18% glucose or 2%-16% sucrose.

Preferably PPM01 medium comprises per liter
0.05-5 g, preferably 0.37 g $MgSO_4\text{-}7H_2O$ and
0.1-10 g, preferably 1 g $(NH_4)_2SO_4$ and
0.05-5 g, preferably 0.46 g betaine and
0.001-0.5 g, preferably 0.05 g Cyanocobalamin (B12) and
1-10 g, preferably 3.74 g $KH_2PO_4$ and
0.1-5 ml, preferably 1 ml trace metal stock,
wherein the trace metal stock comprises per liter 10-100 mM, preferably 60 mM sulfuric acid, 1-10 g, preferably 3.48 g $(NH_4)_2Fe(II)(SO_4)_2\text{-}7H_2O$; 0.1-1 g, preferably 0.35 g $CoSO_4\text{-}7H_2O$; 0.1-1 g, preferably 0.31 g $CuSO_4\text{-}5H_2O$; 0.1-5 g, preferably 0.63 g $ZnSO_4\text{-}7H_2O$; 0.1-1 g, preferably 0.27 g $MnSO_4$—$H_2O$; 0.01-1 g, preferably 0.07 g $NaMoO_4\text{-}2H_2O$ and 0.1-5 g, preferably 0.43 g $H_3BO_3$.

The preferred carbon source in the PPM01 medium is glucose monohydrate, preferably 10-500 g, more preferably 140 g glucose monohydrate per liter medium.

A further embodiment of the invention is a method for producing a recombinant microorganism with enhanced alanine, pyruvate, succinate, aspartate, malate, lactate, valine and/or leucine, preferably succinate or alanine, more preferably alanine yield or productivity, which comprises the following steps:
(I) i) reducing, repressing or deleting of one or more activity and/or expression of the brnQ gene or as defined above under (i) to (v) and/or ii) introducing, increasing, enhancing of one or more activity and/or expression of an argP gene as defined above under (i) to (v) and/or iii) introducing, increasing, enhancing of one or more activity and/or expression of the gcvA gene as defined above under (i) to (v) and/or iv) reducing, repressing or deleting of one or more activity and/or expression of the gcvB gene as defined above under (i) to (v) and/or v) altering activity of the lpxD gene as defined above under (i) to (v) in a microorganism; and (II) generating, identifying and isolating a recombinant microorganism with enhanced alanine, pyruvate, succinate, aspartate, malate, lactate, valine and/or leucine, preferably succinate or alanine, more preferably alanine yield or productivity compared to a corresponding microorganism without the modification as defined above under (I).

In a preferred embodiment the brnQ gene with reduced, repressed or deleted activity and/or expression has a sequence of SEQ ID NO: 3 and/or is encoding a polypeptide of SEQ ID NO: 4.

In a preferred embodiment the argP gene with introduced, increased or enhanced activity and/or expression has a sequence of SEQ ID NO: 47 and/or is encoding a polypeptide of SEQ ID NO: 48.

In a preferred embodiment the gcvA gene with introduced, increased or enhanced activity and/or expression is functionally linked to a promoter having a sequence of SEQ ID NO: 56 or 57.

In a preferred embodiment the gcvB gene with reduced, repressed or deleted activity and/or expression is functionally linked to a promoter having a sequence of SEQ ID NO: 60 or 61.

In a preferred embodiment the lpxD gene with altered activity and/or expression has a sequence of SEQ ID NO: 51 and/or is encoding a polypeptide of SEQ ID NO: 52.

In a preferred embodiment of the method for producing a recombinant microorganism of the invention the method further comprises the step of reducing, repressing or deleting the activity and/or expression of at least one, at least two, at least three, at least four, at least six or all of the pflB gene, adhE gene, ldhA gene, pta gene, ackA gene, frdA gene or dadX gene for example as defined above under (A) to (DD) and (JJ) to (NN) and/or the step of introducing, increasing or enhancing activity and/or expression at least one, at least two, at least three or all of an alaD gene, ygaW gene, a zipA gene or lpd gene for example as defined above under (EE) to (II) and (OO) to (CCC).

In a further preferred embodiment of the method for producing a recombinant microorganism of the invention the nucleic acid molecule as defined in (EE) to (II) is under control of a sequence functioning as a promoter in a microorganism having the sequence of (1) a nucleic acid molecule comprising a sequence of SEQ ID NO: 115 or 116, or
(2) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 115 or 116, or
(3) a nucleic acid molecule hybridizing to a nucleic acid molecule having SEQ ID NO: 115 or 116 under medium stringent conditions, more preferably under high stringent conditions, most preferably under very high stringent conditions or
(4) a fragment of at least 10 nucleotides, preferably at least 20 nucleotides, at least 30 nucleotides or at least 40 nucleotides, more preferably a fragment of at least 50 nucleotides, at least 75 nucleotides or at least 100 nucleotides, even more preferably at least 150 or at least 200 nucleotides of the nucleic acid molecule having SEQ ID NO: 115 or 116. Preferably the fragment of SEQ ID NO: 115 or 116 is a fragment comprising the 3' region of SEQ ID NO: 115 or 116, therefore the fragment comprises a deletion at the 5' end of SEQ ID NO: 115 or 116.

A most preferred method for producing a recombinant microorganism of the invention comprises the step of reducing, repressing or deleting the activity and/or expression of all of the brnQ gene, gcvB gene, pflB gene, adhE gene, ldhA gene, pta gene, ackA gene, frdA gene and dadX gene and the step of introducing, increasing or enhancing activity and/or expression of all of the alaD gene, ygaW gene, zipA gene, lpd gene, argP gene and gcvA gene and the step of altering the activity and/or expression of the lpxD gene.

In one embodiment of the method for producing a recombinant microorganism of the invention the microorganism is selected from the group of prokaryotic microorganisms comprising, *Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Brevibacterium ammoniagenes, Brevibacterium divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Micrococcus sp. CCM825, Morganella morganii, Nocardia opaca, Nocardia rugosa, Planococcus eucinatus, Proteus rettgeri, Propionibacterium shermanii, Pseudomonas synxantha, Pseudomonas azotoformans, Pseudomonas fluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus sp. ATCC 15592, Rhodococcus sp. ATCC 19070, Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces avermitilis, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Escherichia freundii, Microbacterium ammoniaphilum, Serratia marcescens, Salmonella typhimurium, Salmonella schottmulleri, Xanthomonas citri, Synechocystis sp., Synechococcus elongatus, Thermosynechococcus elongatus, Microcystis aeruginosa, Nostoc sp., N. commune, N. sphaericum, Nostoc punctiforme, Spirulina platensis, Lyngbya majuscula, L. lagerheimii, Phormidium tenue, Anabaena sp., Leptolyngbya sp* and so forth.

In some embodiments, the microorganism is a eukaryotic cell. Suitable eukaryotic cells include yeast cells, as for example *Saccharomyces* spec, such as *Saccharomyces cerevisiae*, *Hansenula* spec, such as *Hansenula polymorpha*, *Schizosaccharomyces* spec, such as *Schizosaccharomyces pombe*, *Kluyveromyces* spec, such as *Kluyveromyces lactis* and *Kluyveromyces marxianus*, *Yarrowia* spec, such as *Yarrowia lipolytica*, *Pichia* spec, such as *Pichia methanolica*, *Pichia stipites* and *Pichia pastoris*, *Zygosaccharomyces* spec, such as *Zygosaccharomyces rouxii* and *Zygosaccharomyces bailii*, *Candida* spec, such as *Candida boidinii*, *Candida utilis*, *Candida freyschussii*, *Candida glabrata* and *Candida sonorensis*, *Schwanniomyces* spec, such as *Schwanniomyces occidentalis*, *Arxula* spec, such as *Arxula adeninivorans*, *Ogataea* spec such as *Ogataea minuta*, *Klebsiella* spec, such as *Klebsiella pneumonia*.

Numerous bacterial industrial strains are especially suitable for use in the methods disclosed herein. In some embodiments, the microorganism is a species of the genus *Corynebacterium*, e.g. *C. acetophilum*, *C. glutamicum*, *C. callunae*, *C. acetoacidophilum*, *C. acetoglutamicum*. In some embodiments, the microorganism is a species of the genus *Bacillus*, e.g., *B. thuringiensis*, *B. anthracis*, *B. megaterium*, *B. subtilis*, *B. lentils*, *B. circulans*, *B. pumilus*, *B. lautus*, *B. coagulans*, *B. brevis*, *B. firmus*, *B. alkaophius*, *B. licheniformis*, *B. clausii*, *B. stearothermophilus*, *B. halodurans*, *B. subtilis*, *B. pumilus*, and *B. amyloliquefaciens*. In some embodiments, the microorganism is a species of the genus *Erwinia*, e.g., *E. uredovora*, *E. carotovora*, *E. ananas*, *E. herbicola*, *E. punctata* and *E. terreus*. In some embodiments, the microorganism is a species of the genus *Escherichia*, e.g., *E. coli*. In other embodiments the microorganism is a species of the genus *Pantoea*, e.g., *P. citrea* or *P. agglomerans*. In still other embodiments, the microorganism is a species of the genus *Streptomyces*, e.g., *S. ambofaciens*, *S. achromogenes*, *S. avermitilis*, *S. coelicolor*, *S. aureofaciens*, *S. aureus*, *S. fungicidicus*, *S. griseus* or *S. lividans*. In further embodiments, the microorganism is a species of the genus *Zymomonas*, e.g., *Z. mobilis* or *Z. lipolytica*. In further embodiments, the microorganism is a species of the genus *Rhodococcus*, e.g. *R opacus*.

Preferably the microorganism is selected from the family of Enterobacteriaceae, preferably of the genus *Escherichia*, for example *Escherichia coli* (*E. coli*), preferably the strain *E. coli* W, which corresponds to DSMZ 1116, which corresponds to ATCC9637.

A further embodiment of the invention is a method of producing alanine, pyruvate, succinate, aspartate, malate, lactate, valine and/or leucine, preferably succinate or alanine, more preferably alanine, most preferably L-alanine, comprising culturing one or more recombinant microorganism as defined above under conditions that allow for the production of alanine, pyruvate, succinate, aspartate, malate, lactate, valine and/or leucine, preferably succinate or alanine, more preferably alanine, most preferably L-alanine.

In some embodiments, the recombinant microorganisms encompassed by the invention are grown under batch or continuous fermentations conditions. Classical batch fermentation is a closed system, wherein the compositions of the medium is set at the beginning of the fermentation and is not subject to artificial alterations during the fermentation. A variation of the batch system is a fed-batch fermentation. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. Continuous fermentation which also finds use in the present invention is a system where a defined fermentation medium is added continuously to a bioreactor and an equal amount of conditioned medium (e.g., containing the desired end-products) is removed simultaneously for processing. Continuous fermentation generally maintains the cultures at a constant high density where cells are primarily in the growth phase where production of end products is enhanced. Continuous fermentation systems strive to maintain steady state growth conditions. Methods for modulating nutrients and growth factors for continuous fermentation processes as well as techniques for maximizing the rate of product formation are well known in the art of industrial microbiology.

In some embodiments, fermentations are carried out in a temperature within the range of from about 10° C. to about 60° C., from about 15° C. to about 50° C., from about 20° C. to about 45° C., from about 25° C. to about 45° C., from about 30° C. to about 45° C. and from about 25° C. to about 40° C. In a preferred embodiment the temperature is about 34° C., 35° C. or 36° C. In a most preferred embodiment the temperature is about 37° C. or 38° C.

In some other embodiments, the fermentation is carried out for a period of time within the range of from about 8 hours to 240 hours, from about 8 hours to about 168 hours, from about 10 hours to about 144 hours, from about 15 hours to about 120 hours, or from about 20 hours to about 72 hours. Preferably the fermentation is carried out from about 20 hours to about 40 hours.

In some other embodiments, the fermentation is carried out at a pH in the range of about 4 to about 9, in the range of about 4.5 to about 8.5, in the range of about 5 to about 8, or in the range of about 5.5 to about 7.5. Preferably the fermentation will be carried out at a pH of 7.

In one embodiment of the method of producing alanine, pyruvate, succinate, aspartate, malate, lactate, valine and/or leucine, preferably succinate or alanine, more preferably alanine, the microorganism is cultured in a medium comprising between 1% and 30% (w/v) of a sugar, between 5% and 25% (w/v) of a sugar, between 10% and 20% (w/v) of a sugar, between 11% and 18% (w/v) of a sugar. Preferably the microorganism is cultured in a medium comprising between 12% and 16% (w/v) of a sugar. More preferably the microorganism is cultured in a medium comprising between 13% and 15% (w/v) of a sugar, most preferably the microorganism is cultured in a medium comprising 14% (w/v) of a sugar.

In another embodiment of the method for producing alanine, pyruvate, succinate, aspartate, malate, lactate, valine and/or leucine, preferably succinate or alanine, more preferably alanine the yield of alanine, pyruvate, succinate, aspartate, malate, lactate, valine and/or leucine is at least 80% for example at least 81%, at least 82%, at least 83%, at least 84% or at least 85%. Preferably the yield is at least 86%, at least 87%, at least 88%, at least 89% or at least 90%. More preferably the yield is at least 90.5%, at least 91%, at least 91.5%, at least 92%, at least 92.5%, at least 93%, at least 93.5%, at least 94% or at least 94.5%. In an even more preferred embodiment the yield is at least 95% or at least 95.5%. In a most preferred embodiment, the yield is at least 96%. The percent yield is calculated as gram product produced from gram glucose in the medium. Hence, when the medium contained 100 g glucose and the fermentation yielded 98 g alanine, the yield would be 98%.

In another embodiment of the method for producing alanine preferably L-alanine is produced, wherein the chiral purity of L-alanine is at least 90%, at least 91%, at least 92%, at least 93% or at least 94%. In a preferred embodiment the chiral purity of L-alanine is at least 95% or at least 95.5%. In a more preferred embodiment, the chiral purity of L-alanine is at least 96% or at least 96.5% or at least 97%. In an even more preferred embodiment the chiral purity of L-alanine is at least 97.5%, at least 98% or at least 98.5% for example at least 99%. Even more preferably the chiral purity of L-alanine is at least 99.5% or at least 99.6% for example at least 99.7%, at least 99.8%, or at least 99.9%. In a most preferred embodiment chiral pure L-alanine is produced.

Another embodiment of the invention is a method of culturing or growing any of the genetically modified microorganisms as defined above, the method comprising inoculating a culture medium with one or more genetically modified microorganism and culturing or growing said genetically modified microorganism in culture medium under conditions as defined above.

The use of a recombinant microorganism as defined above or a composition as defined above for the fermentative production of alanine, pyruvate, succinate, aspartate, malate, lactate, valine and/or leucine, preferably succinate or alanine, more preferably alanine, most preferably L-alanine is an additional embodiment of the invention.

The recombinant microorganism according to the present invention is characterized in that, compared to a respective reference microorganism for example a wild type, the expression and/or the activity of the enzyme that is encoded by the brnQ gene and/or the RNA that is encoded by the gcvB gene is decreased and/or the expression and/or the activity of the enzyme that is encoded by the argP gene and/or the gcvA gene is increased and/or the activity of the enzyme encoded by the lpxD gene is altered.

The term "decreased expression and/or activity of", also encompasses a wild type microorganism which has no detectable expression and/or activity of brnQ and/or gcvB.

In one embodiment the decrease of the expression and/or activity of a gene is achieved by a deactivation, mutation or knock-out of the gene. This could be done by deletion of part or total of the coding region and/or the promoter of the gene, by mutation of the gene such as insertion or deletion of a number of nucleotides for example one or two nucleotides leading to a frameshift in the coding region of the gene, introduction of stop codons in the coding region, inactivation of the promoter of the gene by for example deleting or mutating promoter boxes such as ribosomal entry sides, the TATA box and the like. The decrease may also be achieved by degrading the transcript of the gene for example by means of introduction of ribozymes, dsRNA, antisense RNA or antisense oligonucleotides. The decrease of the activity of a gene may be achieved by expressing antibodies or aptamers in the cell specifically binding the target enzyme. Other methods for the decrease of the expression and/or activity of a gene are known to a skilled person.

In a preferred embodiment the decrease of the expression and/or activity of the brnQ gene is achieved by introduction of a mutation into the gene, preferably a deletion. In a further preferred embodiment, the deletion is introduced between position 667 and 764 of SEQ ID NO: 1, thereby deleting 97 nucleotides from the brnQ gene. The resulting truncated nucleic acid has a sequence as depicted in SEQ ID NO: 3 and encodes a truncated protein as depicted in SEQ ID NO: 4.

In a preferred embodiment the increase of the expression and/or activity of the argP gene is achieved by introduction of a mutation into the gene, preferably a point mutation. More preferably it is achieved by mutating the codon at position 286 to 288 of the argP gene of SEQ ID NO: 45 or a corresponding codon of a functional homologous gene. Even more preferably the codon is mutated so that it does encode the amino acid glutamic acid or another acidic amino acid or their amide or an amino acid similar to glutamic acid but not alanine. In a most preferred embodiment the respective codon is mutated so that it encodes the amino acid glutamic acid.

Preferably the increase of the expression and/or activity of the argP gene is achieved by introducing a mutation in the argP gene, wherein the mutated argP gene has the sequence of SEQ ID NO: 47, encoding a protein of SEQ ID NO: 48.

Preferably the increase of the expression and/or activity of the gcvA gene is achieved by introducing a mutation in the promoter of the gcvA gene, wherein the mutated promoter preferably has the sequence of SEQ ID NO: 56 or SEQ ID NO: 57.

In a preferred embodiment the decrease of the expression and/or activity of the gcvB gene is achieved by introduction of a mutation into the promoter. For example, the promoter may be mutated by deleting any one or more of the bases T in position 62 to 68 of SEQ ID NO: 59 or by introducing a point mutation in position 60 of SEQ ID NO: 59, rendering the A at this position into any one of G, C or T. Preferably the mutated promoter has a sequence of SEQ ID NO: 60 or 61.

Preferably the decrease of the expression and/or activity of the gcvB gene is achieved by introducing a mutation in the promoter of the gcvB gene. Preferably the wild-type promoter having SEQ ID NO: 59 is mutated to have the sequence of SEQ ID NO: 60 or 61.

Preferably the altered expression and/or activity of the lpxD gene is achieved by introducing a mutation in the lpxD gene, wherein the mutated lpxD gene has the sequence of SEQ ID NO: 51, encoding a protein of SEQ ID NO: 52.

The reduced expression and/or activity of the RNA or enzymes respectively disclosed herein, in particular the reduced expression and/or reduced activity of the RNA or enzyme encoded by the lactate dehydrogenase (ldhA), pyruvate formate lyase I (pflB), bifunctional acetaldehyde-CoA dehydrogenase/iron-dependent alcohol dehydrogenase/pyruvate-formate lyase deactivase (adhE), phosphate acetyltransferase (pta), fumarate reductase (frdA), gcvB and/or the brnQ, can be a reduction of the expression and/or activity by at least 50%, compared to the expression and/or activity of said RNA or enzyme in a respective reference microorganism for example the wild type of the microorganism, or a reduction of the expression and/or activity by at least 90%, or more preferably a reduction of expression and/or the activity by at least 95%, or more preferably an expression and/or reduction of the activity by at least 98%, or even more preferably a reduction of the expression and/or activity by at least 99% or even more preferably a reduction of the expression and/or the activity by at least 99.9%. In a most preferred embodiment the expression and/or activity of the RNA or enzymes is not detectable in the microorganism of the invention.

The loss of the expression and/or activity of the gcvB gene and/or the brnQ gene and the introduced or increased expression and/or activity of the argP gene and/or the gvcA gene and the altered activity and/or expression of the lpxD gene leads to an improved yield and/or productivity of alanine, pyruvate, succinate, aspartate, malate, lactate, valine and/or leucine, preferably succinate or alanine, more preferably alanine in the recombinant microorganism of the invention compared to a respective reference microorganism. Therefore the loss of the expression and/or activity of the brnQ gene or the gcvB gene and the introduction or increase of the expression and/or activity of the argP gene or the gcvA gene and the alteration of the activity and/or expression of the lpxD gene may be determined by measuring alanine, pyruvate, succinate, aspartate, malate, lactate, valine and/or leucine, preferably succinate or alanine, more preferably alanine yield or productivity of the recombinant microorganism of the invention compared to a respective reference microorganism. Methods for fermentative production of metabolites, for example alanine are known to a skilled person and also described herein. Improved yield of e.g. alanine in fermentation by the microorganism of the invention compared to yield of alanine in fermentation by a respective reference microorganism is a measure for the loss, reduction, introduction or increase or alteration of expression and or activity of the respective gene.

Methods for determining the lactate dehydrogenase (ldhA) expression or activity are, for example, disclosed by Bunch et al. in "The ldhA gene encoding the fermentative lactate de hydrogenase of *Escherichia Coli*", Microbiology (1997), Vol. 143, pages 187-155; or Bergmeyer, H. U., Bergmeyer J. and Grassi, M. (1983-1986) in "Methods of Enzymatic Analysis", 3rd Edition, Volume III, pages 126-133, Verlag Chemie, Weinheim; or Enzymes in Industry: Production and Applications, Second Edition (2004), Wolfgang Aehle, page 23. Preferred is the last method.

Methods for determining the pyruvate formate lyase I (pflB) expression or activity are, for example, disclosed in Knappe J, Blaschkowski H P, Grobner P, Schmitt T (1974). "Pyruvate formate-lyase of *Escherichia coli*: the acetylenzyme intermediate." Eur J Biochem 1974; 50(1); 253-63. PMID: 4615902; in KNAPPE, Joachim, et al. "Pyruvate Formate-Lyase of *Escherichia coli*: the Acetyl-Enzyme Intermediate." European Journal of Biochemistry 50.1 (1974): 253-263; in Wong, Kenny K., et al. "Molecular properties of pyruvate formatelyase activating enzyme." Biochemistry 32.51 (1993): 14102-14110 and in Nnyepi, Mbako R., Yi Peng, and Joan B. Broderick. "Inactivation of *E. coli* pyruvate formate-lyase: Role of AdhE and small molecules." Archives of biochemistry and biophysics 459.1 (2007): 1-9.

Methods for determining the bifunctional acetaldehyde-CoA dehydrogenase/iron-dependent alcohol dehydrogenase/pyruvate-formate lyase deactivase (adhE) expression or activity are, for example, disclosed in Membrillo-Hernandez, Jorge, et al. "Evolution of the adhE Gene Product of *Escherichia coli* from a Functional Reductase to a Dehydrogenase GENETIC AND BIOCHEMICAL STUDIES OF THE MUTANT PROTEINS." Journal of Biological Chemistry 275.43 (2000): 33869-33875 and in Mbako R. Nnyepi, Yi Peng, Joan B. Broderick, Inactivation of *E. coli* pyruvate formate-lyase: Role of AdhE and small molecules, Archives of Biochemistry and Biophysics, Volume 459, Issue 1, 1 Mar. 2007, Pages 1-9.

Methods for determining the phosphate acetyltransferase (pta) expression or activity are, for example, disclosed in Dittrich, Cheryl R., George N. Bennett, and Ka-Yiu San. "Characterization of the Acetate-Producing Pathways in *Escherichia coli*." Biotechnology progress 21.4 (2005): 1062-1067 and in Brown, T. D. K., M. C. Jones-Mortimer, and H. L. Kornberg. "The enzymic interconversion of acetate and acetyl-coenzyme A in *Escherichia coli*." Journal of general microbiology 102.2 (1977): 327-336.

Methods for determining the fumarate reductase (frdA) expression or activity are, for example, disclosed in Dickie, Peter, and Joel H. Weiner. "Purification and characterization of membrane-bound fumarate reductase from anaerobically grown *Escherichia coli*." Canadian journal of biochemistry 57.6 (1979): 813-821; in Cecchini, Gary, et al. "Reconstitution of quinone reduction and characterization of *Escherichia coli* fumarate reductase activity." Journal of Biological Chemistry 261.4 (1986): 1808-1814 or in Schroder, I., et al. "Identification of active site residues of *Escherichia coli* fumarate reductase by site-directed mutagenesis." Journal of Biological Chemistry 266.21 (1991): 13572-13579.

Methods for determining the alanine racemase (dadX) expression or activity are, for example, disclosed in J. Wild, J. Hennig, M. Lobocka, W. Walczak, T. Klopotowski "Identification of the dadX gene coding for the predominant isozyme of alanine racemase in *Escherichia coli* K12" Mol Gen Genet (1985) 198:315-322 and in M. Pulliam Lambert and F. C. Neuhaus "Factors Affecting the Level of Alanine Racemase in *Escherichia coli*" Journal of Bacteriology, March 1972, p. 1156-1161.

Methods for determining the alanine dehydrogenase (alaD) expression or activity are, for example, disclosed in Sakamoto, Y., Nagata, S., Esaki, N., Tanaka, H., Soda, K. "Gene cloning, purification and characterization of thermostable alanine dehydrogenase of *Bacillus stearothermophilus*" J Fermen. Bioeng. 69 (1990):154-158.

The term "reduced expression of an enzyme" includes, for example, the expression of the enzyme by said genetically manipulated (e.g., genetically engineered) microorganism at a lower level than that expressed by a respective reference microorganism for example the wild type of said microorganism. Genetic manipulations for reducing the expression of an enzyme can include, but are not limited to, deleting the gene or parts thereof encoding for the enzyme, altering or modifying regulatory sequences or sites associated with expression of the gene encoding the enzyme (e.g., by removing strong promoters or repressible promoters), modifying proteins (e.g., regulatory proteins, suppressors, enhancers, transcriptional activators and the like) involved in transcription of the gene encoding the enzyme and/or the translation of the gene product, or any other conventional means of decreasing expression of a particular gene routine in the art (including, but not limited to, the use of antisense nucleic acid molecules or other methods to knock-out or block expression of the target protein). Further on, one may introduce destabilizing elements into the mRNA or introduce genetic modifications leading to deterioration of ribosomal binding sites (RBS) of the RNA. It is also possible to change the codon usage of the gene in a way, that the translation efficiency and speed is decreased.

A reduced activity of an enzyme can also be obtained by introducing one or more deleterious gene mutations which lead to a reduced activity of the enzyme. Furthermore, a reduction of the activity of an enzyme may also include an inactivation (or the reduced expression) of activating enzymes which are necessary in order to activate the enzyme the activity of which is to be reduced. By the latter approach the enzyme the activity of which is to be reduced is preferably kept in an inactivated state.

A deleterious mutation according to this application is any mutation within a gene comprising promoter and coding region that lead to a decreased or deleted protein activity of the protein encoded by the coding region of the gene. Such deleterious mutations comprise for example frameshifts, introduction of stop-codons in the coding region, mutation of promoter elements such as the TATA box that prevent transcription and the like.

Microorganisms having a reduced expression and/or activity of the enzyme encoded by the brnQ-gene or the RNA encoded by the gcvB gene or an enhanced or increased expression and/or activity of the proteins encoded by the argP gene or the gcvA gene or an altered activity and/or expression of the protein encoded by the lpxD gene may occur naturally, i.e. due to spontaneous mutations. A microorganism can be modified to lack or to have significantly reduced, enhanced or altered activity of the enzyme or RNA that is encoded by one or more of said genes by various techniques, such as chemical treatment or radiation. To this end, microorganisms will be treated by, e.g., a mutagenizing chemical agent, X-rays, or UV light. In a subsequent step, those microorganisms which have a reduced, enhanced or altered expression and/or activity of the enzyme or RNA that is encoded by one or more of said genes will be selected. Recombinant microorganisms are also obtainable by homologous recombination techniques which aim to mutate, disrupt or excise one or more of said genes in the genome of the microorganism or to substitute one or more of said genes with a corresponding gene that encodes for an enzyme or RNA which, compared to the enzyme or RNA encoded by the wild type gene, has a reduced, enhanced or altered expression and/or activity.

According to one embodiment of the recombinant microorganism according to the present invention, a reduction of the expression and/or activity of the enzyme or RNA encoded by the brnQ-gene or the gcvB gene is achieved by a modification of the brnQ-gene, wherein this/these gene modification(s) is(are) preferably realized by a deletion of one or more of said genes or at least a part thereof, a deletion of a regulatory element of the one or more of said genes or parts thereof, such as a promoter sequence, or by an introduction of at least one deleterious mutation into one or more of said genes.

According to one embodiment of the recombinant microorganism according to the present invention, an increase of the expression and/or activity of the enzyme encoded by the argP-gene and/or the gcvA-gene may be achieved by a modification of the argP-gene and/or the gcvA-gene, wherein this/these gene modification(s) is(are) preferably realized by multiplication of the copy-number of the argP gene and/or the gcvA-gene in the genome of the microorganism, by introducing the gene on a self-replicating expression vector into the microorganism, by exchanging the promoter of the argP-gene and/or the gcvA-gene against a stronger promoter or by converting the endogenous promoter of the gene into a stronger promoter, e.g. by introducing point-mutations into the promoter sequence.

Further the activity of the argP-gene and/or the gcvA-gene and/or the lpxD gene may be enhanced or altered by mutating the gene in order to achieve amino acid exchanges in the protein which improve or alter activity of the gene. Such methods are known to a skilled person.

A mutation into the above-gene can be introduced, for example, by site-directed or random mutagenesis, followed by an introduction of the modified gene into the genome of the microorganism by recombination. Variants of the genes can be generated by mutating the gene sequences by means of PCR. The "Quickchange Site-directed Mutagenesis Kit" (Stratagene) can be used to carry out a directed mutagenesis. A random mutagenesis over the entire coding sequence, or else only part thereof, can be performed with the aid of the "GeneMorph II Random Mutagenesis Kit" (Stratagene). The mutagenesis rate is set to the desired amount of mutations via the amount of the template DNA used. Multiple mutations are generated by the targeted combination of individual mutations or by the sequential performance of several mutagenesis cycles.

In the following, a suitable technique for recombination, in particular for introducing a mutation or for deleting sequences, is described.

This technique is also sometimes referred to as the "Campbell recombination" herein (Leenhouts et al., *Appl Env Microbiol*. (1989), Vol. 55, pages 394-400). "Campbell in", as used herein, refers to a transformant of an original host cell in which an entire circular double stranded DNA molecule (for example a plasmid) has integrated into a chromosome by a single homologous recombination event (a cross in event), and that effectively results in the insertion of a linearized version of said circular DNA molecule into a first DNA sequence of the chromosome that is homologous to a first DNA sequence of the said circular DNA molecule. "Campbelled in" refers to the linearized DNA sequence that has been integrated into the chromosome of a "Campbell in" transformant. A "Campbell in" contains a duplication of the first homologous DNA sequence, each copy of which includes and surrounds a copy of the homologous recombination crossover point.

"Campbell out", as used herein, refers to a cell descending from a "Campbell in" transformant, in which a second homologous recombination event (a cross out event) has occurred between a second DNA sequence that is contained on the linearized inserted DNA of the "Campbelled in" DNA, and a second DNA sequence of chromosomal origin, which is homologous to the second DNA sequence of said linearized insert, the second recombination event resulting in the deletion (jettisoning) of a portion of the integrated DNA sequence, but, importantly, also resulting in a portion (this can be as little as a single base) of the integrated Campbelled in DNA remaining in the chromosome, such that compared to the original host cell, the "Campbell out" cell contains one or more intentional changes in the chromosome (for example, a single base substitution, multiple base substitutions, insertion of a heterologous gene or DNA sequence, insertion of an additional copy or copies of a homologous gene or a modified homologous gene, or insertion of a DNA sequence comprising more than one of these aforementioned examples listed above). A "Campbell out" cell is, preferably, obtained by a counter-selection against a gene that is contained in a portion (the portion that is desired to be jettisoned) of the "Campbelled in" DNA sequence, for example the *Bacillus subtilis* sacB-gene, which is lethal when expressed in a cell that is grown in the presence of about 5% to 10% sucrose. Either with or without a counter-selection, a desired "Campbell out" cell can be obtained or identified by screening for the desired cell, using any screenable phenotype, such as, but not limited to, colony morphology, colony color, presence or absence of antibiotic resistance, presence or absence of a given DNA sequence by polymerase chain reaction, presence or absence of an auxotrophy, presence or absence of an enzyme, colony nucleic acid hybridization, antibody screening, etc. The term "Campbell in" and "Campbell out" can also be used as verbs in various tenses to refer to the method or process described above.

It is understood that the homologous recombination events that leads to a "Campbell in" or "Campbell out" can occur over a range of DNA bases within the homologous DNA sequence, and since the homologous sequences will be identical to each other for at least part of this range, it is not usually possible to specify exactly where the crossover event occurred. In other words, it is not possible to specify precisely which sequence was originally from the inserted DNA, and which was originally from the chromosomal DNA. Moreover, the first homologous DNA sequence and the second homologous DNA sequence are usually separated by a region of partial non-homology, and it is this region of non-homology that remains deposited in a chromosome of the "Campbell out" cell.

Preferably, first and second homologous DNA sequence are at least about 200 base pairs in length, and can be up to several thousand base pairs in length. However, the procedure can be made to work with shorter or longer sequences. For example, a length for the first and second homologous sequences can range from about 500 to 2000 bases, and the obtaining of a "Campbell out" from a "Campbell in" is facilitated by arranging the first and second homologous sequences to be approximately the same length, preferably with a difference of less than 200 base pairs and most preferably with the shorter of the two being at least 70% of the length of the longer in base pairs.

In one embodiment the reduction of the expression and/or activity of brnQ and/or the gcvB gene is achieved by an inactivation of the brnQ-gene and/or the gcvB gene which encodes the branched chain amino acid transporter or a non-protein encoding RNA respectively.

In one embodiment the inactivation of the genes is preferably achieved by a deletion of the gene or at least parts thereof, by a deletion of a regulatory element of the gene or at least a part thereof or by an introduction of at least one deleterious mutation into the gene.

In one embodiment the induction of the expression and/or activity of argP is achieved by an activation of the argP-gene which encodes a protein having a DNA binding/transcription activating activity.

In one embodiment the induction of the expression and/or activity of gcvA is achieved by an activation of the gcvA-gene which encodes a DNA-binding protein.

The terms "alanine, pyruvate, succinate, aspartate, malate, lactate, valine and/or leucine", as used in the context of the present invention, has to be understood in their broadest sense and also encompasses salts thereof, as for example alkali metal salts, like $Na^+$ and $K^+$-salts, or earth alkali salts, like $Mg^{2+}$ and $Ca^{2+}$-salts, or ammonium salts or anhydrides of alanine, pyruvate, succinate, aspartate, malate, lactate, valine and/or leucine.

Preferably, alanine, pyruvate, succinate, aspartate, malate, lactate, valine and/or leucine, preferably succinate or alanine, more preferably alanine is produced under microaerobic conditions. Aerobic or anaerobic conditions may be also used.

Microaerobic means that the concentration of oxygen is less than that in air. According to one embodiment microaerobic means oxygen tension between 5 and 27 mm Hg, preferably between 10 and 20 Hg (Megan Falsetta et al. (2011), The composition and metabolic phenotype of *Neisseria gonorrhoeae* biofilms, Frontiers in Microbiology, Vol 2, page 1 to 11). Preferably the microaerobic conditions are established with 0.1 to 1 vvm air flow.

Anaerobic conditions may be established by means of conventional techniques, as for example by degassing the constituents of the reaction medium and maintaining anaerobic conditions by introducing carbon dioxide or nitrogen or mixtures thereof and optionally hydrogen at a flow rate of, for example, 0.1 to 1 or 0.2 to 0.5 vvm. Aerobic conditions may be established by means of conventional techniques, as for example by introducing air or oxygen at a flow rate of, for example, 0.1 to 1 or 0.2 to 0.5 vvm. If appropriate, a slight over pressure of 0.1 to 1.5 bar may be applied in the process.

According to one embodiment of the process according to the present invention the assimilable carbon source may be glucose, glycerin, glucose, maltose, maltodextrin, fructose, galactose, mannose, xylose, sucrose, arabinose, lactose, raffinose and combinations thereof.

In a preferred embodiment the assimilable carbon source is glucose, sucrose, xylose, arabinose, glycerol or combinations thereof. Preferred carbon sources are glucose, sucrose, glucose and sucrose, glucose and xylose and/or glucose, arabinose and xylose. According to one embodiment of the process according to the present invention the assimilable carbon source may be sucrose, glycerin and/or glucose.

The initial concentration of the assimilable carbon source, preferably the initial concentration is, preferably, adjusted to a value in a range of 5 to 250 g/l, preferably 50 to 200 g/l and more preferably 125 to 150 g/l, most preferably about 140 g/l and may be maintained in said range during cultivation. The pH of the reaction medium may be controlled by addition of suitable bases as for example, gaseous ammonia, $NH_4OH$, $NH_4HCO_3$, $(NH_4)_2CO_3$, $NaOH$, $Na_2CO_3$, $NaHCO_3$, $KOH$, $K_2CO_3$, $KHCO_3$, $Mg(OH)_2$, $MgCO_3$, $Mg(HCO_3)_2$, $Ca(OH)_2$, $CaCO_3$, $Ca(HCO_3)_2$, $CaO$, $CH_6N_2O_2$, $C_2H_7N$ and/or mixtures thereof.

Another embodiment of the invention is a process for fermentative production of alanine, pyruvate, succinate, aspartate, malate, lactate, valine and/or leucine, preferably succinate or alanine, more preferably alanine, most preferably L-alanine comprising the steps of
I) growing the microorganism according to the invention as defined above in a fermenter and
II) recovering alanine, pyruvate, succinate, aspartate, malate, lactate, valine and/or leucine, preferably succinate or alanine, more preferably alanine, most preferably L-alanine from the fermentation broth obtained in I).

The fermentation step I) according to the present invention can, for example, be performed in stirred fermenters, bubble columns and loop reactors. A comprehensive overview of the possible method types including stirrer types and geometric designs can be found in Chmiel: "*Bioprozesstechnik: Einführung in die Bioverfahrenstechnik*", Volume 1. In the process according to the present invention, typical variants available are the following variants known to those skilled in the art or explained, for example, in Chmiel, Hammes and Bailey: "*Biochemical Engineering*", such as batch, fed-batch, repeated fed-batch or else continuous fermentation with and without recycling of the biomass. Depending on the production strain, sparging with air, oxygen, carbon dioxide, hydrogen, nitrogen or appropriate gas mixtures may be effected in order to achieve good yield (YP/S).

Particularly preferred conditions for producing alanine, pyruvate, succinate, aspartate, malate, lactate, valine and/or leucine, preferably succinate or alanine, more preferably alanine, most preferably L-alanine in process step I) are:
Assimilable carbon source: glucose
Temperature: 30 to 45° C.
pH: 6.0 to 7.0
Microaerobic conditions In process step II) the product is recovered from the fermentation broth obtained in process step I).

Usually, the recovery process comprises the step of separating the recombinant microorganisms from the fermentation broth as the so called "biomass". Processes for removing the biomass are known to those skilled in the art, and comprise filtration, sedimentation, flotation or combinations thereof. Consequently, the biomass can be removed, for example, with centrifuges, separators, decanters, filters or in a flotation apparatus. For maximum recovery of the product of value, washing of the biomass is often advisable, for example in the form of a diafiltration. The selection of the method is dependent upon the biomass content in the fermentation broth and the properties of the biomass, and also the interaction of the biomass with the organic compound (e. the product of value). In one embodiment, the fermentation broth can be sterilized or pasteurized. In a further embodiment, the fermentation broth is concentrated. Depending on the requirement, this concentration can be done batch wise or continuously. The pressure and temperature range should be selected such that firstly no product damage occurs, and secondly minimal use of apparatus and energy is necessary. The skillful selection of pressure and temperature levels for a multistage evaporation in particular enables saving of energy.

The recovery process may further comprise additional purification steps in which the fermentation product is further purified. If, however, the fermentation product is converted into a secondary organic product by chemical reactions, a further purification of the fermentation product might, depending on the kind of reaction and the reaction conditions, not necessarily be required. For the purification of the fermentation product obtained in process step II) methods known to the person skilled in the art can be used, as for example crystallization, filtration, electrodialysis and chromatography. The resulting solution may be further purified by means of ion exchange chromatography in order to remove undesired residual ions.

In one embodiment, the reduced, repressed or deleted expression and/or activity of the brnQ gene is achieved by introducing a deletion into the wild-type gene. Preferably it is achieved by introducing a specific mutation between positions 667 and 764 of the wild type gene having SEQ ID NO: 1 or a functional variant thereof.

Therefore a further embodiment of the invention is a recombinant nucleic acid molecule having a sequence selected from the group of
(6) a nucleic acid molecule comprising a sequence of SEQ ID NO: 3, or
(7) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 3, or
(8) a nucleic acid molecule hybridizing to a nucleic acid molecule having SEQ ID NO: 3 under medium stringent conditions, more preferably under high stringent conditions, most preferably under very high stringent conditions, or
(9) a nucleic acid molecule encoding a polypeptide of SEQ ID NO: 4, or
(10) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 4
wherein the microorganism comprising the mutated gene and/or protein as defined but not the wild-type gene and/or protein has an improved Alanine yield in fermentation.

In one embodiment, the enhanced or increased expression and/or activity of the argP gene is achieved by introducing a mutation into the wild-type gene. Preferably it is achieved by introducing a specific mutation at position 286 to 288 of the wild type gene having SEQ ID NO: 45 or a functional variant thereof.

Therefore a further embodiment of the invention is a recombinant nucleic acid molecule having a sequence selected from the group of
(1) a nucleic acid molecule comprising a sequence of SEQ ID NO: 45, or
(2) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 45, or
(3) a nucleic acid molecule hybridizing to a nucleic acid molecule having SEQ ID NO: 45 under medium stringent conditions, more preferably under high stringent conditions, most preferably under very high stringent conditions, or
(4) a nucleic acid molecule encoding a polypeptide of SEQ ID NO: 46, or
(5) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 46, and
wherein the codon of the genes under (1) to (5) corresponding to position 286 to 288 of SEQ ID NO: 45 is not encoding amino acid alanine and is not a stop codon or the amino acid of the proteins encoded by the genes under (1) to (5) corresponding to position 96 of SEQ ID NO: 46 is not alanine, and
wherein the protein encoded by the gene as defined above in (1) to (5) has an enhanced or increased activity compared to the protein having SEQ ID NO: 46, and wherein the microorganism comprising the mutated gene and/or protein as defined above has an improved Alanine yield in fermentation.

Preferably, the recombinant nucleic acid molecule is having a sequence selected from the group of
(6) a nucleic acid molecule comprising a sequence of SEQ ID NO: 47, or
(7) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 47, or
(8) a nucleic acid molecule hybridizing to a nucleic acid molecule having SEQ ID NO: 47 under medium stringent conditions, more preferably under high stringent conditions, most preferably under very high stringent conditions, or
(9) a nucleic acid molecule encoding a polypeptide of SEQ ID NO: 48, or
(10) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 48,
wherein the codon of the genes under (7) to (10) corresponding to position 286 to 288 of SEQ ID NO: 47 is encoding amino acid glutamic acid or a related amino acid or the amino acid of the proteins encoded by the genes under (7) to (10) corresponding to position 96 of SEQ ID NO: 48 is glutamic acid or a related amino acid, and wherein the protein encoded by the gene as defined above in (7) to (10) has an enhanced or increased activity compared to the protein having SEQ ID NO: 48, and wherein the microorganism comprising the mutated gene and/or protein as defined above has an improved Alanine yield in fermentation.

In one embodiment, the enhanced or increased expression and/or activity of the gcvA gene is achieved by introducing a mutation into the promoter of the wild-type gene. Preferably it is achieved by introducing a specific mutation of the promoter of the of the wild type gene having SEQ ID NO: 53 or a functional variant thereof, wherein the mutation corresponds to the mutation introduced in SEQ ID NO: 55 leading to SEQ ID NO: 56 or SEQ ID NO: 57.

Therefore a further embodiment of the invention is a recombinant nucleic acid molecule comprising a sequence selected from the group of

(11) a nucleic acid molecule comprising a sequence of SEQ ID NO: 53, or
(12) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 53, or
(13) a nucleic acid molecule hybridizing to a nucleic acid molecule having SEQ ID NO: 53 under medium stringent conditions, more preferably under high stringent conditions, most preferably under very high stringent conditions, or
(14) a nucleic acid molecule encoding a polypeptide of SEQ ID NO: 54, or
(15) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 54,
functionally linked to a mutated promoter or promoter active in a microorganism which is heterologous to said nucleic acid molecule and
wherein the microorganism comprising the overexpressed gene and/or protein as defined above has an improved alanine yield in fermentation.

In one embodiment, the enhanced or increased yield and/or productivity of alanine or related compounds is achieved by introducing a mutation into the lpxD wild-type gene.

Therefore one embodiment of the invention is a recombinant nucleic acid molecule having a sequence selected from the group of

(16) a nucleic acid molecule comprising a sequence of SEQ ID NO: 49, or
(17) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 49, or
(18) a nucleic acid molecule hybridizing to a nucleic acid molecule having SEQ ID NO: 49 under medium stringent conditions, more preferably under high stringent conditions, most preferably under very high stringent conditions, or
(19) a nucleic acid molecule encoding a polypeptide of SEQ ID NO: 50, or
(20) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 50, and wherein the codon of the genes under (16) to (20) corresponding to position 43 to 45 of SEQ ID NO: 49 is not encoding amino acid alanine and is not a stop codon or the amino acid of the proteins encoded by the genes under (6) to (10) corresponding to position 15 of SEQ ID NO: 50 is not alanine, and wherein the protein encoded by the gene as defined above in (16) to (20) has an altered activity and/or expression compared to the protein having SEQ ID NO: 50, and wherein the microorganism comprising the mutated gene and/or protein as defined above has an improved alanine yield in fermentation.

Preferably, the recombinant nucleic acid molecule is having a sequence selected from the group of

(21) a nucleic acid molecule comprising a sequence of SEQ ID NO: 51, or
(22) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 51, or
(23) a nucleic acid molecule hybridizing to a nucleic acid molecule having SEQ ID NO: 51 under medium stringent conditions, more preferably under high stringent conditions, most preferably under very high stringent conditions, or
(24) a nucleic acid molecule encoding a polypeptide of SEQ ID NO: 52, or
(25) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 52, wherein the codon of the genes under (21) to (25) corresponding to position 43 to 45 of SEQ ID NO: 51 is encoding amino acid threonine or a related amino acid or the amino acid of the proteins encoded by the genes under (21) to (25) corresponding to position 15 of SEQ ID NO: 52 is threonine or a related amino acid, and wherein the protein encoded by the gene as defined above in (21) to (25) has an altered activity and/or expression compared to the protein having SEQ ID NO: 50 and wherein the microorganism comprising the mutated gene and/or protein as defined above has an improved alanine yield in fermentation.

The term "related amino acid" or "conservative amino acid substitution" means that an amino acid is replaced by an amino acid having a similar side-chain. A list of related amino acids is given in the table 2 below. Conservative substitution tables are well known in the art (see for example Creighton (1984) Proteins. W.H. Freeman and Company (Eds) and Table 2 below).

TABLE 2

Examples of conserved amino acid substitutions

| Residue | Conservative Substitutions | Residue | Conservative Substitutions |
|---|---|---|---|
| Ala | Ser | Leu | Ile; Val |
| Arg | Lys | Lys | Arg; Gln |
| Asn | Gln; His | Met | Leu; Ile |
| Asp | Glu | Phe | Met; Leu; Tyr |
| Gln | Asn | Ser | Thr; Gly |
| Cys | Ser | Thr | Ser; Val |
| Glu | Asp | Trp | Tyr |
| Gly | Pro | Tyr | Trp; Phe |
| His | Asn; Gln | Val | Ile; Leu |
| Ile | Leu, Val | | |

In a preferred embodiment the recombinant nucleic acid molecule has SEQ ID NO: 3, 47, 51 and is encoding a protein having SEQ ID NO: 4, 48, 52 respectively.

A further embodiment of the invention is a recombinant amino acid molecule having a sequence selected from the group of
(26) an amino acid molecule comprising a sequence of SEQ ID NO: 4, or
(27) an amino acid molecule having 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 4,
wherein the microorganism comprising the mutated protein as defined but not the wild-type protein has an improved Alanine yield in fermentation.

Preferably the recombinant amino acid molecule of the invention has SEQ ID NO: 4.

A further embodiment of the invention is a recombinant amino acid molecule having a sequence selected from the group of
(28) an amino acid molecule comprising a sequence of SEQ ID NO: 48, or
(29) an amino acid molecule having 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 48,
wherein the amino acid of the protein under (29) corresponding to position 96 of SEQ ID NO: 48 is glutamic acid or a related amino acid, and
wherein the protein as defined above in (29) has an enhanced or increased activity compared to the protein having SEQ ID NO: 46, and
wherein the microorganism comprising the mutated protein as defined but not the wild-type protein has an improved Alanine yield in fermentation.

Preferably the recombinant amino acid molecule of the invention has SEQ ID NO: 48.

A further embodiment of the invention is a recombinant amino acid molecule having a sequence selected from the group of
(30) an amino acid molecule comprising a sequence of SEQ ID NO: 52, or
(31) an amino acid molecule having 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 52,
wherein the amino acid of the protein under (31) corresponding to position 15 of SEQ ID NO: 52 is threonine or a related amino acid, and
wherein the protein as defined above in (31) has an altered activity and/or expression compared to the protein having SEQ ID NO: 50, and
wherein the microorganism comprising the mutated gene and/or protein as defined above has an improved alanine yield in fermentation.

Preferably the recombinant amino acid molecule of the invention has SEQ ID NO: 52.

Definitions

It is to be understood that this invention is not limited to the particular methodology or protocols. It is also to be understood that the terminology used herein is for the purpose of describing particular embodiments only, and is not intended to limit the scope of the present invention which will be limited only by the appended claims. It must be noted that as used herein and in the appended claims, the singular forms "a," "and," and "the" include plural reference unless the context clearly dictates otherwise. Thus, for example, reference to "a vector" is a reference to one or more vectors and includes equivalents thereof known to those skilled in the art, and so forth. The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). As used herein, the word "or" means any one member of a particular list and also includes any combination of members of that list. The words "comprise," "comprising," "include," "including," and "includes" when used in this specification and in the following claims are intended to specify the presence of one or more stated features, integers, components, or steps, but they do not preclude the presence or addition of one or more other features, integers, components, steps, or groups thereof. For clarity, certain terms used in the specification are defined and used as follows:

Coding region: As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5'-side by the nucleotide triplet "ATG" which encodes the initiator methionine, prokaryotes also use the triplets "GTG" and "TTG" as startcodon. On the 3'-side it is bounded by one of the three triplets which specify stop codons (i.e., TAA, TAG, TGA). In addition a gene may include sequences located on both the 5'- and 3'-end of the sequences which are present on the RNA transcript. These sequences are referred to as "flanking" sequences or regions (these flanking sequences are located 5' or 3' to the non-translated sequences present on the mRNA transcript). The 5'-flanking region may contain regulatory sequences such as promoters and enhancers which control or influence the transcription of the gene. The 3'-flanking region may contain sequences which direct the termination of transcription, post-transcriptional cleavage and polyadenylation.

Complementary: "Complementary" or "complementarity" refers to two nucleotide sequences which comprise antiparallel nucleotide sequences capable of pairing with one another (by the base-pairing rules) upon formation of hydrogen bonds between the complementary base residues in the antiparallel nucleotide sequences. For example, the sequence 5'-AGT-3' is complementary to the sequence 5'-ACT-3'. Complementarity can be "partial" or "total." "Partial" complementarity is where one or more nucleic acid bases are not matched according to the base pairing rules. "Total" or "complete" complementarity between nucleic acid molecules is where each and every nucleic acid base is matched with another base under the base pairing rules. The degree of complementarity between nucleic acid molecule strands has significant effects on the efficiency and strength of hybridization between nucleic acid molecule strands. A "complement" of a nucleic acid sequence as used herein refers to a nucleotide sequence whose nucleic acid molecules show total complementarity to the nucleic acid molecules of the nucleic acid sequence.

Endogenous: An "endogenous" nucleotide sequence refers to a nucleotide sequence, which is present in the genome of a wild type microorganism.

Enhanced expression: "enhance" or "increase" the expression of a nucleic acid molecule in a microorganism are used equivalently herein and mean that the level of expression of a nucleic acid molecule in a microorganism is higher compared to a reference microorganism, for example a wild type. The terms "enhanced" or "increased" as used herein mean herein higher, preferably significantly higher expression of the nucleic acid molecule to be expressed. As used herein, an "enhancement" or "increase" of the level of an agent such as a protein, mRNA or RNA means that the level is increased relative to a substantially identical microorganism grown under substantially identical conditions. As used herein, "enhancement" or "increase" of the level of an agent, such as for example a preRNA, mRNA, rRNA, tRNA, expressed by the target gene and/or of the protein product encoded by it, means that the level is increased 50% or more, for example 100% or more, preferably 200% or more, more preferably 5 fold or more, even more preferably 10 fold or more, most preferably 20 fold or more for example 50 fold relative to a suitable reference microorganism. The enhancement or increase can be determined by methods with which the skilled worker is familiar. Thus, the enhancement or increase of the nucleic acid or protein quantity can be determined for example by an immunological detection of the protein. Moreover, techniques such as protein assay, fluorescence, Northern hybridization, nuclease protection assay, reverse transcription (quantitative RT-PCR), ELISA (enzyme-linked immunosorbent assay), Western blotting, radioimmunoassay (RIA) or other immunoassays and fluorescence-activated cell analysis (FACS) can be employed to measure a specific protein or RNA in a microorganism. Depending on the type of the induced protein product, its activity or the effect on the phenotype of the microorganism may also be determined. Methods for determining the protein quantity are known to the skilled worker. Examples, which may be mentioned, are: the micro-Biuret method (Goa J (1953) Scand J Clin Lab Invest 5:218-222), the Folin-Ciocalteau method (Lowry O H et al. (1951) J Biol Chem 193:265-275) or measuring the absorption of CBB G-250 (Bradford M M (1976) Analyt Biochem 72:248-254).

Expression: "Expression" refers to the biosynthesis of a gene product, preferably to the transcription and/or translation of a nucleotide sequence, for example an endogenous gene or a heterologous gene, in a cell. For example, in the case of a structural gene, expression involves transcription of the structural gene into mRNA and—optionally—the subsequent translation of mRNA into one or more polypeptides. In other cases, expression may refer only to the transcription of the DNA harboring an RNA molecule.

Foreign: The term "foreign" refers to any nucleic acid molecule (e.g., gene sequence) which is introduced into a cell by experimental manipulations and may include sequences found in that cell as long as the introduced sequence contains some modification (e.g., a point mutation, the presence of a selectable marker gene, etc.) and is therefore different relative to the naturally-occurring sequence.

Functional linkage: The term "functional linkage" or "functionally linked" is equivalent to the term "operable linkage" or "operably linked" and is to be understood as meaning, for example, the sequential arrangement of a regulatory element (e.g. a promoter) with a nucleic acid sequence to be expressed and, if appropriate, further regulatory elements (such as e.g., a terminator) in such a way that each of the regulatory elements can fulfill its intended function to allow, modify, facilitate or otherwise influence expression of said nucleic acid sequence. As a synonym the wording "operable linkage" or "operably linked" may be used. The expression may result depending on the arrangement of the nucleic acid sequences in relation to sense or antisense RNA. To this end, direct linkage in the chemical sense is not necessarily required. Genetic control sequences such as, for example, enhancer sequences, can also exert their function on the target sequence from positions which are further away, or indeed from other DNA molecules. Preferred arrangements are those in which the nucleic acid sequence to be expressed recombinantly is positioned behind the sequence acting as promoter, so that the two sequences are linked covalently to each other. In a preferred embodiment, the nucleic acid sequence to be transcribed is located behind the promoter in such a way that the transcription start is identical with the desired beginning of the chimeric RNA of the invention. Functional linkage, and an expression construct, can be generated by means of customary recombination and cloning techniques as described (e.g., in Maniatis T, Fritsch E F and Sambrook J (1989) Molecular Cloning: A Laboratory Manual, 2nd Ed., Cold Spring Harbor Laboratory, Cold Spring Harbor (N.Y.); Silhavy et al. (1984) Experiments with Gene Fusions, Cold Spring Harbor Laboratory, Cold Spring Harbor (N.Y.); Ausubel et al. (1987) Current Protocols in Molecular Biology, Greene Publishing Assoc. and Wiley Interscience; Gelvin et al. (Eds) (1990) Plant Molecular Biology Manual; Kluwer Academic Publisher, Dordrecht, The Netherlands). However, further sequences, which, for example, act as a linker with specific cleavage sites for restriction enzymes, or as a signal peptide, may also be positioned between the two sequences. The insertion of sequences may also lead to the expression of fusion proteins. Preferably, the expression construct, consisting of a linkage of a regulatory region for example a promoter and nucleic acid sequence to be expressed, can exist in a vector-integrated form or can be inserted into the genome, for example by transformation.

Gene: The term "gene" refers to a region operably linked to appropriate regulatory sequences capable of regulating the expression of the gene product (e.g., a polypeptide or a functional RNA) in some manner. A gene includes untranslated regulatory regions of DNA (e.g., promoters, enhancers, repressors, etc.) preceding (up-stream) and following (downstream) the coding region (open reading frame, ORF). The term "structural gene" as used herein is intended to mean a DNA sequence that is transcribed into mRNA which is then translated into a sequence of amino acids characteristic of a specific polypeptide.

Genome and genomic DNA: The terms "genome" or "genomic DNA" is referring to the heritable genetic information of a host organism. Said genomic DNA comprises the DNA of the nucleoid but also the DNA of the self-replicating plasmid.

Heterologous: The term "heterologous" with respect to a nucleic acid molecule or DNA refers to a nucleic acid molecule which is operably linked to, or is manipulated to become operably linked to, a second nucleic acid molecule to which it is not operably linked in nature, or to which it is operably linked at a different location in nature. A heterologous expression construct comprising a nucleic acid molecule and one or more regulatory nucleic acid molecule (such as a promoter or a transcription termination signal) linked thereto for example is a constructs originating by experimental manipulations in which either a) said nucleic acid molecule, or b) said regulatory nucleic acid molecule or c) both (i.e. (a) and (b)) is not located in its natural (native) genetic environment or has been modified by experimental manipulations, an example of a modification being a substitution, addition, deletion, inversion or insertion of one or more nucleotide residues. Natural genetic environment refers to the natural genomic locus in the organism of origin, or to the presence in a genomic library. In the case of a genomic library, the natural genetic environment of the sequence of the nucleic acid molecule is preferably retained, at least in part. The environment flanks the nucleic acid sequence at least at one side and has a sequence of at least 50 bp, preferably at least 500 bp, especially preferably at least 1,000 bp, very especially preferably at least 5,000 bp, in length. A naturally occurring expression construct—for example the naturally occurring combination of a promoter with the corresponding gene—becomes a transgenic expression construct when it is modified by non-natural, synthetic "artificial" methods such as, for example, mutagenization. Such methods have been described (U.S. Pat. No. 5,565,350; WO 00/15815). For example a protein encoding nucleic acid molecule operably linked to a promoter, which is not the native promoter of this molecule, is considered to be heterologous with respect to the promoter. Preferably, heterologous DNA is not endogenous to or not naturally associated with the cell into which it is introduced, but has been obtained from another cell or has been synthesized. Heterologous DNA also includes an endogenous DNA sequence, which contains some modification, non-naturally occurring, multiple copies of an endogenous DNA sequence, or a DNA sequence which is not naturally associated with another DNA sequence physically linked thereto. Generally, although not necessarily, heterologous DNA encodes RNA or proteins that are not normally produced by the cell into which it is expressed.

Hybridization: The term "hybridization" as used herein includes "any process by which a strand of nucleic acid molecule joins with a complementary strand through base pairing." (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules. As used herein, the term "Tm" is used in reference to the "melting temperature." The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: $Tm=81.5+0.41(\% G+C)$, when a nucleic acid molecule is in aqueous solution at 1 M NaCl [see e.g., Anderson and Young, Quantitative Filter Hybridization, in Nucleic Acid Hybridization (1985)]. Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6. Suitable hybridization conditions are for example hybridizing under conditions equivalent to hybridization in 7% sodium dodecyl sulfate (SDS), 0.5 M NaPO4, 1 mM EDTA at 50° C. with washing in 2×SSC, 0.1% SDS at 50° C. (low stringency) to a nucleic acid molecule comprising at least 50, preferably at least 100, more preferably at least 150, even more preferably at least 200, most preferably at least 250 consecutive nucleotides of the complement of a sequence. Other suitable hybridizing conditions are hybridization in 7% sodium dodecyl sulfate (SDS), 0.5 M NaPO4, 1 mM EDTA at 50° C. with washing in 1×SSC, 0.1% SDS at 50° C. (medium stringency) or 65° C. (high stringency) to a nucleic acid molecule comprising at least 50, preferably at least 100, more preferably at least 150, even more preferably at least 200, most preferably at least 250 consecutive nucleotides of a complement of a sequence. Other suitable hybridization conditions are hybridization in 7% sodium dodecyl sulfate (SDS), 0.5 M NaPO4, 1 mM EDTA at 50° C. with washing in 0.1×SSC, 0.1% SDS at 65° C. (very high stringency) to a nucleic acid molecule comprising at least 50, preferably at least 100, more preferably at least 150, even more preferably at least 200, most preferably at least 250 consecutive nucleotides of a complement of a sequence.

"Identity": "Identity" when used in respect to the comparison of two or more nucleic acid or amino acid molecules means that the sequences of said molecules share a certain degree of sequence similarity, the sequences being partially identical.

To determine the percentage identity (homology is herein used interchangeably if referring to nucleic acid sequences) of two amino acid sequences or of two nucleic acid molecules, the sequences are written one underneath the other for an optimal comparison (for example gaps may be inserted into the sequence of a protein or of a nucleic acid in order to generate an optimal alignment with the other protein or the other nucleic acid).

The amino acid residues or nucleic acid molecules at the corresponding amino acid positions or nucleotide positions are then compared. If a position in one sequence is occupied by the same amino acid residue or the same nucleic acid molecule as the corresponding position in the other sequence, the molecules are identical at this position. The percentage identity between the two sequences is a function of the number of identical positions shared by the sequences (i.e. % identity=number of identical positions/total number of positions×100). The terms "homology" and "identity" are thus to be considered as synonyms when referring to nucleic acid sequences. When referring to amino acid sequences the term identity refers to identical amino acids at a specific position in a sequence, the term homology refers to homologous amino acids at a specific position in a sequence. Homologous amino acids are amino acids having a similar side chain. Families of amino acid residues having similar side chains have been defined in the art.

A nucleic acid molecule encoding a protein homologous to a protein of the invention can be created by introducing one or more nucleotide substitutions, additions or deletions into a nucleotide sequence such that one or more amino acid substitutions, additions or deletions are introduced into the encoded protein. Mutations can be introduced into one of the sequences of the invention by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in a protein of the invention is preferably replaced with another amino acid residue from the same side chain family.

Alternatively, in another embodiment, mutations can be introduced randomly along all or part of a coding sequence, such as by saturation mutagenesis, and the resultant mutants can be screened for the respective activity described herein to identify mutants that retain their activity. Following mutagenesis of one of the sequences of the invention, the encoded protein can be expressed recombinantly and the activity of the protein can be determined using, for example, assays described herein.

For the determination of the percentage identity of two or more amino acids or of two or more nucleotide sequences several computer software programs have been developed. The identity of two or more sequences can be calculated with for example the software fasta, which presently has been used in the version fasta 3 (W. R. Pearson and D. J. Lipman, PNAS 85, 2444(1988); W. R. Pearson, Methods in Enzymology 183, 63 (1990); W. R. Pearson and D. J. Lipman, PNAS 85, 2444 (1988); W. R. Pearson, Enzymology 183, 63 (1990)). Another useful program for the calculation of identities of different sequences is the standard blast program, which is included in the Biomax pedant software (Biomax, Munich, Federal Republic of Germany). This leads unfortunately sometimes to suboptimal results since blast does not always include complete sequences of the subject and the query. Nevertheless as this program is very efficient it can be used for the comparison of a huge number of sequences. The following settings are typically used for such a comparisons of sequences:

-p Program Name [String]; -d Database [String]; default=nr; -i Query File [File In]; default=stdin; -e Expectation value (E) [Real]; default=10.0; -m alignment view options: 0=pairwise; 1=query-anchored showing identities; 2=query-anchored no identities; 3=flat query-anchored, show identities; 4=flat query-anchored, no identities; 5=query-anchored no identities and blunt ends; 6=flat query-anchored, no identities and blunt ends; 7=XML Blast output; 8=tabular; 9 tabular with comment lines [Integer]; default=0; -o BLAST report Output File [File Out] Optional; default=stdout; -F Filter query sequence (DUST with blastn, SEG with others) [String]; default=T; -G Cost to open a gap (zero invokes default behavior) [Integer]; default=0; -E Cost to extend a gap (zero invokes default behavior) [Integer]; default=0; -X X dropoff value for gapped alignment (in bits) (zero invokes default behavior); blastn 30, megablast 20, tblastx 0, all others 15 [Integer]; default=0; -I Show GI's in deflines [T/F]; default=F; -q Penalty for a nucleotide mismatch (blastn only) [Integer]; default=−3; -r Reward for a nucleotide match (blastn only) [Integer]; default=1; -v Number of database sequences to show one-line descriptions for (V) [Integer]; default=500; -b Number of database sequence to show alignments for (B) [Integer]; default=250; -f Threshold for extending hits, default if zero; blastp 11, blastn 0, blastx 12, tblastn 13; tblastx 13, megablast 0 [Integer]; default=0; -g Perfom gapped alignment (not available with tblastx) [T/F]; default=T; -Q Query Genetic code to use [Integer]; default=1; -D DB Genetic code (for tblast [nx] only) [Integer]; default=1; -a Number of processors to use [Integer]; default=1; -O SeqAlign file [File Out] Optional; -J Believe the query defline [T/F]; default=F; -M Matrix [String]; default=BLOSUM62; -W Word size, default if zero (blastn 11, megablast 28, all others 3) [Integer]; default=0; -z Effective length of the database (use zero for the real size) [Real]; default=0; -K Number of best hits from a region to keep (off by default, if used a value of 100 is recommended) [Integer]; default=0; -P 0 for multiple hit, 1 for single hit [Integer]; default=0; -Y Effective length of the search space (use zero for the real size) [Real]; default=0; -S Query strands to search against database (for blast[nx], and tblastx); 3 is both, 1 is top, 2 is bottom [Integer]; default=3; -T Produce HTML output [T/F]; default=F; -I Restrict search of database to list of GI's [String] Optional; -U Use lower case filtering of FASTA sequence [T/F] Optional; default=F; -y X dropoff value for ungapped extensions in bits (0.0 invokes default behavior); blastn 20, megablast 10, all others 7 [Real]; default=0.0; -Z X dropoff value for final gapped alignment in bits (0.0 invokes default behavior); blastn/megablast 50, tblastx 0, all others 25 [Integer]; default=0; -R PSI-TBLASTN checkpoint file [File In] Optional; -n MegaBlast search [T/F]; default=F; -L Location on query sequence [String] Optional; -A Multiple Hits window size, default if zero (blastn/megablast 0, all others 40 [Integer]; default=0; -w Frame shift penalty (OOF algorithm for blastx) [Integer]; default=0; -t Length of the largest intron allowed in tblastn for linking HSPs (0 disables linking) [Integer]; default=0.

Results of high quality are reached by using the algorithm of Needleman and Wunsch or Smith and Waterman. Therefore programs based on said algorithms are preferred. Advantageously the comparisons of sequences can be done with the program PileUp (J. Mol. Evolution, 25, 351 (1987), Higgins et al., CABIOS 5, 151 (1989)) or preferably with the programs "Gap" and "Needle", which are both based on the algorithms of Needleman and Wunsch (J. Mol. Biol. 48; 443 (1970)), and "BestFit", which is based on the algorithm of Smith and Waterman (Adv. Appl. Math. 2; 482 (1981)). "Gap" and "BestFit" are part of the GCG software-package (Genetics Computer Group, 575 Science Drive, Madison, Wis., USA 53711 (1991); Altschul et al., (Nucleic Acids Res. 25, 3389 (1997)), "Needle" is part of the The European Molecular Biology Open Software Suite (EMBOSS) (Trends in Genetics 16 (6), 276 (2000)). Therefore preferably the calculations to determine the percentages of sequence identity are done with the programs "Gap" or "Needle" over the whole range of the sequences. The following standard adjustments for the comparison of nucleic acid sequences were used for "Needle": matrix:

EDNAFULL, Gap_penalty: 10.0, Extend_penalty: 0.5. The following standard adjustments for the comparison of nucleic acid sequences were used for "Gap": gap weight: 50, length weight: 3, average match: 10.000, average mismatch: 0.000.

For example a sequence, which is said to have 80% identity with sequence SEQ ID NO: 1 at the nucleic acid level is understood as meaning a sequence which, upon comparison with the sequence represented by SEQ ID NO: 1 by the above program "Needle" with the above parameter set, has a 80% identity. Preferably the identity is calculated on the complete length of the query sequence, for example SEQ ID NO:1.

Isolated: The term "isolated" as used herein means that a material has been removed by the hand of man and exists apart from its original, native environment and is therefore not a product of nature. An isolated material or molecule (such as a DNA molecule or enzyme) may exist in a purified form or may exist in a non-native environment such as, for example, in a transgenic host cell. For example, a naturally occurring nucleic acid molecule or polypeptide present in a living cell is not isolated, but the same nucleic acid molecule or polypeptide, separated from some or all of the coexisting materials in the natural system, is isolated. Such nucleic acid molecules can be part of a vector and/or such nucleic acid molecules or polypeptides could be part of a composition, and would be isolated in that such a vector or composition is not part of its original environment. Preferably, the term "isolated" when used in relation to a nucleic acid molecule, as in "an isolated nucleic acid sequence" refers to a nucleic acid sequence that is identified and separated from at least one contaminant nucleic acid molecule with which it is ordinarily associated in its natural source. Isolated nucleic acid molecule is nucleic acid molecule present in a form or setting that is different from that in which it is found in nature. In contrast, non-isolated nucleic acid molecules are nucleic acid molecules such as DNA and RNA, which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs, which encode a multitude of proteins. However, an isolated nucleic acid sequence comprising for example SEQ ID NO: 1 includes, by way of example, such nucleic acid sequences in cells which ordinarily contain SEQ ID NO: 1 where the nucleic acid sequence is in a genomic or plasmid location different from that of natural cells, or is otherwise flanked by a different nucleic acid sequence than that found in nature. The isolated nucleic acid sequence may be present in single-stranded or double-stranded form. When an isolated nucleic acid sequence is to be utilized to express a protein, the nucleic acid sequence will contain at a minimum at least a portion of the sense or coding strand (i.e., the nucleic acid sequence may be single-stranded). Alternatively, it may contain both the sense and anti-sense strands (i.e., the nucleic acid sequence may be double-stranded).

Non-coding: The term "non-coding" refers to sequences of nucleic acid molecules that do not encode part or all of an expressed protein. Non-coding sequences include but are not limited enhancers, promoter regions, 3' untranslated regions, and 5' untranslated regions.

Nucleic acids and nucleotides: The terms "nucleic acids" and "Nucleotides" refer to naturally occurring or synthetic or artificial nucleic acid or nucleotides. The terms "nucleic acids" and "nucleotides" comprise deoxyribonucleotides or ribonucleotides or any nucleotide analogue and polymers or hybrids thereof in either single- or double-stranded, sense or antisense form. Unless otherwise indicated, a particular nucleic acid sequence also implicitly encompasses conservatively modified variants thereof (e.g., degenerate codon substitutions) and complementary sequences, as well as the sequence explicitly indicated. The term "nucleic acid" is used inter-changeably herein with "gene", "cDNA, "mRNA", "oligonucleotide," and "nucleic acid molecule". Nucleotide analogues include nucleotides having modifications in the chemical structure of the base, sugar and/or phosphate, including, but not limited to, 5-position pyrimidine modifications, 8-position purine modifications, modifications at cytosine exocyclic amines, substitution of 5-bromo-uracil, and the like; and 2'-position sugar modifications, including but not limited to, sugar-modified ribonucleotides in which the 2'-OH is replaced by a group selected from H, OR, R, halo, SH, SR, NH2, NHR, NR2, or CN. Short hairpin RNAs (shRNAs) also can comprise non-natural elements such as non-natural bases, e.g., ionosin and xanthine, non-natural sugars, e.g., 2'-methoxy ribose, or non-natural phosphodiester linkages, e.g., methylphosphonates, phosphorothioates and peptides.

Nucleic acid sequence: The phrase "nucleic acid sequence" refers to a single or double-stranded polymer of deoxyribonucleotide or ribonucleotide bases read from the 5'- to the 3'-end. It includes chromosomal DNA, self-replicating plasmids, infectious polymers of DNA or RNA and DNA or RNA that performs a primarily structural role. "Nucleic acid sequence" also refers to a consecutive list of abbreviations, letters, characters or words, which represent nucleotides. In one embodiment, a nucleic acid can be a "probe" which is a relatively short nucleic acid, usually less than 100 nucleotides in length. Often a nucleic acid probe is from about 50 nucleotides in length to about 10 nucleotides in length. A "target region" of a nucleic acid is a portion of a nucleic acid that is identified to be of interest. A "coding region" of a nucleic acid is the portion of the nucleic acid, which is transcribed and translated in a sequence-specific manner to produce into a particular polypeptide or protein when placed under the control of appropriate regulatory sequences. The coding region is said to encode such a polypeptide or protein.

Oligonucleotide: The term "oligonucleotide" refers to an oligomer or polymer of ribonucleic acid (RNA) or deoxyribonucleic acid (DNA) or mimetics thereof, as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. An oligonucleotide preferably includes two or more nucleomonomers covalently coupled to each other by linkages (e.g., phosphodiesters) or substitute linkages.

Overhang: An "overhang" is a relatively short single-stranded nucleotide sequence on the 5'- or 3'-hydroxyl end of a double-stranded oligonucleotide molecule (also referred to as an "extension," "protruding end," or "sticky end").

Polypeptide: The terms "polypeptide", "peptide", "oligopeptide", "polypeptide", "gene product", "expression product" and "protein" are used interchangeably herein to refer to a polymer or oligomer of consecutive amino acid residues.

Promoter: The terms "promoter", or "promoter sequence" are equivalents and as used herein, refer to a DNA sequence which when operably linked to a nucleotide sequence of interest is capable of controlling the transcription of the nucleotide sequence of interest into RNA. A promoter is located 5' (i.e., upstream), proximal to the transcriptional start site of a nucleotide sequence of interest whose transcription into mRNA it controls, and provides a site for specific binding by RNA polymerase and other transcription factors for initiation of transcription. The promoter does not comprise coding regions or 5' untranslated regions. The promoter may for example be heterologous or homologous to the respective cell. A nucleic acid molecule sequence is "heterologous to" an organism or a second nucleic acid molecule sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety). Suitable promoters can be derived from genes of the host cells where expression should occur or from pathogens for this host.

Purified: As used herein, the term "purified" refers to molecules, either nucleic or amino acid sequences that are removed from their natural environment, isolated or separated. "Substantially purified" molecules are at least 60% free, preferably at least 75% free, and more preferably at least 90% free from other components with which they are naturally associated. A purified nucleic acid sequence may be an isolated nucleic acid sequence.

Recombinant: The term "recombinant" with respect to nucleic acid molecules refers to nucleic acid molecules produced by recombinant DNA techniques. The term also comprises nucleic acid molecules which as such does not exist in nature but are modified, changed, mutated or otherwise manipulated by man. Preferably, a "recombinant nucleic acid molecule" is a non-naturally occurring nucleic acid molecule that differs in sequence from a naturally occurring nucleic acid molecule by at least one nucleic acid. A "recombinant nucleic acid molecule" may also comprise a "recombinant construct" which comprises, preferably operably linked, a sequence of nucleic acid molecules not naturally occurring in that order. Preferred methods for producing said recombinant nucleic acid molecule may comprise cloning techniques, directed or non-directed mutagenesis, synthesis or recombination techniques.

Significant increase: An increase for example in enzymatic activity, gene expression, productivity or yield of a certain product, that is larger than the margin of error inherent in the measurement technique, preferably an increase by about 10% or 25% preferably by 50% or 75%, more preferably 2-fold or -5 fold or greater of the activity, expression, productivity or yield of the control enzyme or expression in the control cell, productivity or yield of the control cell, even more preferably an increase by about 10-fold or greater.

Significant decrease: A decrease for example in enzymatic activity, gene expression, productivity or yield of a certain product, that is larger than the margin of error inherent in the measurement technique, preferably a decrease by at least about 5% or 10%, preferably by at least about 20% or 25%, more preferably by at least about 50% or 75%, even more preferably by at least about 80% or 85%, most preferably by at least about 90%, 95%, 97%, 98% or 99%.

Substantially complementary: In its broadest sense, the term "substantially complementary", when used herein with respect to a nucleotide sequence in relation to a reference or target nucleotide sequence, means a nucleotide sequence having a percentage of identity between the substantially complementary nucleotide sequence and the exact complementary sequence of said reference or target nucleotide sequence of at least 60%, more desirably at least 70%, more desirably at least 80% or 85%, preferably at least 90%, more preferably at least 93%, still more preferably at least 95% or 96%, yet still more preferably at least 97% or 98%, yet still more preferably at least 99% or most preferably 100% (the later being equivalent to the term "identical" in this context). Preferably identity is assessed over a length of at least 19 nucleotides, preferably at least 50 nucleotides, more preferably the entire length of the nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J Mol. Biol. 48: 443-453; as defined above). A nucleotide sequence "substantially complementary" to a reference nucleotide sequence hybridizes to the reference nucleotide sequence under low stringency conditions, preferably medium stringency conditions, most preferably high stringency conditions (as defined above).

Transgene: The term "transgene" as used herein refers to any nucleic acid sequence, which is introduced into the genome of a cell by experimental manipulations. A transgene may be an "endogenous DNA sequence," or a "heterologous DNA sequence" (i.e., "foreign DNA"). The term "endogenous DNA sequence" refers to a nucleotide sequence, which is naturally found in the cell into which it is introduced so long as it does not contain some modification (e.g., a point mutation, the presence of a selectable marker gene, etc.) relative to the naturally-occurring sequence.

Transgenic: The term transgenic when referring to an organism means transformed, preferably stably transformed, with a recombinant DNA molecule that preferably comprises a suitable promoter operatively linked to a DNA sequence of interest.

Vector: As used herein, the term "vector" refers to a nucleic acid molecule capable of transporting another nucleic acid molecule to which it has been linked. One type of vector is a genomic integrated vector, or "integrated vector", which can become integrated into the genomic DNA of the host cell. Another type of vector is an episomal vector, i.e., a plasmid or a nucleic acid molecule capable of extra-chromosomal replication. Vectors capable of directing the expression of genes to which they are operatively linked are referred to herein as "expression vectors". In the present specification, "plasmid" and "vector" are used interchangeably unless otherwise clear from the context.

Wild type: The term "wild type", "natural" or "natural origin" means with respect to an organism that said organism is not changed, mutated, or otherwise manipulated by man. With respect to a polypeptide or nucleic acid sequence, that the polypeptide or nucleic acid sequence is naturally occurring or available in at least one naturally occurring organism which is not changed, mutated, or otherwise manipulated by man.

A wild type of a microorganism refers to a microorganism whose genome is present in a state as before the introduction of a genetic modification of a certain gene. The genetic modification may be e.g. a deletion of a gene or a part thereof or a point mutation or the introduction of a gene.

The terms "production" or "productivity" are art-recognized and include the concentration of the fermentation product (for example, alanine) formed within a given time and a given fermentation volume (e.g., kg product per hour per liter). The term "efficiency of production" includes the time required for a particular level of production to be achieved (for example, how long it takes for the cell to attain a particular rate of output of a fine chemical). Productivity may also mean space-time-yield which is defined as the amount of product generated divided by reactor volume and by time.

The term "yield" or "product/carbon yield" is art-recognized and includes the efficiency of the conversion of the carbon source into the product (i.e., fine chemical). This is generally written as, for example, kg product per kg carbon source. By increasing the yield or production of the compound, the quantity of recovered molecules or of useful recovered molecules of that compound in a given amount of culture over a given amount of time is increased.

The term "recombinant microorganism" includes microorganisms which have been genetically modified such that they exhibit an altered or different genotype and/or phenotype (e.g., when the genetic modification affects coding nucleic acid sequences of the microorganism) as compared to the wild type microorganism from which it was derived. A recombinant microorganism comprises at least one recombinant DNA molecule.

The term "recombinant" with respect to DNA refers to DNA molecules produced by man using recombinant DNA techniques. The term comprises DNA molecules which as such do not exist in nature or do not exist in the organism from which the DNA is derived, but are modified, changed, mutated or otherwise manipulated by man. Preferably, a "recombinant DNA molecule" is a non-naturally occurring nucleic acid molecule that differs in sequence from a naturally occurring nucleic acid molecule by at least one nucleic acid. A "recombinant DNA molecule" may also comprise a "recombinant construct" which comprises, preferably operably linked, a sequence of nucleic acid molecules not naturally occurring in that order. Preferred methods for producing said recombinant DNA molecule may comprise cloning techniques, directed or non-directed mutagenesis, gene synthesis or recombination techniques.

An example of such a recombinant DNA is a plasmid into which a heterologous DNA-sequence has been inserted or a gene or promoter which has been mutated compared to gene or promoter from which the recombinant DNA derived. The mutation may be introduced by means of directed mutagenesis technologies known in the art or by random mutagenesis technologies such as chemical, UV light or x-ray mutagenesis or directed evolution technologies.

The term "directed evolution" is used synonymously with the term "metabolic evolution" herein and involves applying a selection pressure that favors the growth of mutants with the traits of interest. The selection pressure can be based on different culture conditions, ATP and growth coupled selection and redox related selection. The selection pressure can be carried out with batch fermentation with serial transferring inoculation or continuous culture with the same pressure.

The term "expression" or "gene expression" means the transcription of a specific gene(s) or specific genetic vector construct. The term "expression" or "gene expression" in particular means the transcription of gene(s) or genetic vector construct into mRNA. The process includes transcription of DNA and may include processing of the resulting RNA-product. The term "expression" or "gene expression" may also include the translation of the mRNA and therewith the synthesis of the encoded protein, i.e. protein expression.

FIG. 1
Clone validation after inactivation of the ackA-pta genes.
FIG. 1 comprises FIGS. 1A and 1B. FIG. 1A: PCR amplicon obtained from genomic DNA of E. coli W ΔackA-pta::FRT with primers P395-ackA-pta-check2 and P395-ackA-pta-check5 (338 bp). M: DNA size marker. FIG. 1B: Sequencing of the PCR amplicon with P395-ackA-pta-check2 and P395-ackA-pta-check5 confirmed basepair-precise modification of the ackA-pta locus. (SEQ ID NOs: 126 and 127.) Nucleotides that were confirmed by sequencing are shown in italics. The remaining FRT site is shown in green, flanking primer binding sites are shown in red. upper case: coding sequence. lower case: intergenic regions.

FIG. 2
Clone validation after inactivation of the adhE gene.
FIG. 2 comprises FIGS. 2A and 2B. FIG. 2A: PCR amplicon obtained from genomic DNA of E. coli W ΔackA-pta::FRT ΔadhE::FRT with primers P395—adhE-check2 and P395-adhE-check5 (569 bp). M: DNA size marker. Fi B: Sequencing of the PCR amplicon with P395-adhE-check2 and P395-adhE-check5 confirmed basepair-precise modification of the adhE locus. (SEQ ID NOs: 128 and 129.) Nucleotides that were confirmed by sequencing are shown in italics. The remaining FRT site is shown in green, flanking primer binding sites are shown in red. upper case: coding sequence. lower case: intergenic regions.

FIG. 3
Clone validation after inactivation of the frdABCD genes.
FIG. 3 comprises FIGS. 3A and 3B. FIG. 3A: PCR amplicon obtained from genomic DNA of E. coli W ΔackA-pta::FRT ΔadhE::FRT ΔfrdABCD::FRT with primers P395-frd-check1 and P395-frd-check4 (797 bp). M: DNA size marker. FIG 3B: Sequencing of the PCR amplicon with P395-frd-check1 and P395-frd-check4 confirmed basepair-precise modification of the frd locus. (SEQ ID NOs: 130 and 131.) Nucleotides that were confirmed by sequencing are shown in italics. The remaining FRT site is shown in green, flanking primer binding sites are shown in red. upper case: coding sequence. lower case: intergenic regions.

FIG. 4
Clone validation after inactivation of the pflB gene.
FIG. 4 comprises FIGS. 4A and 4B. FIG. 4A: PCR amplicon obtained from genomic DNA of E. coli W ΔackA-pta:FRT ΔadhE::FRT ΔfrdABCD::FRT ΔpflB::FRT with primers P395-pflB-check1 and P395-pflB-check3 (511 bp). M: DNA size marker. FIG. 4B: Sequencing of the PCR amplicon with P395-pflB-check1 and P395-pflB-check3 confirmed basepair-precise modification of the pflB locus. (SEQ ID NOs: 132 and 133.) Nucleotides that were confirmed by sequencing are shown in italics. The remaining FRT site is shown in green, flanking primer binding sites are shown in red. upper case: coding sequence. lower case: intergenic regions.

FIG. 5
Clone validation after integration of the alaD-gstear gene.
FIG. 5 comprises FIGS. 5A and 5B. FIG. 5A: PCR amplicon obtained from genomic DNA of E. coli W ΔackA-pta::FRT ΔadhE::FRT ΔfrdABCD::FRT ΔpflB::FRT ΔldhA:: alaD-gstear with primers P395-ldhA-check1 and P395-ldhA-check2 (1833 bp). M: DNA size marker. FIG. 5B: Sequencing of the PCR amplicon with P395-ldhA-check1 and P395-ldhA-check2 confirmed basepair-precise modification of the ldhA locus and integration of alaD-gstear. (SEQ ID NOs: 134 and 135.) Nucleotides that were confirmed by sequencing are shown in italics. The alaD-gstear ORF is shown in cyan, the remaining FRT site is shown in green, flanking primer binding sites are shown in red. upper case: coding sequence. lower case: intergenic regions.

FIG. 6

Metabolic Map of Alanine Synthesis in the Microorganism of the Invention

Red stars depict knockouts of enzyme activity

Green arrow depict introduced enzyme activity

J7 represents ldh—lactate dehydrogenase, KO reduces the production of lactate.

J6 represents frdABCD—fumarate reductase, KO reduces the production of succinate.

J8 represents pfl—pyruvate formate lyase, KO reduces the production of acetate and ethanol.

J10 represents ack-pta—phosphotransacetylase-acetate kinase, KO reduces the production of acetate.

J11 represents adhE-alcohol dehydrogenase, KO reduces the production of ethanol.

FIG. 7

Alanine formation during batch fermentation of E. coli QZ20 and E. coli QZ48 (ArgP A96E) in 500 mL AM 1 medium with 140 g/L glucose. The fermentation was controlled at 37 C, 400 rpm, at pH 6.8 with 5 N NH$_4$OH without aeration.

FIG. 8

The volumetric alanine productivity (space-time-yield), defined as the amount of product generated divided by reactor volume and by time, of E. coli QZ20 and QZ48 (ArgP A96E) after 46 h of batch-fermentation in 500 mL AM 1 medium with 140 g/L glucose as carbon source.

FIG. 9

Alanine formation during batch fermentation of E. coli QZ20/pACYC184 plasmid control and E. coli QZ20/pACYC184-argP in 500 mL AM 1 medium with 140 g/L glucose. The fermentation was controlled at 37 C, 400 rpm, at pH 6.8 with 5 N NH$_4$OH without aeration.

FIG. 10

The volumetric alanine productivity (space-time-yield), defined as the amount of product generated divided by reactor volume and by time, of E. coli QZ20/pACYC184 plasmid control and E. coli QZ20/pACYC184-argP after 20 h of batch-fermentation in 500 mL AM 1 medium with 140 g/L glucose as carbon source.

FIG. 11

Alanine formation during batch fermentation of E. coli QZ20 and E. coli QZ58 (gcvA/B promoter SNP) in 500 mL AM 1 medium with 140 g/L glucose. The fermentation was controlled at 37 C, 400 rpm, at pH 6.8 with 5 N NH$_4$OH without aeration.

FIG. 12

The volumetric alanine productivity (space-time-yield), defined as the amount of product generated divided by reactor volume and by time, of E. coli QZ20 and QZ58 (gcvA/B promoter SNP) after 46 h of batch-fermentation in 500 mL AM 1 medium with 140 g/L glucose as carbon source.

FIG. 13

Alanine formation during batch fermentation of E. coli QZ48 (ArgP A96E) and E. coli QZ66 (Arg A96E, gcvA/B promoter SNP) in 500 mL AM 1 medium with 140 g/L glucose. The fermentation was controlled at 37 C, 400 rpm, at pH 6.8 with 5 N NH$_4$OH without aeration.

FIG. 14

The volumetric alanine productivity (space-time-yield), defined as the amount of product generated divided by reactor volume and by time, of E. coli QZ48 (ArgP A96E) and E. coli QZ66 (ArgP A96E, gcvA/B promoter SNP) after 46 h of batch-fermentation in 500 mL AM 1 medium with 140 g/L glucose as carbon source.

FIG. 15

Relative gene transcription analysis of (A) gcvA and (B) gcvB in E. coli QZ20 and QZ23 at 8 h, 11 h and 28 h during batch-fermentation relative to E. coli QZ20 8 h. All qPCR-derived data were normalized versus the rrsA gene as reference.

FIG. 16

Alanine formation during batch fermentation of E. coli QZ20/pACYC184 plasmid control, E. coli QZ20/pACYC184-gcvA and E. coli QZ20/pACYC184-gcvB in 500 mL AM 1 medium with 140 g/L glucose. The fermentation was controlled at 37 C, 400 rpm, at pH 6.8 with 5 N NH$_4$OH without aeration.

FIG. 17

The volumetric alanine productivity (space-time-yield), defined as the amount of product generated divided by reactor volume and by time, of E. coli QZ20 with plasmid control pACYC184, pACYC184-gcvA and pACYC184-gcvB after 46 h of batch-fermentation in 500 mL AM 1 medium with 140 g/L glucose as carbon source.

FIG. 18

Alanine formation during batch fermentation of E. coli QZ20 and E. coli QZ71 (gcvB knock-out) in 500 mL AM 1 medium with 140 g/L glucose. The fermentation was controlled at 37 C, 400 rpm, at pH 6.8 with 5 N NH$_4$OH without aeration.

FIG. 19

The volumetric alanine productivity (space-time-yield), defined as the amount of product generated divided by reactor volume and by time, of E. coli QZ20 and E. coli QZ71 (gcvB knock-out) after 46 h of batch-fermentation in 500 mL AM 1 medium with 140 g/L glucose as carbon source.

FIG. 20

Alanine formation during batch fermentation of E. coli QZ20, E. coli QZ57 (brnQΔ667-764) and E. coli QZ69 (brnQ KO) in 500 mL AM 1 medium with 140 g/L glucose. The fermentation was controlled at 37 C, 400 rpm, at pH 6.8 with 5 N NH$_4$OH without aeration.

FIG. 21

The volumetric alanine productivity (space-time-yield), defined as the amount of product generated divided by reactor volume and by time, of E. coli QZ20, E. coli QZ57 (brnQΔ667-764) and E. coli QZ69 (brnQ KO) after 46 h of batch-fermentation in 500 mL AM 1 medium with 140 g/L glucose as carbon source.

FIG. 22

Alanine formation during batch fermentation of E. coli QZ20 and E. coli QZ56 (LpxD A15T) in 500 mL AM 1 medium with 140 g/L glucose. The fermentation was controlled at 37 C, 400 rpm, at pH 6.8 with 5 N NH$_4$OH without aeration.

FIG. 23

The volumetric alanine productivity (space-time-yield), defined as the amount of product generated divided by reactor volume and by time, of E. coli QZ20 and QZ56 (LpxD A15T) after 46 h of batch-fermentation in 500 mL AM 1 medium with 140 g/L glucose as carbon source.

FIG. 24

Alanine formation during batch fermentation of E. coli QZ68 (argP A96E, gcvA/B promoter SNP, brnQΔ667-764) and E. coli QZ70 (argP A96E, gcvA/B promoter SNP, brnQΔ667-764, lpxD A15T) in 500 mL AM 1 medium with 140 g/L glucose. The fermentation was controlled at 37 C, 400 rpm, at pH 6.8 with 5 N NH$_4$OH without aeration.

FIG. 25

The volumetric alanine productivity (space-time-yield), defined as the amount of product generated divided by reactor volume and by time, of E. coli QZ68 (argP A96E, gcvA/B promoter SNP, brnQΔ667-764) and E. coli QZ70 (argP A96E, gcvA/B promoter SNP, brnQΔ667-764, lpxD A15T) after 46 h of batch-fermentation in 500 mL AM 1 medium with 140 g/L glucose as carbon source.

FIG. 26

Enantiomeric excess of alanine samples taken from E. coli strain QZ30 and E. coli strain QZ23 at various time-points during batch-fermentation in 500 mL AM 1 medium with 140 g/L glucose as carbon source. The fermentation was controlled at 37 C, 400 rpm, at pH 6.8 with 5 N NH$_4$OH without aeration.

EXAMPLES

Chemicals and Common Methods

Unless indicated otherwise, cloning procedures carried out for the purposes of the present invention including restriction digest, agarose gel electrophoresis, purification of nucleic acids, ligation of nucleic acids, transformation, selection and cultivation of bacterial cells are performed as described (Sambrook et al., 1989). Sequence analyses of recombinant DNA are performed with a laser fluorescence DNA sequencer (Applied Biosystems, Foster City, Calif., USA) using the Sanger technology (Sanger et al., 1977). Unless described otherwise, chemicals and reagents are obtained from Sigma Aldrich (Sigma Aldrich, St. Louis, USA), from Promega (Madison, Wis., USA), Duchefa (Haarlem, The Netherlands) or Invitrogen (Carlsbad, Calif., USA). Restriction endonucleases are from New England Biolabs (Ipswich, Mass., USA) or Roche Diagnostics GmbH (Penzberg, Germany). Oligonucleotides are synthesized by Eurofins MWG Operon (Ebersberg, Germany).

Example 1

E. coli W (LU17032) was engineered for L-alanine production by inactivation of the ackA-pta, adhE, frdABCD and pflB ORFs and replacement of the ldhA ORF by a codon-optimized variant of the alaD gene (alaD-gstear).

The ackA-pta, adhE, frdABCD and pflB ORFs were inactivated by insertion of an FRT-flanked kanamycin resistance cassette, followed by removal of the antibiotic resistance cassette by FLP recombination.

The ldhA gene was replaced by alaD-gstear and a downstream FRT-flanked zeocin resistance cassette, which was finally removed by FLP recombination.

Materials and Methods

Bacterial Culture

E. coli W (LU17032) was cultured in Luria-Bertani (LB) liquid medium or on Luria-Bertani solid medium. Occasionally, clones were passaged over M9 minimal agar containing 10 mM Sucrose to confirm W strain identity. Antibiotics were added to the liquid and solid media as appropriate, to final concentrations of 15 µg/ml (kanamycin, chloramphenicol), 25 µg/ml (zeocin) or 3 µg/ml (tetracyclin).

Red/ET Recombination

Red/ET recombination was performed using standard protocols of Gene Bridges GmbH (www.genebridges.com). Briefly, Red/ET-proficient E. coli W was aerobically grown at 30° C. to an OD600 nm of ~0.3. Expression of red genes was induced by adding 50 µl of 10% (w/v) L-arabinose, followed by a temperature increase to 37° C. Arabinose was omitted from uninduced control cultures. After 35 min of incubation at 37° C. the cells were washed twice with ice cold 10% (v/v) glycerol and electroporated with 500 ng of PCR product at 1.35 kV, 10 µF, 6000. The cells were then resuspended in 1 ml ice-cold LB medium and aerobically grown at 37° C. for approximately 1.5 h. Cultures were then plated on LB agar containing 15 µg/ml kanamycin (knock-outs) or 25 µg/ml zeocin (knockin).

FLP Recombination

Flanking FRT sites allowed removal of antibiotic resistance markers by FLP recombination following modification of the E. coli chromosome. FLP recombination leaves a single FRT site (34 bp) as well as short flanking sequences (approx. 20 bp each) which are used as primer binding sites in the amplification of the cassettes.

To perform FLP recombination, plasmid 708-FLPe (Tab. 1) encoding FLP recombinase was introduced into the Red/ET recombinants by electroporation. KanR CmR or ZeoR CmR transformants were used to inoculate 0.2 ml LB cultures, which were incubated at 30° C. for 3 h. FLP activity was then induced by a temperature shift to 37° C., followed by a three-hour incubation at 37° C. Single colonies obtained from these cultures were subsequently screened for a CmS and KanS or ZeoS phenotype.

DNA Preparation and Analysis

E. coli genomic DNA (gDNA) was isolated from overnight cultures with the Gentra Puregene Yeast/Bact. Kit B (Qiagen, Hilden, Germany). PCR products harbouring knockout or knockin cassettes were amplified from template plasmids with PRECISOR high-fidelity DNA polymerase (BioCat, Heidelberg) and analytical PCR reactions were performed with the PCR Extender System (SPRIME GmbH, Hamburg, Germany), according to the manufacturer's recommendations. PCR amplicons were purified using the GeneJET PCR Purification Kit or the GeneJET Gel Extraction Kit (Fermentas, St. Leon-Rot, Germany) and sequencing was performed by GATC BioTech (Konstanz, Germany) or BioSpring (Frankfurt am Main, Germany).

TABLE 1

Plasmids and primers

| plasmids | Relevant characteristics/ oligo sequences (5' → 3') | Source |
| --- | --- | --- |
| pRed/ET | red expression plasmid, pSC101-based, Tc$^R$ | Gene Bridges |
| 708-FLPe | FLP recombinase expression plasmid, pSC101-based, Cm$^R$ | Gene Bridges |
| pQZ11 | pUC57-based plasmid with chloramphenicol acetyl-transferase (cat)-levansucrase (sacB) cassette, ampR | Gene-script |
| pACYC184 | E. coli cloning vector, p15A ori, Cm$^R$, Tc$^R$ | NEB |
| primers (BioSpring) | Sequence | SEQ ID NO |
| P395-ackA-pta-check1 | 5'-ACTGCGGTAGTTCTTCACTG-3' | SEQ ID NO: 17 |
| P395-ackA-pta-check2 | 5'-AGTACCTTTCTGGTTTAGCCG-3' | SEQ ID NO: 18 |
| P395-ackA-pta-check3 | 5'-GATAGCAGAAACGGAACCAC-3' | SEQ ID NO: 19 |

TABLE 1-continued

Plasmids and primers

| Name | Sequence | SEQ ID |
|---|---|---|
| P395-ackA-pta-check4 | 5'-GGTGCTGTTCACACTACCGC-3' | SEQ ID NO: 20 |
| P395-ackA-pta-check5 | 5'-TGACGAGATTACTGCTGCTG-3' | SEQ ID NO: 21 |
| P395-ackA-pta-check6 | 5'-ATTTCCGGTTCAGATATCCGC-3' | SEQ ID NO: 22 |
| P395-adhE-check1 | 5'-GGGTTGACCAGCGCAAATAAC-3' | SEQ ID NO: 23 |
| P395-adhE-check2 | 5'-CAGAAGTGAGTAATCTTGCTTAC-3' | SEQ ID NO: 24 |
| P395-adhE-check3 | 5'-GATCACTTTATCTTCGACGATAC-3' | SEQ ID NO: 25 |
| P395-adhE-check4 | 5'-GCGAACGTGGATAAACTGTCTG-3' | SEQ ID NO: 26 |
| P395-adhE-check5 | 5'-GCTCTTAAGCACCGACGTTGAC-3' | SEQ ID NO: 27 |
| P395-adhE-check6 | 5'-GTCGGCTCATTAACGGCTATTC-3' | SEQ ID NO: 28 |
| P395-frd-check1 | 5'-GACGGATCTCCGCCATAATC-3' | SEQ ID NO: 29 |
| P395-frd-check2 | 5'-TCGCCACCCGCTACTGTATC-3' | SEQ ID NO: 30 |
| P395-frd-check3 | 5'-CAAAGCGTTCTGACGAACCGG-3' | SEQ ID NO: 31 |
| P395-frd-check4 | 5'-TGTGCGATGCACAATATCGTTG-3' | SEQ ID NO: 32 |
| P395-pflB-check1 | 5'-TTGGTTGGGTTGACATACTGG-3' | SEQ ID NO: 33 |
| P395-pflB-check2 | 5'-TGAACTTCATCACTGATAACC-3' | SEQ ID NO: 34 |
| P395-pflB-check3 | 5'-TTCAAAGGAGTGAATGCGACC-3' | SEQ ID NO: 35 |
| P395-pflB-check4 | 5'-GTCGCGGTTATGACAATACAGG-3' | SEQ ID NO: 36 |
| P395-ldhA-check1 | 5'-TACCGTGCCGACGTTCAATAAC-3' | SEQ ID NO: 37 |
| P395-ldhA-check2 | 5'-CATCAGCAGGCTTAGCGCAAC-3' | SEQ ID NO: 38 |
| P395-ldhA-check3 | 5'-ACCTTTACGCGTAATGCGTG-3' | SEQ ID NO: 39 |
| P395-ldhA-check4 | 5'-ACCGTTTACGCTTTCCAGCAC-3' | SEQ ID NO: 40 |
| P395-csc-check1 | 5'-CGAATTATCGATCTCGCTCAAC-3' | SEQ ID NO: 41 |
| P395-csc-check2 | 5'-CGTCTATATTGCTGAAGGTACAG-3' | SEQ ID NO: 42 |
| P395-csc-check3 | 5'-TCGAAGGTCCATTCACGCAAC-3' | SEQ ID NO: 43 |
| P395-csc-check4 | 5'-GATTCCCACCGCAACGTTAG-3' | SEQ ID NO: 44 |
| PargP_1_F | 5'-ttgctggaagaagagtggctgggcgatgaacaaaccggttcgactccgctgatatcggaagcccgggccaac-3' | SEQ ID NO: 62 |
| PargP_1_R | 5'tcagccaacacaggagccagtgcaggaagcaaccacgtcgccagactgtccacctgagacaacttgttacagctc-3' | SEQ ID NO: 63 |
| PargP_2_F | 5'-actggatgcggtgatacgtgaacg-3' | SEQ ID NO: 64 |
| PargP_2_R | 5'-accactggcgctttcagtaatgcc-3' | SEQ ID NO: 65 |
| PargP_seq_F | 5'-ttaccaggagcagacaacagc-3' | SEQ ID NO: 66 |
| PargP_seq_R | 5'-ggcagatcgaagttttgctgc-3' | SEQ ID NO: 67 |
| PargP-pACYC_F | 5'-tatcatcgataagcttatgttacccgccgacggcttcg-3' | SEQ ID NO: 68 |
| PargP-pACYC_R | 5'-aagggcatcggtcgacgtgaggataacgcctgatatgtgc-3' | SEQ ID NO: 69 |
| PgcvA_1_F | 5'-taataggttacacagtgtgatctaattgttaaattcatttaacatcaaaggatatcggaagcccgggccaac-3' | SEQ ID NO: 70 |
| PgcvA_1_R | 5'-aaactcgtaaggcatttagcggtggtaatcgtttagacatggcttttaaacacctgagacaacttgttacagctc-3' | SEQ ID NO: 71 |
| PgcvA_2_F | 5'-cgcagaccaattgcaaacac-3' | SEQ ID NO: 72 |
| PgcvA_2_R | 5'-ctcgcgcagcagaagagctt-3' | SEQ ID NO: 73 |
| PgcvA_seq_F | 5'-agcagatcaaccgtactgac-3' | SEQ ID NO: 74 |
| PgcvA_seq_R | 5'-agtttacgcgtcgcttcggt-3' | SEQ ID NO: 75 |
| PgcvA-pACYC_F | 5'-tatcatcgataagcttaagtgccgccactataggtatttgc-3' | SEQ ID NO: 76 |
| PgcvA-pACYC_R | 5'-aagggcatcggtcgactggtcatggtcgtaccctacg-3' | SEQ ID NO: 77 |
| PgcvB_1_F | 5'-tgacgtgaaagagatggtcgaactggatcagtaattcgcgatcgcaaggtgatatcggaagcccgggccaac-3' | SEQ ID NO: 78 |
| PgcvB_1_R | 5'-attataaattgtccgttgagcttctaccagcaaataccttatagtggcggccacctgagacaacttgttacagctc-3' | SEQ ID NO: 79 |
| PgcvB_seq_F | 5'-gccgcaattatttctgcctgtatgc-3' | SEQ ID NO: 80 |
| PgcvB_seq_R | 5'-cacaaaaagctcttctgctgcgcg-3' | SEQ ID NO: 81 |
| PgcvB-pACYC_F | 5'-tatcatcgataagcttggtcgaactggatcagtaattcgc-3' | SEQ ID NO: 82 |
| PgcvB-pACYC_R | 5'-aagggcatcggtcgaccggtggtaatcgtttagacatggc-3' | SEQ ID NO: 83 |
| PbrnQ_1_F | 5'-tatcgttattgttaacgcggcgcgttctcgtggcgttaccgaagcgcgatatcggaagcccgggccaac-3' | SEQ ID NO: 84 |
| PbrnQ_1_R | 5'-gaacgtaagcatgcagaatagcagcgccgtttgcagactgatcgaccagcacctgagacaacttgttacagctc-3' | SEQ ID NO: 85 |

TABLE 1-continued

Plasmids and primers

| | | |
|---|---|---|
| PbrnQ_2_F | 5'-ggataccgtgggcaacttccttgc-3' | SEQ ID NO: 86 |
| PbrnQ_2_R | 5'-gttagaaaccaccatcgagaagccg-3' | SEQ ID NO: 87 |
| PbrnQ_seq_F | 5'-cgctgtttatctacagcctgg-3' | SEQ ID NO: 88 |
| PbrnQ_seq_R | 5'-ggataaatagcggtcagcacc-3' | SEQ ID NO: 89 |
| PlpxD_1C_F | 5'-catcggtaaaacctggtaagtgttctccacaaaggaatgtagtggtagtgtagcgatatcggaagccctgggccaac-3' | SEQ ID NO: 90 |
| PlpxD_1C_R | 5'-ggtgcagttctttgcgtggcccggcgatctttatattgatcgcctaaagtcatccacctgagacaacttgttacagctc-3' | SEQ ID NO: 91 |
| PlpxD_fix_F | 5'-cgatcaacgaatataactcgctgcg-3' | SEQ ID NO: 92 |
| PlpxD_fix_R | 5'-ataataacacggcctgccgcaatcg-3' | SEQ ID NO: 93 |
| PlpxD_flank_F | 5'-atgctgtaggcggtaacgccat-3' | SEQ ID NO: 94 |
| PlpxD_flank_R | 5'-atacgttgttacccagcttcgc-3' | SEQ ID NO: 95 |
| PlpxD-pACYC_F | 5'-tatcatcgataagcttaaatccgttgccaacagccagg-3' | SEQ ID NO: 96 |
| PlpxD-pACYC_R | 5'-aagggcatcggtcgacaacacggcctgccgcaatcg-3' | SEQ ID NO: 97 |
| PargP_RT_F | 5'-gcccggactacagaacattacagg-3' | SEQ ID NO: 99 |
| PargP_RT_R | 5'-tgagacggctgattgtgtaatgc-3' | SEQ ID NO: 100 |
| PgcvA_RT_F | 5'-ccatttaagtttcactcgcgcagc-3' | SEQ ID NO: 101 |
| PgcvA_RT_R | 5'-ggcggcggaacagttttagc-3' | SEQ ID NO: 102 |
| PgcvB_RT_F | 5'-taggcggtgctacattaatcactatgg-3' | SEQ ID NO: 103 |
| PgcvB_RT_R | 5'-tgttgtgtttgcaattggtctgc-3' | SEQ ID NO: 104 |
| PlpxD_RT_F | 5'-gatatcgtcatcaccggcgttgc-3' | SEQ ID NO: 105 |
| PlpxD_RT_R | 5'-gcacaagcctaaatgctcacgg-3' | SEQ ID NO: 106 |
| PrrsA_RT_F | 5'-ctcttgccatcggatgtgcccag-3' | SEQ ID NO: 107 |
| PrrsA_RT_R | 5'-ccagtgtggctggtcatcctctca-3' | SEQ ID NO: 108 |

1.1. ackA-Pta Locus—Targeting of ackA-Pta

Approximately 500 ng of the ΔackA-pta PCR construct (1737 bp) were electroporated into Red/ET-proficient E. coli W cells. Eight KanR transformants were analysed for correct integration of the resistance marker cassette by PCR with genome-specific primers. Three clones were subjected to FLP recombination, which was performed as described in Material and Methods (data not shown).

Clone validation. Inactivation of the ackA-pta locus and removal of the kanamycin resistance cassette were confirmed by PCR across the remaining FRT scar. One clone that yielded the correct PCR signal was also confirmed by sequencing (FIG. 1).

1.2 adhE Locus—Targeting of adhE

Approximately 500 ng of the ΔadhE PCR construct (1093 bp) were electroporated into Red/ET-proficient E. coli W cells harbouring the ΔackA-pta::FRT modification. Eight KanR transformants were analysed for correct integration of the resistance marker cassette by PCR with genome-specific primers. Two clones were subjected to FLP recombination, which was performed as described in Material and Methods (data not shown).

Clone validation. Inactivation of the adhE locus and removal of the kanamycin resistance cassette were confirmed by PCR across the remaining FRT scar. One clone that yielded the correct PCR signal was also confirmed by sequencing (FIG. 2).

1.3 Frd Locus—Targeting of frdABCD

Approximately 500 ng of the ΔfrdABCD PCR construct (1093 bp) were electroporated into Red/ET-proficient E. coli W cells harbouring the ΔackA-pta::FRT and ΔadhE::FRT modifications. Eight KanR transformants were analysed for correct integration of the resistance marker cassette by PCR with genome-specific primers. One clone was subjected to FLP recombination, which was performed as described in material and Methods (data not shown). Clone validation. Inactivation of the frd locus and removal of the kanamycin resistance cassette were confirmed by PCR across the remaining FRT scar. One clone that yielded the correct PCR signal was also confirmed by sequencing (FIG. 3).

1.4 pflB Locus—Targeting of pflB

Approximately 500 ng of the ΔpflB PCR construct (1093 bp) were electroporated into Red/ET-proficient E. coli W cells harbouring the ΔackA-pta::FRT, ΔadhE::FRT and ΔfrdABCD::FRT modifications. Eight KanR transformants were analysed for correct integration of the resistance marker cassette by PCR with genome-specific primers. Four clones were subjected to FLP recombination, which was performed as described in Material and Methods (data not shown).

Clone validation. Inactivation of the pflB locus and removal of the kanamycin resistance cassette were confirmed by PCR across the remaining FRT scar. One clone that yielded the correct PCR signal was also confirmed by sequencing (FIG. 4).

1.5 ldhA Locus—Knockin of alaD-Gstear

Approximately 500 ng of the ΔldhA::alaD-gstear PCR construct (1783 bp) were electroporated into Red/ET-proficient E. coli W cells harbouring the ΔackA-pta::FRT, ΔadhE::FRT, ΔfrdABCD::FRT and ΔpflB::FRT modifications. Four ZeoR transformants were analysed for correct integration of the resistance marker cassette by PCR with genome-specific primers. One clone was subjected to FLP recombination, which was performed as described in material and Methods (data not shown).

Clone validation. Integration of alaD-gstear and removal of the zeocin resistance cassette were confirmed by PCR across the remaining FRT scar. One clone that yielded the correct PCR signal was also confirmed by sequencing (FIG. 5).

Example 2 HPLC Detection and Quantification of Alanine

The following HPLC method for the alanine detection in the cell culture media was used: Column: Aminex HPX-87C column (Bio-Rad), 300×7.8 mm, i.d. particle size 9 μm Mobile phase: Ca(NO3)2 at 0.1 mol/L 90%, Acetonitrile 10%
Flow rate: 0.6 mL/min
Column temperature: 60° C.
Detection: Refractive index detector Under above method, major estimated components in the cell culture sample matrix can be well separated from alanine, without interfering alanine's quantitation.

The amount of the alanine in the sample was determined by external standard calibration method. Standard samples containing alanine from 0.5 to 10.0 g/L were injected and the peak areas were used for calibration. Linear regression coefficient of the calibration curve was 0.9995.

Samples are injected once at 20 μL. Peak areas are used to calculate the amount presenting in the sample by Waters LC Millenium software.

Example 3 HPLC Detection and Quantification of Glucose, Succinate, Lactate, Formate, Acetate and Ethanol HPLC method used
Column: Aminex HPX-87H column (Bio-Rad), 300×7.8 mm, i.d. particle size 9 μm
Mobile phase: H2SO4 4 mM
Flow rate: 0.4 mL/min
Column temperature: 45° C.
Detection: Refractive index detector The amount of the analytes was determined by external standard calibration method. Standard samples containing glucose from 0.1 to 38.0 g/L, succinate, lactate, formate, acetate and ethanol from 0.05 to 10.0 g/L were injected and the peak areas were used for calibration. Linear regression coefficients for all six calibration curves were better than 0.999.

Samples are injected once at 20 μL. Peak areas are used to calculate the amount presenting in the sample by Waters LC Millenium software.

Example 4 Metabolic Evolution of the *E. coli* W Stem Derived from Example 1 for Improved Alanine Yield The *E. coli* stem comprising all mutations as described in Example 1, named *E. coli* Ex1 or QZ16, was used for a metabolic evolution procedure in order to improve the alanine yield of the *E. coli* Ex1 stem.

The metabolic evolution was performed as follows: In a first and second evolution round continuous evolution was performed for 500 hours and 750 hours respectively in NBS medium 5% glucose.
NBS medium:
3.5 g KH2PO4
5.0 g K2HPO4
3.5 g (NH4)2HPO4
0.25 g MgSO4-7H2O
15 mg CaCL2-2H2O
0.5 mg Thiamine
1 ml trace metal stock
The trace metal stock was prepared in 0.1 M HCL, 1.6 g FeCL$_3$-6H$_2$O; 0.2 g CoCl$_2$-6H$_2$O; 0.1 g CuCl$_2$-2H$_2$O; 0.2 g ZnCl$_2$; 0.2 g NaMoO4-2H$_2$O; 0.05 g H$_3$BO$_3$.

Cells were streaked on LB plates and tested for alanine yield. The best *E. coli* stem (*E. coli* Ev1 or QZ17) resulted in fermentation with NBS medium comprising 5% glucose for 24 and 48 h at 37° C. in alanine yield between 84%-86% compared to the alanine yield of the starting stem *E. coli* Ex1 resulting in 80%-83%.

*E. coli* Ev1 was used for further evolution steps which were performed as batch evolution for 20 days. 5% of the cells were reinoculated in fresh medium every 24 h, 48 h, 72 h and so forth in AM1 medium comprising 14% glucose at 37° C.
AM1 medium:
19.92 mm (NH4)2HPO4=2.6 g/L MW: 132.07
7.56 mm NH4H2PO4=0.87 g/L MW: 115
2.0 mm KCl=0.15 g/L MW: 74.55
1.5 mm MgSO4-7H2O=0.37 g/L MW: 246.5
15 g/L Ammonium sulfate was added in the last step
1 mm betain
1 ml Trace metal stock"
To make 1 L trace metal stock:
The trace metal stock was prepared in 0.12 M HCL, 2.4 g FeCL$_3$-6H$_2$O; 0.3 g CoCl$_2$-6H$_2$O; 0.21 g CuCl$_2$-2H$_2$O; 0.3 g ZnCl$_2$; 0.27 g NaMoO4-2H$_2$O; 0.068 g H$_3$BO$_3$; 0.5 g MnCl2-4H$_2$O From this evolution the stem *E. coli* Ev2, also named QZ18 was isolated. This stem was tested in fermentation which was performed in a fermenter with AM1 medium 14% glucose. The stem *E. coli* Ev2 had an alanine yield between 92%-94% compared to an alanine yield of *E. coli* Ev1 of 91%-92% under same conditions.

After further batch evolution steps for 300 h in AM1 medium comprising 12% glucose and subsequent 10 batch evolution steps in the AM1 comprising 12% glucose, the stem *E. coli* Ev3, also named QZ20 was isolated.

Testing for alanine yield revealed that the stem *E. coli* Ev3 had an alanine yield between 94%-96% in AM1 medium comprising 12% glucose compared to an alanine yield of *E. coli* Ev2 of 92%-93% under same conditions.

Further sequential batch evolution as described before for a period of 1000 h in AM1 medium with 14% glucose was performed with *E. coli* Ev3 and stem *E. coli* Ev4, also named QZ23, was isolated. *E. coli* Ev4 was tested in comparison with *E. coli* Ev3 in AM1 medium with 14% glucose. The stem *E. coli* Ev4 showed an increased alanine productivity (spacetime-yield), defined as the amount of product generated divided by reactor volume and by time, of 2.0-2.4 g/(Lh) compared to 1.0-1.3 g(/Lh) of stem *E. coli* Ev3 after 46 h of fermentation.

Example 5 Determination of Mutations in the Stem *E. coli* Ev4 Compared to *E. coli* Ev3

The genome of the *E. coli* stems *E. coli* Ev4 and *E. coli* Ev3 were sequenced and the results compared in order to determine the mutations that lead to the increased alanine productivity of stem *E. coli* Ev4.

A mutation in the brnQ gene was identified which changed the sequence of the brnQ gene from SEQ ID NO: 1, encoding the protein having SEQ ID NO: 2 in stem *E. coli* Ev3 to SEQ ID NO: 3, encoding the protein having SEQ ID NO: 4 in stem *E. coli* Ev4.

Further, a mutation in the argP gene was identified which changed the sequence of the argP gene from SEQ ID NO: 45, encoding the protein having SEQ ID NO: 46 in stem *E. coli* Ev3 to SEQ ID NO: 47, encoding the protein having SEQ ID NO: 48 in stem *E. coli* Ev4.

Further, a mutation in the promoter of the gcvA gene was identified which changed the sequence of the promoter of the gcvA gene from SEQ ID NO: 55 in stem *E. coli* Ev3 to SEQ ID NO: 56 in stem *E. coli* Ev4. In an independent strain also exhibiting enhanced alanine yield, another mutation was identified changing the sequence of the promoter of the gcvA gene from SEQ ID NO: 55 to SEQ ID NO: 57.

Further, a mutation in the promoter of the gcvB gene was identified which changed the sequence of the promoter of the gcvB gene from SEQ ID NO: 59 in stem *E. coli* Ex1 to SEQ ID NO: 60 in stem *E. coli* Ev1. In another independent strain exhibiting increased alanine yield another mutation in the promoter of the gcvB gene was identified changing the promoter sequence from SEQ ID NO: 59 to SEQ ID NO: 61.

Further, a mutation in the lpxD gene was identified which changed the sequence of the lpxD gene from SEQ ID NO: 49, encoding the protein having SEQ ID NO: 50 in stem *E. coli* Ev3 to SEQ ID NO: 51, encoding the protein having SEQ ID NO: 52 in stem *E. coli* Ev4.

In order to determine the importance of the identified mutations for alanine yield and productivity, mutations were sequentially introduced into an *E. coli* strain comprising the mutations as described in Example 1 and the mutations as described in PCT/IB2014/064426 comprising mutations in the ygaW gene, the zipA gene, the lpd gene and a mutation in the promoter controlling expression of the alaD gene as also described above. These mutations were evaluated for their effect on alanine productivity. Expression levels of mutated genes or genes under the control of mutated promoter regions were monitored by qPCR.

Example 6 Confirming the Effect of a SNP in the argP (iciA) Gene

ArgP (or iciA) is a transcriptional regulator. It controls genes involved in the arginine transport system and genes involved in DNA replication. A SNP leading to a A96E mutation in the ArgP protein was identified in *E. coli* QZ23 and was evaluated for its effect on alanine productivity.

Strain Construction of *E. coli* QZ48

An argP-cat-sacB cassette with selectable chloramphenicol resistance marker and counter-selectable sacB marker (confers sucrose sensitivity) was amplified from template vector pQZ11 (Genescript) with primers PargP_1_F and PargP_1_R (see Table 1) with Phusion Hot Start High-Fidelity DNA Polymerase (Thermo). The PCR product was DpnI (NEB) digested at 37 C for 1 h to reduce plasmid template background and gel extracted from a 1% agarose gel with the QIAquick Gel Extraction Kit (Qiagen). The argP SNP cassette (543 bp) was amplified from QZ23 genomic DNA with primers PargP_2_F and PargP_2_R (see Table 1) with Phusion Hot Start High-Fidelity DNA Polymerase (Thermo) and purified with the QIAquick PCR Purification Kit (Qiagen).

For Red/ET recombination the Genebridges Red/ET Recombination Kit was used according to manufacturer's protocol. Approximately 200 ng of the argP-cat-sacB cassette were electroporated into Red/ET-proficient *E. coli* QZ20 cells. Cultures were plated on LB agar plates with 10 ug/mL chloramphenicol for selection of positive transformants after electroporation. Several colonies were screened for integration of the marker cassette by PCR with the genome-specific primers PargP_seq_F and PargP_seq_R (see Table 1). A PCR confirmed clone was used for a second Red/ET recombination with the argP SNP cassette to replace the cat-sacB marker cassette. Cultures were plated on LB agar plates with 6% sucrose without NaCl for selection of positive transformants after electroporation. Several clones were tested with the genome-specific primers PargP_seq_F and PargP_seq_R (see Table 1) for loss of the cat-sacB marker cassette. At least one clone that yielded a PCR product of the correct size was also confirmed by sequencing (Genewiz). The heat-sensitive recombineering plasmid pRedET (amp) was cured from strains at 42 C overnight on LB plates before strains were tested in the bioreactor. The SNP leading to the ArgP A96E mutation was introduced into strain *E. coli* QZ20. The resulting strain was designated as QZ48.

Fermentation Trial of *E. coli* QZ20 in Comparison to *E. coli* QZ48

*E. coli* strain QZ48 was tested for its performance during fermentation in a lab-scale bioreactor. Cell growth and alanine formation were monitored in comparison to *E. coli* strain QZ20.

Precultures were grown in shake flasks with LB medium, 20% filling volume at 37 C and 200 rpm overnight. The fermentation was performed in the DASGIP 1.5 L parallel bioreactor system (Eppendorf) in 500 mL AM 1 medium (2.6 g/L (NH4)2HPO4, 0.87 g/L NH4H2PO4, 0.15 g/L Kill, 0.37 g/L MgSO4.7H2O, 15 g/L (NH4)2SO4, 1 mM betaine, 1 ml/L trace metal stock solution). The trace metal stock comprised 1.6 g/L FeCL3.6H2O; 0.2 g/L CoCl2.6H2O; 0.1 g/L CuCl2.2H2O; 0.2 g/L ZnCl2; 0.2 g/L NaMoO4.2H2O; 0.05 g/L H3BO3, 0.1 M HCL. 140 g/L Glucose were used as the carbon source in the fermentation medium. *E. coli* cells equivalent to an OD600•mL of 7 were harvested via centrifugation and resuspended in 5 mL AM 1 medium. # OD600•mL=(OD600 of undiluted culture)×(culture volume in mL). The 5 mL resuspended cells were used to inoculate the 500 mL fermentation medium in the 1.5 L DASGIP bioreactor. Each strain was run in duplicates at 37 C and 400 rpm stirrer speed. 5N NH$_4$OH was used to control the pH to 6.8 and provide the culture with ammonium as an alanine precursor throughout the fermentation. No air was sparged during the fermentation and the vessel was not pressurized so that after the initial consumption of dissolved oxygen in the medium by the cells the fermentation was run under microaerobic conditions. Samples were taken throughout the fermentation and analyzed by HPLC for alanine and glucose concentrations.

Figure 7:
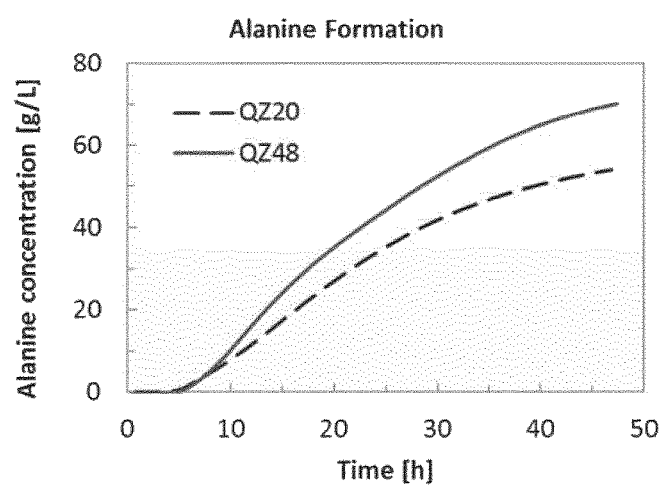

The ArgP A96E mutation in QZ48 had a strong influence on alanine formation (FIG. 7).

Figure 8:
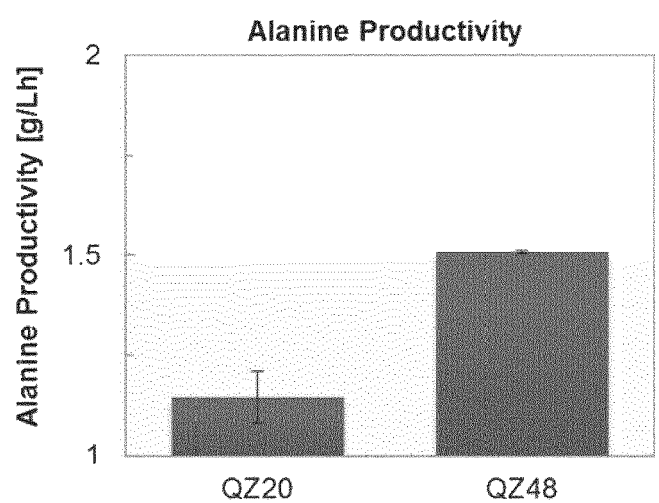

The volumetric alanine productivity (space-time-yield), defined as the amount of product generated divided by reactor volume and by time, of QZ20 after 46 h was 1.15±0.06 g/(Lh). *E. coli* QZ48 showed an increased volumetric alanine productivity of 1.51±0.01 g/(Lh) after 46 h (FIG. 8).

Construction of pACYC184-argP Plasmid

To test the influence of argP overexpression, plasmid pACYC184-argP (p15 ori, CmR, ~15 copies per cell) was constructed via commercial InFusion cloning technology (Clontech, Mountain View, Calif., USA). First the vector pACYC184 (Table 1) was obtained via NEB (Ipswich, Mass., USA) and linearized with HindIII and SalI restriction endonucleases, also from NEB. This digest removed most of the tetracycline-resistance gene. Separately, the argP ORF was PCR amplified from wild-type *E. coli* W DNA with Phusion polymerase (Thermo Scientific, Waltham, Mass.) with the primers PargP-pACYC_F and PargP-pACYC_R (Table 1). The primers contained additional 15 bp overhangs homologous to the linearized vector ends to facilitate seamless cloning. The InFusion reaction was then performed as according to the manufacturer's protocol with both purified linearized vector backbone and argP insert. The resulting InFusion products were then used to transform QZ20 via electroporation and selection on LB chloramphenicol plates.

Positive clones were PCR identified, confirmed by DNA sequencing, and used in the fermentations for the overexpression studies.

Fermentation Comparison Between QZ20/pACYC184 and QZ20/pACYC184-argP

Figure 9:
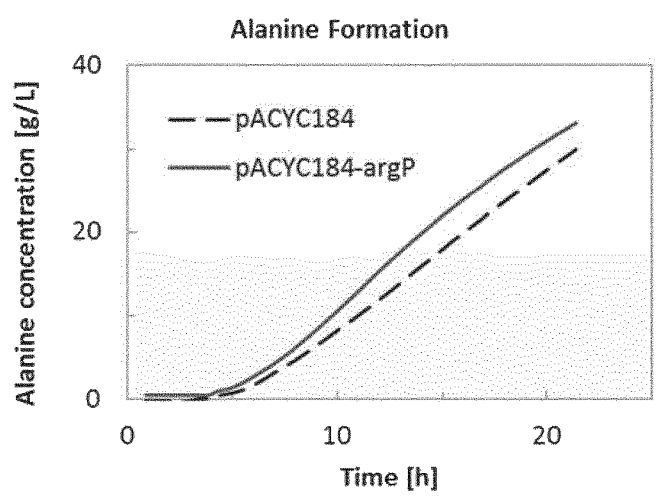
Figure 10:
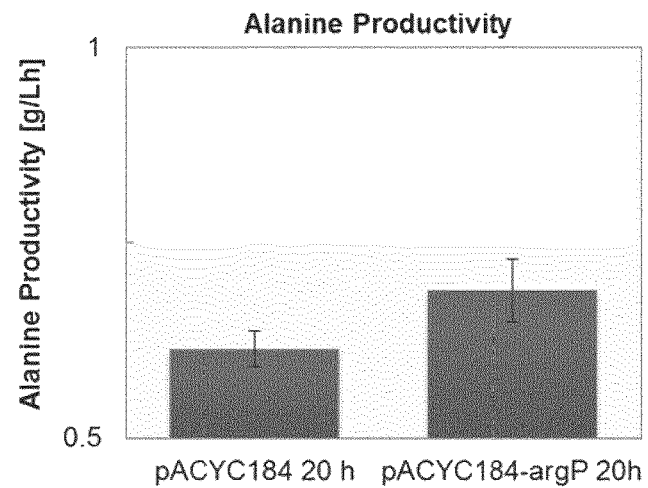

Precultures were grown in shake flasks with LB medium, 20% filling volume at 37 C and 200 rpm overnight. The fermentation was performed in the DASGIP 1.5 L parallel bioreactor system with 14% glucose in AM 1 medium. All fermentation conditions were as described before.

argP overexpression led to an accelerated alanine formation rate and higher alanine titer after 20 h of fermentation (FIG. 9). The volumetric alanine productivity (space-time-yield), defined as the amount of product generated divided by reactor volume and by time, of QZ20/pACYC-argP after 20 h was 0.69±0.04 g/(Lh) compared to 0.61±0.02 g/(Lh) of the strain with the pACYC184 plasmid control (FIG. 10).

Example 7 Confirmation of the Effect of a SNP in the gcvA/gcvB Promoter Region

Strain Construction of QZ58 and QZ66 The gcvA-cat-sacB cassette was amplified from vector pQZ11 (Genescript) with primers PgcvA_1_F/R (Table 1). The gcvA/B SNP cassette (320 bp) was amplified from the genomic DNA of strain QZ23 with primers PgcvA_2_F/R (Table 1). Red/ET recombineering was conducted as described previously. Clones were tested by colony PCR with PgcvA_seq_F/R sequencing primers. The SNP in the gcvA/B promoter region was introduced into $E.$ $coli$ QZ20 and the resulting strain designated as QZ58. The SNP was also introduced into QZ48 (argP SNP) and the resulting strain designated as QZ66.

Fermentation Trial of QZ58 and QZ66

Figure 11:
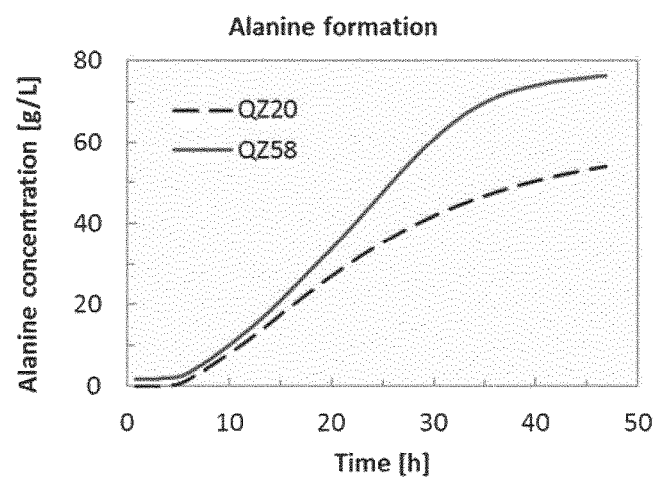
Figure 12:
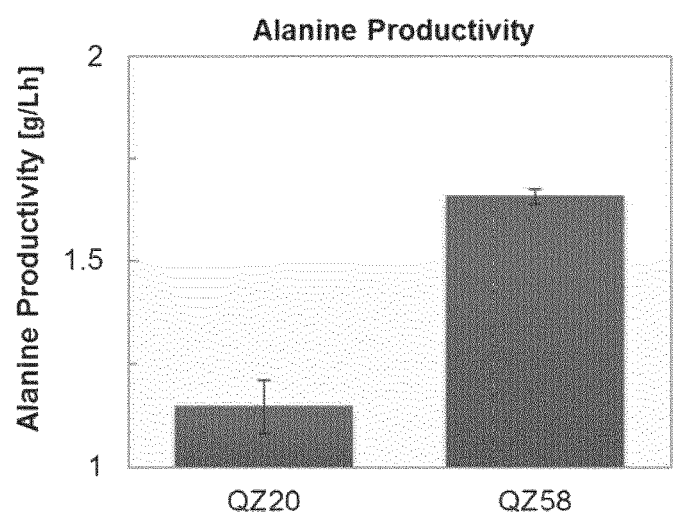
Figure 13:
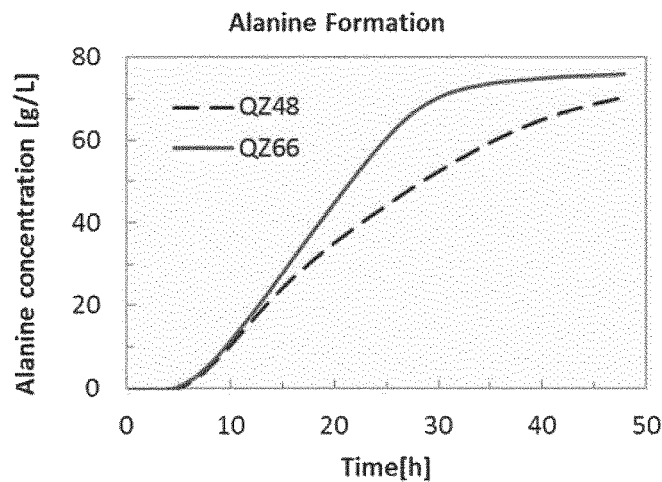
Figure 14:
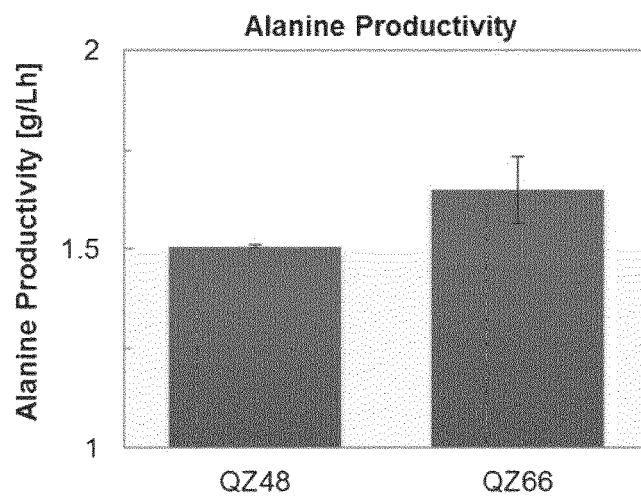

Strain QZ58 (gcvA/B promoter SNP) was tested for its performance during fermentation as described before. Alanine formation was monitored in comparison to strain QZ20. The gcvA/B promoter SNP had a significant influence on alanine formation resulting in a higher alanine formation rate and an alanine titer of ca 76 g/L alanine compared to ca 54 g/L produced by QZ20 after 46 h (FIG. 11). The volumetric alanine productivity of QZ58 was 1.66±0.02 g/(Lh) compared to 1.15±0.06 g/(Lh) in QZ20 after 46 h (FIG. 12). The gcvA/B promoter SNP was also added on top of the argP SNP in QZ48 and the resulting strain QZ66 was tested during alanine fermentation in comparison to QZ48. The additional gcvA/B promoter mutation on top of the argP mutation in QZ66 led to an faster alanine formation rate compared to QZ48 and a higher alanine yield after 46 h of ca 76 g/L compared to ca 70 g/L in QZ48 (FIG. 13). The volumetric alanine productivity of QZ66 was 1.65±0.08 g/(Lh) compared to 1.51±0.01 g/(Lh) of QZ48 after 46 h (FIG. 14).

RT-qPCR Analysis of gcvA and gcvB Transcription Levels

Transcription levels of gcvA and gcvB were determined via quantitative reverse transcription PCR (RT-qPCR). The iTaq Universal One-Step Kit from Biorad was used for SYBR Green-based one-step reverse transcription (RT)-qPCR reactions. From a parallel batch-fermentation of $E.$ $coli$ QZ20 and $E.$ $coli$ QZ23 that was conducted as described previously, culture samples were taken at 8 h, 11 h and 28 h. Samples were immediately treated with RNAprotect Bacteria Reagent (Qiagen) to stabilize the RNA. RNA was extracted from the samples with the AurumTotal RNA Mini Kit (Biorad) according to the manufacturer's manual. The isolated RNA was further treated with the DNA-free DNA Removal Kit (lifetechnologies) to remove contaminating genomic DNA and reduce background during qPCR. The RNA was quantified spectrophotometrically at $\lambda=260$ nm.

A 7-step 10-fold dilution series of 100 ng $E.$ $coli$ QZ20 RNA was tested with the RT-qPCR primers (Table 1) PgcvA_RT_F/R for the gcvA gene, PgcvB_RT_F/R for the gcvB regulatory RNA and rrsA_RT_F and PrrsA_RT_R, specific for the ribosomal 16 S RNA coding PrrsA gene, which served as a reference gene during qPCR trials. The suitable linear dynamic range of RNA dilutions that led to signal amplification efficiencies 90%<E<110% and a linear regression factor $R2>0.985$ were determined for each RT-qPCR primer set. rrsA was tested for its suitability as an internal reference gene for normalization and found to be expressed stable among all the tested samples (data not shown). RT-qPCR reactions were carried out with the CFX96 Touch Real-Time PCR Detection System (Biorad) according to the manufacturer's protocol. Relative quantification of gene expression was calculated with $E.$ $coli$ QZ20 8 h RNA as the internal calibrator according to the ΔΔCt method (Livak and Schmittgen 2001).

Figure 15:
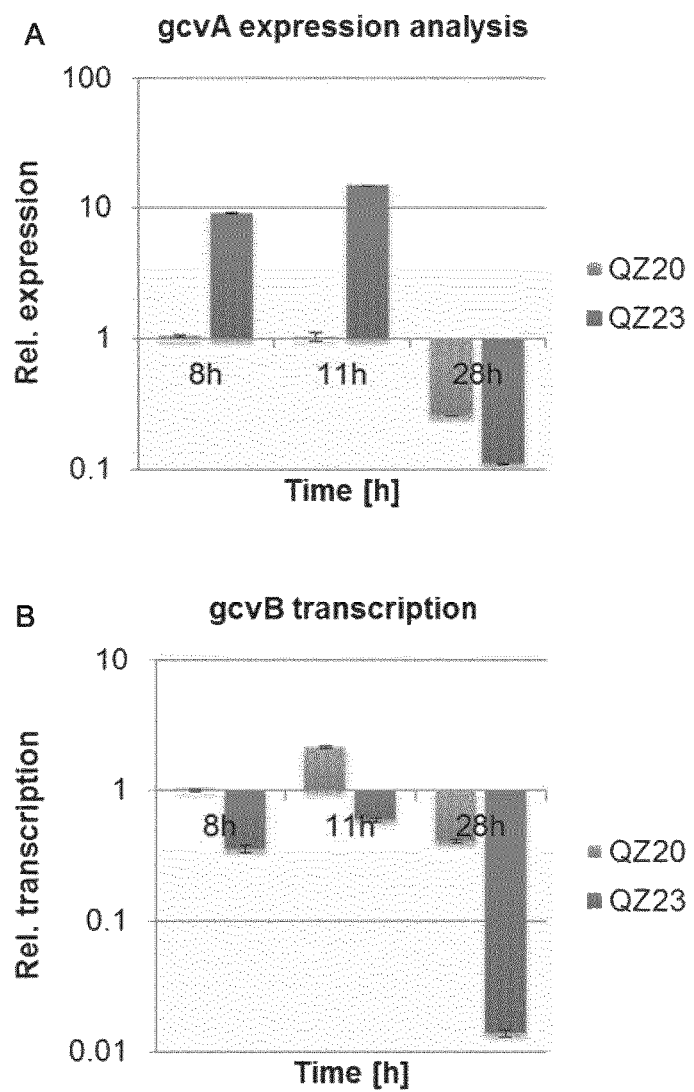

The qPCR results confirmed the overexpression of gcvA in QZ23 compared to QZ20 during exponential phase after 8 h and 11 h of fermentation. Down-regulation of gcvA was observed in 28 h samples when cell densities were declining (FIG. 15A). The gcvB regulatory protein was down-regulated in QZ23 compared to QZ20 during exponential phase after 8 h and 11 h of fermentation. An overall down-regulation of gcvB transcription was observed in 28 h samples when cell densities were declining (FIG. 15B).

Construction of pACYC184-gcvA and pACYC184-gcvB Plasmid

Since the gcvA/B promoter SNP led to overexpression of gcvA, it needed to be confirmed that it was in fact the gcvA overexpression that resulted in increased alanine productivity. Therefore plasmid pACYC184-gcvA was constructed via commercial InFusion cloning technology (Clontech, Mountain View, Calif., USA). First the vector pACYC184 (Table 1) was obtained via NEB (Ipswich, Mass., USA) and linearized with HindIII and SalI restriction endonucleases, also from NEB. This digest removed most of the tetracycline-resistance gene. Separately, the gcvA ORF was PCR amplified from wild-type $E.$ $coli$ W DNA with Phusion polymerase (Thermo Scientific, Waltham, Mass.) with the primers PgcvA-pACYC_F and PgcvA-pACYC_R (Table 1). Likewise to test the effect of gcvB overexpression, plasmid pACYC184-gcvB was constructed. The gcvB transcription unit was PCR amplified with the primers PgcvB-pACYC_F and PgcvB-pACYC_R (Table 1).

The primers contained additional 15 bp overhangs homologous to the linearized vector ends to facilitate seamless cloning. The InFusion reaction was then performed as according to the manufacturer's protocol with both purified linearized vector backbone and gcvA and gcvB insert, respectively. The resulting InFusion products were then used to transform QZ20 via electroporation and selection on LB chloramphenicol plates. Positive clones were PCR identified, confirmed by DNA sequencing, and used in the fermentations for the overexpression studies.

Fermentation Comparison Between QZ20/pACYC184, QZ20/pACYC184-gcvA and QZ20/pACYC-gcvB Precultures were grown in shake flasks with LB medium, 20% filling volume at 37 C and 200 rpm overnight. The fermentation was performed in the DASGIP 1.5 L parallel bioreactor system with 14% glucose in AM 1 medium. All fermentation conditions were as described before.

Figure 16:
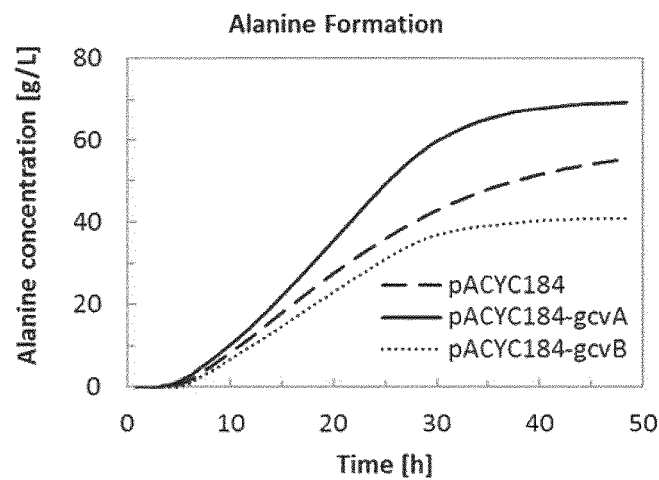
Figure 17:
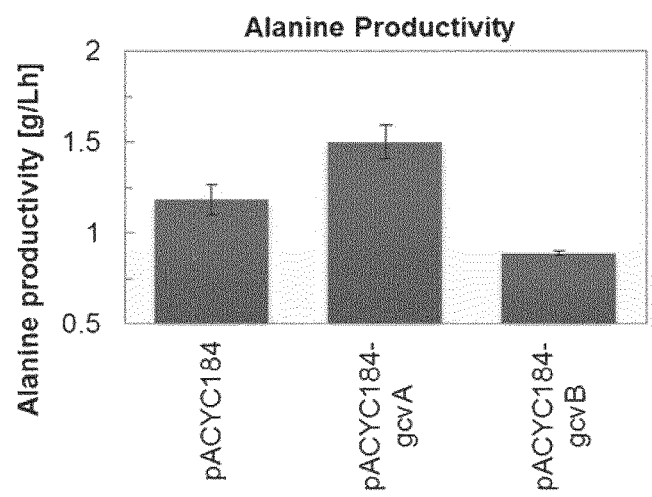

The fermentation trial confirmed that overexpression of gcvA from plasmid pACYC184-gcvA resulted in a higher alanine formation rate and titer compared to the empty plasmid control (FIG. 16). In contrast overexpression of the gcvB small regulatory RNA from plasmid pACYC184-gcvB led to a significant reduction of alanine formation rate and titer. E. coli QZ20/pACYC184-gcvA showed a volumetric alanine productivity of 1.50±0.09 g/(Lh) compared to 1.18±0.08 g/(Lh) of QZ20 with the plasmid control. E. coli QZ20/pACYC184-gcvB showed a reduced volumetric alanine productivity of 0.89±0.01 g/(Lh) compared to the plasmid control (FIG. 17).

Strain Construction of QZ20 gcvB Knock-Out QZ71

Since overexpression of the regulatory RNA gcvB from plasmid pACYC184-gcvB led to significant reduction of alanine productivity, gcvB was knocked out in QZ20 and tested for performance. The gcvB-cat-sacB cassette was amplified from vector pQZ11 (Genescript) with primers PgcvB_1_F/R (Table 1). The gcvB deletion cassette (400 bp) was ordered as dsDNA gBlock from IDT (SEQ ID NO: 98). Red/ET recombineering was conducted as described previously. Clones were tested by colony PCR with PgcvB_seq_F/R sequencing primers. The gcvB deletion was introduced into E. coli QZ20 and the resulting strain designated as QZ71.

Fermentation Trial of QZ71

Strain QZ71 (gcvB knock-out) was tested for its performance during fermentation as described before. Alanine formation was monitored in comparison to strain QZ20.

Figure 18:
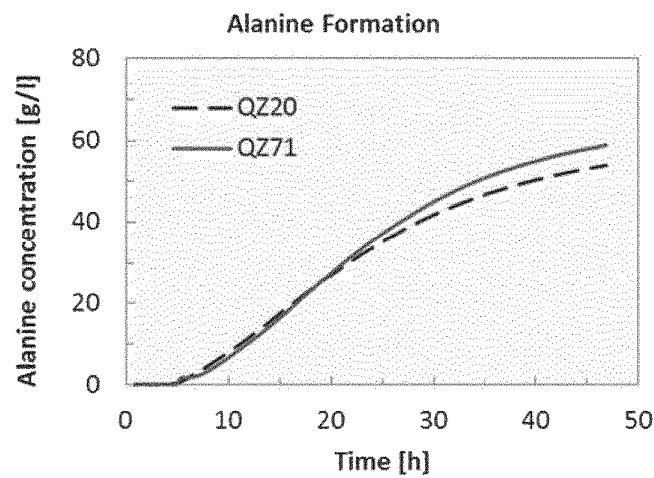
Figure 19:
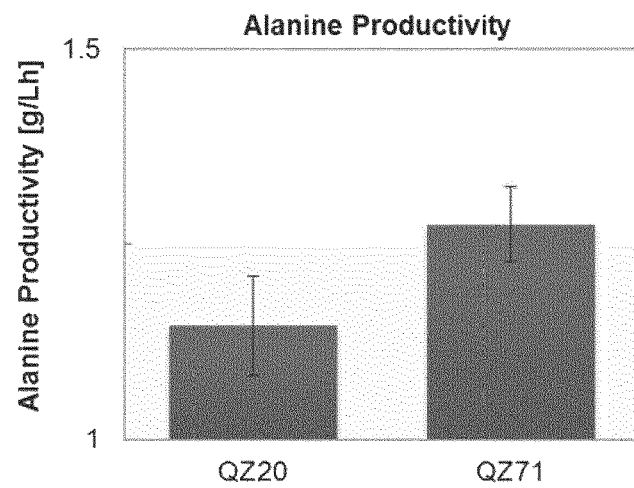

Deletion of the gcvB regulatory RNA from QZ20 resulted in an increase in alanine titer compared to QZ20 (FIG. 18). The volumetric alanine productivity of QZ71 was 1.28±0.05 g/(Lh) compared to 1.15±0.06 g/(Lh) of QZ20 after 46 h (FIG. 19).

Example 8 Confirming the Effect of a Deletion in the brnQ Gene (Δ667-764)

BrnQ is a putative 439 AA branched chain amino acid transporter that transports leucine, valine, and isoleucine into the cell as a sodium/branched chain amino acid symporter. In QZ23 a 97 bp deletion (Δ667-764) was identified that causes a reading frame shift. While the first 222 amino acids of the 439 AA protein are unaltered, 31 AAs are changed due to the frame-shift and the residual C-terminal chain is truncated due to an occurring stop codon. Since it was assumed that the 97 bp partial deletion found in the brnQ gene in QZ23 leads to an abolished BrnQ activity, a complete deletion of the brnQ gene (knock-out) was tested in addition to the partial brnQ deletion.

Strain Construction of QZ57 and QZ69

The brnQ-cat-sacB cassette was amplified from vector pQZ11 (Genescript) with primers PbrnQ_1_F/R (Table 1). The brnQ partial deletion cassette (462 bp) was amplified from the genomic DNA of strain QZ23 with primers PbrnQ_2_F/R (Table 1). The brnQ KO cassette (500 bp) was ordered as dsDNA gBlock from IDT (SEQ ID NO: 117). Red/ET recombineering was conducted as described previously. Clones were tested by colony PCR with PbrnQ_seq_F/R sequencing primers. The brnQ partial deletion was introduced into E. coli QZ20 and the resulting strain designated as QZ57. The brnQ complete deletion was introduced into E. coli QZ20 and the resulting strain designated as QZ69.

Fermentation Trial of QZ57 and QZ69

Strain QZ57 (brnQ Δ667-764) and QZ69 (brnQ KO) were tested for their performance during fermentation as described before. Alanine formation was monitored in comparison to strain QZ20.

Figure 20:
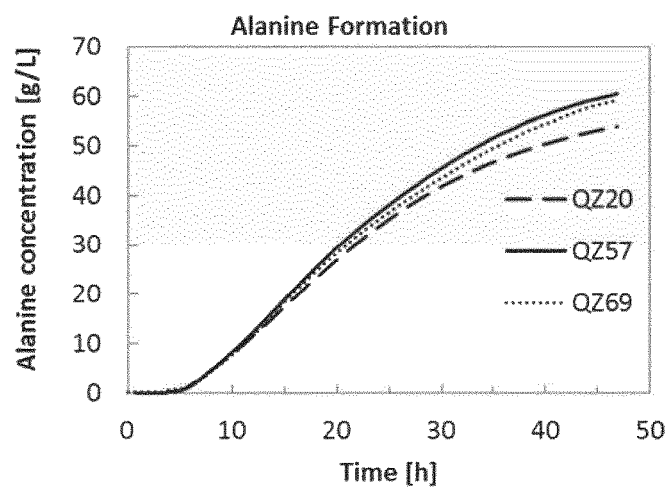
Figure 21:
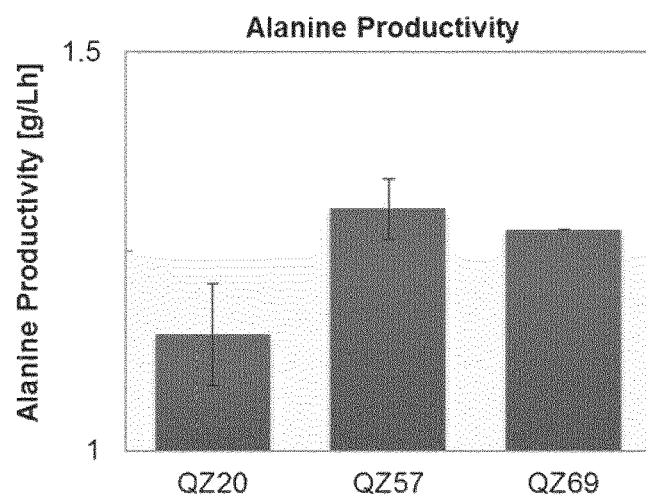

The 97 bp brnQ deletion in QZ57 and the complete brnQ knockout performed comparable. Both resulted in higher alanine formation and alanine titer than QZ20 (FIG. 20). The volumetric alanine productivity of QZ57 was 1.30±0.04 g/(Lh) and the productivity of QZ69 was 1.28 g/(Lh) compared to 1.15±0.06 g/(Lh) in QZ20 after 46 h (FIG. 21).

Example 9 Confirming the Effect of a SNP in the lpxD Gene

In QZ23 a SNP was detected in the lpxD gene leading to a A15T mutation of the encoded enzyme. UDP-3-O-(3-hydroxymyristoyl) glucosamine-N-acetyltransferase encoded by LpxD is an essential enzyme involved in the biosynthesis of lipid A. Lipid A is an integral part of the E. coli outer membrane lipopolysaccharide (LPS).

Strain Construction of QZ56 and QZ70

The lpxD-cat-sacB cassette was amplified from vector pQZ11 (Genescript) with primers PlpxD_1 C_F/R (Table 1). The lpxD SNP cassette (2588 bp) was amplified from the genomic DNA of strain QZ23 with primers lpxD_fix_F/R (Table 1). Red/ET recombineering was conducted as described previously. Clones were tested by colony PCR with PlpxD_flank_F/R sequencing primers. The lpxD SNP was introduced into E. coli QZ20 and the resulting strain designated as QZ56. The lpxD SNP was also introduced into QZ68 (argP SNP, gcvA/B promoter SNP, brnQ Δ667-764) and the resulting strain designated as QZ70.

Fermentation Trial of QZ56 and QZ70

Figure 22:
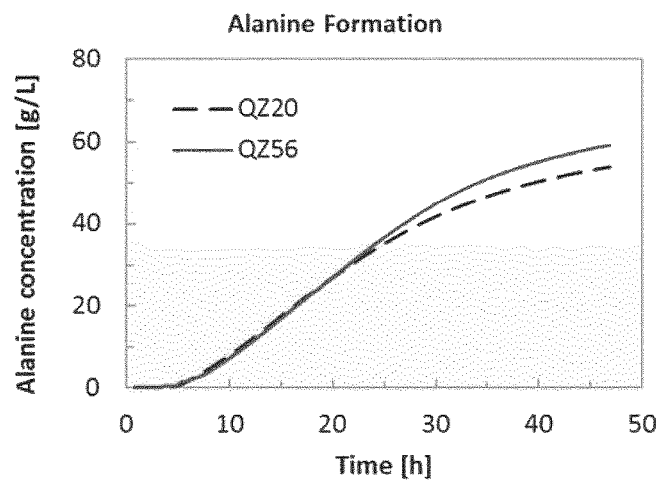
Figure 23:
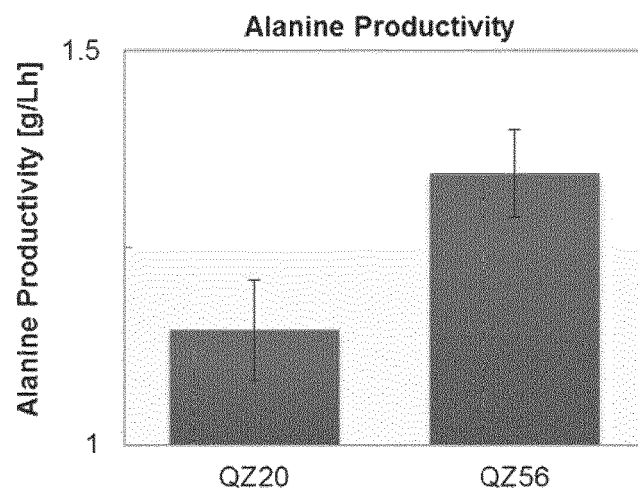

Strain QZ56 (lpxD SNP) was tested for its performance during fermentation as described before. Alanine formation was monitored in comparison to strain QZ20. The LpxD A15T mutation in QZ56 resulted in an increased alanine titer compared to QZ20 (FIG. 22). The volumetric alanine productivity of QZ56 was 1.34±0.06 g/(Lh) compared to 1.15±0.06 g/(Lh) in QZ20 after 46 h (FIG. 23).

Figure 24:
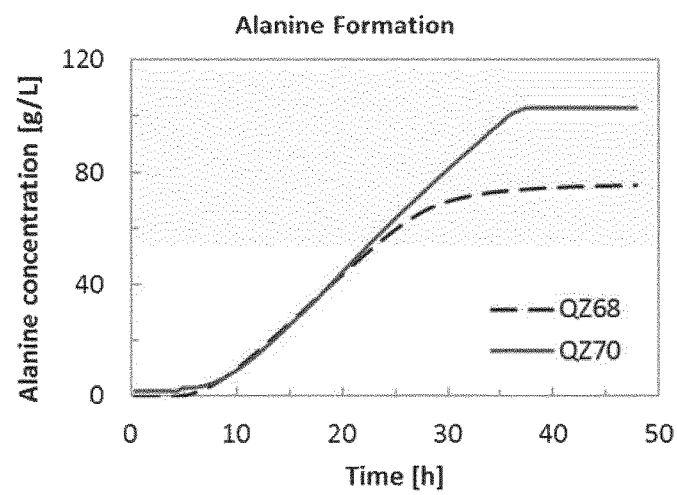
Figure 25:
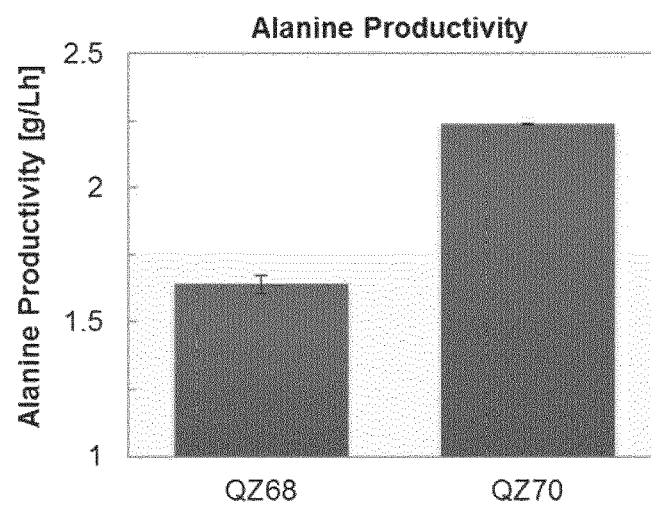

The lpxD SNP was also introduced into QZ68 (argP SNP, gcvA/B promoter SNP, brnQ Δ667-764) and the resulting strain QZ70 was tested during alanine fermentation in comparison to QZ68. The LpxD A15T mutation had a strong influence on alanine formation. The alanine formation rate between QZ68 and QZ70 was comparable, however the alanine titer of QZ68 plateaued at around 75 g/L, while alanine formation continued in QZ70 until all glucose in the medium was consumed and an alanine titer of 102 g/L was reached after ca 37 h (FIG. 24). The volumetric alanine productivity of QZ70 was 2.24±0.002 g/(Lh) compared to 1.64±0.03 g/(Lh) of QZ68 after 46 h (FIG. 25).

Example 10 Construction of an E. coli Strain with Deleted dadX Gene Leads to Higher Enantiomeric Excess of L-Alanine E. coli strain QZ30 was constructed by deleting the alanine racemase dadX gene (SEQ ID NO: 118) from the genome of E. coli strain QZ23. The dadX ORFs was inactivated by insertion of an FRT-flanked kanamycin resistance cassette, followed by removal of the antibiotic resistance cassette by FLP recombination as described before. The Genebridges Red/ET Recombination Kit was used according to manufacturer's protocol. The FRT-flanked kanamycin cassette was amplified from the pRED/ET plasmid (Gene Bridges) with primers PdadX_KO_F (SEQ ID NO: 122) and PdadX_KO_R (SEQ ID NO: 123), which each contains 50 bp homologous region to the dadX ORF for insertion of the kanamycin resistance cassette. Successful deletion of the dadX ORF was checked via PCR with the primers PdadX_seq_F (SEQ ID NO: 124) and PdadX_seq_F (SEQ ID NO: 125) and confirmed by sequencing of the genome region.

E. coli strain QZ30 with inactivated dadX gene was cultivated in comparison to E. coli strain QZ23 with intact dadX in a lab-scale bioreactor and the formed alanine was tested for chirality.

Precultures were grown in shake flasks with LB medium, 20% filling volume at 37 C and 200 rpm overnight. The fermentation was performed in the DASGIP 1.5 L parallel bioreactor system (Eppendorf) in 500 mL AM 1 medium (2.6 g/L $(NH_4)_2HPO_4$, 0.87 g/L $NH_4H_2PO_4$, 0.15 g/L Kill, 0.37 g/L $MgSO_4.7H_2O$, 15 g/L $(NH_4)_2SO_4$, 1 mM betaine, 1 ml/L trace metal stock solution). The trace metal stock comprised 1.6 g/L $FeCL_3.6H_2O$; 0.2 g/L $CoCl_2.6H_2O$; 0.1 g/L $CuCl_2.2H_2O$; 0.2 g/L $ZnCl_2$; 0.2 g/L $NaMoO_4.2H_2O$; 0.05 g/L $H_3BO_3$, 0.1 M HCL. 140 g/L Glucose were used as the carbon source in the fermentation medium. E. coli cells equivalent to an OD600•mL of 7 were harvested via centrifugation and resuspended in 5 mL AM 1 medium. # OD600•mL=(OD600 of undiluted culture)×(culture volume in mL). The 5 mL resuspended cells were used to inoculate the 500 mL fermentation medium in the 1.5 L DASGIP bioreactor. Each strain was run in duplicates at 37 C and 400 rpm stirrer speed. 5N $NH_4OH$ was used to control the pH to 6.8 and provide the culture with ammonium as an alanine precursor throughout the fermentation. No air was sparged during the fermentation and the vessel was not pressurized so that after the initial consumption of dissolved oxygen in the medium by the cells the fermentation was run under microaerobic conditions. Samples were taken throughout the fermentation and analyzed by HPLC for alanine concentration and chirality.

Figure 26:
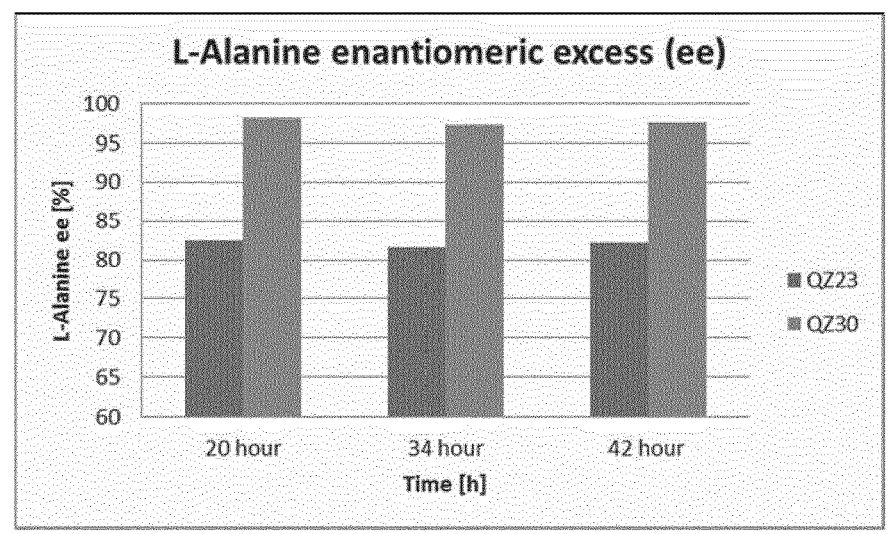

It was found that the E. coli strain QZ30 with inactivated dadX gene consistently produced alanine with a higher enantiomeric excess (ee) of L-alanine >95%, compared to E. coli QZ23 with intact dadX (FIG. 26). After 20 h of cultivation QZ30 produced L-alanine with an enantiomeric excess of 98.09% compared to 82.5% produced by QZ23. After 34 h of cultivation the ee of L-alanine produced by QZ30 was 97.27% compared to 81.65% for QZ23 and after 42 h of cultivation the ee was 97.49% L-alanine produced by QZ30 compared to 82.2% produced by QZ23.

We claim:

1. A recombinant microorganism having a higher yield and/or productivity of alanine in fermentative production compared to a respective reference microorganism, the recombinant microorganism comprising:
   (A) a reduced, repressed or deleted activity and/or expression of a dadX gene, wherein the dadX gene is selected from the group consisting of:
      (i) a nucleic acid molecule comprising SEQ ID NO: 118,
      (ii) a nucleic acid molecule having at least 80% identity to SEQ ID NO: 118,
      (iii) a nucleic acid molecule encoding the polypeptide comprising SEQ ID NO: 119, and
      (iv) a nucleic acid molecule encoding a polypeptide having at least 80% identity to SEQ ID NO: 119,
   and
   (B) at least one of:
      a) a reduced, repressed or deleted activity and/or expression of a brnQ gene or a homolog or functional variant thereof,
      b) an introduced, increased, enhanced or altered activity and/or expression of a argP gene or a homolog or functional variant thereof, wherein the argP gene or a homolog or functional variant thereof is selected from:
         (I) a nucleic acid molecule comprising SEQ ID NO: 45 or a nucleic acid molecule having at least 80% identity to SEQ ID NO: 45, wherein the codon encoding the amino acid alanine corresponding to position 286 to 288 of SEQ ID NO: 45 has been replaced by a codon encoding the amino acid glutamic acid or an amino acid related to glutamic acid, or
         (II) a nucleic acid molecule encoding the polypeptide of SEQ ID NO: 46 or a polypeptide having 80% identity to SEQ ID NO: 46, wherein the amino acid of the protein corresponding to position 96 of SEQ ID NO: 46 is not alanine,
      c) an introduced, increased, enhanced or altered activity and/or expression of a gcvA gene or a homolog or functional variant thereof, and/or
      d) an altered lpxD gene or a functional homologous gene thereof, wherein the lpxD gene or functional homologous gene thereof is selected from:
         (I) a nucleic acid molecule comprising SEQ ID NO: 49 or a nucleic acid molecule having at least 80% identity to SEQ ID NO: 49, wherein the codon corresponding to position 43 to 45 of SEQ ID NO: 49 is encoding amino acid threonine or an amino acid related to threonine, or
         (II) a nucleic acid molecule encoding the polypeptide of SEQ ID NO: 50 or a polypeptide having at least 80% identity to SEQ ID NO: 50, wherein the amino acid of the protein corresponding to position 15 of SEQ ID NO: 50 is not alanine.

2. The recombinant microorganism according to claim 1, wherein the brnQ gene is selected from the group consisting of:
   (i) a nucleic acid molecule comprising SEQ ID NO: 1,
   (ii) a nucleic acid molecule having at least 80% identity to SEQ ID NO: 1,
   (iii) a nucleic acid molecule encoding the polypeptide comprising SEQ ID NO: 2, and
   (iv) a nucleic acid molecule encoding a polypeptide having at least 80% identity to SEQ ID NO: 2.

3. The recombinant microorganism according to claim 1, wherein the gcvA gene is selected from the group consisting of:
   (i) a nucleic acid molecule comprising SEQ ID NO: 53,
   (ii) a nucleic acid molecule having at least 80% identity to SEQ ID NO: 53,
   (iii) a nucleic acid molecule encoding the polypeptide comprising SEQ ID NO: 54, and
   (iv) a nucleic acid molecule encoding a polypeptide having at least 80% identity to SEQ ID NO: 54.

4. The recombinant microorganism according to claim 1, further comprising a gcvB gene or a functional homologous gene thereof having reduced or repressed expression of said gcvB gene or functional homologous gene or wherein said gcvB gene or functional homologous gene is deleted.

5. The recombinant microorganism according to claim 4, wherein the gcvB gene is selected from the group consisting of:
   (i) a nucleic acid molecule comprising SEQ ID NO: 58, and
   (ii) a nucleic acid molecule having at least 80% identity to SEQ ID NO: 58.

6. The recombinant microorganism according to claim 1, further comprising an introduced, increased or enhanced activity and/or expression of an alaD gene, wherein the alaD gene is selected from the group consisting of:
(i) a nucleic acid molecule comprising SEQ ID NO: 15,
(ii) a nucleic acid molecule having at least 80% identity to SEQ ID NO: 15,
(iii) a nucleic acid molecule encoding the polypeptide comprising SEQ ID NO: 16, and
(iv) a nucleic acid molecule encoding a polypeptide having at least 80% identity to SEQ ID NO: 16.

7. The recombinant microorganism according to claim 1, further comprising a reduced, repressed or deleted activity and/or expression of a pflB gene, wherein the pflB gene is selected from the group consisting of:
(i) a nucleic acid molecule comprising SEQ ID NO: 5,
(ii) a nucleic acid molecule having at least 80% identity to SEQ ID NO: 5,
(iii) a nucleic acid molecule encoding the polypeptide comprising SEQ ID NO: 6, and
(iv) a nucleic acid molecule encoding a polypeptide having at least 80% identity to SEQ ID NO: 6.

8. The recombinant microorganism according to claim 1, further comprising a reduced, repressed or deleted activity and/or expression of an adhE gene, wherein the adhE gene is selected from the group consisting of:
(i) a nucleic acid molecule comprising SEQ ID NO: 7,
(ii) a nucleic acid molecule having at least 80% identity to SEQ ID NO: 7,
(iii) a nucleic acid molecule encoding the polypeptide comprising SEQ ID NO: 8, and
(iv) a nucleic acid molecule encoding a polypeptide having at least 80% identity to SEQ ID NO: 8.

9. The recombinant microorganism according to claim 1, further comprising a reduced, repressed or deleted activity and/or expression of an ldhA gene, wherein the ldhA gene is selected from the group consisting of:
(i) a nucleic acid molecule comprising SEQ ID NO: 9,
(ii) a nucleic acid molecule having at least 80% identity to SEQ ID NO: 9,
(iii) a nucleic acid molecule encoding the polypeptide comprising SEQ ID NO: 10, and
(iv) a nucleic acid molecule encoding a polypeptide having at least 80% identity to SEQ ID NO: 10.

10. The recombinant microorganism according to claim 1, further comprising a reduced, repressed or deleted activity and/or expression of a pta gene, wherein the pta gene is selected from the group consisting of:
(i) a nucleic acid molecule comprising SEQ ID NO: 11,
(ii) a nucleic acid molecule having at least 80% identity to SEQ ID NO: 11,
(iii) a nucleic acid molecule encoding the polypeptide comprising SEQ ID NO: 12, and
(iv) a nucleic acid molecule encoding a polypeptide having at least 80% identity to SEQ ID NO: 12.

11. The recombinant microorganism according to claim 1, further comprising a reduced, repressed or deleted activity and/or expression of an ackA gene, wherein the ackA gene is selected from the group consisting of:
(i) a nucleic acid molecule comprising SEQ ID NO: 120,
(ii) a nucleic acid molecule having at least 80% identity to SEQ ID NO: 120,
(iii) a nucleic acid molecule encoding the polypeptide comprising SEQ ID NO: 121, and
(iv) a nucleic acid molecule encoding a polypeptide having at least 80% identity to SEQ ID NO: 121.

12. The recombinant microorganism according to claim 1, further comprising a reduced, repressed or deleted activity and/or expression of an frdA gene, wherein the frdA gene is selected from the group consisting of:
(i) a nucleic acid molecule comprising SEQ ID NO: 13,
(ii) a nucleic acid molecule having at least 80% identity to SEQ ID NO: 13,
(iii) a nucleic acid molecule encoding the polypeptide comprising SEQ ID NO: 14, and
(iv) a nucleic acid molecule encoding a polypeptide having at least 80% identity to SEQ ID NO: 14.

13. The recombinant microorganism according to claim 1, further comprising an introduced, increased or enhanced activity and/or expression of an ygaW gene, wherein the ygaW gene is selected from the group consisting of:
(i) a nucleic acid molecule comprising SEQ ID NO: 109,
(ii) a nucleic acid molecule having at least 80% identity to SEQ ID NO: 109,
(iii) a nucleic acid molecule encoding the polypeptide comprising SEQ ID NO: 110, and
(iv) a nucleic acid molecule encoding a polypeptide having at least 80% identity to SEQ ID NO: 110.

14. The recombinant microorganism according to claim 1, further comprising an introduced, increased or enhanced activity and/or expression of a zipA gene, wherein the zipA gene is selected from the group consisting of:
(i) a nucleic acid molecule comprising SEQ ID NO: 111,
(ii) a nucleic acid molecule having at least 80% identity to SEQ ID NO: 111,
(iii) a nucleic acid molecule encoding the polypeptide comprising SEQ ID NO: 112, and
(iv) a nucleic acid molecule encoding a polypeptide having at least 80% identity to SEQ ID NO: 112.

15. The recombinant microorganism according to claim 1, further comprising an introduced, increased or enhanced activity and/or expression of an lpd gene, wherein the lpd gene is selected from the group consisting of:
(i) a nucleic acid molecule comprising SEQ ID NO: 113,
(ii) a nucleic acid molecule having at least 80% identity to SEQ ID NO: 113,
(iii) a nucleic acid molecule encoding the polypeptide comprising SEQ ID NO: 114, and
(iv) a nucleic acid molecule encoding a polypeptide having at least 80% identity to SEQ ID NO: 114.

16. The recombinant microorganism according to claim 6, wherein the alaD gene is operably linked to a promoter having a sequence selected from the group consisting of:
(i) SEQ ID NO: 115 or 116,
(ii) a nucleic acid molecule having at least 80% identity to SEQ ID NO: 115 or 116, and
(iii) a fragment comprising at least 10 consecutive nucleotides of the nucleic acid having sequence SEQ ID NO: 115.

17. The recombinant microorganism according to claim 1, wherein the microorganism is selected from a genus of the group consisting of: *Corynebacterium, Bacillus, Erwinia, Escherichia, Pantoea, Streptomyces, Zymomonas, Rhodococcus* and *Saccharomyces*.

18. A method of producing pyruvate, succinate, aspartate, malate, lactate, valine, leucine and/or alanine comprising culturing one or more recombinant microorganism according to claim 1 under conditions that allow for the production of pyruvate, succinate, aspartate, malate, lactate, valine, leucine and/or alanine.

19. The method according to claim 18, wherein the microorganism is cultured in a medium comprising between 0.5% and 30% (w/v) of a sugar.

20. The method according to claim 18, wherein the yield of pyruvate, succinate, aspartate, malate, lactate, valine, leucine and/or alanine is at least 80% yield.

21. The method according to claim 18, wherein the chiral purity of L-alanine is at least 95%.

22. A method of culturing or growing a genetically modified microorganism comprising:
   I) inoculating a culture medium with one or more genetically modified microorganism according to claim 1, and
   II) culturing or growing said genetically modified microorganism in said culture medium.

23. A process for fermentative production of pyruvate, succinate, aspartate, malate, lactate, valine, leucine and/or alanine comprising:
   I) growing the microorganism according to claim 1 in broth in a fermenter to obtain fermentation broth, and
   II) recovering pyruvate, succinate, aspartate, malate, lactate, valine, leucine and/or alanine from the fermentation broth.

* * * * *

SEQUENCE LISTING

```
<160> NUMBER OF SEQ ID NOS: 135

<210> SEQ ID NO 1
<211> LENGTH: 1320
<212> TYPE: DNA
<213> ORGANISM: Escherichia coli
<220> FEATURE:
<221> NAME/KEY: misc_feature
<222> LOCATION: (1)..(1320)
<223> OTHER INFORMATION: brnQ

<400> SEQUENCE: 1
atgacccatc aattaagatc gcgcgatatc atcgctctgg gctttatgac atttgcgttg      60
ttcgtcggcg caggtaacat tattttccct ccaatggtcg gcttgcaggc aggcgaacac     120
gtctggactg cggcattcgg cttcctcatt actgccgttg gcctgccggt attaacggta     180
gtggcgctgg caaaagttgg cggcggtgtt gacagcctca gcacgccaat cggtaaagtc     240
gctggcgtgc tgctggcaac ggtttgttac ctggcggtgg ggccgctttt cgctacgccg     300
cgtacagcta ccgtttcctt tgaagtgggg attgcgccgc tgacgggtga ttccgcgctg     360
ccgctgttta tctacagcct ggtctatttc gctatcgtta ttctggtttc gctctatccg     420
ggcaagctgc tggataccgt gggcaacttc cttgcgccgc tgaaaattat cgcgctggtc     480
atcctgtctg ttgccgcgat tgtctggccg gcgggttcta tcagcacggc gactgaggct     540
tatcaaaacg ctgcgttttc taacggcttc gttaacggct atctgaccat ggatacgctg     600
ggcgcaatgg tgtttggtat cgttattgtt aacgcggcgc gttctcgtgg cgttaccgaa     660
gcgcgtctgc tgacccgtta taccgtctgg gctggcctga tggcgggtgt tggtctgact     720
ctgctgtacc tggcgctgtt ccgtctgggt tcagacagcg cgtcgctggt cgatcagtct     780
gcaaacggcg ctgctattct gcatgcttac gttcagcaca cctttggcgg cggcgtagc     840 ttcctgctgg cggcgttaat cttcatcgcc tgcctggtaa cggcagttgg cctgacctgt     900
gcttgtgcag aattctttgc ccagtacgta ccgctctctt atcgtacgct ggtgtttatc     960
ctcggcggct tctcgatggt ggtttctaac ctcggcttaa gccagctgat ccagatctcc    1020
```

```
gtaccggtgc tgaccgctat ttatccgccg tgtatcgcac tggttgtatt aagtttttaca    1080 cgctcatggt ggcataattc gtcccgcgtg attgctccgc cgatgtttat cagcctgctt    1140
tttggtattc tcgacgggat caaagcatct gcattcagcg atatcttacc gtcctgggcg    1200
cagcgtttac cgctggccga acaaggtctg gcgtggttaa tgccaacagt ggtgatggtg    1260
gttctggcca ttatctggga tcgcgcggca ggtcgtcagg tgacctccag cgctcactaa    1320
```

```
<210> SEQ ID NO 2
<211> LENGTH: 439
<212> TYPE: PRT
<213> ORGANISM: Escherichia coli
<220> FEATURE:
<221> NAME/KEY: MISC_FEATURE
<222> LOCATION: (1)..(439)
<223> OTHER INFORMATION: brnQ

<400> SEQUENCE: 2
```

```
Met Thr His Gln Leu Arg Ser Arg Asp Ile Ile Ala Leu Gly Phe Met
1               5                   10                  15

Thr Phe Ala Leu Phe Val Gly Ala Gly Asn Ile Ile Phe Pro Pro Met
            20                  25                  30

Val Gly Leu Gln Ala Gly Glu His Val Trp Thr Ala Ala Phe Gly Phe
        35                  40                  45

Leu Ile Thr Ala Val Gly Leu Pro Val Leu Thr Val Val Ala Leu Ala
    50                  55                  60

Lys Val Gly Gly Gly Val Asp Ser Leu Ser Thr Pro Ile Gly Lys Val
65                  70                  75                  80

Ala Gly Val Leu Leu Ala Thr Val Cys Tyr Leu Ala Val Gly Pro Leu
                85                  90                  95

Phe Ala Thr Pro Arg Thr Ala Thr Val Ser Phe Glu Val Gly Ile Ala
            100                 105                 110

Pro Leu Thr Gly Asp Ser Ala Leu Pro Leu Phe Ile Tyr Ser Leu Val
        115                 120                 125

Tyr Phe Ala Ile Val Ile Leu Val Ser Leu Tyr Pro Gly Lys Leu Leu
    130                 135                 140

Asp Thr Val Gly Asn Phe Leu Ala Pro Leu Lys Ile Ile Ala Leu Val
145                 150                 155                 160

Ile Leu Ser Val Ala Ala Ile Val Trp Pro Ala Gly Ser Ile Ser Thr
                165                 170                 175

Ala Thr Glu Ala Tyr Gln Asn Ala Ala Phe Ser Asn Gly Phe Val Asn
            180                 185                 190

Gly Tyr Leu Thr Met Asp Thr Leu Gly Ala Met Val Phe Gly Ile Val
        195                 200                 205

Ile Val Asn Ala Ala Arg Ser Arg Gly Val Thr Glu Ala Arg Leu Leu
    210                 215                 220

Thr Arg Tyr Thr Val Trp Ala Gly Leu Met Ala Gly Val Gly Leu Thr
225                 230                 235                 240

Leu Leu Tyr Leu Ala Leu Phe Arg Leu Gly Ser Asp Ser Ala Ser Leu
                245                 250                 255

Val Asp Gln Ser Ala Asn Gly Ala Ala Ile Leu His Ala Tyr Val Gln
            260                 265                 270

His Thr Phe Gly Gly Gly Ser Phe Leu Leu Ala Ala Leu Ile Phe
        275                 280                 285

Ile Ala Cys Leu Val Thr Ala Val Gly Leu Thr Cys Ala Cys Ala Glu
    290                 295                 300
```

```
Phe Phe Ala Gln Tyr Val Pro Leu Ser Tyr Arg Thr Leu Val Phe Ile
305                 310                 315                 320

Leu Gly Gly Phe Ser Met Val Val Ser Asn Leu Gly Leu Ser Gln Leu
            325                 330                 335

Ile Gln Ile Ser Val Pro Val Leu Thr Ala Ile Tyr Pro Pro Cys Ile
        340                 345                 350

Ala Leu Val Val Leu Ser Phe Thr Arg Ser Trp Trp His Asn Ser Ser
        355                 360                 365

Arg Val Ile Ala Pro Pro Met Phe Ile Ser Leu Leu Phe Gly Ile Leu
    370                 375                 380

Asp Gly Ile Lys Ala Ser Ala Phe Ser Asp Ile Leu Pro Ser Trp Ala
385                 390                 395                 400

Gln Arg Leu Pro Leu Ala Glu Gln Gly Leu Ala Trp Leu Met Pro Thr
            405                 410                 415

Val Val Met Val Val Leu Ala Ile Ile Trp Asp Arg Ala Ala Gly Arg
            420                 425                 430

Gln Val Thr Ser Ser Ala His
            435
```

```
<210> SEQ ID NO 3
<211> LENGTH: 1223
<212> TYPE: DNA
<213> ORGANISM: Escherichia coli
<220> FEATURE:
<221> NAME/KEY: misc_feature
<222> LOCATION: (1)..(1223)
<223> OTHER INFORMATION: brnQ Mut

<400> SEQUENCE: 3
```

```
atgacccatc aattaagatc gcgcgatatc atcgctctgg gctttatgac atttgcgttg      60
ttcgtcggcg caggtaacat tatttttccct ccaatggtcg gcttgcaggc aggcgaacac   120
gtctggactg cggcattcgg cttcctcatt actgccgttg gcctgccggt attaacggta   180
gtggcgctgg caaaagttgg cggcggtgtt gacagcctca gcacgccaat cggtaaagtc   240
gctggcgtgc tgctggcaac ggtttgttac ctggcggtgg ggccgctttt cgctacgccg   300
cgtacagcta ccgtttcctt tgaagtgggg attgcgccgc tgacgggtga ttccgcgctg   360
ccgctgttta tctacagcct ggtctatttc gctatcgtta ttctggtttc gctctatccg   420
ggcaagctgc tggataccgt gggcaacttc cttgcgccgc tgaaaattat cgcgctggtc   480
atcctgtctg ttgccgcgat tgtctggccg gcgggttcta tcagcacggc gactgaggct   540
tatcaaaacg ctgcgttttc taacggcttc gttaacggct atctgaccat ggatacgctg   600
ggcgcaatgg tgtttggtat cgttattgtt aacgcggcgc gttctcgtgg cgttaccgaa   660
gcgcgtcgct ggtcgatcag tctgcaaacg cgctgctat tctgcatgct tacgttcagc   720
acacctttgg cggcggcggt agcttcctgc tggcggcgtt aatcttcatc gcctgcctgg   780
taacggcagt tggcctgacc tgtgcttgtg cagaattctt tgcccagtac gtaccgctct   840
cttatcgtac gctggtgttt atcctcggcg gcttctcgat ggtggtttct aacctcggct   900
taagccagct gatccagatc tccgtaccgg tgctgaccgc tatttatccg ccgtgtatcg   960
cactggttgt attaagtttt acacgctcat ggtggcataa ttcgtcccgc gtgattgctc  1020
cgccgatgtt tatcagcctg ctttttggta ttctcgacgg gatcaaagca tctgcattca  1080
gcgatatctt accgtcctgg gcgcagcgtt taccgctggc cgaacaaggt ctggcgtggt  1140
taatgccaac agtggtgatg gtggttctgg ccattatctg ggatcgcgcg gcaggtcgtc  1200
```
aggtgacctc cagcgctcac taa                                              1223

<210> SEQ ID NO 4
<211> LENGTH: 253
<212> TYPE: PRT
<213> ORGANISM: Escherichia coli
<220> FEATURE:
<221> NAME/KEY: MISC_FEATURE
<222> LOCATION: (1)..(439)
<223> OTHER INFORMATION: brnQ_1 Mut1

<400> SEQUENCE: 4

Met Thr His Gln Leu Arg Ser Arg Asp Ile Ile Ala Leu Gly Phe Met
1               5                   10                  15

Thr Phe Ala Leu Phe Val Gly Ala Gly Asn Ile Ile Phe Pro Pro Met
            20                  25                  30

Val Gly Leu Gln Ala Gly Glu His Val Trp Thr Ala Ala Phe Gly Phe
        35                  40                  45

Leu Ile Thr Ala Val Gly Leu Pro Val Leu Thr Val Val Ala Leu Ala
    50                  55                  60

Lys Val Gly Gly Gly Val Asp Ser Leu Ser Thr Pro Ile Gly Lys Val
65                  70                  75                  80

Ala Gly Val Leu Leu Ala Thr Val Cys Tyr Leu Ala Val Gly Pro Leu
                85                  90                  95

Phe Ala Thr Pro Arg Thr Ala Thr Val Ser Phe Glu Val Gly Ile Ala
            100                 105                 110

Pro Leu Thr Gly Asp Ser Ala Leu Pro Leu Phe Ile Tyr Ser Leu Val
        115                 120                 125

Tyr Phe Ala Ile Val Ile Leu Val Ser Leu Tyr Pro Gly Lys Leu Leu
    130                 135                 140

Asp Thr Val Gly Asn Phe Leu Ala Pro Leu Lys Ile Ile Ala Leu Val
145                 150                 155                 160

Ile Leu Ser Val Ala Ala Ile Val Trp Pro Ala Gly Ser Ile Ser Thr
                165                 170                 175

Ala Thr Glu Ala Tyr Gln Asn Ala Ala Phe Ser Asn Gly Phe Val Asn
            180                 185                 190

Gly Tyr Leu Thr Met Asp Thr Leu Gly Ala Met Val Phe Gly Ile Val
        195                 200                 205

Ile Val Asn Ala Ala Arg Ser Arg Gly Val Thr Glu Ala Arg Arg Trp
    210                 215                 220

Ser Ile Ser Leu Gln Thr Ala Leu Leu Phe Cys Met Leu Thr Phe Ser
225                 230                 235                 240

Thr Pro Leu Ala Ala Ala Val Ala Ser Cys Trp Arg Arg
                245                 250

<210> SEQ ID NO 5
<211> LENGTH: 2283
<212> TYPE: DNA
<213> ORGANISM: Escherichia coli
<220> FEATURE:
<221> NAME/KEY: misc_feature
<222> LOCATION: (1)..(2283)
<223> OTHER INFORMATION: pflB

<400> SEQUENCE: 5
atgtccgagc ttaatgaaaa gttagccaca gcctgggaag gttttaccaa aggtgactgg      60
cagaatgaag taaacgtccg tgacttcatt cagaaaaact acactccgta cgagggtgac     120
gagtccttcc tggctggcgc tactgaagcg accaccaccc tgtgggacaa agtaatggaa     180

```
ggcgttaaac tggaaaaccg cactcacgcg ccagttgact ttgacaccgc tgttgcttcc    240
accatcacct ctcacgacgc tggctacatc aacaaagcgt tggaaaaagt tgttggtcta    300
cagactgaag ctccgctgaa acgtgctctt atcccgttcg gtggtatcaa aatgatcgag    360
ggttcctgca aagcgtacaa ccgcgaactg gacccgatga tcaaaaaaat cttcactgaa    420
taccgtaaaa ctcacaacca gggcgtgttc gacgtttaca ctccggacat cctgcgttgc    480
cgtaaatccg tgttctgac cggtctgcca gatgcttatg ccgtggccg tatcatcggt    540 gactaccgtc gcgttgcgct gtacggtatc gactacctga tgaaagacaa atacgctcag    600
ttcacctctc tgcaggctga tctggaaaac ggcgtaaacc tggaacagac tatccgtctg    660
cgcgaagaaa tcgctgaaca gcaccgcgct ctgggtcaga tgaaagaaat ggctgcgaaa    720
tacggctacg acatctctgg tccggctacc aacgctcagg aagctatcca gtggacttac    780
ttcggctacc tggctgctgt taagtctcag aacggtgctg caatgtcctt cggtcgtacc    840 tccacctcc tggatgtgta catcgaacgt gacctgaaag ctggcaagat caccgaacaa    900
gaagcgcagg aaatggttga ccacctggtc atgaaactgc gtatggttcg cttcctgcgt    960
actccggaat acgatgaact gttctctggc gacccgatct gggcaaccga atctatcggt   1020
ggtatgggcc tcgacggtcg taccctggtt accaaaaaca gcttccgttt cctgaacacc   1080
ctgtacacca tgggtccgtc tccggaaccg aacatgacca ttctgtggtc tgaaaaactg   1140
ccgctgaact tcaagaaatt cgccgctaaa gtgtccatcg acacctcttc tctgcaatat   1200
gagaacgatg acctgatgcg tccggacttc aacaacgatg actacgctat tgcttgctgc   1260
gtaagcccga tgatcgttgg taaacaaatg cagttcttcg gtgcgcgtgc aaacctggcg   1320
aaaaccatgc tgtacgcaat caacggcggc gttgacgaaa aactgaaaat gcaggttggt   1380
ccgaagtctg aaccgatcaa aggcgatgtc ctgaactatg atgaagtgat ggagcgcatg   1440
gatcacttca tggactggct ggctaaacag tacatcactg cactgaacat catccactac   1500
atgcacgaca agtacagcta cgaagcctct ctgatggcgc tgcacgaccg tgacgttatc   1560
cgcaccatgg cgtgtggtat cgctggtctg tccgttgctg ctgactccct gtctgcaatc   1620
aaatatgcga agtttaaacc gattcgtgac gaagacggtc tggctatcga cttcgaaatc   1680
gaaggcgaat accgcagtt tggtaacaat gatccgcgtg tagatgacct ggctgttgac   1740
ctggtagaac gtttcatgaa gaaaattcag aaactgcaca cctaccgtga cgctatcccg   1800
actcagtctg ttctgaccat cacttctaac gttgtgtatg gtaagaaaac tggtaacacc   1860
ccagacggtc gtcgtgctgg cgcgccgttc ggaccgggtg ctaacccgat gcacggtcgt   1920
gaccagaaag gtgctgtagc gtctctgact ccgttgcta aactaccgtt tgcttacgct   1980
aaagatggta tctcctacac cttctctatc gttccgaacg cactgggtaa agacgacgaa   2040
gttcgtaaga ccaacctggc tggtctgatg gatggttact tccaccacga agcatccatc   2100
gaaggtggtc agcacctgaa cgttaacgtg atgaaccgtg aaatgctgct cgacgcgatg   2160
gaaaacccgg aaaaatatcc gcagctgacc atccgtgtat ctggctacgc agtacgtttc   2220
aactcgctga ctaaagaaca gcagcaggac gttattactc gtaccttcac tcaatctatg   2280
taa                                                                 2283

<210> SEQ ID NO 6
<211> LENGTH: 760
<212> TYPE: PRT
<213> ORGANISM: Escherichia coli
<220> FEATURE:
```

-continued

<221> NAME/KEY: MISC_FEATURE
<222> LOCATION: (1)..(760)
<223> OTHER INFORMATION: pflB

<400> SEQUENCE: 6

Met Ser Glu Leu Asn Glu Lys Leu Ala Thr Ala Trp Glu Gly Phe Thr
1               5                   10                  15

Lys Gly Asp Trp Gln Asn Glu Val Asn Val Arg Asp Phe Ile Gln Lys
            20                  25                  30

Asn Tyr Thr Pro Tyr Glu Gly Asp Glu Ser Phe Leu Ala Gly Ala Thr
        35                  40                  45

Glu Ala Thr Thr Thr Leu Trp Asp Lys Val Met Glu Gly Val Lys Leu
    50                  55                  60

Glu Asn Arg Thr His Ala Pro Val Asp Phe Asp Thr Ala Val Ala Ser
65                  70                  75                  80

Thr Ile Thr Ser His Asp Ala Gly Tyr Ile Asn Lys Ala Leu Glu Lys
                85                  90                  95

Val Val Gly Leu Gln Thr Glu Ala Pro Leu Lys Arg Ala Leu Ile Pro
            100                 105                 110

Phe Gly Gly Ile Lys Met Ile Glu Gly Ser Cys Lys Ala Tyr Asn Arg
        115                 120                 125

Glu Leu Asp Pro Met Ile Lys Lys Ile Phe Thr Glu Tyr Arg Lys Thr
130                 135                 140

His Asn Gln Gly Val Phe Asp Val Tyr Thr Pro Asp Ile Leu Arg Cys
145                 150                 155                 160

Arg Lys Ser Gly Val Leu Thr Gly Leu Pro Asp Ala Tyr Gly Arg Gly
                165                 170                 175

Arg Ile Ile Gly Asp Tyr Arg Arg Val Ala Leu Tyr Gly Ile Asp Tyr
            180                 185                 190

Leu Met Lys Asp Lys Tyr Ala Gln Phe Thr Ser Leu Gln Ala Asp Leu
        195                 200                 205

Glu Asn Gly Val Asn Leu Glu Gln Thr Ile Arg Leu Arg Glu Glu Ile
    210                 215                 220

Ala Glu Gln His Arg Ala Leu Gly Gln Met Lys Glu Met Ala Ala Lys
225                 230                 235                 240

Tyr Gly Tyr Asp Ile Ser Gly Pro Ala Thr Asn Ala Gln Glu Ala Ile
                245                 250                 255

Gln Trp Thr Tyr Phe Gly Tyr Leu Ala Ala Val Lys Ser Gln Asn Gly
            260                 265                 270

Ala Ala Met Ser Phe Gly Arg Thr Ser Thr Phe Leu Asp Val Tyr Ile
        275                 280                 285

Glu Arg Asp Leu Lys Ala Gly Lys Ile Thr Glu Gln Glu Ala Gln Glu
    290                 295                 300

Met Val Asp His Leu Val Met Lys Leu Arg Met Val Arg Phe Leu Arg
305                 310                 315                 320

Thr Pro Glu Tyr Asp Glu Leu Phe Ser Gly Asp Pro Ile Trp Ala Thr
                325                 330                 335

Glu Ser Ile Gly Gly Met Gly Leu Asp Gly Arg Thr Leu Val Thr Lys
            340                 345                 350

Asn Ser Phe Arg Phe Leu Asn Thr Leu Tyr Thr Met Gly Pro Ser Pro
        355                 360                 365

Glu Pro Asn Met Thr Ile Leu Trp Ser Glu Lys Leu Pro Leu Asn Phe
    370                 375                 380

Lys Lys Phe Ala Ala Lys Val Ser Ile Asp Thr Ser Ser Leu Gln Tyr

```
            385                 390                 395                 400
        Glu Asn Asp Asp Leu Met Arg Pro Asp Phe Asn Asn Asp Asp Tyr Ala
                            405                 410                 415

Ile Ala Cys Cys Val Ser Pro Met Ile Val Gly Lys Gln Met Gln Phe
                        420                 425                 430

Phe Gly Ala Arg Ala Asn Leu Ala Lys Thr Met Leu Tyr Ala Ile Asn
                    435                 440                 445

Gly Gly Val Asp Glu Lys Leu Lys Met Gln Val Gly Pro Lys Ser Glu
                450                 455                 460

Pro Ile Lys Gly Asp Val Leu Asn Tyr Asp Glu Val Met Glu Arg Met
        465                 470                 475                 480

Asp His Phe Met Asp Trp Leu Ala Lys Gln Tyr Ile Thr Ala Leu Asn
                            485                 490                 495

Ile Ile His Tyr Met His Asp Lys Ser Tyr Glu Ala Ser Leu Met
                        500                 505                 510

Ala Leu His Asp Arg Asp Val Ile Arg Thr Met Ala Cys Gly Ile Ala
                    515                 520                 525

Gly Leu Ser Val Ala Ala Asp Ser Leu Ser Ala Ile Lys Tyr Ala Lys
                530                 535                 540

Val Lys Pro Ile Arg Asp Glu Asp Gly Leu Ala Ile Asp Phe Glu Ile
        545                 550                 555                 560

Glu Gly Glu Tyr Pro Gln Phe Gly Asn Asn Asp Pro Arg Val Asp Asp
                            565                 570                 575

Leu Ala Val Asp Leu Val Glu Arg Phe Met Lys Lys Ile Gln Lys Leu
                        580                 585                 590

His Thr Tyr Arg Asp Ala Ile Pro Thr Gln Ser Val Leu Thr Ile Thr
                    595                 600                 605

Ser Asn Val Val Tyr Gly Lys Lys Thr Gly Asn Thr Pro Asp Gly Arg
                610                 615                 620

Arg Ala Gly Ala Pro Phe Gly Pro Gly Ala Asn Pro Met His Gly Arg
        625                 630                 635                 640

Asp Gln Lys Gly Ala Val Ala Ser Leu Thr Ser Val Ala Lys Leu Pro
                            645                 650                 655

Phe Ala Tyr Ala Lys Asp Gly Ile Ser Tyr Thr Phe Ser Ile Val Pro
                        660                 665                 670

Asn Ala Leu Gly Lys Asp Asp Glu Val Arg Lys Thr Asn Leu Ala Gly
                    675                 680                 685

Leu Met Asp Gly Tyr Phe His His Glu Ala Ser Ile Glu Gly Gly Gln
                690                 695                 700

His Leu Asn Val Asn Val Met Asn Arg Glu Met Leu Leu Asp Ala Met
        705                 710                 715                 720

Glu Asn Pro Glu Lys Tyr Pro Gln Leu Thr Ile Arg Val Ser Gly Tyr
                            725                 730                 735

Ala Val Arg Phe Asn Ser Leu Thr Lys Glu Gln Gln Gln Asp Val Ile
                        740                 745                 750

Thr Arg Thr Phe Thr Gln Ser Met
                    755                 760

<210> SEQ ID NO 7
<211> LENGTH: 2676
<212> TYPE: DNA
<213> ORGANISM: Escherichia coli
<220> FEATURE:
<221> NAME/KEY: misc_feature
<222> LOCATION: (1)..(2676)
```

<223> OTHER INFORMATION: adhE

<400> SEQUENCE: 7

```
atggctgtta ctaatgtcgc tgaacttaac gcactcgtag agcgtgtaaa aaaagcccag      60
cgtgaatatg ccagtttcac tcaagagcaa gtagacaaaa tcttccgcgc cgccgctctg     120
gctgctgcag atgctcgaat cccactcgcg aaaatggccg ttgccgaatc cggcatgggt     180
atcgtcgaag ataaagtgat caaaaaccac tttgcttctg aatatatcta caacgcctat     240
aaagatgaaa aacctgtggt tgttctgtct gaagacgaca cttttggtac catcactatc     300
gctgaaccaa tcggtattat ttgcggtatc gttccgacca ctaacccgac ttcaactgct     360
atcttcaaat cgctgatcag tctgaagacc cgtaacgcca ttatcttctc cccgcacccg     420
cgtgcaaaag atgccaccaa caaagcggct gatatcgttc tgcaggctgc tatcgctgcc     480
ggtgctccga agatctgat cggctggatc gatcaacctt ctgttgaact gtctaacgca     540
ctgatgcacc acccagacat caacctgatc ctcgcgactg gtggtccggg catggttaaa     600
gccgcataca gctccggtaa accagctatc ggtgtaggcg cgggcaacac tccagttgtt     660
atcgatgaaa ctgctgatat caaacgtgca gttgcatctg tactgatgtc caaaaccttc     720
gacaacggcg taatctgtgc ttctgaacag tctgttgttg ttgttgactc tgtttatgac     780
gctgtacgtg aacgttttgc aacccacggc ggctatctgt tgcagggtaa agagctgaaa     840
gctgttcagg atgttatcct gaaaaacggt gcgctgaacg cggctatcgt tggtcagcca     900
gcctataaaa ttgctgaact ggcaggcttc tctgtaccag aaaacaccaa gattctgatc     960
ggtgaagtga ccgttgttga tgaaagcgaa ccgttcgcac atgaaaaact gtcccccgact    1020
ctggcaatgt accgcgctaa agatttcgaa gacgcggtag aaaagcaga gaaactggtt    1080
gctatgggcg gtatcggtca tacctcttgc ctgtacactg accaggataa ccaaccggct    1140
cgcgttctt acttcggtca gaaaatgaaa acggctcgta tcctgattaa cacccccagcg    1200
tctcagggtg gtatcggtga cctgtataac ttcaaactcg caccttccct gactctgggt    1260
tgtggttctt ggggtggtaa ctccatctct gaaaacgttg gtccgaaaca cctgatcaac    1320
aagaaaaccg ttgctaagcg agctgaaaac atgttgtggc acaaacttcc gaaatctatc    1380
tacttccgcc gtggctccct gccaatcgcg ctggatgaag tgattactga tggccacaaa    1440
cgtgcgctca tcgtgactga ccgcttcctg ttcaacaatg ttatgctga tcagatcact    1500
tccgtactga aagcagcagg cgttgaaact gaagtcttct tcgaagtaga agcggacccg    1560
accctgagca tcgttcgtaa aggtgcagaa ctggcaaact ccttcaaacc agacgtgatt    1620
atcgcgctgg gtggtggttc cccgatggac gccgcgaaga tcatgtgggt tatgtacgaa    1680
catccggaaa ctcacttcga agagctggcg ctgcgctta tggatatccg taacgtatc    1740
tacaagttcc cgaaaatggg cgtgaaagcg aaaatgatcg ctgtcaccac cacttctggt    1800
acaggttctg aagtcactcc gtttgcggtt gtaactgacg acgctactgg tcagaaatat    1860
ccgctggcag actatgcgct gactccggat atggcgattg tcgacgccaa cctggttatg    1920
gacatgccga gtccctgtg tgctttcggt ggtctggacg cagtaactca cgccatggaa    1980
gcttatgttt ctgtactggc atctgagttc tctgatggtc aggctctgca ggcactgaaa    2040
ctgctgaaag aatatctgcc agcgtcctac cacgaagggt ctaaaaatcc ggtagcgcgt    2100
gaacgtgttc acagtgcagc gactatcgcg ggtatcgcgt ttgcgaacgc cttcctgggt    2160
gtatgtcact caatggcgca caaactgggt tcccagttcc atattccgca cggtctggca    2220
aacgccctgc tgatttgtaa cgttattcgc tacaatgcga acgacaaccc gaccaagcag    2280
```

```
actgcattca gccagtatga ccgtccgcag gctcgccgtc gttatgctga aattgccgac    2340
cacttgggtc tgagcgcacc gggcgaccgt actgctgcta agatcgagaa actgctggca    2400
tggctggaaa cgctgaaagc tgaactgggt attccgaaat ctatccgtga agctggcgtt    2460
caggaagcag acttcctggc gaacgtggat aaactgtctg aagatgcgtt cgatgaccag    2520
tgcaccggcg ctaacccgcg ttacccgctg atctccgagc tgaaacagat cctgctggat    2580
acctactacg tcgtgatta tgtagaaggt gaaactgcag cgaaaaaaga agccgctccg    2640
gctaaagctg agaaaaaagc gaaaaaatcc gcttaa                             2676
```

<210> SEQ ID NO 8
<211> LENGTH: 891
<212> TYPE: PRT
<213> ORGANISM: Escherichia coli
<220> FEATURE:
<221> NAME/KEY: MISC_FEATURE
<222> LOCATION: (1)..(891)
<223> OTHER INFORMATION: adhE
<400> SEQUENCE: 8

```
Met Ala Val Thr Asn Val Ala Glu Leu Asn Ala Leu Val Glu Arg Val
1               5                   10                  15

Lys Lys Ala Gln Arg Glu Tyr Ala Ser Phe Thr Gln Glu Gln Val Asp
                20                  25                  30

Lys Ile Phe Arg Ala Ala Ala Leu Ala Ala Ala Asp Ala Arg Ile Pro
            35                  40                  45

Leu Ala Lys Met Ala Val Ala Glu Ser Gly Met Gly Ile Val Glu Asp
    50                  55                  60

Lys Val Ile Lys Asn His Phe Ala Ser Glu Tyr Ile Tyr Asn Ala Tyr
65                  70                  75                  80

Lys Asp Glu Lys Thr Cys Gly Val Leu Ser Glu Asp Asp Thr Phe Gly
                85                  90                  95

Thr Ile Thr Ile Ala Glu Pro Ile Gly Ile Ile Cys Gly Ile Val Pro
            100                 105                 110

Thr Thr Asn Pro Thr Ser Thr Ala Ile Phe Lys Ser Leu Ile Ser Leu
    115                 120                 125

Lys Thr Arg Asn Ala Ile Ile Phe Ser Pro His Pro Arg Ala Lys Asp
130                 135                 140

Ala Thr Asn Lys Ala Ala Asp Ile Val Leu Gln Ala Ala Ile Ala Ala
145                 150                 155                 160

Gly Ala Pro Lys Asp Leu Ile Gly Trp Ile Asp Gln Pro Ser Val Glu
                165                 170                 175

Leu Ser Asn Ala Leu Met His His Pro Asp Ile Asn Leu Ile Leu Ala
            180                 185                 190

Thr Gly Gly Pro Gly Met Val Lys Ala Ala Tyr Ser Ser Gly Lys Pro
    195                 200                 205

Ala Ile Gly Val Gly Ala Gly Asn Thr Pro Val Val Ile Asp Glu Thr
210                 215                 220

Ala Asp Ile Lys Arg Ala Val Ala Ser Val Leu Met Ser Lys Thr Phe
225                 230                 235                 240

Asp Asn Gly Val Ile Cys Ala Ser Glu Gln Ser Val Val Val Val Asp
                245                 250                 255

Ser Val Tyr Asp Ala Val Arg Glu Arg Phe Ala Thr His Gly Gly Tyr
            260                 265                 270

Leu Leu Gln Gly Lys Glu Leu Lys Ala Val Gln Asp Val Ile Leu Lys
```

```
                    275                 280                 285
Asn Gly Ala Leu Asn Ala Ala Ile Val Gly Gln Pro Ala Tyr Lys Ile
290                 295                 300
Ala Glu Leu Ala Gly Phe Ser Val Pro Glu Asn Thr Lys Ile Leu Ile
305                 310                 315                 320
Gly Glu Val Thr Val Asp Glu Ser Glu Pro Phe Ala His Glu Lys
                325                 330                 335
Leu Ser Pro Thr Leu Ala Met Tyr Arg Ala Lys Asp Phe Glu Asp Ala
                340                 345                 350
Val Glu Lys Ala Glu Lys Leu Val Ala Met Gly Gly Ile Gly His Thr
                355                 360                 365
Ser Cys Leu Tyr Thr Asp Gln Asp Asn Gln Pro Ala Arg Val Ser Tyr
370                 375                 380
Phe Gly Gln Lys Met Lys Thr Ala Arg Ile Leu Ile Asn Thr Pro Ala
385                 390                 395                 400
Ser Gln Gly Gly Ile Gly Asp Leu Tyr Asn Phe Lys Leu Ala Pro Ser
                405                 410                 415
Leu Thr Leu Gly Cys Gly Ser Trp Gly Gly Asn Ser Ile Ser Glu Asn
                420                 425                 430
Val Gly Pro Lys His Leu Ile Asn Lys Lys Thr Val Ala Lys Arg Ala
                435                 440                 445
Glu Asn Met Leu Trp His Lys Leu Pro Lys Ser Ile Tyr Phe Arg Arg
                450                 455                 460
Gly Ser Leu Pro Ile Ala Leu Asp Glu Val Ile Thr Asp Gly His Lys
465                 470                 475                 480
Arg Ala Leu Ile Val Thr Asp Arg Phe Leu Phe Asn Asn Gly Tyr Ala
                485                 490                 495
Asp Gln Ile Thr Ser Val Leu Lys Ala Ala Gly Val Glu Thr Glu Val
                500                 505                 510
Phe Phe Glu Val Glu Ala Asp Pro Thr Leu Ser Ile Val Arg Lys Gly
                515                 520                 525
Ala Glu Leu Ala Asn Ser Phe Lys Pro Asp Val Ile Ile Ala Leu Gly
                530                 535                 540
Gly Gly Ser Pro Met Asp Ala Ala Lys Ile Met Trp Val Met Tyr Glu
545                 550                 555                 560
His Pro Glu Thr His Phe Glu Glu Leu Ala Leu Arg Phe Met Asp Ile
                565                 570                 575
Arg Lys Arg Ile Tyr Lys Phe Pro Lys Met Gly Val Lys Ala Lys Met
                580                 585                 590
Ile Ala Val Thr Thr Thr Ser Gly Thr Gly Ser Glu Val Thr Pro Phe
                595                 600                 605
Ala Val Val Thr Asp Asp Ala Thr Gly Gln Lys Tyr Pro Leu Ala Asp
                610                 615                 620
Tyr Ala Leu Thr Pro Asp Met Ala Ile Val Asp Ala Asn Leu Val Met
625                 630                 635                 640
Asp Met Pro Lys Ser Leu Cys Ala Phe Gly Gly Leu Asp Ala Val Thr
                645                 650                 655
His Ala Met Glu Ala Tyr Val Ser Val Leu Ala Ser Glu Phe Ser Asp
                660                 665                 670
Gly Gln Ala Leu Gln Ala Leu Lys Leu Leu Lys Glu Tyr Leu Pro Ala
                675                 680                 685
Ser Tyr His Glu Gly Ser Lys Asn Pro Val Ala Arg Glu Arg Val His
                690                 695                 700
```

| Ser | Ala | Thr | Ile | Ala | Gly | Ile | Ala | Phe | Asn | Ala | Phe | Leu | Gly |
| 705 | | | | 710 | | | | 715 | | | | 720 | |

| Val | Cys | His | Ser | Met | Ala | His | Lys | Leu | Gly | Ser | Gln | Phe | His | Ile | Pro |
| | | | | 725 | | | | | 730 | | | | | 735 | |

His Gly Leu Ala Asn Ala Leu Leu Ile Cys Asn Val Ile Arg Tyr Asn
            740                 745                 750

Ala Asn Asp Asn Pro Thr Lys Gln Thr Ala Phe Ser Gln Tyr Asp Arg
        755                 760                 765

Pro Gln Ala Arg Arg Tyr Ala Glu Ile Ala Asp His Leu Gly Leu
    770             775                 780

Ser Ala Pro Gly Asp Arg Thr Ala Ala Lys Ile Glu Lys Leu Leu Ala
785                 790                 795                 800

Trp Leu Glu Thr Leu Lys Ala Glu Leu Gly Ile Pro Lys Ser Ile Arg
                805                 810                 815

Glu Ala Gly Val Gln Glu Ala Asp Phe Leu Ala Asn Val Asp Lys Leu
                820                 825                 830

Ser Glu Asp Ala Phe Asp Asp Gln Cys Thr Gly Ala Asn Pro Arg Tyr
            835                 840                 845

Pro Leu Ile Ser Glu Leu Lys Gln Ile Leu Leu Asp Thr Tyr Tyr Gly
    850                 855                 860

Arg Asp Tyr Val Glu Gly Glu Thr Ala Ala Lys Lys Glu Ala Ala Pro
865                 870                 875                 880

Ala Lys Ala Glu Lys Lys Ala Lys Lys Ser Ala
                885                 890

```
<210> SEQ ID NO 9
<211> LENGTH: 990
<212> TYPE: DNA
<213> ORGANISM: Escherichia coli
<220> FEATURE:
<221> NAME/KEY: misc_feature
<222> LOCATION: (1)..(990)
<223> OTHER INFORMATION: ldhA

<400> SEQUENCE: 9
atgaaactcg ccgtttatag cacaaaacag tacgacaaga gtacctgca  acaggtgaac      60 gagtcctttg gctttgagct ggaatttttt gactttctgc tgacggaaaa aaccgctaaa     120
actgccaatg gctgcgaagc ggtatgtatt ttcgtaaacg atgacggcag ccgcccggtg     180
ctggaagagc tgaaaaagca cggcgttaaa tatatcgccc tgcgctgtgc cggtttcaat     240
aacgtcgacc ttgacgcggc aaaagaactg gggctgaaag tagtccgtgt tccagcctat     300
gatccagagg ccgttgctga acacgccatc ggtatgatga tgacgctgaa ccgccgtatt     360
caccgcgcgt atcagcgtac ccgtgacgct aacttctctc tggaaggtct gaccggcttt     420
actatgtatg gcaaaacggc aggcgttatc ggtaccggta aaatcggtgt ggcgatgctg     480
cgcattctga aggttttgg tatgcgtctg ctggcgttcg atccgtatcc aagtgcagcg     540
gcgctggaac tcggtgtgga gtatgtcgat ctgccaaccc tgttctctga atcagacgtt     600
atctctctgc actgcccgct gacaccggaa aactaccatc tgttgaacga agccgccttc     660
gatcagatga aaaatggcgt gatgatcgtc aataccagtc gcggtgcatt gattgattct     720
caggcagcaa ttgaagcgct gaaaaatcag aaaattggtt cgttgggtat ggacgtgtat     780
gagaacgaac gcgatctatt ctttgaagat aaatccaacg acgtaattca ggatgacgta     840
ttccgtcgcc tgtctgcctg ccacaacgtg ctatttaccg ggcaccaggc attcctgaca     900
```

```
gcagaagctc tgaccagtat ttctcagact acgctgcaaa acttaagcaa tctggaaaaa       960
ggcgaaacct gcccgaacga actggtttaa                                        990
```

<210> SEQ ID NO 10
<211> LENGTH: 329
<212> TYPE: PRT
<213> ORGANISM: Escherichia coli
<220> FEATURE:
<221> NAME/KEY: MISC_FEATURE
<222> LOCATION: (1)..(329)
<223> OTHER INFORMATION: ldhA

<400> SEQUENCE: 10

```
Met Lys Leu Ala Val Tyr Ser Thr Lys Gln Tyr Asp Lys Lys Tyr Leu
1               5                   10                  15

Gln Gln Val Asn Glu Ser Phe Gly Phe Glu Leu Glu Phe Phe Asp Phe
            20                  25                  30

Leu Leu Thr Glu Lys Thr Ala Lys Thr Ala Asn Gly Cys Glu Ala Val
        35                  40                  45

Cys Ile Phe Val Asn Asp Asp Gly Ser Arg Pro Val Leu Glu Glu Leu
    50                  55                  60

Lys Lys His Gly Val Lys Tyr Ile Ala Leu Arg Cys Ala Gly Phe Asn
65                  70                  75                  80

Asn Val Asp Leu Asp Ala Ala Lys Glu Leu Gly Leu Lys Val Val Arg
                85                  90                  95

Val Pro Ala Tyr Asp Pro Glu Ala Val Ala Glu His Ala Ile Gly Met
            100                 105                 110

Met Met Thr Leu Asn Arg Arg Ile His Arg Ala Tyr Gln Arg Thr Arg
        115                 120                 125

Asp Ala Asn Phe Ser Leu Glu Gly Leu Thr Gly Phe Thr Met Tyr Gly
    130                 135                 140

Lys Thr Ala Gly Val Ile Gly Thr Gly Lys Ile Gly Val Ala Met Leu
145                 150                 155                 160

Arg Ile Leu Lys Gly Phe Gly Met Arg Leu Leu Ala Phe Asp Pro Tyr
                165                 170                 175

Pro Ser Ala Ala Ala Leu Glu Leu Gly Val Glu Tyr Val Asp Leu Pro
            180                 185                 190

Thr Leu Phe Ser Glu Ser Asp Val Ile Ser Leu His Cys Pro Leu Thr
        195                 200                 205

Pro Glu Asn Tyr His Leu Leu Asn Glu Ala Ala Phe Asp Gln Met Lys
    210                 215                 220

Asn Gly Val Met Ile Val Asn Thr Ser Arg Gly Ala Leu Ile Asp Ser
225                 230                 235                 240

Gln Ala Ala Ile Glu Ala Leu Lys Asn Gln Lys Ile Gly Ser Leu Gly
                245                 250                 255

Met Asp Val Tyr Glu Asn Glu Arg Asp Leu Phe Phe Glu Asp Lys Ser
            260                 265                 270

Asn Asp Val Ile Gln Asp Asp Val Phe Arg Arg Leu Ser Ala Cys His
    275                 280                 285

Asn Val Leu Phe Thr Gly His Gln Ala Phe Leu Thr Ala Glu Ala Leu
    290                 295                 300

Thr Ser Ile Ser Gln Thr Thr Leu Gln Asn Leu Ser Asn Leu Glu Lys
305                 310                 315                 320

Gly Glu Thr Cys Pro Asn Glu Leu Val
                325
```

<210> SEQ ID NO 11
<211> LENGTH: 2145
<212> TYPE: DNA
<213> ORGANISM: Escherichia coli
<220> FEATURE:
<221> NAME/KEY: misc_feature
<222> LOCATION: (1)..(2145)
<223> OTHER INFORMATION: pta

<400> SEQUENCE: 11

```
gtgtcccgta ttattatgct gatccctacc ggaaccagcg tcggtctgac cagcgtcagc      60
cttggcgtga tccgtgcaat ggaacgcaaa ggcgttcgtc tgagcgtttt caaacctatc     120
gctcagccgc gtaccggtgg cgatgcgccc gatcagacta cgactatcgt gcgtgcgaac     180
tcttccacca cgacggccgc tgaaccgctg aaaatgagct acgttgaagg tctgctttcc     240
agcaatcaga aagatgtgct gatggaagag atcgtcgcaa actaccacgc taacaccaaa     300
gacgctgaag tcgttctggt tgaaggtctg gtcccgacac gtaagcacca gtttgcccag     360
tctctgaact acgaaatcgc taaaacgctg aatgcgaaa tcgtcttcgt tatgtctcag     420
ggcactgaca ccccggaaca gctgaaagag cgtatcgaac tgacccgcaa cagcttcggc     480
ggtgccaaaa acaccaacat caccggcgtt atcgttaaca aactgaacgc accggttgat     540
gaacagggtc gtactcgccc ggatctgtcc gagattttcg acgactcttc caaagctaaa     600
gtaaacaatg ttgatccggc gaagctgcaa gaatccagcc cgctgccggt tctcggcgct     660
gtgccgtgga gctttgacct gatcgcgact cgtgcgatcg atatggctcg ccacctgaat     720
gcgaccatca tcaacgaagg cgacatcaat actcgccgcg ttaaatccgt cactttctgc     780
gcacgcagca ttccgcacat gctggagcac ttccgtgccg ttctctgct ggtgacttcc     840
gcagaccgtc ctgacgtgct ggtggccgct gcctggcag ccatgaacgg cgtagaaatc     900
ggtgccctgc tgctgactgg cggctacgaa atggacgcgc gcatttctaa actgtgcgaa     960
cgtgctttcg ctaccggcct gccggtattt atggtgaaca ccaacacctg gcagacctct    1020
ctgagcctgc agagcttcaa cctggaagtt ccggttgacg atcacgagcg tatcgagaaa    1080
gttcaggaat acgttgctaa ctacatcaac gctgactgga tcgaatctct gactgccact    1140
tctgagcgca gccgtcgtct gtctccgcct gcgttccgtt atcagctgac tgaacttgcg    1200
cgcaaagcgg gcaaacgtat cgtactgccg gaaggtgacg aaccgcgtac cgttaaagca    1260
gccgctatct gtgctgaacg tggtatcgca acttgcgtac tgctgggtaa tccggcagag    1320
atcaaccgtg ttgcagcgtc tcagggtgta gaactgggtg cagggattga atcgttgat    1380
ccagaagtgg ttcgcgaaag ctatgttggt cgtctggtcg aactgcgtaa gaacaaaggc    1440
atgaccgaaa ccgttgcccg cgaacagctg gaagacaacg tggtgctcgg tacgctgatg    1500
ctggaacagg atgaagttga tggtctggtt ccggtgctg ttcacactac cgcaaacacc    1560
atccgtccgc cgctgcagct gatcaaaact gcaccgggca gctccctggt atcttccgtg    1620
ttcttcatgc tgctgccgga acaggtttac gtttacggtg actgtgcgat caaccccggat    1680
ccgaccgctg aacagctggc agaaatcgcg attcagtccg ctgattccgc tgcggccttc    1740
ggtatcgaac cgcgcgttgc tatgctctcc tactccaccg gtacttctgg tgcaggtagc    1800
gacgtagaaa aagttcgcga agcaactcgt ctggcgcagg aaaaacgtcc tgacctgatg    1860
atcgacggtc cgctgcagta cgacgctgcg gtaatggctc acgttgcgaa atccaaagcg    1920
ccgaactctc cggttgcagg tcgcgctacc gtgttcatct cccgggatct gaacaccggt    1980
aacaccacct acaaagcggt acagcgttct gccgacctga tctccatcgg gccgatgctg    2040
```
cagggtatgc gcaagccggt taacgacctg tcccgtggcg cactggttga cgatatcgtc    2100
tacaccatcg cgctgactgc gattcagtct gcacagcagc agtaa                    2145

<210> SEQ ID NO 12
<211> LENGTH: 714
<212> TYPE: PRT
<213> ORGANISM: Escherichia coli
<220> FEATURE:
<221> NAME/KEY: MISC_FEATURE
<222> LOCATION: (1)..(714)
<223> OTHER INFORMATION: pta

<400> SEQUENCE: 12

```
Met Ser Arg Ile Ile Met Leu Ile Pro Thr Gly Thr Ser Val Gly Leu
1               5                   10                  15

Thr Ser Val Ser Leu Gly Val Ile Arg Ala Met Glu Arg Lys Gly Val
            20                  25                  30

Arg Leu Ser Val Phe Lys Pro Ile Ala Gln Pro Arg Thr Gly Gly Asp
        35                  40                  45

Ala Pro Asp Gln Thr Thr Thr Ile Val Arg Ala Asn Ser Ser Thr Thr
    50                  55                  60

Thr Ala Ala Glu Pro Leu Lys Met Ser Tyr Val Glu Gly Leu Leu Ser
65                  70                  75                  80

Ser Asn Gln Lys Asp Val Leu Met Glu Glu Ile Val Ala Asn Tyr His
                85                  90                  95

Ala Asn Thr Lys Asp Ala Glu Val Val Leu Val Glu Gly Leu Val Pro
            100                 105                 110

Thr Arg Lys His Gln Phe Ala Gln Ser Leu Asn Tyr Glu Ile Ala Lys
        115                 120                 125

Thr Leu Asn Ala Glu Ile Val Phe Val Met Ser Gln Gly Thr Asp Thr
    130                 135                 140

Pro Glu Gln Leu Lys Glu Arg Ile Glu Leu Thr Arg Asn Ser Phe Gly
145                 150                 155                 160

Gly Ala Lys Asn Thr Asn Ile Thr Gly Val Ile Val Asn Lys Leu Asn
                165                 170                 175

Ala Pro Val Asp Glu Gln Gly Arg Thr Arg Pro Asp Leu Ser Glu Ile
            180                 185                 190

Phe Asp Asp Ser Ser Lys Ala Lys Val Asn Asn Val Asp Pro Ala Lys
        195                 200                 205

Leu Gln Glu Ser Ser Pro Leu Pro Val Leu Gly Ala Val Pro Trp Ser
    210                 215                 220

Phe Asp Leu Ile Ala Thr Arg Ala Ile Asp Met Ala Arg His Leu Asn
225                 230                 235                 240

Ala Thr Ile Ile Asn Glu Gly Asp Ile Asn Thr Arg Arg Val Lys Ser
                245                 250                 255

Val Thr Phe Cys Ala Arg Ser Ile Pro His Met Leu Glu His Phe Arg
            260                 265                 270

Ala Gly Ser Leu Leu Val Thr Ser Ala Asp Arg Pro Asp Val Leu Val
        275                 280                 285

Ala Ala Cys Leu Ala Ala Met Asn Gly Val Glu Ile Gly Ala Leu Leu
    290                 295                 300

Leu Thr Gly Gly Tyr Glu Met Asp Ala Arg Ile Ser Lys Leu Cys Glu
305                 310                 315                 320

Arg Ala Phe Ala Thr Gly Leu Pro Val Phe Met Val Asn Thr Asn Thr
                325                 330                 335
```

Trp Gln Thr Ser Leu Ser Leu Gln Ser Phe Asn Leu Glu Val Pro Val
                340                 345                 350

Asp Asp His Glu Arg Ile Glu Lys Val Gln Glu Tyr Val Ala Asn Tyr
                355                 360                 365

Ile Asn Ala Asp Trp Ile Glu Ser Leu Thr Ala Thr Ser Glu Arg Ser
370                 375                 380

Arg Arg Leu Ser Pro Pro Ala Phe Arg Tyr Gln Leu Thr Glu Leu Ala
385                 390                 395                 400

Arg Lys Ala Gly Lys Arg Ile Val Leu Pro Glu Gly Asp Glu Pro Arg
                405                 410                 415

Thr Val Lys Ala Ala Ile Cys Ala Glu Arg Gly Ile Ala Thr Cys
                420                 425                 430

Val Leu Leu Gly Asn Pro Ala Glu Ile Asn Arg Val Ala Ala Ser Gln
                435                 440                 445

Gly Val Glu Leu Gly Ala Gly Ile Glu Ile Val Asp Pro Glu Val Val
                450                 455                 460

Arg Glu Ser Tyr Val Gly Arg Leu Val Glu Leu Arg Lys Asn Lys Gly
465                 470                 475                 480

Met Thr Glu Thr Val Ala Arg Glu Gln Leu Glu Asp Asn Val Val Leu
                485                 490                 495

Gly Thr Leu Met Leu Glu Gln Asp Glu Val Asp Gly Leu Val Ser Gly
                500                 505                 510

Ala Val His Thr Thr Ala Asn Thr Ile Arg Pro Pro Leu Gln Leu Ile
                515                 520                 525

Lys Thr Ala Pro Gly Ser Ser Leu Val Ser Ser Val Phe Phe Met Leu
                530                 535                 540

Leu Pro Glu Gln Val Tyr Val Tyr Gly Asp Cys Ala Ile Asn Pro Asp
545                 550                 555                 560

Pro Thr Ala Glu Gln Leu Ala Glu Ile Ala Ile Gln Ser Ala Asp Ser
                565                 570                 575

Ala Ala Ala Phe Gly Ile Glu Pro Arg Val Ala Met Leu Ser Tyr Ser
                580                 585                 590

Thr Gly Thr Ser Gly Ala Gly Ser Asp Val Glu Lys Val Arg Glu Ala
                595                 600                 605

Thr Arg Leu Ala Gln Glu Lys Arg Pro Asp Leu Met Ile Asp Gly Pro
                610                 615                 620

Leu Gln Tyr Asp Ala Ala Val Met Ala Asp Val Ala Lys Ser Lys Ala
625                 630                 635                 640

Pro Asn Ser Pro Val Ala Gly Arg Ala Thr Val Phe Ile Phe Pro Asp
                645                 650                 655

Leu Asn Thr Gly Asn Thr Thr Tyr Lys Ala Val Gln Arg Ser Ala Asp
                660                 665                 670

Leu Ile Ser Ile Gly Pro Met Leu Gln Gly Met Arg Lys Pro Val Asn
                675                 680                 685

Asp Leu Ser Arg Gly Ala Leu Val Asp Asp Ile Val Tyr Thr Ile Ala
                690                 695                 700

Leu Thr Ala Ile Gln Ser Ala Gln Gln Gln
705                 710

<210> SEQ ID NO 13
<211> LENGTH: 1809
<212> TYPE: DNA
<213> ORGANISM: Escherichia coli
<220> FEATURE:

<221> NAME/KEY: misc_feature
<222> LOCATION: (1)..(1809)
<223> OTHER INFORMATION: frdA

<400> SEQUENCE: 13

```
gtgcaaacct tcaagccga tcttgccatt gtaggcgccg gtggcgcggg attacgtgct      60
gcaattgctg ccgcgcaggc aaatccgaat gcaaaaatcg cactaatctc aaaagtatac    120
ccgatgcgta gccataccgt tgctgcagaa ggggctccg ccgctgtcgc gcaggatcat     180
gacagcttcg aatatcactt tcacgataca gtagcgggtg gcgactggtt gtgtgagcag    240
gatgtcgtgg attatttcgt ccaccactgc ccaaccgaaa tgacccaact ggaactgtgg    300
ggatgcccat ggagccgtcg cccggatggt agcgtcaacg tacgtcgctt cggcggcatg    360
aaaatcgagc gcacctggtt cgccgccgat aagaccggct tccatatgct gcacacgctg    420
ttccagacct ctctgcaatt cccgcagatc cagcgttttg acgaacattt cgtgctggat    480
attctggttg atgatggtca tgttcgcggc ctggtagcaa tgaacatgat ggaaggcacg    540
ctggtgcaga tccgtgctaa cgcggtcgtt atggctactg gcggtgcggg tcgcgtttat    600
cgttacaaca ccaacggcgg catcgttacc ggtgacggta tgggtatggc gctaagccac    660
ggcgttccgc tgcgtgacat ggaattcgtt cagtatcacc caaccggtct gccaggttcc    720
ggtatcctga tgaccgaagg ctgccgcggt gaaggcggta ttctggtcaa caaaaatggc    780
taccgttatc tgcaagatta cggcatgggc ccggaaactc cgctgggcga ccgaaaaac    840
aaatatatgg aactgggtcc acgcgacaaa gtttctcagg ccttctggca cgaatggcgt    900
aaaggcaaca ccatctccac gccgcgtggc gatgtggttt atctcgacct gcgtcacctc    960
ggcgagaaaa aactgcatga acgtctgccg ttcatctgcg aactggcgaa agcgtacgtt   1020
ggcgtcgatc cggttaaaga accgattccg gtacgtccga ccgcacacta ccatgggc    1080
ggtatcgaaa ccgatcagaa ctgtgaaacc cgcattaaag gtctgttcgc cgtgggtgaa   1140
tgttcctctg ttggtctgca cggtgcaaac cgtctgggtt ctaactccct ggcggaactg   1200
gtggtcttcg gccgtctggc cggtgaacaa gcgacagagc gtgcagcaac tgccggtaat   1260
ggcaacgaag cggcaattga agcgcaggca gctggcgttg aacaacgtct gaaagatctg   1320
gttaaccagg atggcggcga aaactgggcg aagatccgcg acgaaatggg cctggcaatg   1380
gaagaaggtt gcggtatcta ccgtacgccg gaactgatgc agaaaaccat cgacaagctg   1440
gcagagctgc aggaacgctt caagcgcgtg cgcatcaccg acacctccag cgtgttcaac   1500
accgacctgc tctacaccat tgaactgggc cacggtctga cgttgctga atgtatggcg    1560
cactccgcaa tggcacgtaa agagtcccgc ggcgcacacc agcgtctgga cgaaggttgc   1620
accgagcgtg acgacgtcaa cttcctcaaa cacacccctcg ccttccgcga tgctgatggc   1680
acgactcgcc tggagtacag cgacgtgaag attactacgc tgccgccagc taaacgcgtt   1740
tacggtggcg aagcggatgc agccgataag gcggaagcag ccaataagaa ggagaaggcg   1800
aatggctga                                                          1809
```

<210> SEQ ID NO 14
<211> LENGTH: 602
<212> TYPE: PRT
<213> ORGANISM: Escherichia coli
<220> FEATURE:
<221> NAME/KEY: MISC_FEATURE
<222> LOCATION: (1)..(602)
<223> OTHER INFORMATION: frdA

<400> SEQUENCE: 14

```
Met Gln Thr Phe Gln Ala Asp Leu Ala Ile Val Gly Ala Gly Gly Ala
1               5                   10                  15

Gly Leu Arg Ala Ala Ile Ala Ala Gln Ala Asn Pro Asn Ala Lys
            20                  25                  30

Ile Ala Leu Ile Ser Lys Val Tyr Pro Met Arg Ser His Thr Val Ala
            35                  40                  45

Ala Glu Gly Gly Ser Ala Ala Val Ala Gln Asp His Asp Ser Phe Glu
        50                  55                  60

Tyr His Phe His Asp Thr Val Ala Gly Gly Asp Trp Leu Cys Glu Gln
65                  70                  75                  80

Asp Val Val Asp Tyr Phe Val His His Cys Pro Thr Glu Met Thr Gln
                85                  90                  95

Leu Glu Leu Trp Gly Cys Pro Trp Ser Arg Arg Pro Asp Gly Ser Val
                100                 105                 110

Asn Val Arg Arg Phe Gly Gly Met Lys Ile Glu Arg Thr Trp Phe Ala
            115                 120                 125

Ala Asp Lys Thr Gly Phe His Met Leu His Thr Leu Phe Gln Thr Ser
        130                 135                 140

Leu Gln Phe Pro Gln Ile Gln Arg Phe Asp Glu His Phe Val Leu Asp
145                 150                 155                 160

Ile Leu Val Asp Asp Gly His Val Arg Gly Leu Val Ala Met Asn Met
                165                 170                 175

Met Glu Gly Thr Leu Val Gln Ile Arg Ala Asn Ala Val Val Met Ala
            180                 185                 190

Thr Gly Gly Ala Gly Arg Val Tyr Arg Tyr Asn Thr Asn Gly Gly Ile
            195                 200                 205

Val Thr Gly Asp Gly Met Gly Met Ala Leu Ser His Gly Val Pro Leu
    210                 215                 220

Arg Asp Met Glu Phe Val Gln Tyr His Pro Thr Gly Leu Pro Gly Ser
225                 230                 235                 240

Gly Ile Leu Met Thr Glu Gly Cys Arg Gly Glu Gly Gly Ile Leu Val
                245                 250                 255

Asn Lys Asn Gly Tyr Arg Tyr Leu Gln Asp Tyr Gly Met Gly Pro Glu
            260                 265                 270

Thr Pro Leu Gly Glu Pro Lys Asn Lys Tyr Met Glu Leu Gly Pro Arg
        275                 280                 285

Asp Lys Val Ser Gln Ala Phe Trp His Glu Trp Arg Lys Gly Asn Thr
    290                 295                 300

Ile Ser Thr Pro Arg Gly Asp Val Val Tyr Leu Asp Leu Arg His Leu
305                 310                 315                 320

Gly Glu Lys Lys Leu His Glu Arg Leu Pro Phe Ile Cys Glu Leu Ala
                325                 330                 335

Lys Ala Tyr Val Gly Val Asp Pro Val Lys Glu Pro Ile Pro Val Arg
            340                 345                 350

Pro Thr Ala His Tyr Thr Met Gly Gly Ile Glu Thr Asp Gln Asn Cys
        355                 360                 365

Glu Thr Arg Ile Lys Gly Leu Phe Ala Val Gly Glu Cys Ser Ser Val
    370                 375                 380

Gly Leu His Gly Ala Asn Arg Leu Gly Ser Asn Ser Leu Ala Glu Leu
385                 390                 395                 400

Val Val Phe Gly Arg Leu Ala Gly Glu Gln Ala Thr Glu Arg Ala Ala
                405                 410                 415
```

```
Thr Ala Gly Asn Gly Asn Glu Ala Ala Ile Glu Ala Gln Ala Ala Gly
                420                 425                 430

Val Glu Gln Arg Leu Lys Asp Leu Val Asn Gln Asp Gly Gly Glu Asn
            435                 440                 445

Trp Ala Lys Ile Arg Asp Glu Met Gly Leu Ala Met Glu Glu Gly Cys
        450                 455                 460

Gly Ile Tyr Arg Thr Pro Glu Leu Met Gln Lys Thr Ile Asp Lys Leu
465                 470                 475                 480

Ala Glu Leu Gln Glu Arg Phe Lys Arg Val Arg Ile Thr Asp Thr Ser
                485                 490                 495

Ser Val Phe Asn Thr Asp Leu Leu Tyr Thr Ile Glu Leu Gly His Gly
            500                 505                 510

Leu Asn Val Ala Glu Cys Met Ala His Ser Ala Met Ala Arg Lys Glu
        515                 520                 525

Ser Arg Gly Ala His Gln Arg Leu Asp Glu Gly Cys Thr Glu Arg Asp
530                 535                 540

Asp Val Asn Phe Leu Lys His Thr Leu Ala Phe Arg Asp Ala Asp Gly
545                 550                 555                 560

Thr Thr Arg Leu Glu Tyr Ser Asp Val Lys Ile Thr Thr Leu Pro Pro
                565                 570                 575

Ala Lys Arg Val Tyr Gly Gly Glu Ala Asp Ala Ala Asp Lys Ala Glu
            580                 585                 590

Ala Ala Asn Lys Lys Glu Lys Ala Asn Gly
        595                 600

<210> SEQ ID NO 15
<211> LENGTH: 1119
<212> TYPE: DNA
<213> ORGANISM: G. stearothermophilus
<220> FEATURE:
<221> NAME/KEY: misc_feature
<222> LOCATION: (1)..(1119)
<223> OTHER INFORMATION: alaD

<400> SEQUENCE: 15
atgaaaattg catccctaa agagattaag aacaatgaaa accgtgtagc aatcaccccg      60
gcaggtgtta tgactctggt taaagcgggc acgatgtgt acgtcgaaac cgaagcgggt     120
gccggcagcg gcttcagcga cagcgagtat gagaaggcgg gtgcggttat tgtgactaag    180
gcggaggacg cttgggcagc cgaaatggtt ctgaaggtga agaaccgct ggcggaggag     240 tttcgctatt ttcgtccggg tctgattttg ttcacctacc tgcacctggc tgcggccgag    300
gcgctgacca aggcactggt ggagcagaag gttgttggca tcgcgtacga aacggttcaa    360
ctggcgaatg gttccctgcc gctgctgacc cctatgtctg aagttgcggg tcgcatgagc    420
gttcaagtcg gcgctcagtt tctggagaaa ccgcacggtg gcaagggcat tttgctgggt    480
ggtgttccgg tgtccgccg tggtaaagtg acgatcattg gcgtggtac ggccggtacg     540 aacgcggcca agattgccgt aggtctgggt gcagatgtga ccattctgga catcaacgcg    600
gaacgtttgc gtgagctgga cgacctgttt ggcgaccaag tcaccaccct gatgagcaac    660
agctaccaca tcgcggagtg cgtccgtgaa agcgatttgg tcgttggtgc ggtgctgatc    720
ccgggtgcaa aagccccgaa actggtgacc gaggagatgg tccgtagcat gaccccgggt    780
tcggttctgg tcgacgtggc aattgaccag ggcggtatct tcgaaaccac cgaccgcgtc    840
acgacccatg atgacccgac ctatgtgaaa catggcgtgg ttcactatgc ggtcgcgaat    900
atgccgggtg cagtgccgcg cacgtccacg ttcgcgctga cgaacgtgac gattccatac    960
```

-continued

```
gctctgcaga tcgccaataa gggctatcgt gcggcgtgtc tggataatcc ggcattgctg      1020
aaaggcatca ataccctgga tggtcatatc gtttacgagg ctgtggctgc agcacacaac      1080
atgccgtaca ctgatgtcca tagcttgctg caaggctaa                            1119
```

<210> SEQ ID NO 16
<211> LENGTH: 372
<212> TYPE: PRT
<213> ORGANISM: G. stearothermophilus
<220> FEATURE:
<221> NAME/KEY: MISC_FEATURE
<222> LOCATION: (1)..(372)
<223> OTHER INFORMATION: alaD

<400> SEQUENCE: 16

```
Met Lys Ile Gly Ile Pro Lys Glu Ile Lys Asn Asn Glu Asn Arg Val
1               5                   10                  15

Ala Ile Thr Pro Ala Gly Val Met Thr Leu Val Lys Ala Gly His Asp
            20                  25                  30

Val Tyr Val Glu Thr Glu Ala Gly Ala Gly Ser Gly Phe Ser Asp Ser
        35                  40                  45

Glu Tyr Glu Lys Ala Gly Ala Val Ile Val Thr Lys Ala Glu Asp Ala
    50                  55                  60

Trp Ala Ala Glu Met Val Leu Lys Val Lys Glu Pro Leu Ala Glu Glu
65                  70                  75                  80

Phe Arg Tyr Phe Arg Pro Gly Leu Ile Leu Phe Thr Tyr Leu His Leu
                85                  90                  95

Ala Ala Ala Glu Ala Leu Thr Lys Leu Val Glu Gln Lys Val Val
            100                 105                 110

Gly Ile Ala Tyr Glu Thr Val Gln Leu Ala Asn Gly Ser Leu Pro Leu
        115                 120                 125

Leu Thr Pro Met Ser Glu Val Ala Gly Arg Met Ser Val Gln Val Gly
130                 135                 140

Ala Gln Phe Leu Glu Lys Pro His Gly Gly Lys Gly Ile Leu Leu Gly
145                 150                 155                 160

Gly Val Pro Gly Val Arg Arg Gly Lys Val Thr Ile Ile Gly Gly Gly
                165                 170                 175

Thr Ala Gly Thr Asn Ala Ala Lys Ile Ala Val Gly Leu Gly Ala Asp
            180                 185                 190

Val Thr Ile Leu Asp Ile Asn Ala Glu Arg Leu Arg Glu Leu Asp Asp
        195                 200                 205

Leu Phe Gly Asp Gln Val Thr Thr Leu Met Ser Asn Ser Tyr His Ile
    210                 215                 220

Ala Glu Cys Val Arg Glu Ser Asp Leu Val Val Gly Ala Val Leu Ile
225                 230                 235                 240

Pro Gly Ala Lys Ala Pro Lys Leu Val Thr Glu Glu Met Val Arg Ser
                245                 250                 255

Met Thr Pro Gly Ser Val Leu Val Asp Val Ala Ile Asp Gln Gly Gly
            260                 265                 270

Ile Phe Glu Thr Thr Asp Arg Val Thr Thr His Asp Asp Pro Thr Tyr
        275                 280                 285

Val Lys His Gly Val Val His Tyr Ala Val Ala Asn Met Pro Gly Ala
    290                 295                 300

Val Pro Arg Thr Ser Thr Phe Ala Leu Thr Asn Val Thr Ile Pro Tyr
305                 310                 315                 320
```

-continued

```
Ala Leu Gln Ile Ala Asn Lys Gly Tyr Arg Ala Ala Cys Leu Asp Asn
            325                 330                 335

Pro Ala Leu Leu Lys Gly Ile Asn Thr Leu Asp Gly His Ile Val Tyr
        340                 345                 350

Glu Ala Val Ala Ala Ala His Asn Met Pro Tyr Thr Asp Val His Ser
    355                 360                 365

Leu Leu Gln Gly
    370

<210> SEQ ID NO 17
<211> LENGTH: 20
<212> TYPE: DNA
<213> ORGANISM: Artificial sequence
<220> FEATURE:
<223> OTHER INFORMATION: Primer P395-ackA-pta-check1

<400> SEQUENCE: 17
actgcggtag ttcttcactg                                              20

<210> SEQ ID NO 18
<211> LENGTH: 21
<212> TYPE: DNA
<213> ORGANISM: Artificial sequence
<220> FEATURE:
<223> OTHER INFORMATION: Primer P395-ackA-pta-check2

<400> SEQUENCE: 18
agtacctttc tggtttagcc g                                            21

<210> SEQ ID NO 19
<211> LENGTH: 20
<212> TYPE: DNA
<213> ORGANISM: Artificial sequence
<220> FEATURE:
<223> OTHER INFORMATION: Primer P395-ackA-pta-check3

<400> SEQUENCE: 19
gatagcagaa acggaaccac                                              20

<210> SEQ ID NO 20
<211> LENGTH: 20
<212> TYPE: DNA
<213> ORGANISM: Artificial sequence
<220> FEATURE:
<223> OTHER INFORMATION: Primer P395-ackA-pta-check4

<400> SEQUENCE: 20
ggtgctgttc acactaccgc                                              20

<210> SEQ ID NO 21
<211> LENGTH: 20
<212> TYPE: DNA
<213> ORGANISM: Artificial sequence
<220> FEATURE:
<223> OTHER INFORMATION: Primer P395-ackA-pta-check5

<400> SEQUENCE: 21
tgacgagatt actgctgctg                                              20

<210> SEQ ID NO 22
<211> LENGTH: 21
<212> TYPE: DNA
<213> ORGANISM: Artificial sequence
<220> FEATURE:
<223> OTHER INFORMATION: Primer P395-ackA-pta-check6
```

```
<400> SEQUENCE: 22
atttccggtt cagatatccg c                                              21

<210> SEQ ID NO 23
<211> LENGTH: 21
<212> TYPE: DNA
<213> ORGANISM: Artificial sequence
<220> FEATURE:
<223> OTHER INFORMATION: Primer P395-adhE-check1

<400> SEQUENCE: 23
gggttgacca gcgcaaataa c                                              21

<210> SEQ ID NO 24
<211> LENGTH: 23
<212> TYPE: DNA
<213> ORGANISM: Artificial sequence
<220> FEATURE:
<223> OTHER INFORMATION: Primer P395-adhE-check2

<400> SEQUENCE: 24
cagaagtgag taatcttgct tac                                            23

<210> SEQ ID NO 25
<211> LENGTH: 23
<212> TYPE: DNA
<213> ORGANISM: Artificial sequence
<220> FEATURE:
<223> OTHER INFORMATION: Primer P395-adhE-check3

<400> SEQUENCE: 25
gatcacttta tcttcgacga tac                                            23

<210> SEQ ID NO 26
<211> LENGTH: 22
<212> TYPE: DNA
<213> ORGANISM: Artificial sequence
<220> FEATURE:
<223> OTHER INFORMATION: Primer P395-adhE-check4

<400> SEQUENCE: 26
gcgaacgtgg ataaactgtc tg                                             22

<210> SEQ ID NO 27
<211> LENGTH: 22
<212> TYPE: DNA
<213> ORGANISM: Artificial sequence
<220> FEATURE:
<223> OTHER INFORMATION: Primer P395-adhE-check5

<400> SEQUENCE: 27
gctcttaagc accgacgttg ac                                             22

<210> SEQ ID NO 28
<211> LENGTH: 22
<212> TYPE: DNA
<213> ORGANISM: Artificial sequence
<220> FEATURE:
<223> OTHER INFORMATION: Primer P395-adhE-check6

<400> SEQUENCE: 28
gtcggctcat taacggctat tc                                             22

<210> SEQ ID NO 29
```

```
<211> LENGTH: 20
<212> TYPE: DNA
<213> ORGANISM: Artificial sequence
<220> FEATURE:
<223> OTHER INFORMATION: Primer P395-frd-check1

<400> SEQUENCE: 29
gacggatctc cgccataatc                                              20

<210> SEQ ID NO 30
<211> LENGTH: 20
<212> TYPE: DNA
<213> ORGANISM: Artificial sequence
<220> FEATURE:
<223> OTHER INFORMATION: Primer P395-frd-check2

<400> SEQUENCE: 30
tcgccacccg ctactgtatc                                              20

<210> SEQ ID NO 31
<211> LENGTH: 21
<212> TYPE: DNA
<213> ORGANISM: Artificial sequence
<220> FEATURE:
<223> OTHER INFORMATION: Primer P395-frd-check3

<400> SEQUENCE: 31
caaagcgttc tgacgaaccg g                                            21

<210> SEQ ID NO 32
<211> LENGTH: 22
<212> TYPE: DNA
<213> ORGANISM: Artificial sequence
<220> FEATURE:
<223> OTHER INFORMATION: Primer P395-frd-check4

<400> SEQUENCE: 32
tgtgcgatgc acaatatcgt tg                                           22

<210> SEQ ID NO 33
<211> LENGTH: 21
<212> TYPE: DNA
<213> ORGANISM: Artificial sequence
<220> FEATURE:
<223> OTHER INFORMATION: Primer P395-pflB-check1

<400> SEQUENCE: 33
ttggttgggt tgacatactg g                                            21

<210> SEQ ID NO 34
<211> LENGTH: 21
<212> TYPE: DNA
<213> ORGANISM: Artificial sequence
<220> FEATURE:
<223> OTHER INFORMATION: Primer P395-pflB-check2

<400> SEQUENCE: 34
tgaacttcat cactgataac c                                            21

<210> SEQ ID NO 35
<211> LENGTH: 21
<212> TYPE: DNA
<213> ORGANISM: Artificial sequence
<220> FEATURE:
<223> OTHER INFORMATION: Primer P395-pflB-check3

<400> SEQUENCE: 35
```
ttcaaaggag tgaatgcgac c                                              21

<210> SEQ ID NO 36
<211> LENGTH: 22
<212> TYPE: DNA
<213> ORGANISM: Artificial sequence
<220> FEATURE:
<223> OTHER INFORMATION: Primer P395-pflB-check4

<400> SEQUENCE: 36
gtcgcggtta tgacaataca gg                                             22

<210> SEQ ID NO 37
<211> LENGTH: 22
<212> TYPE: DNA
<213> ORGANISM: Artificial sequence
<220> FEATURE:
<223> OTHER INFORMATION: Primer P395-ldhA-check1

<400> SEQUENCE: 37
taccgtgccg acgttcaata ac                                             22

<210> SEQ ID NO 38
<211> LENGTH: 21
<212> TYPE: DNA
<213> ORGANISM: Artificial sequence
<220> FEATURE:
<223> OTHER INFORMATION: Primer P395-ldhA-check2

<400> SEQUENCE: 38
catcagcagg cttagcgcaa c                                              21

<210> SEQ ID NO 39
<211> LENGTH: 20
<212> TYPE: DNA
<213> ORGANISM: Artificial sequence
<220> FEATURE:
<223> OTHER INFORMATION: Primer P395-ldhA-check3

<400> SEQUENCE: 39
acctttacgc gtaatgcgtg                                                20

<210> SEQ ID NO 40
<211> LENGTH: 21
<212> TYPE: DNA
<213> ORGANISM: Artificial sequence
<220> FEATURE:
<223> OTHER INFORMATION: Primer P395-ldhA-check4

<400> SEQUENCE: 40
accgtttacg ctttccagca c                                              21

<210> SEQ ID NO 41
<211> LENGTH: 22
<212> TYPE: DNA
<213> ORGANISM: Artificial sequence
<220> FEATURE:
<223> OTHER INFORMATION: Primer P395-csc-check1

<400> SEQUENCE: 41
cgaattatcg atctcgctca ac                                             22

<210> SEQ ID NO 42
<211> LENGTH: 23
<212> TYPE: DNA

<213> ORGANISM: Artificial sequence
<220> FEATURE:
<223> OTHER INFORMATION: Primer P395-csc-check2

<400> SEQUENCE: 42
cgtctatatt gctgaaggta cag                                          23

<210> SEQ ID NO 43
<211> LENGTH: 21
<212> TYPE: DNA
<213> ORGANISM: Artificial sequence
<220> FEATURE:
<223> OTHER INFORMATION: Primer P395-csc-check3

<400> SEQUENCE: 43
tcgaaggtcc attcacgcaa c                                            21

<210> SEQ ID NO 44
<211> LENGTH: 20
<212> TYPE: DNA
<213> ORGANISM: Artificial sequence
<220> FEATURE:
<223> OTHER INFORMATION: Primer P395-csc-check4

<400> SEQUENCE: 44
gattcccacc gcaacgttag                                              20

<210> SEQ ID NO 45
<211> LENGTH: 894
<212> TYPE: DNA
<213> ORGANISM: Escherichia coli
<220> FEATURE:
<221> NAME/KEY: misc_feature
<222> LOCATION: (1)..(894)
<223> OTHER INFORMATION: argP

<400> SEQUENCE: 45
atgaaacgcc cggactacag aacattacag gcactggatg cggtgatacg tgaacgagga    60
tttgagcgcg cggcacaaaa gctgtgcatt acacaatcag ccgtctcaca gcgcattaag   120
caactggaaa atatgttcgg gcagccgctg ttggtgcgta ccgtaccgcc gcgcccgacg   180
gaacaagggc aaaaactgct ggcactgctg cgccaggtgg agttgctgga agaagagtgg   240
ctgggcgatg aacaaaccgg ttcgactccg ctgctgcttt cactggcggt caacgccgac   300
agtctggcga cgtggttgct tcctgcactg gctcctgtgt tggctgattc gcctatccgc   360
ctcaacttgc aggtagaaga tgaaacccgc actcaggaac gtctgcgccg cggcgaagtg   420
gtcggcgcgg tgagtattca acatcaggcg ctgccgagtt gtcttgtcga taaacttggt   480
gcgctcgact atctgttcgt cagctcaaaa ccctttgccg aaaaatatttt ccctaacggc   540 gtaacgcgtt cggcattact gaaagcgcca gtggtcgcgt ttgaccatct tgacgatatg   600
caccaggcct ttttgcagca aaacttcgat ctgcctccag gcagcgtgcc ctgccatatc   660
gttaattctt cagaagcgtt cgtacaactt gctcgccagg gcaccacctg ctgtatgatc   720
ccgcacctgc aaatcgagaa agaactggcc agcggtgaac tgattgactt aacgccgggg   780
ctatttcaac gccggatgct ctactggcac cgctttgctc ctgaaagccg catgatgcgt   840
aaagtcactg atgcgttgct cgattatggt cacaaagtcc ttcgtcagga ttaa          894

<210> SEQ ID NO 46
<211> LENGTH: 297
<212> TYPE: PRT
<213> ORGANISM: Escherichia coli
<220> FEATURE:
<221> NAME/KEY: MISC_FEATURE
<222> LOCATION: (1)..(297)
<223> OTHER INFORMATION: argP

<400> SEQUENCE: 46

```
Met Lys Arg Pro Asp Tyr Arg Thr Leu Gln Ala Leu Asp Ala Val Ile
1               5                   10                  15

Arg Glu Arg Gly Phe Glu Arg Ala Ala Gln Lys Leu Cys Ile Thr Gln
            20                  25                  30

Ser Ala Val Ser Gln Arg Ile Lys Gln Leu Glu Asn Met Phe Gly Gln
        35                  40                  45

Pro Leu Leu Val Arg Thr Val Pro Pro Arg Pro Thr Glu Gln Gly Gln
    50                  55                  60

Lys Leu Leu Ala Leu Leu Arg Gln Val Glu Leu Glu Glu Glu Trp
65                  70                  75                  80

Leu Gly Asp Glu Gln Thr Gly Ser Thr Pro Leu Leu Ser Leu Ala
            85                  90                  95

Val Asn Ala Asp Ser Leu Ala Thr Trp Leu Leu Pro Ala Leu Ala Pro
            100                 105                 110

Val Leu Ala Asp Ser Pro Ile Arg Leu Asn Leu Gln Val Glu Asp Glu
        115                 120                 125

Thr Arg Thr Gln Glu Arg Leu Arg Arg Gly Glu Val Val Gly Ala Val
130                 135                 140

Ser Ile Gln His Gln Ala Leu Pro Ser Cys Leu Val Asp Lys Leu Gly
145                 150                 155                 160

Ala Leu Asp Tyr Leu Phe Val Ser Ser Lys Pro Phe Ala Glu Lys Tyr
                165                 170                 175

Phe Pro Asn Gly Val Thr Arg Ser Ala Leu Leu Lys Ala Pro Val Val
            180                 185                 190

Ala Phe Asp His Leu Asp Asp Met His Gln Ala Phe Leu Gln Asn
        195                 200                 205

Phe Asp Leu Pro Pro Gly Ser Val Pro Cys His Ile Val Asn Ser Ser
    210                 215                 220

Glu Ala Phe Val Gln Leu Ala Arg Gln Gly Thr Thr Cys Cys Met Ile
225                 230                 235                 240

Pro His Leu Gln Ile Glu Lys Glu Leu Ala Ser Gly Glu Leu Ile Asp
                245                 250                 255

Leu Thr Pro Gly Leu Phe Gln Arg Arg Met Leu Tyr Trp His Arg Phe
            260                 265                 270

Ala Pro Glu Ser Arg Met Met Arg Lys Val Thr Asp Ala Leu Leu Asp
        275                 280                 285

Tyr Gly His Lys Val Leu Arg Gln Asp
    290                 295
```

<210> SEQ ID NO 47
<211> LENGTH: 894
<212> TYPE: DNA
<213> ORGANISM: Escherichia coli
<220> FEATURE:
<221> NAME/KEY: misc_feature
<222> LOCATION: (1)..(894)
<223> OTHER INFORMATION: argP Mut

<400> SEQUENCE: 47
atgaaacgcc cggactacag aacattacag gcactggatg cggtgatacg tgaacgagga    60
tttgagcgcg cggcacaaaa gctgtgcatt acacaatcag ccgtctcaca gcgcattaag   120

```
caactggaaa atatgttcgg gcagccgctg ttggtgcgta ccgtaccgcc gcgcccgacg    180
gaacaagggc aaaaactgct ggcactgctg cgccaggtgg agttgctgga agaagagtgg    240
ctgggcgatg aacaaaccgg ttcgactccg ctgctgcttt cactggaggt caacgccgac    300
agtctggcga cgtggttgct tcctgcactg gctcctgtgt tggctgattc gcctatccgc    360
ctcaacttgc aggtagaaga tgaaacccgc actcaggaac gtctgcgccg cggcgaagtg    420
gtcggcgcgt gagtattca acatcaggcg ctgccgagtt gtcttgtcga taaacttggt    480
gcgctcgact atctgttcgt cagctcaaaa ccctttgccg aaaaatattt ccctaacggc    540
gtaacgcgtt cggcattact gaaagcgcca gtggtcgcgt ttgaccatct tgacgatatg    600
caccaggcct ttttgcagca aaacttcgat ctgcctccag gcagcgtgcc ctgccatatc    660
gttaattctt cagaagcgtt cgtacaactt gctcgccagg gcaccacctg ctgtatgatc    720 cgcacctgc aaatcgagaa agaactggcc agcggtgaac tgattgactt aacgccgggg    780
ctatttcaac gccggatgct ctactggcac cgctttgctc ctgaaagccg catgatgcgt    840
aaagtcactg atgcgttgct cgattatggt cacaaagtcc ttcgtcagga ttaa           894
```

```
<210> SEQ ID NO 48
<211> LENGTH: 297
<212> TYPE: PRT
<213> ORGANISM: Escherichia coli
<220> FEATURE:
<221> NAME/KEY: MISC_FEATURE
<222> LOCATION: (1)..(297)
<223> OTHER INFORMATION: argP Mut

<400> SEQUENCE: 48
```

```
Met Lys Arg Pro Asp Tyr Arg Thr Leu Gln Ala Leu Asp Ala Val Ile
1               5                   10                  15

Arg Glu Arg Gly Phe Glu Arg Ala Ala Gln Lys Leu Cys Ile Thr Gln
                20                  25                  30

Ser Ala Val Ser Gln Arg Ile Lys Gln Leu Glu Asn Met Phe Gly Gln
            35                  40                  45

Pro Leu Leu Val Arg Thr Val Pro Pro Arg Pro Thr Glu Gln Gly Gln
        50                  55                  60

Lys Leu Leu Ala Leu Leu Arg Gln Val Glu Leu Glu Glu Glu Trp
65                  70                  75                  80

Leu Gly Asp Glu Gln Thr Gly Ser Thr Pro Leu Leu Ser Leu Glu
                85                  90                  95

Val Asn Ala Asp Ser Leu Ala Thr Trp Leu Leu Pro Ala Leu Ala Pro
            100                 105                 110

Val Leu Ala Asp Ser Pro Ile Arg Leu Asn Leu Gln Val Glu Asp Glu
        115                 120                 125

Thr Arg Thr Gln Glu Arg Leu Arg Arg Gly Glu Val Val Gly Ala Val
    130                 135                 140

Ser Ile Gln His Gln Ala Leu Pro Ser Cys Leu Val Asp Lys Leu Gly
145                 150                 155                 160

Ala Leu Asp Tyr Leu Phe Val Ser Ser Lys Pro Phe Ala Glu Lys Tyr
                165                 170                 175

Phe Pro Asn Gly Val Thr Arg Ser Ala Leu Leu Lys Ala Pro Val Val
            180                 185                 190

Ala Phe Asp His Leu Asp Asp Met His Gln Ala Phe Leu Gln Gln Asn
        195                 200                 205

Phe Asp Leu Pro Pro Gly Ser Val Pro Cys His Ile Val Asn Ser Ser
```

Glu Ala Phe Val Gln Leu Ala Arg Gln Gly Thr Thr Cys Cys Met Ile
225                 230                 235                 240

Pro His Leu Gln Ile Glu Lys Glu Leu Ala Ser Gly Glu Leu Ile Asp
            245                 250                 255

Leu Thr Pro Gly Leu Phe Gln Arg Arg Met Leu Tyr Trp His Arg Phe
        260                 265                 270

Ala Pro Glu Ser Arg Met Met Arg Lys Val Thr Asp Ala Leu Leu Asp
        275                 280                 285

Tyr Gly His Lys Val Leu Arg Gln Asp
    290                 295

<210> SEQ ID NO 49
<211> LENGTH: 1026
<212> TYPE: DNA
<213> ORGANISM: Escherichia coli
<220> FEATURE:
<221> NAME/KEY: misc_feature
<222> LOCATION: (1)..(1026)
<223> OTHER INFORMATION: lpxD

<400> SEQUENCE: 49
atgccttcaa ttcgactggc tgatttagcg cagcagttgg atgcagaact acacggtgat      60
ggcgatatcg tcatcaccgg cgttgcgtcc atgcaatctg cacaaacagg tcacattacg     120
ttcatggtta acccaaaata ccgtgagcat ttaggcttgt gccaggcgtc cgcggttgtc     180
atgacccagg acgatcttcc tttcgcgaaa agtgccgcgc tggtagtgaa gaatccctac     240
ctgacttacg cgcgcatggc gcaaatttta gataccacgc cgcagcccgc gcagaacatt     300
gcacccagtg cggtgatcga cgcgacggcg aagctgggta caacgtatc gattggcgct     360
aacgcggtga ttgagtccgg cgttgaactg ggcgataacg tgattatcgg tgccggttgc     420
ttcgtaggta aaaacagcaa aatcggtgca ggttcgcgtc tctgggcgaa cgtaaccatt     480
taccatgaga tccagatcgg tcagaattgc ctgatccagt ccggaacagt ggtaggcgca     540
gacggctttg gttatgccaa cgatcgtggt aactgggtga agatcccaca gattggtcgc     600
gtaattattg gcgatcgcgt ggagatcggt gcctgcacaa ccatcgatcg cggcgcgctg     660
gatgacacta ttattggcaa tggcgtgatc attgataacc agtgccagat tgcacataac     720
gtcgtgattg gcgacaatac ggcggttgcc ggtggcgtca ttatggcggg cagcctgaaa     780
attggtcgtt actgcatgat cggcggagcc agcgtaatca acgggcatat ggaaatatgc     840
gacaaagtga cggttacggg catgggtatg gtgatgcgtc ccatcactga accaggcgtc     900
tattcctcag gcattccgct gcaacccaac aaagtctggc gcaaaaccgc tgcactggtg     960
atgaacattg atgacatgag caagcgtctg aaatcgcttg agcgcaaggt taatcaacaa    1020
gactaa                                                                1026

<210> SEQ ID NO 50
<211> LENGTH: 341
<212> TYPE: PRT
<213> ORGANISM: Escherichia coli
<220> FEATURE:
<221> NAME/KEY: MISC_FEATURE
<222> LOCATION: (1)..(341)
<223> OTHER INFORMATION: lpxD

<400> SEQUENCE: 50

Met Pro Ser Ile Arg Leu Ala Asp Leu Ala Gln Gln Leu Asp Ala Glu
1               5                   10                  15

Leu His Gly Asp Gly Asp Ile Val Ile Thr Gly Val Ala Ser Met Gln
           20                  25                  30

Ser Ala Gln Thr Gly His Ile Thr Phe Met Val Asn Pro Lys Tyr Arg
       35                  40                  45

Glu His Leu Gly Leu Cys Gln Ala Ser Ala Val Met Thr Gln Asp
50                  55                  60

Asp Leu Pro Phe Ala Lys Ser Ala Ala Leu Val Val Lys Asn Pro Tyr
65                  70                  75                  80

Leu Thr Tyr Ala Arg Met Ala Gln Ile Leu Asp Thr Thr Pro Gln Pro
               85                  90                  95

Ala Gln Asn Ile Ala Pro Ser Ala Val Ile Asp Ala Thr Ala Lys Leu
           100                 105                 110

Gly Asn Asn Val Ser Ile Gly Ala Asn Ala Val Ile Glu Ser Gly Val
           115                 120                 125

Glu Leu Gly Asp Asn Val Ile Ile Gly Ala Gly Cys Phe Val Gly Lys
130                 135                 140

Asn Ser Lys Ile Gly Ala Gly Ser Arg Leu Trp Ala Asn Val Thr Ile
145                 150                 155                 160

Tyr His Glu Ile Gln Ile Gly Gln Asn Cys Leu Ile Gln Ser Gly Thr
               165                 170                 175

Val Val Gly Ala Asp Gly Phe Gly Tyr Ala Asn Asp Arg Gly Asn Trp
           180                 185                 190

Val Lys Ile Pro Gln Ile Gly Arg Val Ile Ile Gly Asp Arg Val Glu
           195                 200                 205

Ile Gly Ala Cys Thr Thr Ile Asp Arg Gly Ala Leu Asp Asp Thr Ile
210                 215                 220

Ile Gly Asn Gly Val Ile Ile Asp Asn Gln Cys Gln Ile Ala His Asn
225                 230                 235                 240

Val Val Ile Gly Asp Asn Thr Ala Val Ala Gly Gly Val Ile Met Ala
               245                 250                 255

Gly Ser Leu Lys Ile Gly Arg Tyr Cys Met Ile Gly Gly Ala Ser Val
           260                 265                 270

Ile Asn Gly His Met Glu Ile Cys Asp Lys Val Thr Val Thr Gly Met
           275                 280                 285

Gly Met Val Met Arg Pro Ile Thr Glu Pro Gly Val Tyr Ser Ser Gly
290                 295                 300

Ile Pro Leu Gln Pro Asn Lys Val Trp Arg Lys Thr Ala Ala Leu Val
305                 310                 315                 320

Met Asn Ile Asp Asp Met Ser Lys Arg Leu Lys Ser Leu Glu Arg Lys
               325                 330                 335

Val Asn Gln Gln Asp
           340

<210> SEQ ID NO 51
<211> LENGTH: 1026
<212> TYPE: DNA
<213> ORGANISM: Escherichia coli
<220> FEATURE:
<221> NAME/KEY: misc_feature
<222> LOCATION: (1)..(1026)
<223> OTHER INFORMATION: lpxD Mut

<400> SEQUENCE: 51
atgccttcaa ttcgactggc tgatttagcg cagcagttgg atacagaact acacggtgat      60
ggcgatatcg tcatcaccgg cgttgcgtcc atgcaatctg cacaaacagg tcacattacg     120

```
ttcatggtta acccaaaata ccgtgagcat ttaggcttgt gccaggcgtc cgcggttgtc    180
atgacccagg acgatcttcc tttcgcgaaa agtgccgcgc tggtagtgaa gaatccctac    240
ctgacttacg cgcgcatggc gcaaattta gataccacgc cgcagcccgc gcagaacatt    300
gcacccagtg cggtgatcga cgcgacggcg aagctgggta caacgtatc gattggcgct    360 aacgcggtga ttgagtccgg cgttgaactg ggcgataacg tgattatcgg tgccggttgc    420
ttcgtaggta aaacagcaa atcggtgca ggttcgcgtc tctgggcgaa cgtaaccatt    480
taccatgaga tccagatcgg tcagaattgc ctgatccagt ccggaacagt ggtaggcgca    540
gacggctttg gttatgccaa cgatcgtggt aactgggtga agatcccaca gattggtcgc    600
gtaattattg gcgatcgcgt ggagatcggt gcctgcacaa ccatcgatcg cggcgcgctg    660
gatgacacta ttattggcaa tggcgtgatc attgataacc agtgccagat tgcacataac    720
gtcgtgattg gcgacaatac ggcggttgcc ggtggcgtca ttatggcggg cagcctgaaa    780
attggtcgtt actgcatgat cggcggagcc agcgtaatca acgggcatat ggaaatatgc    840
gacaaagtga cggttacggg catgggtatg gtgatgcgtc ccatcactga accaggcgtc    900
tattcctcag gcattccgct gcaacccaac aaagtctggc gcaaaaccgc tgcactggtg    960
atgaacattg atgacatgag caagcgtctg aaatcgcttg agcgcaaggt taatcaacaa   1020
gactaa                                                             1026
```

<210> SEQ ID NO 52
<211> LENGTH: 341
<212> TYPE: PRT
<213> ORGANISM: Escherichia coli
<220> FEATURE:
<221> NAME/KEY: MISC_FEATURE
<222> LOCATION: (1)..(341)
<223> OTHER INFORMATION: lpxD Mut

<400> SEQUENCE: 52

```
Met Pro Ser Ile Arg Leu Ala Asp Leu Ala Gln Gln Leu Asp Thr Glu
  1               5                  10                  15

Leu His Gly Asp Gly Asp Ile Val Ile Thr Gly Val Ala Ser Met Gln
             20                  25                  30

Ser Ala Gln Thr Gly His Ile Thr Phe Met Val Asn Pro Lys Tyr Arg
         35                  40                  45

Glu His Leu Gly Leu Cys Gln Ala Ser Ala Val Val Met Thr Gln Asp
     50                  55                  60

Asp Leu Pro Phe Ala Lys Ser Ala Ala Leu Val Val Lys Asn Pro Tyr
 65                  70                  75                  80

Leu Thr Tyr Ala Arg Met Ala Gln Ile Leu Asp Thr Thr Pro Gln Pro
                 85                  90                  95

Ala Gln Asn Ile Ala Pro Ser Ala Val Ile Asp Ala Thr Ala Lys Leu
            100                 105                 110

Gly Asn Asn Val Ser Ile Gly Ala Asn Ala Val Ile Glu Ser Gly Val
        115                 120                 125

Glu Leu Gly Asp Asn Val Ile Ile Gly Ala Gly Cys Phe Val Gly Lys
    130                 135                 140

Asn Ser Lys Ile Gly Ala Gly Ser Arg Leu Trp Ala Asn Val Thr Ile
145                 150                 155                 160

Tyr His Glu Ile Gln Ile Gly Gln Asn Cys Leu Ile Gln Ser Gly Thr
                165                 170                 175

Val Val Gly Ala Asp Gly Phe Gly Tyr Ala Asn Asp Arg Gly Asn Trp
```

```
                180                 185                 190
Val Lys Ile Pro Gln Ile Gly Arg Val Ile Gly Asp Arg Val Glu
            195                 200                 205
Ile Gly Ala Cys Thr Thr Ile Asp Arg Gly Ala Leu Asp Thr Ile
            210                 215                 220
Ile Gly Asn Gly Val Ile Asp Asn Gln Cys Gln Ile Ala His Asn
225                 230                 235                 240
Val Val Ile Gly Asp Asn Thr Ala Val Ala Gly Val Ile Met Ala
                245                 250                 255
Gly Ser Leu Lys Ile Gly Arg Tyr Cys Met Ile Gly Gly Ala Ser Val
            260                 265                 270
Ile Asn Gly His Met Glu Ile Cys Asp Lys Val Thr Val Thr Gly Met
            275                 280                 285
Gly Met Val Met Arg Pro Ile Thr Glu Pro Gly Val Tyr Ser Ser Gly
            290                 295                 300
Ile Pro Leu Gln Pro Asn Lys Val Trp Arg Lys Thr Ala Ala Leu Val
305                 310                 315                 320
Met Asn Ile Asp Asp Met Ser Lys Arg Leu Lys Ser Leu Glu Arg Lys
                325                 330                 335
Val Asn Gln Gln Asp
        340

<210> SEQ ID NO 53
<211> LENGTH: 918
<212> TYPE: DNA
<213> ORGANISM: Escherichia coli
<220> FEATURE:
<221> NAME/KEY: misc_feature
<222> LOCATION: (1)..(918)
<223> OTHER INFORMATION: gcvA

<400> SEQUENCE: 53
atgtctaaac gattaccacc gctaaatgcc ttacgagttt ttgatgccgc agcacgccat      60
ttaagtttca ctcgcgcagc agaagagctt tttgtgaccc aggccgcagt aagtcatcaa     120
atcaagtctc ttgaggattt tctggggcta aaactgttcc gccgccgtaa tcgttcactc     180
ctgctgaccg aggaaggtca agctatttc ctcgatatca aagagatatt ttcgcaatta     240
accgaagcga cgcgtaaact ccaggcccgt agcgccaagg gggcgttgac ggtcagttta     300
ctccccagtt tcgccattca ttggttggtt ccgcgacttt ccagctttaa ttcagcttat     360
ccgggaattg acgttcgaat ccaggcggtt gatcgtcagg aagataagct ggcggatgat     420
gttgatgtgg cgatatttta tggtcgggc aactggccgg ggctacgggt ggaaaaactg     480
tacgccgaat atttattgcc ggtgtgttcg ccgctactgc tgacaggcga aaaacccttg     540
aagaccccgg aagatctggc taaacatacg ttattacatg atgcgtcacg ccgtgactgg     600
cagacatata cccgacagtt gggggttaaat catatcaacg ttcagcaagg gccaattttt     660
agtcatagcg ccatggtgct gcaagcgct attcacgggc agggagtggc gctggcaaat     720
aacgtgatgg cgcaatctga atcgaggcc ggacgtcttg tttgcccgtt taatgatgtt     780
ctggtcagta aaaacgcttt ttatctggtt tgtcatgaca gccaggcaga actgggtaaa     840
atagccgcct ttcgccaatg gatcctggcg aaagccgctg ctgaacaaga aaaattccgc     900
tttcgttatg aacaataa                                                  918

<210> SEQ ID NO 54
<211> LENGTH: 305
```

<212> TYPE: PRT
<213> ORGANISM: Escherichia coli
<220> FEATURE:
<221> NAME/KEY: MISC_FEATURE
<222> LOCATION: (1)..(305)
<223> OTHER INFORMATION: gcvA

<400> SEQUENCE: 54

```
Met Ser Lys Arg Leu Pro Pro Leu Asn Ala Leu Arg Val Phe Asp Ala
1               5                   10                  15

Ala Ala Arg His Leu Ser Phe Thr Arg Ala Ala Glu Glu Leu Phe Val
            20                  25                  30

Thr Gln Ala Ala Val Ser His Gln Ile Lys Ser Leu Glu Asp Phe Leu
        35                  40                  45

Gly Leu Lys Leu Phe Arg Arg Arg Asn Arg Ser Leu Leu Leu Thr Glu
50                  55                  60

Glu Gly Gln Ser Tyr Phe Leu Asp Ile Lys Glu Ile Phe Ser Gln Leu
65                  70                  75                  80

Thr Glu Ala Thr Arg Lys Leu Gln Ala Arg Ser Ala Lys Gly Ala Leu
                85                  90                  95

Thr Val Ser Leu Leu Pro Ser Phe Ala Ile His Trp Leu Val Pro Arg
            100                 105                 110

Leu Ser Ser Phe Asn Ser Ala Tyr Pro Gly Ile Asp Val Arg Ile Gln
        115                 120                 125

Ala Val Asp Arg Gln Glu Asp Lys Leu Ala Asp Asp Val Asp Val Ala
    130                 135                 140

Ile Phe Tyr Gly Arg Gly Asn Trp Pro Gly Leu Arg Val Glu Lys Leu
145                 150                 155                 160

Tyr Ala Glu Tyr Leu Leu Pro Val Cys Ser Pro Leu Leu Thr Gly
                165                 170                 175

Glu Lys Pro Leu Lys Thr Pro Glu Asp Leu Ala Lys His Thr Leu Leu
            180                 185                 190

His Asp Ala Ser Arg Arg Asp Trp Gln Thr Tyr Thr Arg Gln Leu Gly
        195                 200                 205

Leu Asn His Ile Asn Val Gln Gln Gly Pro Ile Phe Ser His Ser Ala
    210                 215                 220

Met Val Leu Gln Ala Ala Ile His Gly Gln Gly Val Ala Leu Ala Asn
225                 230                 235                 240

Asn Val Met Ala Gln Ser Glu Ile Glu Ala Gly Arg Leu Val Cys Pro
                245                 250                 255

Phe Asn Asp Val Leu Val Ser Lys Asn Ala Phe Tyr Leu Val Cys His
            260                 265                 270

Asp Ser Gln Ala Glu Leu Gly Lys Ile Ala Ala Phe Arg Gln Trp Ile
        275                 280                 285

Leu Ala Lys Ala Ala Ala Glu Gln Glu Lys Phe Arg Phe Arg Tyr Glu
    290                 295                 300

Gln
305
```

<210> SEQ ID NO 55
<211> LENGTH: 350
<212> TYPE: DNA
<213> ORGANISM: Escherichia coli
<220> FEATURE:
<221> NAME/KEY: misc_feature
<222> LOCATION: (1)..(350)
<223> OTHER INFORMATION: gcvA WT Promoter

```
<400> SEQUENCE: 55
ttcgcgatcg caaggtaaaa aaaagcaccg caattaggcg gtgctacatt aatcactatg    60
gacagacagg gtaaatgtac aggaagtgaa aaaaggtagc tttgctacca tggtctgaat   120
cgcagaccaa ttgcaaacac aacaacacaa catcacaacc gtaagccaaa agttcaccag   180
aacacgcatt ccgataaaac ttttcgttcc ggctcaggaa gtgccgccac tataggtatt   240
tgctggtaga agctcaacgg acaatttata atggctcaga ttaaaaaaac taataggtta   300
cacagtgtga tctaattgtt aaattcattt aacatcaaag tttaaaagcc              350

<210> SEQ ID NO 56
<211> LENGTH: 349
<212> TYPE: DNA
<213> ORGANISM: Escherichia coli
<220> FEATURE:
<221> NAME/KEY: misc_feature
<222> LOCATION: (1)..(349)
<223> OTHER INFORMATION: gcvA Mut Promoter1

<400> SEQUENCE: 56
ttcgcgatcg caaggtaaaa aaaagcaccg caattaggcg gtgctacatt aatcactatg    60
gacagacagg gtaaatgtac aggaagtgaa aaaaggtagc tttgctacca tggtctgaat   120
cgcagaccaa ttgcaaacac aacaacacaa catcacaacc gtaagccaaa agttcaccag   180
aacacgcatt ccgataaaac ttttcgttcc ggctcaggaa gtgccgccac tataggtatt   240
tgctggtaga agctcaacgg acaatttata atggctcaga ttaaaaaact aataggttac   300
acagtgtgat ctaattgtta aattcattta acatcaaagt ttaaaagcc               349

<210> SEQ ID NO 57
<211> LENGTH: 350
<212> TYPE: DNA
<213> ORGANISM: Escherichia coli
<220> FEATURE:
<221> NAME/KEY: misc_feature
<222> LOCATION: (1)..(350)
<223> OTHER INFORMATION: gcvA Mut Promoter2

<400> SEQUENCE: 57
ttcgcgatcg caaggtaaaa aaaagcaccg caattaggcg gtgctacatt aatcactatg    60
gacagacagg gtaaatgtac aggaagtgaa aaaaggtagc tttgctacca tggtctgaat   120
cgcagaccaa ttgcaaacac aacaacacaa catcacaacc gtaagccaaa agttcaccag   180
aacacgcatt ccgataaaac ttttcgttcc ggctcaggaa gtgccgccac tataggtatt   240
tgctggtaga agctcaacgg acaatttata atggctcaga ttaaaaaaac aaataggtta   300
cacagtgtga tctaattgtt aaattcattt aacatcaaag tttaaaagcc              350

<210> SEQ ID NO 58
<211> LENGTH: 206
<212> TYPE: DNA
<213> ORGANISM: Escherichia coli
<220> FEATURE:
<221> NAME/KEY: misc_feature
<222> LOCATION: (1)..(206)
<223> OTHER INFORMATION: gcvB

<400> SEQUENCE: 58
acttcctgag ccggaacgaa aagtttttatc ggaatgcgtg ttctggtgaa cttttggctt    60
acggttgtga tgttgtgttg ttgtgtttgc aattggtctg cgattcagac catggtagca   120
aagctacctt ttttcacttc ctgtacattt accctgtctg tccatagtga ttaatgtagc   180
```

```
accgcctaat tgcggtgctt tttttt                                         206

<210> SEQ ID NO 59
<211> LENGTH: 128
<212> TYPE: DNA
<213> ORGANISM: Escherichia coli
<220> FEATURE:
<221> NAME/KEY: misc_feature
<222> LOCATION: (1)..(128)
<223> OTHER INFORMATION: gcvB WT Promoter

<400> SEQUENCE: 59
ggcttttaaa ctttgatgtt aaatgaattt aacaattaga tcacactgtg taacctatta    60 gttttttaa tctgagccat tataaattgt ccgttgagct tctaccagca aatacctata   120
gtggcggc                                                            128

<210> SEQ ID NO 60
<211> LENGTH: 127
<212> TYPE: DNA
<213> ORGANISM: Escherichia coli
<220> FEATURE:
<221> NAME/KEY: misc_feature
<222> LOCATION: (1)..(127)
<223> OTHER INFORMATION: gcvB Mut1 Promoter

<400> SEQUENCE: 60
ggcttttaaa ctttgatgtt aaatgaattt aacaattaga tcacactgtg taacctatta    60
gttttttaat ctgagccatt ataaattgtc cgttgagctt ctaccagcaa atacctatag   120
tggcggc                                                             127

<210> SEQ ID NO 61
<211> LENGTH: 128
<212> TYPE: DNA
<213> ORGANISM: Escherichia coli
<220> FEATURE:
<221> NAME/KEY: misc_feature
<222> LOCATION: (1)..(128)
<223> OTHER INFORMATION: gcvB Mut2 Promoter

<400> SEQUENCE: 61
ggcttttaaa ctttgatgtt aaatgaattt aacaattaga tcacactgtg taacctattt    60 gttttttaa tctgagccat tataaattgt ccgttgagct tctaccagca aatacctata   120
gtggcggc                                                            128

<210> SEQ ID NO 62
<211> LENGTH: 73
<212> TYPE: DNA
<213> ORGANISM: Artificial sequence
<220> FEATURE:
<223> OTHER INFORMATION: Primer argP_1_F

<400> SEQUENCE: 62
ttgctggaag aagagtggct gggcgatgaa caaaccggtt cgactccgct gatatcggaa    60
gccctgggcc aac                                                       73

<210> SEQ ID NO 63
<211> LENGTH: 75
<212> TYPE: DNA
<213> ORGANISM: Artificial sequence
<220> FEATURE:
<223> OTHER INFORMATION: Primer argP_1_R
```

<400> SEQUENCE: 63
tcagccaaca caggagccag tgcaggaagc aaccacgtcg ccagactgtc cacctgagac    60
aacttgttac agctc    75

<210> SEQ ID NO 64
<211> LENGTH: 24
<212> TYPE: DNA
<213> ORGANISM: Artificial sequence
<220> FEATURE:
<223> OTHER INFORMATION: Primer argP_2_F

<400> SEQUENCE: 64
actggatgcg gtgatacgtg aacg    24

<210> SEQ ID NO 65
<211> LENGTH: 24
<212> TYPE: DNA
<213> ORGANISM: Artificial sequence
<220> FEATURE:
<223> OTHER INFORMATION: Primer argP_2_R

<400> SEQUENCE: 65
accactggcg ctttcagtaa tgcc    24

<210> SEQ ID NO 66
<211> LENGTH: 21
<212> TYPE: DNA
<213> ORGANISM: Artificial sequence
<220> FEATURE:
<223> OTHER INFORMATION: Primer argP_seq_F

<400> SEQUENCE: 66
ttaccaggag cagacaacag c    21

<210> SEQ ID NO 67
<211> LENGTH: 21
<212> TYPE: DNA
<213> ORGANISM: Artificial sequence
<220> FEATURE:
<223> OTHER INFORMATION: Primer argP_seq_R

<400> SEQUENCE: 67
ggcagatcga agttttgctg c    21

<210> SEQ ID NO 68
<211> LENGTH: 38
<212> TYPE: DNA
<213> ORGANISM: Artificial sequence
<220> FEATURE:
<223> OTHER INFORMATION: Primer argP-pACYC_F

<400> SEQUENCE: 68
tatcatcgat aagcttatgt tacccgccga cggcttcg    38

<210> SEQ ID NO 69
<211> LENGTH: 40
<212> TYPE: DNA
<213> ORGANISM: Artificial sequence
<220> FEATURE:
<223> OTHER INFORMATION: Primer argP-pACYC_R

<400> SEQUENCE: 69
aagggcatcg gtcgacgtga ggataacgcc tgatatgtgc    40

<210> SEQ ID NO 70
<211> LENGTH: 73
<212> TYPE: DNA
<213> ORGANISM: Artificial sequence
<220> FEATURE:
<223> OTHER INFORMATION: Primer gcvA_1_F

<400> SEQUENCE: 70

```
taataggtta cacagtgtga tctaattgtt aaattcattt aacatcaaag gatatcggaa      60
gccctgggcc aac                                                        73
```

<210> SEQ ID NO 71
<211> LENGTH: 75
<212> TYPE: DNA
<213> ORGANISM: Artificial sequence
<220> FEATURE:
<223> OTHER INFORMATION: Primer gcvA_1_R

<400> SEQUENCE: 71

```
aaactcgtaa ggcatttagc ggtggtaatc gtttagacat ggcttttaaa cacctgagac      60
aacttgttac agctc                                                      75
```

<210> SEQ ID NO 72
<211> LENGTH: 20
<212> TYPE: DNA
<213> ORGANISM: Artificial sequence
<220> FEATURE:
<223> OTHER INFORMATION: Primer gcvA_2_F

<400> SEQUENCE: 72

```
cgcagaccaa ttgcaaacac                                                 20
```

<210> SEQ ID NO 73
<211> LENGTH: 20
<212> TYPE: DNA
<213> ORGANISM: Artificial sequence
<220> FEATURE:
<223> OTHER INFORMATION: Primer gcvA_2_R

<400> SEQUENCE: 73

```
ctcgcgcagc agaagagctt                                                 20
```

<210> SEQ ID NO 74
<211> LENGTH: 20
<212> TYPE: DNA
<213> ORGANISM: Artificial sequence
<220> FEATURE:
<223> OTHER INFORMATION: Primer gcvA_seq_F

<400> SEQUENCE: 74

```
agcagatcaa ccgtactgac                                                 20
```

<210> SEQ ID NO 75
<211> LENGTH: 20
<212> TYPE: DNA
<213> ORGANISM: Artificial sequence
<220> FEATURE:
<223> OTHER INFORMATION: Primer gcvA_seq_R

<400> SEQUENCE: 75

```
agtttacgcg tcgcttcggt                                                 20
```

<210> SEQ ID NO 76
<211> LENGTH: 41
<212> TYPE: DNA

```
<213> ORGANISM: Artificial sequence
<220> FEATURE:
<223> OTHER INFORMATION: Primer gcvA-pACYC_F

<400> SEQUENCE: 76
tatcatcgat aagcttaagt gccgccacta taggtatttg c                          41

<210> SEQ ID NO 77
<211> LENGTH: 37
<212> TYPE: DNA
<213> ORGANISM: Artificial sequence
<220> FEATURE:
<223> OTHER INFORMATION: Primer gcvA-pACYC_R

<400> SEQUENCE: 77
aagggcatcg gtcgactggt catggtcgta ccctacg                               37

<210> SEQ ID NO 78
<211> LENGTH: 73
<212> TYPE: DNA
<213> ORGANISM: Artificial sequence
<220> FEATURE:
<223> OTHER INFORMATION: Primer gcvB_1_F

<400> SEQUENCE: 78
tgacgtgaaa gagatggtcg aactggatca gtaattcgcg atcgcaaggt gatatcggaa      60
gccctgggcc aac                                                         73

<210> SEQ ID NO 79
<211> LENGTH: 75
<212> TYPE: DNA
<213> ORGANISM: Artificial sequence
<220> FEATURE:
<223> OTHER INFORMATION: Primer gcvB_1_R

<400> SEQUENCE: 79
attataaatt gtccgttgag cttctaccag caaatacctα tagtggcggc cacctgagac      60
aacttgttac agctc                                                       75

<210> SEQ ID NO 80
<211> LENGTH: 25
<212> TYPE: DNA
<213> ORGANISM: Artificial sequence
<220> FEATURE:
<223> OTHER INFORMATION: Primer gcvB_seq_F

<400> SEQUENCE: 80
gccgcaatta tttctgcctg tatgc                                            25

<210> SEQ ID NO 81
<211> LENGTH: 24
<212> TYPE: DNA
<213> ORGANISM: Artificial sequence
<220> FEATURE:
<223> OTHER INFORMATION: Primer gcvB_seq_R

<400> SEQUENCE: 81
cacaaaaagc tcttctgctg cgcg                                             24

<210> SEQ ID NO 82
<211> LENGTH: 40
<212> TYPE: DNA
<213> ORGANISM: Artificial sequence
<220> FEATURE:
<223> OTHER INFORMATION: Primer gcvB-pACYC_F
```

<400> SEQUENCE: 82
tatcatcgat aagcttggtc gaactggatc agtaattcgc                                    40

<210> SEQ ID NO 83
<211> LENGTH: 40
<212> TYPE: DNA
<213> ORGANISM: Artificial sequence
<220> FEATURE:
<223> OTHER INFORMATION: Primer gcvB-pACYC_R

<400> SEQUENCE: 83
aagggcatcg gtcgaccggt ggtaatcgtt tagacatggc                                    40

<210> SEQ ID NO 84
<211> LENGTH: 73
<212> TYPE: DNA
<213> ORGANISM: Artificial sequence
<220> FEATURE:
<223> OTHER INFORMATION: Primer brnQ_1_F

<400> SEQUENCE: 84
tatcgttatt gttaacgcgg cgcgttctcg tggcgttacc gaagcgcgtc gatatcggaa             60
gccctgggcc aac                                                                 73

<210> SEQ ID NO 85
<211> LENGTH: 75
<212> TYPE: DNA
<213> ORGANISM: Artificial sequence
<220> FEATURE:
<223> OTHER INFORMATION: Primer brnQ_1_R

<400> SEQUENCE: 85
gaacgtaagc atgcagaata gcagcgccgt ttgcagactg atcgaccagc cacctgagac             60
aacttgttac agctc                                                               75

<210> SEQ ID NO 86
<211> LENGTH: 24
<212> TYPE: DNA
<213> ORGANISM: Artificial sequence
<220> FEATURE:
<223> OTHER INFORMATION: Primer brnQ_2_F

<400> SEQUENCE: 86
ggataccgtg ggcaacttcc ttgc                                                     24

<210> SEQ ID NO 87
<211> LENGTH: 25
<212> TYPE: DNA
<213> ORGANISM: Artificial sequence
<220> FEATURE:
<223> OTHER INFORMATION: Primer brnQ_2_R

<400> SEQUENCE: 87
gttagaaacc accatcgaga agccg                                                    25

<210> SEQ ID NO 88
<211> LENGTH: 21
<212> TYPE: DNA
<213> ORGANISM: Artificial sequence
<220> FEATURE:
<223> OTHER INFORMATION: Primer brnQ_seq_F

<400> SEQUENCE: 88
cgctgtttat ctacagcctg g                                              21

<210> SEQ ID NO 89
<211> LENGTH: 21
<212> TYPE: DNA
<213> ORGANISM: Artificial sequence
<220> FEATURE:
<223> OTHER INFORMATION: Primer brnQ_seq_R

<400> SEQUENCE: 89
ggataaatag cggtcagcac c                                              21

<210> SEQ ID NO 90
<211> LENGTH: 77
<212> TYPE: DNA
<213> ORGANISM: Artificial sequence
<220> FEATURE:
<223> OTHER INFORMATION: Primer lpxD_1C_F

<400> SEQUENCE: 90
catcggtaaa acctggtaag tgttctccac aaaggaatgt agtggtagtg tagcgatatc    60
ggaagccctg ggccaac                                                   77

<210> SEQ ID NO 91
<211> LENGTH: 78
<212> TYPE: DNA
<213> ORGANISM: Artificial sequence
<220> FEATURE:
<223> OTHER INFORMATION: Primer lpxD_1C_R

<400> SEQUENCE: 91
ggtgcagttc tttgcgtggc ccggcgatct tatattgatc gcctaaagtc atccacctga    60
gacaacttgt tacagctc                                                  78

<210> SEQ ID NO 92
<211> LENGTH: 25
<212> TYPE: DNA
<213> ORGANISM: Artificial sequence
<220> FEATURE:
<223> OTHER INFORMATION: Primer lpxD_fix_F

<400> SEQUENCE: 92
cgatcaacga atataactcg ctgcg                                          25

<210> SEQ ID NO 93
<211> LENGTH: 25
<212> TYPE: DNA
<213> ORGANISM: Artificial sequence
<220> FEATURE:
<223> OTHER INFORMATION: Primer lpxD_fix_R

<400> SEQUENCE: 93
ataataacac ggcctgccgc aatcg                                          25

<210> SEQ ID NO 94
<211> LENGTH: 22
<212> TYPE: DNA
<213> ORGANISM: Artificial sequence
<220> FEATURE:
<223> OTHER INFORMATION: Primer lpxD_flank_F

<400> SEQUENCE: 94
atgctgtagg cggtaacgcc at                                             22

```
<210> SEQ ID NO 95
<211> LENGTH: 22
<212> TYPE: DNA
<213> ORGANISM: Artificial sequence
<220> FEATURE:
<223> OTHER INFORMATION: Primer lpxD_flank_R

<400> SEQUENCE: 95
atacgttgtt acccagcttc gc                                              22

<210> SEQ ID NO 96
<211> LENGTH: 38
<212> TYPE: DNA
<213> ORGANISM: Artificial sequence
<220> FEATURE:
<223> OTHER INFORMATION: Primer lpxD-pACYC_F

<400> SEQUENCE: 96
tatcatcgat aagcttaaat ccgttgccaa cagccagg                             38

<210> SEQ ID NO 97
<211> LENGTH: 36
<212> TYPE: DNA
<213> ORGANISM: Artificial sequence
<220> FEATURE:
<223> OTHER INFORMATION: Primer lpxD-pACYC_R

<400> SEQUENCE: 97
aagggcatcg gtcgacaaca cggcctgccg caatcg                               36

<210> SEQ ID NO 98
<211> LENGTH: 400
<212> TYPE: DNA
<213> ORGANISM: Escherichia coli
<220> FEATURE:
<221> NAME/KEY: misc_feature
<222> LOCATION: (1)..(400)
<223> OTHER INFORMATION: gcvB_KO_Fix

<400> SEQUENCE: 98
tgccctgagc gcctgttccg gttcgaacta tgtgatgcac accaatgacg gacgtaccat     60
cgtctctgac ggcaaaccac agactgataa cgataccggt atgatttcgt ataaagacgc   120
taatggcaac aaacagcaga tcaaccgtac tgacgtgaaa gagatggtcg aactggatca   180
gtaattcgcg atcgcaaggt gccgccacta taggtatttg ctggtagaag ctcaacggac   240
aatttataat ggctcagatt aaaaaaacta ataggttaca cagtgtgatc taattgttaa   300
attcatttaa catcaaagtt taaaagccat gtctaaacga ttaccaccgc taaatgcctt   360
acgagttttt gatgccgcag cacgccattt aagtttcact                         400

<210> SEQ ID NO 99
<211> LENGTH: 24
<212> TYPE: DNA
<213> ORGANISM: Artificial sequence
<220> FEATURE:
<223> OTHER INFORMATION: Primer argP_RT_F

<400> SEQUENCE: 99
gcccggacta cagaacatta cagg                                            24

<210> SEQ ID NO 100
<211> LENGTH: 23
<212> TYPE: DNA
<213> ORGANISM: Artificial sequence
<220> FEATURE:
```

```
<223> OTHER INFORMATION: Primer argP_RT_R

<400> SEQUENCE: 100
tgagacggct gattgtgtaa tgc                                          23

<210> SEQ ID NO 101
<211> LENGTH: 24
<212> TYPE: DNA
<213> ORGANISM: Artificial sequence
<220> FEATURE:
<223> OTHER INFORMATION: Primer gcvA_RT_F

<400> SEQUENCE: 101
ccatttaagt ttcactcgcg cagc                                         24

<210> SEQ ID NO 102
<211> LENGTH: 20
<212> TYPE: DNA
<213> ORGANISM: Artificial sequence
<220> FEATURE:
<223> OTHER INFORMATION: Primer gcvA_RT_R

<400> SEQUENCE: 102
ggcggcggaa cagttttagc                                              20

<210> SEQ ID NO 103
<211> LENGTH: 27
<212> TYPE: DNA
<213> ORGANISM: Artificial sequence
<220> FEATURE:
<223> OTHER INFORMATION: Primer gcvB_RT_F

<400> SEQUENCE: 103
taggcggtgc tacattaatc actatgg                                      27

<210> SEQ ID NO 104
<211> LENGTH: 23
<212> TYPE: DNA
<213> ORGANISM: Artificial sequence
<220> FEATURE:
<223> OTHER INFORMATION: Primer gcvB_RT_R

<400> SEQUENCE: 104
tgttgtgttt gcaattggtc tgc                                          23

<210> SEQ ID NO 105
<211> LENGTH: 23
<212> TYPE: DNA
<213> ORGANISM: Artificial sequence
<220> FEATURE:
<223> OTHER INFORMATION: Primer lpxD_RT_F

<400> SEQUENCE: 105
gatatcgtca tcaccggcgt tgc                                          23

<210> SEQ ID NO 106
<211> LENGTH: 22
<212> TYPE: DNA
<213> ORGANISM: Artificial sequence
<220> FEATURE:
<223> OTHER INFORMATION: Primer lpxD_RT_R

<400> SEQUENCE: 106
gcacaagcct aaatgctcac gg                                           22
```

<210> SEQ ID NO 107
<211> LENGTH: 23
<212> TYPE: DNA
<213> ORGANISM: Artificial sequence
<220> FEATURE:
<223> OTHER INFORMATION: Primer rrsA_RT_F

<400> SEQUENCE: 107
ctcttgccat cggatgtgcc cag                                              23

<210> SEQ ID NO 108
<211> LENGTH: 24
<212> TYPE: DNA
<213> ORGANISM: Artificial sequence
<220> FEATURE:
<223> OTHER INFORMATION: Primer rrsA_RT_R

<400> SEQUENCE: 108
ccagtgtggc tggtcatcct ctca                                             24

<210> SEQ ID NO 109
<211> LENGTH: 450
<212> TYPE: DNA
<213> ORGANISM: E.coli
<220> FEATURE:
<221> NAME/KEY: misc_feature
<222> LOCATION: (1)..(450)
<223> OTHER INFORMATION: ygaW

<400> SEQUENCE: 109
atgttctcac cgcagtcacg cttgcgtcat gcagttgcag atacgttcgc gatggttgtt      60
tactgttctg tcgtgaacat gtgtattgaa gttttcctct ccggaatgag cttcgaacag     120
tctttttatt ccagattggt agcgattccg gtgaacatct taattgcatg gccatacggt     180
atgtaccgtg atctgtttat gcgcgcggca cgcaaagtta gcccgtcggg ctggataaaa     240
aatctggctg atatcctggc ttatgtgacg ttccagtcac cggtgtatgt ggcgatcttg     300
ttagtggtgg gcgcagactg gcatcagatt atggcggcgg tcagttcaaa catcgttgtt     360
tcgatgttga tgggggcggt ttatggctac ttcctcgatt attgccgccg actgtttaaa     420
gtcagccgtt accagcaggt aaaagcctga                                      450

<210> SEQ ID NO 110
<211> LENGTH: 149
<212> TYPE: PRT
<213> ORGANISM: E.coli
<220> FEATURE:
<221> NAME/KEY: MISC_FEATURE
<222> LOCATION: (1)..(149)
<223> OTHER INFORMATION: ygaW

<400> SEQUENCE: 110

Met Phe Ser Pro Gln Ser Arg Leu Arg His Ala Val Ala Asp Thr Phe
1               5                   10                  15

Ala Met Val Val Tyr Cys Ser Val Val Asn Met Cys Ile Glu Val Phe
                20                  25                  30

Leu Ser Gly Met Ser Phe Glu Gln Ser Phe Tyr Ser Arg Leu Val Ala
            35                  40                  45

Ile Pro Val Asn Ile Leu Ile Ala Trp Pro Tyr Gly Met Tyr Arg Asp
        50                  55                  60

Leu Phe Met Arg Ala Ala Arg Lys Val Ser Pro Ser Gly Trp Ile Lys
65                  70                  75                  80

Asn Leu Ala Asp Ile Leu Ala Tyr Val Thr Phe Gln Ser Pro Val Tyr 85                  90                  95
Val Ala Ile Leu Leu Val Val Gly Ala Asp Trp His Gln Ile Met Ala
                100                 105                 110

Ala Val Ser Ser Asn Ile Val Val Ser Met Leu Met Gly Ala Val Tyr
            115                 120                 125

Gly Tyr Phe Leu Asp Tyr Cys Arg Arg Leu Phe Lys Val Ser Arg Tyr
    130                 135                 140

Gln Gln Val Lys Ala
145

<210> SEQ ID NO 111
<211> LENGTH: 987
<212> TYPE: DNA
<213> ORGANISM: E.coli
<220> FEATURE:
<221> NAME/KEY: misc_feature
<222> LOCATION: (1)..(987)
<223> OTHER INFORMATION: zipA

<400> SEQUENCE: 111
atgatgcagg atttgcgtct gatattaatc attgttggcg cgatcgccat aatcgcttta      60
ctggtacatg gtttctggac cagccgtaaa gaacgatctt ctatgttccg cgatcggcca     120
ttaaaacgaa tgaagtcaaa acgtgacgac gattcttatg acgaggatgt cgaagatgat     180
gagggcgttg gtgaggttcg tgttcaccgc gtgaatcatg ccccggctaa cgctcaggag     240
catgaggctg ctcgtccgtc gccgcaacac cagtaccaac cgccttatgc gtctgcgcag     300
ccgcgtcaac cggtccagca gccgcctgaa gcgcaggtac cgccgcaaca tgctccgcgt     360
ccagcgcagc cggtgcagca gcctgcctat cagccgcagc ctgaacagcc gttgcagcag     420
ccagtttcgc cacaggtcgc gccagcgccg cagcctgtgc attcagcacc gcaaccggca     480
caacaggctt ccagcctgc agaacccgta gcggcaccac agcctgagcc tgtagcggaa     540
ccggctccag ttatggataa accgaagcgc aaagaagcgg tgattatcat gaacgtcgcg     600
gcgcatcacg gtagcgagct aaacggtgaa ctgcttctta acagcattca acaagcgggc     660 ttcattttg gcgatatgaa tatttaccat cgtcatctta gcccggatgg cagcggcccg     720
gcgttattca gcctggcgaa tatggtgaaa ccgggaacct tgatcctga atgaaggat     780 ttcactactc cgggtgtcac catctttatg caggtaccgt cttacggtga cgagctgcag     840
aacttcaagc tgatgctgca atctgcgcag catattgccg atgaagtggg cggtgtcgtg     900
cttgacgatc agcgccgtat gatgactccg cagaaattgc gcgagtacca ggacatcatc     960
cgcgaagtca agacgccaa cgcctga                                         987

<210> SEQ ID NO 112
<211> LENGTH: 328
<212> TYPE: PRT
<213> ORGANISM: E.coli
<220> FEATURE:
<221> NAME/KEY: MISC_FEATURE
<222> LOCATION: (1)..(328)
<223> OTHER INFORMATION: zipA

<400> SEQUENCE: 112

Met Met Gln Asp Leu Arg Leu Ile Leu Ile Ile Val Gly Ala Ile Ala
1               5                   10                  15

Ile Ile Ala Leu Leu Val His Gly Phe Trp Thr Ser Arg Lys Glu Arg
            20                  25                  30

Ser Ser Met Phe Arg Asp Arg Pro Leu Lys Arg Met Lys Ser Lys Arg

|   |   |   | 35  |   |   |   | 40  |   |   |   | 45  |   |   |
|---|---|---|-----|---|---|---|-----|---|---|---|-----|---|---|

Asp Asp Asp Ser Tyr Asp Glu Asp Val Glu Asp Glu Gly Val Gly
50                  55                  60

Glu Val Arg Val His Arg Val Asn His Ala Pro Ala Asn Ala Gln Glu
65                  70                  75                  80

His Glu Ala Ala Arg Pro Ser Pro Gln His Gln Tyr Gln Pro Pro Tyr
                85                  90                  95

Ala Ser Ala Gln Pro Arg Gln Pro Val Gln Gln Pro Pro Glu Ala Gln
                100                 105                 110

Val Pro Pro Gln His Ala Pro Arg Pro Ala Gln Pro Val Gln Gln Pro
            115                 120                 125

Ala Tyr Gln Pro Gln Pro Glu Gln Pro Leu Gln Gln Pro Val Ser Pro
        130                 135                 140

Gln Val Ala Pro Ala Pro Gln Pro Val His Ser Ala Pro Gln Pro Ala
145                 150                 155                 160

Gln Gln Ala Phe Gln Pro Ala Glu Pro Val Ala Ala Pro Gln Pro Glu
                165                 170                 175

Pro Val Ala Glu Pro Ala Pro Val Met Asp Lys Pro Lys Arg Lys Glu
                180                 185                 190

Ala Val Ile Ile Met Asn Val Ala Ala His His Gly Ser Glu Leu Asn
            195                 200                 205

Gly Glu Leu Leu Leu Asn Ser Ile Gln Gln Ala Gly Phe Ile Phe Gly
210                 215                 220

Asp Met Asn Ile Tyr His Arg His Leu Ser Pro Asp Gly Ser Gly Pro
225                 230                 235                 240

Ala Leu Phe Ser Leu Ala Asn Met Val Lys Pro Gly Thr Phe Asp Pro
                245                 250                 255

Glu Met Lys Asp Phe Thr Thr Pro Gly Val Thr Ile Phe Met Gln Val
                260                 265                 270

Pro Ser Tyr Gly Asp Glu Leu Gln Asn Phe Lys Leu Met Leu Gln Ser
            275                 280                 285

Ala Gln His Ile Ala Asp Glu Val Gly Gly Val Val Leu Asp Asp Gln
        290                 295                 300

Arg Arg Met Met Thr Pro Gln Lys Leu Arg Glu Tyr Gln Asp Ile Ile
305                 310                 315                 320

Arg Glu Val Lys Asp Ala Asn Ala
                325

```
<210> SEQ ID NO 113
<211> LENGTH: 1425
<212> TYPE: DNA
<213> ORGANISM: E.coli
<220> FEATURE:
<221> NAME/KEY: misc_feature
<222> LOCATION: (1)..(1425)
<223> OTHER INFORMATION: lpd

<400> SEQUENCE: 113
atgagtactg aaatcaaaac tcaggtcgtg gtacttgggg caggccccgc aggttactcc      60
gctgccttcc gttgcgctga tttaggtctg gaaaccgtaa tcgtagaacg ttacaacacc     120
cttggcggtg tttgcctgaa cgtcggctgt atcccttcta aagcactgct gcacgtagca     180
aaagttatcg aagaagccaa agcgctggct gaacacggta tcgtcttcgg cgaaccgaaa     240
accgatattg acaagattcg tacctggaaa gagaaagtga tcaatcagct gaccggtggt     300
ctggctggta tggcgaaagg ccgcaaagtc aaagtggtca acggtctggg taaatttacc     360
```

```
ggggctaaca ccctggaagt tgaaggtgag aacggtaaaa ccgtgatcaa cttcgacaac    420
gcgatcattg cagcgggttc tcgcccgatc caactgccgt ttattccgca tgaagatccg    480
cgtatctggg actccactga cgcgctggaa ctgaaagaag taccagaacg cctgctggta    540
atgggtggcg gtatcatcgg tctggaaatg ggcaccgtat accacgcgct gggttcacag    600
attgacgtgg ttgaaatgtt cgaccaggtt atcccggcag ctgacaaaga catcgttaaa    660
gtcttcacca gcgtatcag caagaaattc aacctgatgc tggaaaccaa agttaccgcc    720
gttgaagcga agaagacgg tatttatgtg acgatggaag caaaaaagc acccgctgaa    780 ccgcagcgtt acgacgccgt gctggtagcg attggtcgtg tgccgaacgg taaaaacctc    840
gacgcaggca agctggcgt ggaagtggac gaccgtggtt tcatccgcgt tgacaaacag    900
ctgcgtacca acgtaccgca catctttgct atcggcgata cgtcggtca gccgatgctg    960 gcacacaaag gtgttcacga aggtcacgtt gccgctgaag ttatcgccgg taagaaacac   1020
tacttcgatc cgaaagttat cccgtccatc gcctataccg aaccagaagt tgcatgggta   1080
ggtctgactg agaaagaagc gaaagagaaa ggcatcagct atgaaaccgc caccttcccg   1140
tgggctgctt ctggtcgtgc tatcgcttcc gactgcgcag acggtatgac caagctgatt   1200
ttcgacaaag aatctcaccg tgtgatcggt ggtgcgattg tcggtaccaa cggcggcgag   1260
ctgctgggtg aaatcggcct ggcaatcgaa atgggttgtg atgctgaaga catcgcactg   1320
accatccacg cgcacccgac tctgcacgag tctgtgggcc tggcggcaga agtgttcgaa   1380
ggtagcatta ccgacctgcc gaacccgaaa gcgaagaaga gtaa                    1425
```

<210> SEQ ID NO 114
<211> LENGTH: 474
<212> TYPE: PRT
<213> ORGANISM: E.coli
<220> FEATURE:
<221> NAME/KEY: MISC_FEATURE
<222> LOCATION: (1)..(474)
<223> OTHER INFORMATION: lpd

<400> SEQUENCE: 114

```
Met Ser Thr Glu Ile Lys Thr Gln Val Val Leu Gly Ala Gly Pro
1               5                   10                  15

Ala Gly Tyr Ser Ala Ala Phe Arg Cys Ala Asp Leu Gly Leu Glu Thr
            20                  25                  30

Val Ile Val Glu Arg Tyr Asn Thr Leu Gly Gly Val Cys Leu Asn Val
        35                  40                  45

Gly Cys Ile Pro Ser Lys Ala Leu Leu His Val Ala Lys Val Ile Glu
    50                  55                  60

Glu Ala Lys Ala Leu Ala Glu His Gly Ile Val Phe Gly Glu Pro Lys
65                  70                  75                  80

Thr Asp Ile Asp Lys Ile Arg Thr Trp Lys Glu Lys Val Ile Asn Gln
                85                  90                  95

Leu Thr Gly Gly Leu Ala Gly Met Ala Lys Gly Arg Lys Val Lys Val
            100                 105                 110

Val Asn Gly Leu Gly Lys Phe Thr Gly Ala Asn Thr Leu Glu Val Glu
        115                 120                 125

Gly Glu Asn Gly Lys Thr Val Ile Asn Phe Asp Asn Ala Ile Ile Ala
    130                 135                 140

Ala Gly Ser Arg Pro Ile Gln Leu Pro Phe Ile Pro His Glu Asp Pro
145                 150                 155                 160
```

Arg Ile Trp Asp Ser Thr Asp Ala Leu Glu Leu Lys Glu Val Pro Glu
            165                 170                 175
Arg Leu Leu Val Met Gly Gly Ile Ile Gly Leu Glu Met Gly Thr
        180                 185                 190
Val Tyr His Ala Leu Gly Ser Gln Ile Asp Val Val Glu Met Phe Asp
            195                 200                 205
Gln Val Ile Pro Ala Ala Asp Lys Asp Ile Val Lys Val Phe Thr Lys
        210                 215                 220
Arg Ile Ser Lys Lys Phe Asn Leu Met Leu Glu Thr Lys Val Thr Ala
225                 230                 235                 240
Val Glu Ala Lys Glu Asp Gly Ile Tyr Val Thr Met Glu Gly Lys Lys
            245                 250                 255
Ala Pro Ala Glu Pro Gln Arg Tyr Asp Ala Val Leu Val Ala Ile Gly
        260                 265                 270
Arg Val Pro Asn Gly Lys Asn Leu Asp Ala Gly Lys Ala Gly Val Glu
            275                 280                 285
Val Asp Asp Arg Gly Phe Ile Arg Val Asp Lys Gln Leu Arg Thr Asn
        290                 295                 300
Val Pro His Ile Phe Ala Ile Gly Asp Ile Val Gly Gln Pro Met Leu
305                 310                 315                 320
Ala His Lys Gly Val His Glu Gly His Val Ala Ala Glu Val Ile Ala
            325                 330                 335
Gly Lys Lys His Tyr Phe Asp Pro Lys Val Ile Pro Ser Ile Ala Tyr
        340                 345                 350
Thr Glu Pro Glu Val Ala Trp Val Gly Leu Thr Glu Lys Glu Ala Lys
            355                 360                 365
Glu Lys Gly Ile Ser Tyr Glu Thr Ala Thr Phe Pro Trp Ala Ala Ser
        370                 375                 380
Gly Arg Ala Ile Ala Ser Asp Cys Ala Asp Gly Met Thr Lys Leu Ile
385                 390                 395                 400
Phe Asp Lys Glu Ser His Arg Val Ile Gly Gly Ala Ile Val Gly Thr
            405                 410                 415
Asn Gly Gly Glu Leu Leu Gly Glu Ile Gly Leu Ala Ile Glu Met Gly
        420                 425                 430
Cys Asp Ala Glu Asp Ile Ala Leu Thr Ile His Ala His Pro Thr Leu
            435                 440                 445
His Glu Ser Val Gly Leu Ala Ala Glu Val Phe Glu Gly Ser Ile Thr
        450                 455                 460
Asp Leu Pro Asn Pro Lys Ala Lys Lys Lys
465                 470

<210> SEQ ID NO 115
<211> LENGTH: 269
<212> TYPE: DNA
<213> ORGANISM: E.coli
<220> FEATURE:
<221> NAME/KEY: misc_feature
<222> LOCATION: (1)..(269)
<223> OTHER INFORMATION: ldhA mut Promoter

<400> SEQUENCE: 115
catagtaaat tcccccacca gtttaaccgg cggctgattt tcaaacgcga cgacatccag      60
ttcgctgact gtaagttgtt gcccttcag ctggccttga aatttaactt tttcgccctg     120
ataacgcagt tgctggatat cagaggttaa tgcgagagag agttttccct gccattcctg     180
ccagggagaa aaaatcagtt tatcgatatt gattttgtaa aatattttta gtagcttaaa     240
tgtgattcaa catcactgga gaaagtctt                                    269

<210> SEQ ID NO 116
<211> LENGTH: 50
<212> TYPE: DNA
<213> ORGANISM: E.coli
<220> FEATURE:
<221> NAME/KEY: misc_feature
<222> LOCATION: (1)..(50)
<223> OTHER INFORMATION: ldhA mut Promoter fragment

<400> SEQUENCE: 116
tattgatttt gtaaaatatt tttagtagct taaatgtgat tcaacatcac              50

<210> SEQ ID NO 117
<211> LENGTH: 500
<212> TYPE: DNA
<213> ORGANISM: E.coli
<220> FEATURE:
<221> NAME/KEY: misc_feature
<222> LOCATION: (1)..(500)
<223> OTHER INFORMATION: brnQ_KO_fix

<400> SEQUENCE: 117
gtgatttctt atcgctatat acctctggtt tttagatccc tccttgcttt aaaacgttat   60
aagcgtttaa attgcgcttc aggtgctgtc atactgactg cattaacgcg gtaaatcgaa   120
aaactattct tcgccgcgcc tggttgggag tatttcccgc taaaattgtt taaatatacc   180
gctgtatcat ccccagggat tggcacaaaa atttaacgtt acaacaccac atccacaggc   240
agtatgattt atcactgaac atttgtttta accacggggc tgcgatgccc cgtggttttt   300
tattgtgttg atgggttagg aattgatgga agtaagaac aagctaaagc gtgggctaag    360
tacccgccac atacgcttta tggcactggg ttcagcaatt ggcaccgggc tgttttacgg   420
ttcggcagac gccatcaaaa tggccggtcc gagcgtgttg ttggcctata ttatcggtgg   480
tatcgcggcg tatatcatta                                              500

<210> SEQ ID NO 118
<211> LENGTH: 1071
<212> TYPE: DNA
<213> ORGANISM: E. coli
<220> FEATURE:
<221> NAME/KEY: misc_feature
<222> LOCATION: (1)..(1071)
<223> OTHER INFORMATION: dadX

<400> SEQUENCE: 118
atgacccgtc cgatacaggc cagcctcgat ctgcaggcat taaaacagaa tctgtccatt   60
gtccgccagg ccgcgccgca cgcgcgcgtc tggtcggtgg taaaagcgaa cgcttacggg   120
catggtattg agcgtatctg gagcgcgctc ggggccaccg atggctttgc attacttaac   180
ctggaagagg caataacgtt acgtgagcgc ggctggaagg ggccgatcct gatgctggaa   240
ggatttttcc atgctcagga tctggagatt tatgaccagc accgcctgac cacctgcgta   300
cacagcaact ggcagctcaa agcactgcaa aatgcgcggc taaaagcacc gttggatatt   360
tatcttaaag tgaacagtgg gatgaatcgg ttgggcttcc agcccgatcg cgtgcttacc   420
gtctggcagc agttgcgggc aatggcgaat gttggcgaga tgaccctgat gtcgcatttt   480
gccgaagcgg aacatcctga tggaatttcc agcgcgatgg cgcgtattga gcaggcggcg   540
gaagggctgg agtgtcggcg ttcgttgtcc aattcggcgg cgactctgtg gcacccggaa   600

```
gcgcattttg actgggttcg gcctggcatt attttgtatg gcgcttcgcc gtccggtcag   660
tggcgtgata tcgccaatac cggattacgt ccggtgatga cgctaagcag tgagattatt   720
ggtgtccaga cgctaaaagc gggtgagcgt gtgggctacg gcggtcgcta tactgcgcgc   780
gatgaacagc gaatcggcat tgtcgccgca gggtacgccg acggttatcc gcgccacgcg   840
cctaccggta cccctgtttt agtggacggc gtgcgcacca tgacggtggg gaccgtctcg   900
atggatatgc tagcggtcga tttaacgcct tgcccgcagg cggggattgg tacgccggtt   960
gagctgtggg gcaaggagat caaaattgat gatgtcgccg ccgctgccgg aacggtgggc  1020
tatgagttga tgtgcgcgct ggcgttacgc gtcccggttg tgacagtgta a           1071
```

<210> SEQ ID NO 119
<211> LENGTH: 356
<212> TYPE: PRT
<213> ORGANISM: E. coli
<220> FEATURE:
<221> NAME/KEY: MISC_FEATURE
<222> LOCATION: (1)..(356)
<223> OTHER INFORMATION: dadX

<400> SEQUENCE: 119

```
Met Thr Arg Pro Ile Gln Ala Ser Leu Asp Leu Gln Ala Leu Lys Gln
1               5                   10                  15

Asn Leu Ser Ile Val Arg Gln Ala Ala Pro His Ala Arg Val Trp Ser
            20                  25                  30

Val Val Lys Ala Asn Ala Tyr Gly His Gly Ile Glu Arg Ile Trp Ser
        35                  40                  45

Ala Leu Gly Ala Thr Asp Gly Phe Ala Leu Leu Asn Leu Glu Glu Ala
    50                  55                  60

Ile Thr Leu Arg Glu Arg Gly Trp Lys Gly Pro Ile Leu Met Leu Glu
65                  70                  75                  80

Gly Phe Phe His Ala Gln Asp Leu Glu Ile Tyr Asp Gln His Arg Leu
                85                  90                  95

Thr Thr Cys Val His Ser Asn Trp Gln Leu Lys Ala Leu Gln Asn Ala
            100                 105                 110

Arg Leu Lys Ala Pro Leu Asp Ile Tyr Leu Lys Val Asn Ser Gly Met
        115                 120                 125

Asn Arg Leu Gly Phe Gln Pro Asp Arg Val Leu Thr Val Trp Gln Gln
    130                 135                 140

Leu Arg Ala Met Ala Asn Val Gly Glu Met Thr Leu Met Ser His Phe
145                 150                 155                 160

Ala Glu Ala Glu His Pro Asp Gly Ile Ser Ser Ala Met Ala Arg Ile
                165                 170                 175

Glu Gln Ala Ala Glu Gly Leu Glu Cys Arg Arg Ser Leu Ser Asn Ser
            180                 185                 190

Ala Ala Thr Leu Trp His Pro Glu Ala His Phe Asp Trp Val Arg Pro
        195                 200                 205

Gly Ile Ile Leu Tyr Gly Ala Ser Pro Ser Gly Gln Trp Arg Asp Ile
    210                 215                 220

Ala Asn Thr Gly Leu Arg Pro Val Met Thr Leu Ser Ser Glu Ile Ile
225                 230                 235                 240

Gly Val Gln Thr Leu Lys Ala Gly Glu Arg Val Gly Tyr Gly Gly Arg
                245                 250                 255

Tyr Thr Ala Arg Asp Glu Gln Arg Ile Gly Ile Val Ala Ala Gly Tyr
            260                 265                 270
```

```
Ala Asp Gly Tyr Pro Arg His Ala Pro Thr Gly Thr Pro Val Leu Val
        275                 280                 285

Asp Gly Val Arg Thr Met Thr Val Gly Thr Val Ser Met Asp Met Leu
    290                 295                 300

Ala Val Asp Leu Thr Pro Cys Pro Gln Ala Gly Ile Gly Thr Pro Val
305                 310                 315                 320

Glu Leu Trp Gly Lys Glu Ile Lys Ile Asp Asp Val Ala Ala Ala
                325                 330                 335

Gly Thr Val Gly Tyr Glu Leu Met Cys Ala Leu Ala Leu Arg Val Pro
                340                 345                 350

Val Val Thr Val
        355
```

<210> SEQ ID NO 120
<211> LENGTH: 1203
<212> TYPE: DNA
<213> ORGANISM: Escherichia coli
<220> FEATURE:
<221> NAME/KEY: misc_feature
<222> LOCATION: (1)..(1203)
<223> OTHER INFORMATION: ackA

<400> SEQUENCE: 120

```
atgtcgagta agttagtact ggttctgaac tgcggtagtt cttcactgaa atttgccatc      60
atcgatgcag taaatggtga agagtacctt tctggtttag ccgaatgttt ccacctgccc     120
gaagcacgta tcaaatggaa atggacggca aataaacagg aagcggcttt aggtgcaggc     180
gccgctcaca gcgaagcgct caactttatc gttaatacta ttctggcaca aaaccagaa     240
ctgtctgcgc agctgactgc tatcggtcac cgtatcgtac acggcggcga aaagtatacc     300
agctccgtag tgatcgatga gtctgttatt cagggtatca aagatgcagc ttcttttgca     360
ccgctgcaca acccggctca cctgatcggt atcgaagaag ctctgaaatc tttcccacag     420
ctgaaagaca aaaacgttgc tgtatttgac accgcgttcc accagactat gccggaagag     480
tcttacctct acgccctgcc ttacaacctg tacaaagagc acggcatccg tcgttacggc     540
gcgcacggca ccagccactt ctatgtaacc caggaagcgg caaaaatgct gaacaaaccg     600
gtagaagaac tgaacatcat cacctgccac ctgggcaacg gtggttccgt ttctgctatc     660
cgcaacggta aatgcgttga cacctctatg ggcctgaccc cgctggaagg tctggtcatg     720
ggtacccgtt ctggtgatat cgatccggcg atcatcttcc acctgcacga cacctggc     780
atgagcgttg acgcaatcaa caaactgctg accaaagagt ctggcctgct gggtctgacc     840
gaagtgacca gcgactgccg ctatgttgaa gacaactacg cgacgaaaga agacgcgaag     900
cgcgcaatgg acgtttactg ccaccgcctg gcgaaataca tcggtgccta cactgcgctg     960
atggatggtc gtctggacgc tgttgtattc actggtggta tcggtgaaaa tgccgcaatg    1020
gttcgtgaac tgtctctggg caaactgggc gtgctgggct ttgaagttga tcatgaacgc    1080
aacctggctg cacgtttcgg caaatctggt ttcatcaaca agaaggtac ccgtcctgcg    1140
gtggttatcc caaccaacga gaactggtt atcgcgcaag acgcgagccg cctgactgcc    1200
tga                                                                 1203
```

<210> SEQ ID NO 121
<211> LENGTH: 400
<212> TYPE: PRT
<213> ORGANISM: Escherichia coli
<220> FEATURE:
<221> NAME/KEY: MISC_FEATURE
<222> LOCATION: (1)..(400)
<223> OTHER INFORMATION: ackA

<400> SEQUENCE: 121

```
Met Ser Ser Lys Leu Val Leu Val Leu Asn Cys Gly Ser Ser Ser Leu
1               5                   10                  15

Lys Phe Ala Ile Ile Asp Ala Val Asn Gly Glu Glu Tyr Leu Ser Gly
                20                  25                  30

Leu Ala Glu Cys Phe His Leu Pro Glu Ala Arg Ile Lys Trp Lys Met
            35                  40                  45

Asp Gly Asn Lys Gln Glu Ala Leu Gly Ala Gly Ala His Ser
        50                  55                  60

Glu Ala Leu Asn Phe Ile Val Asn Thr Ile Leu Ala Gln Lys Pro Glu
65                  70                  75                  80

Leu Ser Ala Gln Leu Thr Ala Ile Gly His Arg Ile Val His Gly Gly
                85                  90                  95

Glu Lys Tyr Thr Ser Ser Val Val Ile Asp Glu Ser Val Ile Gln Gly
            100                 105                 110

Ile Lys Asp Ala Ala Ser Phe Ala Pro Leu His Asn Pro Ala His Leu
        115                 120                 125

Ile Gly Ile Glu Glu Ala Leu Lys Ser Phe Pro Gln Leu Lys Asp Lys
130                 135                 140

Asn Val Ala Val Phe Asp Thr Ala Phe His Gln Thr Met Pro Glu Glu
145                 150                 155                 160

Ser Tyr Leu Tyr Ala Leu Pro Tyr Asn Leu Tyr Lys Glu His Gly Ile
                165                 170                 175

Arg Arg Tyr Gly Ala His Gly Thr Ser His Phe Tyr Val Thr Gln Glu
            180                 185                 190

Ala Ala Lys Met Leu Asn Lys Pro Val Glu Glu Leu Asn Ile Ile Thr
        195                 200                 205

Cys His Leu Gly Asn Gly Gly Ser Val Ser Ala Ile Arg Asn Gly Lys
210                 215                 220

Cys Val Asp Thr Ser Met Gly Leu Thr Pro Leu Glu Gly Leu Val Met
225                 230                 235                 240

Gly Thr Arg Ser Gly Asp Ile Asp Pro Ala Ile Ile Phe His Leu His
                245                 250                 255

Asp Thr Leu Gly Met Ser Val Asp Ala Ile Asn Lys Leu Leu Thr Lys
            260                 265                 270

Glu Ser Gly Leu Leu Gly Leu Thr Glu Val Thr Ser Asp Cys Arg Tyr
        275                 280                 285

Val Glu Asp Asn Tyr Ala Thr Lys Glu Asp Ala Lys Arg Ala Met Asp
290                 295                 300

Val Tyr Cys His Arg Leu Ala Lys Tyr Ile Gly Ala Tyr Thr Ala Leu
305                 310                 315                 320

Met Asp Gly Arg Leu Asp Ala Val Val Phe Thr Gly Gly Ile Gly Glu
                325                 330                 335

Asn Ala Ala Met Val Arg Glu Leu Ser Leu Gly Lys Leu Gly Val Leu
            340                 345                 350

Gly Phe Glu Val Asp His Glu Arg Asn Leu Ala Ala Arg Phe Gly Lys
        355                 360                 365

Ser Gly Phe Ile Asn Lys Glu Gly Thr Arg Pro Ala Val Val Ile Pro
370                 375                 380

Thr Asn Glu Glu Leu Val Ile Ala Gln Asp Ala Ser Arg Leu Thr Ala
385                 390                 395                 400
```

<210> SEQ ID NO 122
<211> LENGTH: 72
<212> TYPE: DNA
<213> ORGANISM: Artificial sequence
<220> FEATURE:
<223> OTHER INFORMATION: Primer dadX_KO_F

<400> SEQUENCE: 122
catggtattg agcgtatctg gagcgcgctc ggggccaccg atggctttgc aattaaccct    60
cactaaaggg cg    72

<210> SEQ ID NO 123
<211> LENGTH: 73
<212> TYPE: DNA
<213> ORGANISM: Artificial sequence
<220> FEATURE:
<223> OTHER INFORMATION: Primer dadX_KO_R

<400> SEQUENCE: 123
accaataccc gcctgcgggc aaggcgttaa atcgaccgct agcatatcca taatacgact    60
cactataggg ctc    73

<210> SEQ ID NO 124
<211> LENGTH: 20
<212> TYPE: DNA
<213> ORGANISM: Artificial sequence
<220> FEATURE:
<223> OTHER INFORMATION: Primer dadX_seq_F

<400> SEQUENCE: 124
ggctggacga tggcttgcgg    20

<210> SEQ ID NO 125
<211> LENGTH: 20
<212> TYPE: DNA
<213> ORGANISM: Artificial sequence
<220> FEATURE:
<223> OTHER INFORMATION: Primer dadX_seq_R

<400> SEQUENCE: 125
gtgcggtgag ttcaggttcc    20

<210> SEQ ID NO 126
<211> LENGTH: 1107
<212> TYPE: DNA
<213> ORGANISM: Artificial Sequence
<220> FEATURE:
<223> OTHER INFORMATION: Synthetic DNA construct
<220> FEATURE:
<221> NAME/KEY: CDS
<222> LOCATION: (407)..(619)
<223> OTHER INFORMATION: ackA-partial

<400> SEQUENCE: 126
gtctttgagt aatgctgtcc ccggcgaaac aagctaaaaa aattaacaga acgattatcc    60
ggcgttgaca tgcttcacct caacttcaca tataaagatt caaaaatttg tgcaaattca    120
caactcagcg ggacaacgtt caaaacattt tgtcttccat acccactatc aggtatcctt    180
tagcagcctg aaggcctaag tagtacatat tcattgagtc gtcaaattca tatacattat    240
gccattggct gaaaattacg caaaatggca tagactcaag atatttcttc catcatgcaa    300
aaaaaatttg cagtgcatga tgttaatcat aaatgtcggt gtcatcatgc gctacgctct    360

```
atggctccct gacgtttttt tagccacgta tcaattatag gtactt atg tcg agt      415
                                                   Met Ser Ser
                                                     1 aag tta gta ctg gtt ctg aac tgc ggt agt tct tca ctg aaa ttt gcc      463
Lys Leu Val Leu Val Leu Asn Cys Gly Ser Ser Ser Leu Lys Phe Ala
  5              10                  15 atc atc gat gca gta aat ggt gaa gag tac ctt tct ggt tta gcc gaa      511
Ile Ile Asp Ala Val Asn Gly Glu Glu Tyr Leu Ser Gly Leu Ala Glu
 20              25                  30                  35 tgt ttc cac ctg ccc gaa gca cgt atc aaa tgg aaa atg gac ggc aat      559
Cys Phe His Leu Pro Glu Ala Arg Ile Lys Trp Lys Met Asp Gly Asn
             40                  45                  50 aaa cag gaa gcg gct tta ggt gca ggc gcc gct cac agc gaa gcg ctc      607
Lys Gln Glu Ala Ala Leu Gly Ala Gly Ala Ala His Ser Glu Ala Leu
         55                  60                  65 aac ttt atc aat taaccctcac taaagggcgg ccgcgaagtt cctattctct          659
Asn Phe Ile Asn
         70 agaaagtata ggaacttcct cgagccctat agtgagtcgt attagccgat gctgcagggt    719 atgcgcaagc cggttaacga cctgtcccgt ggcgcactgg ttgacgatat cgtctacacc    779 atcgcgctga ctgcgattca gtctgcacag cagcagtaat ctcgtcatca tccgcagctt    839 tgcgctgcgg atatctgaac cggaaataat cactatttcc ggttttttat tctcttaatc    899 tgcattaatc ctttctgatt atcttgctta actgcgctgc atcaatgaat tgcgccattt    959 cactttgcat acttaccact ttgttttgtg caagggaata tttgcgctat gtccgcaatc   1019 actgaatcca aaccaacaag aagatgggca atgcccgata cgttggtgat tatctttttt   1079 gttgctattt taaccagcct tgccacct                                      1107
```

<210> SEQ ID NO 127
<211> LENGTH: 71
<212> TYPE: PRT
<213> ORGANISM: Artificial Sequence
<220> FEATURE:
<223> OTHER INFORMATION: Synthetic Construct

<400> SEQUENCE: 127

Met Ser Ser Lys Leu Val Leu Val Leu Asn Cys Gly Ser Ser Ser Leu
 1               5                  10                  15

Lys Phe Ala Ile Ile Asp Ala Val Asn Gly Glu Glu Tyr Leu Ser Gly
             20                  25                  30

Leu Ala Glu Cys Phe His Leu Pro Glu Ala Arg Ile Lys Trp Lys Met
         35                  40                  45

Asp Gly Asn Lys Gln Glu Ala Ala Leu Gly Ala Gly Ala Ala His Ser
     50                  55                  60

Glu Ala Leu Asn Phe Ile Asn
 65                  70

<210> SEQ ID NO 128
<211> LENGTH: 1177
<212> TYPE: DNA
<213> ORGANISM: Artificial Sequence
<220> FEATURE:
<223> OTHER INFORMATION: Synthetic DNA construct
<220> FEATURE:
<221> NAME/KEY: CDS
<222> LOCATION: (631)..(693)
<223> OTHER INFORMATION: adhE-partial

<400> SEQUENCE: 128

```
caggttggct gtaaggttag ttttgtttcg cgctgccgct gtctgataac tggtcatgct        60
gataaagacg ggaataatcc ctaccgggtt gaccagcgca ataacccga tgaaaattt         120 gaagtaaacg ggaaaatcaa aaaaggtctg aatcacggtt agctccgaag caaaagccgg      180
ataatgttag ccataaataa ggttgaaaag acgcgctgac aatacgcctt ttgacagcat       240
ttttcacctc ctaactactt aaaattgcta tcattcgtta ttgttatcta gttgtgcaaa      300
acatgctaat gtagccacca atcatacta caatttatta actgttagct ataatggcga       360
aaagcgatgc tgaaaggtgt cagctttgca aaaatttgat ttggatcacg taatcagtac     420
ccagaagtga gtaatcttgc ttcgccacc tggaagtgac gcattagaga taataactct       480 aatgttaaa ctctttagt aaatcacagt gagtgtgagc gcgagtaagc ttttgatttt        540
cataggttaa gcaaatcatc accgcactga ctatactctc gtattcgagc agatgattta    600
```
ctaaaaaagt ttaacattat caggagagca atg gct gtt act aat gtc gct gaa        654
                                   Met Ala Val Thr Asn Val Ala Glu
                                    1               5 ctt aac gca ctc gta gag cgt gta aaa att aac cct cac taaagggcgg          703
Leu Asn Ala Leu Val Glu Arg Val Lys Ile Asn Pro His
    10              15                  20

```
aagttcctat tctctagaaa gtataggaac ttcgagccct aatgaactcc gtgctaaaga       763
agccgctccg gctaaagctg agaaaaaagc gaaaaaatcc gcttaatcag tagcgctgtc     823
tggcaatata acggcccct tctggggccg ttttttttgtt tacccaaagc aacttttcca       883
taaaccgaca gcattagcct tcatcatatt tgcgacgatg taacgcct aaacacaggg         943 atattgtact ttcaggtca caagtcaacg tcggtgctta agagccctgt gaggcgtata       1003
gcggcgttaa aaaactgccg agaagggtat atagcccgga agaagtgcgt aaaacgaact    1063
gacaggataa aagtgccctg ctcacccctgt cagtaaagaa attcttatta atcgtggcga    1123
tgcctttcct gaatagccgt taatgagccg acttgtaacg cctctatata gtgt            1177
```

<210> SEQ ID NO 129
<211> LENGTH: 21
<212> TYPE: PRT
<213> ORGANISM: Artificial Sequence
<220> FEATURE:
<223> OTHER INFORMATION: Synthetic Construct

<400> SEQUENCE: 129

Met Ala Val Thr Asn Val Ala Glu Leu Asn Ala Leu Val Glu Arg Val
1               5                   10                  15

Lys Ile Asn Pro His
            20

<210> SEQ ID NO 130
<211> LENGTH: 1134
<212> TYPE: DNA
<213> ORGANISM: Artificial Sequence
<220> FEATURE:
<223> OTHER INFORMATION: Synthetic DNA construct
<220> FEATURE:
<221> NAME/KEY: CDS
<222> LOCATION: (579)..(641)
<223> OTHER INFORMATION: frdA-partial

<400> SEQUENCE: 130

```
ccagcaggcg tttcatatgg tattccgggc tggtcattaa ccagagattc atccctgcg        60 aatgcccggg gccaacgaaa cgtgtctcaa acgggaccaa atgaatatcg gttaccgtcg     120
cctggctcat acaaggcgtc tccacctcca gcactccacg atcggcaaag aaacgacgga    180
```

```
tctccgccat aatcgccgcg cgttttaata agttaggaat ggatgcgctc ggctgccagg      240
atgccgtttc gctcatagtt aaatctccag tttttgacaa gggcacgaag tctactcgca      300
acgcgacggc gagacaaatt ttacgcagga atcaaacagc ggtgggcagt gactaaaaaa      360
agcacgatct gatggtttag taattaaatt aatcatcttc agtgataatt tagccctctt      420
gcgcactaaa aaaatcgatc tcgtcaaatt tcagacttat ccatcagact atactgttgt      480
acctataaag gagcagtgga atagcgttcg cagaccgtaa ctttcaggta cttaccctga      540
agtacgtggc tgtgggataa aaacaatctg aggaatg gtg caa acc ttt caa gcc      596
                                         Val Gln Thr Phe Gln Ala
                                           1               5 gat ctt gcc att gta ggc gcc ggt ggc gcg gga att aac cct cac           641
Asp Leu Ala Ile Val Gly Ala Gly Gly Ala Gly Ile Asn Pro His
        10                  15                  20 taaagggcgg aagttcctat tctctagaaa gtataggaac ttcgagccct aatgaactcc      701
gtgctaacgc gatgcacgat ctgaaaattc acgtgcctgc gggcaaatgg gttttctacg      761
gtctggctgc tatcctgaca gttgtcacgc tgattggtat cgttacaatc taacgtatcg      821
ccaatgtaaa tccggcccgc ctatggcggg ccgttttgta tggaaaccag accttatgtt      881
caaaacgacg ctctgcgcct tattaattac ctcctcttgc tccacatttg ctgcccctca      941
acaaatcaac gatattgtgc atcgcacaat taccccgctt atagagcaac aaaagatccc     1001
cggtatggcg gtggcggtaa tttatcaggg taaaccttat tactttacct ggggctatgc     1061
ggacatcgcc aaaagcagc ccgtcacaca gcaaacgttg tttgagttag gttcggtcag     1121
caaaacattt acg                                                        1134

<210> SEQ ID NO 131
<211> LENGTH: 21
<212> TYPE: PRT
<213> ORGANISM: Artificial Sequence
<220> FEATURE:
<223> OTHER INFORMATION: Synthetic Construct

<400> SEQUENCE: 131

Val Gln Thr Phe Gln Ala Asp Leu Ala Ile Val Gly Ala Gly Gly Ala
 1               5                  10                  15

Gly Ile Asn Pro His
            20

<210> SEQ ID NO 132
<211> LENGTH: 757
<212> TYPE: DNA
<213> ORGANISM: Artificial Sequence
<220> FEATURE:
<223> OTHER INFORMATION: Synthetic DNA construct
<220> FEATURE:
<221> NAME/KEY: CDS
<222> LOCATION: (247)..(309)
<223> OTHER INFORMATION: pflB partial

<400> SEQUENCE: 132
taatccgcga cttcgcatct ccggaattct ggaccgctgt cggttctgca ccggaaaatt       60
tttctcacct gaccgtgatg aacttcatca ctgataacct gattccggtt acgatcggta      120
atattatcgg cggtggtttg ttggttgggt tgacatactg ggtcatttac ctgcgtgaaa      180
acgatcacca ttaatggttg tcgaagtacg cagtaaataa aaaatccact taagaaggta      240 ggtgtt atg tcc gag ctt aat gaa aag tta gcc aca gcc tgg gaa ggt        288
       Met Ser Glu Leu Asn Glu Lys Leu Ala Thr Ala Trp Glu Gly
```

```
                      1               5                   10
ttt acc aaa att aac cct cac taaagggcgg aagttcctat tctctagaaa       339
Phe Thr Lys Ile Asn Pro His
 15                  20 gtataggaac ttcgagccct aatgaactcc gtgctaaaga acagcagcag gacgttatta   399
ctcgtacctt cactcaatct atgtaattag atttgactga aatcgtacag taaaaagcgt   459
acaataaagg ctccacgaaa gtggggcctt ttttagcacg agagcctttt ttgtcagcta   519
tctatacttt aaggtgactg ccaaaacaga ctcgacgtag ccttcgagct gcgcaccaac   579
acggcctcag atgggccaca tctggagaaa caccgcaatg tcagttattg gtcgcattca   639
ctcctttgaa tcctgtggaa ccgtagacgg cccaggtatt cgctttatca ccttttttcca  699 gggctgcctg atgcgctgcc tgtattgtca taaccgcgac acctgggata cgcatggc     757

<210> SEQ ID NO 133
<211> LENGTH: 21
<212> TYPE: PRT
<213> ORGANISM: Artificial Sequence
<220> FEATURE:
<223> OTHER INFORMATION: Synthetic Construct

<400> SEQUENCE: 133

Met Ser Glu Leu Asn Glu Lys Leu Ala Thr Ala Trp Glu Gly Phe Thr
 1               5                  10                  15

Lys Ile Asn Pro His
            20

<210> SEQ ID NO 134
<211> LENGTH: 2022
<212> TYPE: DNA
<213> ORGANISM: Artificial Sequence
<220> FEATURE:
<223> OTHER INFORMATION: Synthetic DNA construct
<220> FEATURE:
<221> NAME/KEY: CDS
<222> LOCATION: (553)..(1671)
<223> OTHER INFORMATION: Geobacillus stearothermophilus alaD

<400> SEQUENCE: 134
gagggttttt ggagcagctg gcgattgctc cgtctgcggc aatttcgcca gacaagcaga    60
atcaagttct accgtgccga cgttcaataa ccagcggctg ggatgtgaaa ggctggcgtt   120
ggtgatatgc gcaagctgac aatctcccac cagataacgg agatcgggaa tgattaaacc   180
tttacgcgta atgcgtgggc tttcatctaa tgcaatacgt gtcccgagcg gtagccagat   240
gcccgccagc gtgggaaccc acagcccgag cgtcatcagc agcgtcaacg gcacaagaat   300
aatcagtaat aacagcgcga gaaccggcttt atatttaccc agcatgggta gttaatatcc   360
tgatttagcg aaaaattaag cattcaatac gggtattgtg gcatgtttaa ccgttcagtt    420
gaaggttgcg cctacactaa gcatagttgt tgatgaattt ttcaatatcg ccatagcttt   480
caattatatt tgaaattttg taaaatattt ttagtagctt aaatgtgatt caacatcact   540
ggagaaagtc tt atg aaa att ggc atc cct aaa gag att aag aac aat gaa   591
               Met Lys Ile Gly Ile Pro Lys Glu Ile Lys Asn Asn Glu
                1               5                  10 aac cgt gta gca atc acc ccg gca ggt gtt atg act ctg gtt aaa gcg   639
Asn Arg Val Ala Ile Thr Pro Ala Gly Val Met Thr Leu Val Lys Ala
 15                  20                  25 ggc cac gat gtg tac gtc gaa acc gaa gcg ggt gcc ggc agc ggc ttc   687
Gly His Asp Val Tyr Val Glu Thr Glu Ala Gly Ala Gly Ser Gly Phe
 30                  35                  40                  45
```

```
agc gac agc gag tat gag aag gcg ggt gcg gtt att gtg act aag gcg     735
Ser Asp Ser Glu Tyr Glu Lys Ala Gly Ala Val Ile Val Thr Lys Ala
                50                  55                  60 gag gac gct tgg gca gcc gaa atg gtt ctg aag gtg aaa gaa ccg ctg     783
Glu Asp Ala Trp Ala Ala Glu Met Val Leu Lys Val Lys Glu Pro Leu
            65                  70                  75 gcg gag gag ttt cgc tat ttt cgt ccg ggt ctg att ttg ttc acc tac     831
Ala Glu Glu Phe Arg Tyr Phe Arg Pro Gly Leu Ile Leu Phe Thr Tyr
        80                  85                  90 ctg cac ctg gct gcg gcc gag gcg ctg acc aag gca ctg gtg gag cag     879
Leu His Leu Ala Ala Ala Glu Ala Leu Thr Lys Ala Leu Val Glu Gln
    95                  100                 105 aag gtt gtt ggc atc gcg tac gaa acg gtt caa ctg gcg aat ggt tcc     927
Lys Val Val Gly Ile Ala Tyr Glu Thr Val Gln Leu Ala Asn Gly Ser
110                 115                 120                 125 ctg ccg ctg ctg acc cct atg tct gaa gtt gcg ggt cgc atg agc gtt     975
Leu Pro Leu Leu Thr Pro Met Ser Glu Val Ala Gly Arg Met Ser Val
                130                 135                 140 caa gtc ggc gct cag ttt ctg gag aaa ccg cac ggt ggc aag ggc att    1023
Gln Val Gly Ala Gln Phe Leu Glu Lys Pro His Gly Gly Lys Gly Ile
            145                 150                 155 ttg ctg ggt ggt gtt ccg ggt gtc cgc cgt ggt aaa gtg acg atc att    1071
Leu Leu Gly Gly Val Pro Gly Val Arg Arg Gly Lys Val Thr Ile Ile
        160                 165                 170 ggc ggt ggt acg gcc ggt acg aac gcg gcc aag att gcc gta ggt ctg    1119
Gly Gly Gly Thr Ala Gly Thr Asn Ala Ala Lys Ile Ala Val Gly Leu
    175                 180                 185 ggt gca gat gtg acc att ctg gac atc aac gcg gaa cgt ttg cgt gag    1167
Gly Ala Asp Val Thr Ile Leu Asp Ile Asn Ala Glu Arg Leu Arg Glu
190                 195                 200                 205 ctg gac gat ctg ttt ggc gac caa gtc acc acc ctg atg agc aac agc    1215
Leu Asp Asp Leu Phe Gly Asp Gln Val Thr Thr Leu Met Ser Asn Ser
                210                 215                 220 tac cac atc gcg gag tgc gtc cgt gaa agc gat ttg gtc gtt ggt gcg    1263
Tyr His Ile Ala Glu Cys Val Arg Glu Ser Asp Leu Val Val Gly Ala
            225                 230                 235 gtg ctg atc ccg ggt gca aaa gcc ccg aaa ctg gtg acc gag gag atg    1311
Val Leu Ile Pro Gly Ala Lys Ala Pro Lys Leu Val Thr Glu Glu Met
        240                 245                 250 gtc cgt agc atg acc ccg ggt tcg gtt ctg gtc gac gtg gca att gac    1359
Val Arg Ser Met Thr Pro Gly Ser Val Leu Val Asp Val Ala Ile Asp
    255                 260                 265 cag ggc ggt atc ttc gaa acc acc gac cgc gtc acg acc cat gat gac    1407
Gln Gly Gly Ile Phe Glu Thr Thr Asp Arg Val Thr Thr His Asp Asp
270                 275                 280                 285 ccg acc tat gtg aaa cat ggc gtg gtt cac tat gcg gtc gcg aat atg    1455
Pro Thr Tyr Val Lys His Gly Val Val His Tyr Ala Val Ala Asn Met
                290                 295                 300 ccg ggt gca gtg ccg cgc acg tcc acg ttc gcg ctg acg aac gtg acg    1503
Pro Gly Ala Val Pro Arg Thr Ser Thr Phe Ala Leu Thr Asn Val Thr
            305                 310                 315 att cca tac gct ctg cag atc gcc aat aag ggc tat cgt gcg gcg tgt    1551
Ile Pro Tyr Ala Leu Gln Ile Ala Asn Lys Gly Tyr Arg Ala Ala Cys
        320                 325                 330 ctg gat aat ccg gca ttg ctg aaa ggc atc aat acc ctg gat ggt cat    1599
Leu Asp Asn Pro Ala Leu Leu Lys Gly Ile Asn Thr Leu Asp Gly His
    335                 340                 345 atc gtt tac gag gct gtg gct gca gca cac aac atg ccg tac act gat    1647
Ile Val Tyr Glu Ala Val Ala Ala Ala His Asn Met Pro Tyr Thr Asp
```

```
                350           355           360           365
gtc cat agc ttg ctg caa ggc taa aattaccct cactaaaggg cggaagttcc       1701
Val His Ser Leu Leu Gln Gly
                370 tattctctag aaagtatagg aacttcgagc cctaatgaac tccgtgctat cttgccgctc     1761 ccctgcattc caggggagct gattcagata atccccaatg acctttcatc ctctattctt    1821 aaaatagccc tgagtcagaa actgtaattg agaaccacaa tgaagaaagt agccgcgctc    1881 gttgcgctaa gcctgctgat ggcgggatgt gtaagtaatg acaaaattgc tgtaacgcca    1941 gaacagttac agcatcatcg ttttgtgctg gaaagcgtaa acggtaagcc cgtgaccaac    2001 gataaaaatc cgccagaaat c                                              2022
```

<210> SEQ ID NO 135
<211> LENGTH: 372
<212> TYPE: PRT
<213> ORGANISM: Artificial Sequence
<220> FEATURE:
<223> OTHER INFORMATION: Synthetic Construct

<400> SEQUENCE: 135

```
Met Lys Ile Gly Ile Pro Lys Glu Ile Lys Asn Asn Glu Asn Arg Val
1               5                   10                  15

Ala Ile Thr Pro Ala Gly Val Met Thr Leu Val Lys Ala Gly His Asp
            20                  25                  30

Val Tyr Val Glu Thr Glu Ala Gly Ala Gly Ser Gly Phe Ser Asp Ser
        35                  40                  45

Glu Tyr Glu Lys Ala Gly Ala Val Ile Val Thr Lys Ala Glu Asp Ala
    50                  55                  60

Trp Ala Ala Glu Met Val Leu Lys Val Lys Glu Pro Leu Ala Glu Glu
65                  70                  75                  80

Phe Arg Tyr Phe Arg Pro Gly Leu Ile Leu Phe Thr Tyr Leu His Leu
                85                  90                  95

Ala Ala Ala Glu Ala Leu Thr Lys Ala Leu Val Glu Gln Lys Val Val
            100                 105                 110

Gly Ile Ala Tyr Glu Thr Val Gln Leu Ala Asn Gly Ser Leu Pro Leu
        115                 120                 125

Leu Thr Pro Met Ser Glu Val Ala Gly Arg Met Ser Val Gln Val Gly
130                 135                 140

Ala Gln Phe Leu Glu Lys Pro His Gly Gly Lys Gly Ile Leu Leu Gly
145                 150                 155                 160

Gly Val Pro Gly Val Arg Arg Gly Lys Val Thr Ile Ile Gly Gly Gly
                165                 170                 175

Thr Ala Gly Thr Asn Ala Ala Lys Ile Ala Val Gly Leu Gly Ala Asp
            180                 185                 190

Val Thr Ile Leu Asp Ile Asn Ala Glu Arg Leu Arg Glu Leu Asp Asp
        195                 200                 205

Leu Phe Gly Asp Gln Val Thr Thr Leu Met Ser Asn Ser Tyr His Ile
    210                 215                 220

Ala Glu Cys Val Arg Glu Ser Asp Leu Val Val Gly Ala Val Leu Ile
225                 230                 235                 240

Pro Gly Ala Lys Ala Pro Lys Leu Val Thr Glu Met Val Arg Ser
                245                 250                 255

Met Thr Pro Gly Ser Val Leu Val Asp Val Ala Ile Asp Gln Gly Gly
            260                 265                 270
```

```
Ile Phe Glu Thr Thr Asp Arg Val Thr Thr His Asp Pro Thr Tyr
    275                 280                 285

Val Lys His Gly Val Val His Tyr Ala Val Ala Asn Met Pro Gly Ala
    290                 295                 300

Val Pro Arg Thr Ser Thr Phe Ala Leu Thr Asn Val Thr Ile Pro Tyr
305                 310                 315                 320

Ala Leu Gln Ile Ala Asn Lys Gly Tyr Arg Ala Ala Cys Leu Asp Asn
                325                 330                 335

Pro Ala Leu Leu Lys Gly Ile Asn Thr Leu Asp Gly His Ile Val Tyr
            340                 345                 350

Glu Ala Val Ala Ala Ala His Asn Met Pro Tyr Thr Asp Val His Ser
        355                 360                 365

Leu Leu Gln Gly
    370
```